US012655192B2

(12) United States Patent
Velasquez et al.

(10) Patent No.: US 12,655,192 B2
(45) Date of Patent: Jun. 16, 2026

(54) GRP78 TARGETED ADOPTIVE CELL THERAPY

(71) Applicant: St. Jude Children's Research Hospital, Inc., Memphis, TN (US)

(72) Inventors: Mireya Paulina Velasquez, Memphis, TN (US); Stephen Gottschalk, Germantown, TN (US); Nikhil Hebbar, Cordova, TN (US); Rebecca Epperly, Memphis, TN (US); Abishek Vaidya, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 759 days.

(21) Appl. No.: 17/919,728

(22) PCT Filed: Apr. 23, 2021

(86) PCT No.: PCT/US2021/028830
§ 371 (c)(1),
(2) Date: Oct. 18, 2022

(87) PCT Pub. No.: WO2021/216994
PCT Pub. Date: Oct. 28, 2021

(65) Prior Publication Data
US 2023/0312671 A1       Oct. 5, 2023

Related U.S. Application Data

(60) Provisional application No. 63/015,119, filed on Apr. 24, 2020.

(51) Int. Cl.
*A61K 40/11* (2025.01)
*A61K 40/31* (2025.01)
(Continued)

(52) U.S. Cl.
CPC .......... *C07K 14/7051* (2013.01); *A61K 40/11* (2025.01); *A61K 40/31* (2025.01);
(Continued)

(58) Field of Classification Search
CPC . C07K 14/7051; A61P 35/00; A61K 40/4262; A61K 40/31; A61K 40/11
See application file for complete search history.

(56) References Cited

U.S. PATENT DOCUMENTS

| | | | | |
|---|---|---|---|---|
| 6,900,292 | B2 * | 5/2005 | Sun ...................... | C07K 14/505 |
| | | | | 530/397 |
| 2011/0319336 | A1 * | 12/2011 | Kawakami .............. | A61P 35/00 |
| | | | | 435/254.2 |
| 2019/0112380 | A1 * | 4/2019 | Chaudhary ........ | C07K 16/2896 |

FOREIGN PATENT DOCUMENTS

| | | | | |
|---|---|---|---|---|
| WO | WO-2018022479 | A1 * | 2/2018 | ......... G01N 33/6854 |
| WO | 2019090003 | A1 | 5/2019 | |

(Continued)

OTHER PUBLICATIONS

U.S. Appl. No. 18/727,752, filed Jul. 10, 2024, Velasquez.*
(Continued)

*Primary Examiner* — Julie Wu
(74) *Attorney, Agent, or Firm* — Troutman Pepper Locke LLP

(57) ABSTRACT

The present invention provides a chimeric antigen receptor (CAR) comprising an extracellular target-binding domain comprising at least one glucose-regulated-protein 78 (GRP78)-binding moiety. The present invention further provides polynucleotides and recombinant vectors encoding such CARs. The present invention further provides isolated host cells and methods for preparing isolated host cells expressing the CARs. The present invention further provides pharmaceutical compositions comprising the host cells and
(Continued)

10C3 Dylight488 Ab      Biotin-Ahx-CTVALPGGYVRVC methods for treating a tumor using the pharmaceutical compositions.

27 Claims, 53 Drawing Sheets

Specification includes a Sequence Listing.

(51) Int. Cl.

| | |
|---|---|
| *A61K 40/42* | (2025.01) |
| *A61P 35/00* | (2006.01) |
| *C07K 14/705* | (2006.01) |
| *C12N 15/63* | (2006.01) |

(52) U.S. Cl.
CPC .......... *A61K 40/4262* (2025.01); *A61P 35/00* (2018.01); *C12N 15/63* (2013.01); *A61K 2239/31* (2023.05); *C07K 2319/02* (2013.01); *C07K 2319/03* (2013.01)

(56) References Cited

FOREIGN PATENT DOCUMENTS

| | | | |
|---|---|---|---|
| WO | WO-2019089982 A1 * | 5/2019 | ......... A61K 40/4215 |
| WO | 2019154313 A1 | 8/2019 | |

OTHER PUBLICATIONS

"Pre-clinical evaluation of CD38 chimeric antigen receptor engineered T cells for the treatment of multiple myeloma," Drent et al., Plasma Cell Disorders (Year: 2016).*

GenBank: LR584050.1; Echeneis naucrates genome assembly, chromosome: 9; https://www.ncbi.nim.nih.gov/nuccore/1610704160?sat=49&satkey=43513024; Aug. 21, 2021.

International Search Report mailed Oct. 4, 2021 for International Patent Application No. PCT/US2021/028830, which was filed Apr. 23, 2021 and published as WO 2021/216994 on Oct. 28, 2021 (Applicant: St. Jude Children's Research Hospital, Inc. // Inventor: Mireya Paulina Velasquez // (17 pages).

* cited by examiner

FIG. 3B
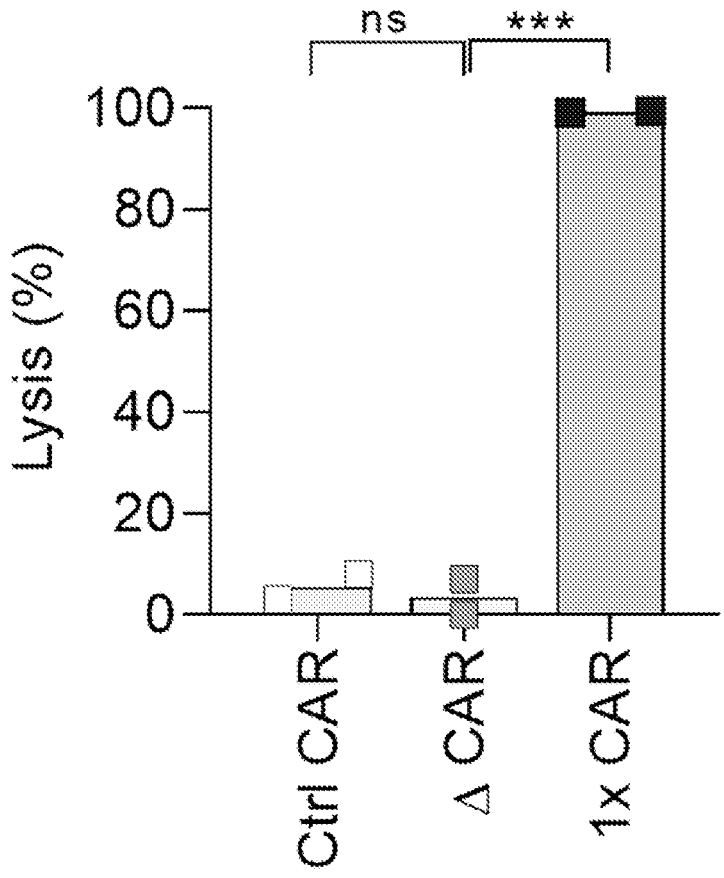

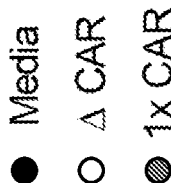
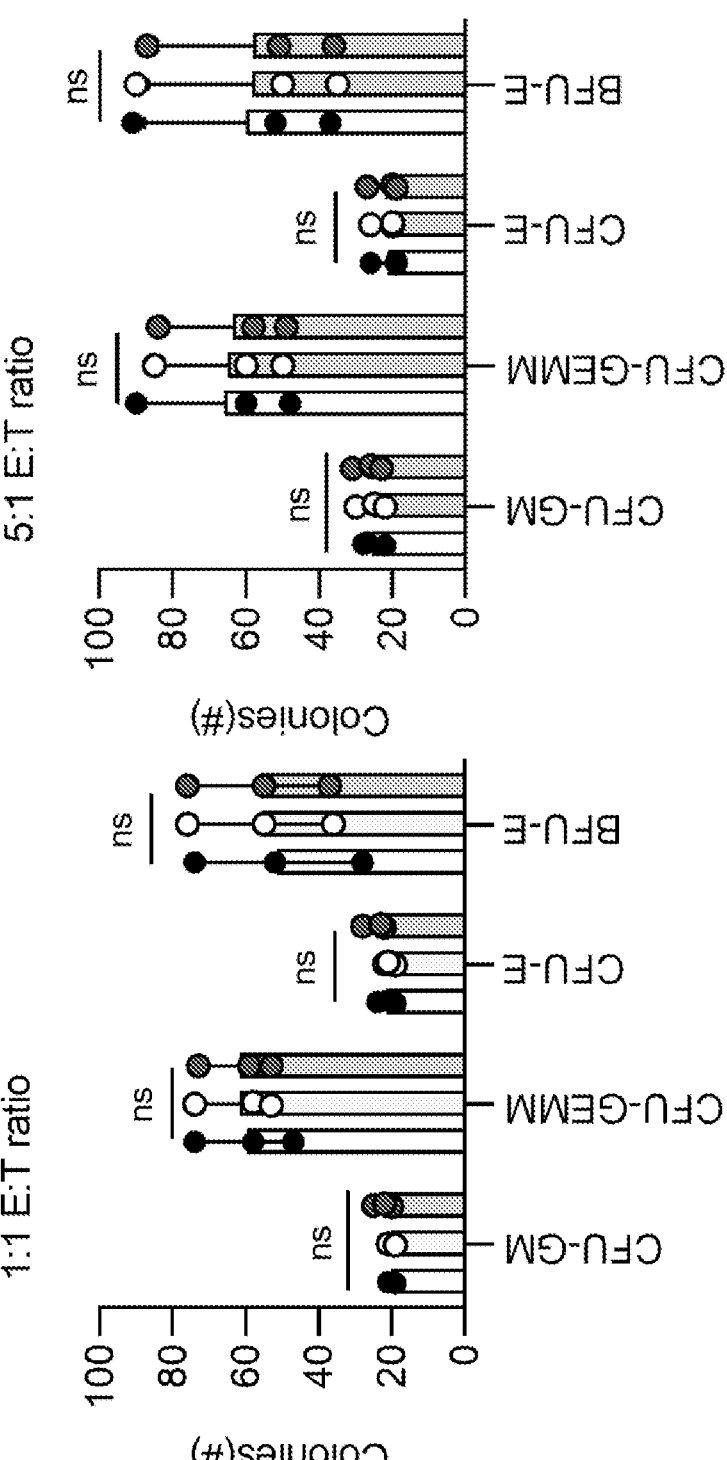
FIG. 3E

FIG. 4A

AML- MOLM13 (intravenous) –
$3 \times 10^6$ T cells

AML- MOLM13 (intravenous) - 10x10⁶ T cells

CAR-T cell dose -  3x10⁶ cells

FIG. 6A

GRP78 Peptide-CAR Component Sequences

Leader: IgG Heavy chain signal peptide
MDWIWRILFL VGAATGAHS

GRP78 peptide sequence:
CTVALPGGYVRVC

Linker:
GGGGS

*mutIgG4 Hinge*
*ESKYGPPCPS CPAPEFEGGP SVFLFPPKPK DTLMISRTPE VTCVVVDVSQ EDPEVQFNWY*
*VDGVEVHNAK TKPREEQFQS TYRVVSVLTV LHQDWLNGKE YKCKVSNKGL PSSIEKTISK*
*AKGQPREPQV YTLPPSQEEM TKNQVSLTCL VKGFYPSDIA VEWESNGQPE NNYKTTPPVL*
*DSDGSFFLYS RLTVDKSRWQ EGNVFSCSVM HEALHNHYTQ KSLSLSLGK*

*CD28 Transmembrane domain*
*FWVLVVVGGV LACYSLLVTV AFIIFWV*

CD28 Costim/Endodomain:
RSKRSRLLHS DYMNMTPRRP GPTRKHYQPY APPRDFAAYRS

*CD3ζ Endodomain:*
*RVKFSRSADA PAYQQGQNQL YNELNLGRRE EYDVLDKRRG RDPEMGGKPR RKNPQEGLYN*
*ELQKDKMAEA YSEIGMKGER RRGKGHDGLY QGLSTATKDT YDALHMQALP PR*

T2A Ribosomal Skip:
EGRGSLLTCG DVEENPGP

Truncated CD19:
MPPPRLLFFL LFLTPMEVRP EEPLVVKVEE GDNAVLQCLK GTSDGPTQQL TWSRESPLKP
FLKLSLGLPG LGIHMRPLAI WLFIFNVSQQ MGGFYLCQPG PPSEKAWQPG WTVNVEGSGE
LFRWNVSDLG GLGCGLKNRS SEGPSSPSGK LMSPKLYVWA KDRPEIWEGE PPCLPPRDSL
NQSLSQDLTM APGSTLWLSC GVPPDSVSRG PLSWTHVHPK GPKSLLSLEL KDDRPARDMW
VMETGLLLPR ATAQDAGKYY CHRGNLTMSF HLEITARPVL WHWLLRTGGW KVSAVTLAYL
IFCLCSLVGI LHLQRALVLR RKRKRMTDPT RRF

FIG. 6B

GRP78 1X Peptide.mutIgG4H.CD28TM.CD3ζ.T2A.tCd19

<u>Nucleotide sequence</u>
ATGGACTGGATTTGGCGGATCCTGTTTCTCGTGGGAGCCGCCACAGGCGCCCATTCTTGTACTGTGGCCCTT
CCTGGTGGATACGTTAGAGTGTGCGAATTC*GAGTCTAAGTACGGCCCTCCTTGTCCTAGCTGCCCCGCTCCT*
*GAATTTGAAGGCGGCCCTTCCGTGTTCCTGTTTCCTCCAAAGCCTAAGGACACCCTGATGATCAGCAGAACC*
*CCTGAAGTGACCTGCGTGGTGGTGGACGTGTCCCAAGAGGATCCTGAGGTGCAGTTCAATTGGTACGTGGAC*
*GGCGTGGAAGTGCACAACGCCAAGACCAAGCCTAGAGAGGAACAGTTCCAGAGCACCTACAGAGTGGTGTCC*
*GTGCTGACAGTGCTGCACCAGGATTGGCTGAACGGCAAAGAGTACAAGTGCAAGGTGTCCAACAAGGGCCTG*
*CCTAGCAGCATCGAGAAAACCATCAGCAAGGCCAAGGGCCAGCCAAGAGAACCCCAGGTGTACACACTGCCT*
*CCAAGCCAAGAGGAAATGACCAAGAACCAGGTGTCCCTGACCTGCCTGGTCAAGGGCTTCTACCCTTCCGAT*
*ATCGCCGTGGAATGGGAGAGCAATGGCCAGCCTGAGAACAACTACAAGACCACACCTCCTGTGCTGGACAGC*
*GACGGCTCATTCTTCCTGTACAGCAGACTGACCGTGGACAAGAGCAGATGGCAAGAGGGCAACGTGTTCAGC*
*TGCAGCGTGATGCACGAGGCCCTGCACAACCACTACACCCAGAAGTCTCTGAGCCTGAGCCTCGGCAAG*GGC
TCC*TTCTGGGTGCTCGTTGTTGTTGGCGGCGTGCTGGCCTGTTACAGCCTGCTGGTTACCGTGGCCTTCATC*
ATCTTTTGGGTCCGAAGCAAGCGGAGCCGGCTGCTGCACAGCGATTACATGAACATGACCCCTCGGAGGCCC
GGACCAACCAGAAAGCACTACCAGCCTTACGCTCCTCCTAGAGACTTCGCCGCCTACCGGTCC*AGAGTGAAG*
*TTCAGCAGATCCGCCGATGCTCCCGCCTATCAGCAGGGACAGAACCAGCTGTACAACGAGCTGAACCTGGGG*
*AGAAGAGAAGAGTACGACGTGCTGGATAAGCGGAGAGGCAGAGATCCTGAGATGGGCGGCAAGCCCAGACGG*
*AAGAATCCTCAAGAGGGCCTGTATAATGAGCTGCAGAAAGACAAGATGGCCGAGGCCTACAGCGAGATCGGA*
*ATGAAGGGCGAGCGCAGAAGAGGCAAGGGACACGATGGACTGTACCAGGGACTGAGCACCGCCACCAAGGAT*
*ACCTATGACGCACTGCACATGCAGGCCCTGCCACCTAGA*AGATCTGGCTCTGGCGAAGGCAGAGGCTCTCTG
CTGACATGTGGCGACGTGGAAGAGAATCCTGGACCTATGCCTCCCCCCAGACTGCTGTTCTTCCTGCTGTTC
CTGACCCCTATGGAAGTGCGGCCCGAGGAACCCCTGGTCGTGAAAGTGGAAGAGGGCGACAACGCCGTGCTG
CAGTGTCTGAAGGGCACCTCCGATGGCCCTACCCAGCAGCTGACCTGGTCCAGAGAGAGCCCCCTGAAGCCC
TTCCTGAAGCTGTCTCTGGGCCTGCCTGGCCTGGGCATCCATATGAGGCCACTGGCCATCTGGCTGTTCATC
TTCAACGTGTCCCAGCAGATGGGAGGCTTCTACCTGTGCCAGCCTGGCCCACCTTCTGAGAAGGCTTGGCAG
CCTGGCTGGACCGTGAACGTGGAAGGATCTGGCGAGCTGTTCCGGTGGAACGTGTCCGATCTGGGCGGCCTG
GGATGCGGCCTGAAGAACAGATCTAGCGAGGGCCCCAGCAGCCCCAGCGGCAAACTGATGAGCCCCAAGCTG
TACGTGTGGGCCAAGGACAGACCCGAGATTTGGGAGGGCGAGCCCCCTTGCCTGCCCCCTAGAGATAGCCTG
AACCAGAGCCTGAGCCAGGACCTGACAATGGCCCCTGGCAGCACACTGGCTGAGCTGTGGCGTGCCACCC
GACTCTGTGTCTAGAGGCCCTCTGAGCTGGACCCACGTGCACCCTAAGGGCCCTAAGAGCCTGCTGTCCCTG
GAACTGAAGGACGACAGGCCCGCCAGAGATATGTGGGTCATGGAAACCGGCCTGCTGCTGCCTAGAGCCACA
GCCCAGGATGCCGGCAAGTACTACTGCCACAGAGGCAACCTGACCATGAGCTTCCACCTGGAAATCACCGCC
AGACCCGTGCTGTGGCACTGGCTGCTGAGAACCGGCGGATGGAAAGTGTCCGCCGTGACTCTGGCCTACCTG
ATCTTCTGCCTGTGCTCCCTCGTGGGCATCCTGCATCTGCAGAGGGCTCTGGTGCTGCGGCGGAAGCGGAAG
AGAATGACCGACCCTACCCGGCGGTTCTAA <u>Amino acid Sequence:</u>
MDWIWRILFLVGAATGAHSCTVALPGGYVRVCEF*ESKYGPPCPSCPAPEFEGGPSVFLFPPKPKDTLMISRT*
*PEVTCVVVDVSQEDPEVQFNWYVDGVEVHNAKTKPREEQFQSTYRVVSVLTVLHQDWLNGKEYKCKVSNKGL*
*PSSIEKTISKAKGQPREPQVYTLPPSQEEMTKNQVSLTCLVKGFYPSDIAVEWESNGQPENNYKTTPPVLDS*
*DGSFFLYSRLTVDKSRWQEGNVFSCSVMHEALHNHYTQKSLSLSLGK*GS*FWVLVVVGGVLACYSLLVTVAFI*
*IFWVRSKRSRLLHSDYMNMTPRRPGPTRKHYQPYAPPRDFAAYRS**RVKFSRSADAPAYQQGQNQLYNELNLG*
*RREEYDVLDKRRGRDPEMGGKPRRKNPQEGLYNELQKDKMAEAYSEIGMKGERRRGKGHDGLYQGLSTATKD*
*TYDALHMQALPPR*RSGSGEGRGSLLTCGDVEENPGPMPPPRLLFFLLFLTPMEVRPEEPLVVKVEEGDNAVL
QCLKGTSDGPTQQLTWSRESPLKPFLKLSLGLPGLGIHMRPLAIWLFIFNVSQQMGGFYLCQPGPPSEKAWQ
PGWTVNVEGSGELFRWNVSDLGGLGCGLKNRSSEGPSSPSGKLMSPKLYVWAKDRPEIWEGEPPCLPPRDSL
NQSLSQDLTMAPGSTLWLSCGVPPDSVSRGPLSWTHVHPKGPKSLLSLELKDDRPARDMWVMETGLLLPRAT
AQDAGKYYCHRGNLTMSFHLEITARPVLWHWLLRTGGWKVSAVTLAYLIFCLCSLVGILHLQRALVLRRKRK
RMTDPTRRF*

FIG. 6C

GRP78 2X Peptide.mutIgG4H.CD28TM.CD3ζ.T2A.tCD19

Nucleotide sequence:
ATGGACTGGATTTGGCGGATCCTGTTTCTCGTGGGAGCCGCCACAGGCGCCCATTCTTGTACTGTG
GCCCTTCCTGGTGGATACGTTAGAGTGTGCGGTGGCGGCGGAAGCTGTACTGTGGCCCTTCCTGGT
GGATACGTTAGAGTGTGCGAATTCGAGTCTAAGTACGGCCCTCCTTGTCCTAGCTGCCCCGCTCCT
GAATTTGAAGGCGGCCCTTCCGTGTTCCTGTTTCCTCCAAAGCCTAAGGACACCCTGATGATCAGC
AGAACCCCTGAAGTGACCTGCGTGGTGGTGGACGTGTCCCAAGAGGATCCTGAGGTGCAGTTCAAT
TGGTACGTGGACGGCGTGGAAGTGCACAACGCCAAGACCAAGCCTAGAGAGGAACAGTTCCAGAGC
ACCTACAGAGTGGTGTCCGTGCTGACAGTGCTGCACCAGGATTGGCTGAACGGCAAAGAGTACAAG
TGCAAGGTGTCCAACAAGGGCCTGCCTAGCAGCATCGAGAAAACCATCAGCAAGGCCAAGGGCCAG
CCAAGAGAACCCCAGGTGTACACACTGCCTCCAAGCCAAGAGGAAATGACCAAGAACCAGGTGTCC
CTGACCTGCCTGGTCAAGGGCTTCTACCCTTCCGATATCGCCGTGGAATGGGAGAGCAATGGCCAG
CCTGAGAACAACTACAAGACCACACCTCCTGTGCTGGACAGCGACGGCTCATTCTTCCTGTACAGC
AGACTGACCGTGGACAAGAGCAGATGGCAAGAGGGCAACGTGTTCAGCTGCAGCGTGATGCACGAG
GCCCTGCACAACCACTACACCCAGAAGTCTCTGAGCCTGAGCCTCGGCAAGGGCTCCTTCTGGGTG
CTCGTTGTTGTTGGCGGCGTGCTGGCCTGTTACAGCCTGCTGGTTACCGTGGCCTTCATCATCTTT
TGGGTCCGAAGCAAGCGGAGCCGGCTGCTGCACAGCGATTACATGAACATGACCCCTCGGAGGCCC
GGACCAACCAGAAAGCACTACCAGCCTTACGCTCCTCCTAGAGACTTCGCCGCCTACCGGTCCAGA
GTGAAGTTCAGCAGATCCGCCGATGCTCCCGCCTATCAGCAGGGACAGAACCAGCTGTACAACGAG
CTGAACCTGGGGAGAAGAGAAGAGTACGACGTGCTGGATAAGCGGAGAGGCAGAGATCCTGAGATG
GGCGGCAAGCCCAGACGGAAGAATCCTCAAGAGGGCCTGTATAATGAGCTGCAGAAAGACAAGATG
GCCGAGGCCTACAGCGAGATCGGAATGAAGGGCGAGCGCAGAAGAGGCAAGGGACACGATGGACTG
TACCAGGGACTGAGCACCGCCACCAAGGATACCTATGACGCACTGCACATGCAGGCCCTGCCACCT
AGAAGATCTGGCTCTGGCGAAGGCAGAGGCTCTCTGCTGACATGTGGCGACGTGGAAGAGAATCCT
GGACCTATGCCTCCCCCCAGACTGCTGTTCTTCCTGCTGTTCCTGACCCCTATGGAAGTGCGGCCC
GAGGAACCCCTGGTCGTGAAAGTGGAAGAGGGCGACAACGCCGTGCTGCAGTGTCTGAAGGGCACC
TCCGATGGCCCTACCCAGCAGCTGACCTGGTCCAGAGAGAGCCCCCTGAAGCCCTTCCTGAAGCTG
TCTCTGGGCCTGCCTGGCCTGGGCATCCATATGAGGCCACTGGCCATCTGGCTGTTCATCTTCAAC
GTGTCCCAGCAGATGGGAGGCTTCTACCTGTGCCAGCCTGGCCCACCTTCTGAGAAGGCTTGGCAG
CCTGGCTGGACCGTGAACGTGGAAGGATCTGGCGAGCTGTTCCGGTGGAACGTGTCCGATCTGGGC
GGCCTGGGATGCGGCCTGAAGAACAGATCTAGCGAGGGCCCCAGCAGCCCCAGCGGCAAACTGATG
AGCCCCAAGCTGTACGTGTGGGCCAAGGACAGACCCGAGATTTGGGAGGGCGAGCCCCCTTGCCTG
CCCCCTAGAGATAGCCTGAACCAGAGCCTGAGCCAGGACCTGACAATGGCCCCTGGCAGCACACTG
TGGCTGAGCTGTGGCGTGCCACCCGACTCTGTGTCTAGAGGCCCTCTGAGCTGGACCCACGTGCAC
CCTAAGGGCCCTAAGAGCCTGCTGTCCCTGGAACTGAAGGACGACAGGCCCGCCAGAGATATGTGG
GTCATGGAAACCGGCCTGCTGCTGCCTAGAGCCACAGCCCAGGATGCCGGCAAGTACTACTGCCAC
AGAGGCAACCTGACCATGAGCTTCCACCTGGAAATCACCGCCAGACCCGTGCTGTGGCACTGGCTG
CTGAGAACCGGCGGATGGAAAGTGTCCGCCGTGACTCTGGCCTACCTGATCTTCTGCCTGTGCTCC
CTCGTGGGCATCCTGCATCTGCAGAGGGCTCTGGTGCTGCGGCGGAAGCGGAAGAGAATGACCGAC
CCTACCCGGCGGTTCTAA Amino acid sequence:
MDWIWRILFLVGAATGAHSCTVALPGGYVRVCGGGGSCTVALPGGYVRVCEFESKYGPPCPSCPAP
EFEGGPSVFLFPPKPKDTLMISRTPEVTCVVVDVSQEDPEVQFNWYVDGVEVHNAKTKPREEQFQS
TYRVVSVLTVLHQDWLNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKSRWQEGNVFSCSVMHE
ALHNHYTQKSLSLSLGKGSFWVLVVVGGVLACYSLLVTVAFIIFWVRSKRSRLLHSDYMNMTPRRP
GPTRKHYQPYAPPRDFAAYRSRVKFSRSADAPAYQQGQNQLYNELNLGRREEYDVLDKRRGRDPEM
GGKPRRKNPQEGLYNELQKDKMAEAYSEIGMKGERRRGKGHDGLYQGLSTATKDTYDALHMQALPP
RRSGSGEGRGSLLTCGDVEENPGPMPPPRLLFFLLFLTPMEVRPEEPLVVKVEEGDNAVLQCLKGT
SDGPTQQLTWSRESPLKPFLKLSLGLPGLGIHMRPLAIWLFIFNVSQQMGGFYLCQPGPPSEKAWQ
PGWTVNVEGSGELFRWNVSDLGGLGCGLKNRSSEGPSSPSGKLMSPKLYVWAKDRPEIWEGEPPCL
PPRDSLNQSLSQDLTMAPGSTLWLSCGVPPDSVSRGPLSWTHVHPKGPKSLLSLELKDDRPARDMW
VMETGLLLPRATAQDAGKYYCHRGNLTMSFHLEITARPVLWHWLLRTGGWKVSAVTLAYLIFCLCS
LVGILHLQRALVLRRKRKRMTDPTRRF*

FIG. 6D

GRP78 3X Peptide.mutIgG4H.CD28TM.CD3ζ.T2A.tCd19

Nucleotide sequence:
ATGGACTGGATTTGGCGGATCCTGTTTCTCGTGGGAGCCGCCACAGGCGCCCATTCTTGTACTGTGG
CCCTTCCTGGTGGATACGTTAGAGTGTGCGGTGGCGGCGGAAGCTGTACTGTGGCCCTTCCTGGTGG
ATACGTTAGAGTGTGCGGTGGCGGCGGAAGCTGTACTGTGGCCCTTCCTGGTGGATACGTTAGAGTG
TGCGAATTCGAGTCTAAGTACGGCCCTCCTTGTCCTAGCTGCCCCGCTCCTGAATTTGAAGGCGGCC
CTTCCGTGTTCCTGTTTCCTCCAAAGCCTAAGGACACCCTGATGATCAGCAGAACCCCTGAAGTGAC
CTGCGTGGTGGTGGACGTGTCCCAAGAGGATCCTGAGGTGCAGTTCAATTGGTACGTGGACGGCGTG
GAAGTGCACAACGCCAAGACCAAGCCTAGAGAGGAACAGTTCCAGAGCACCTACAGAGTGGTGTCCG
TGCTGACAGTGCTGCACCAGGATTGGCTGAACGGCAAAGAGTACAAGTGCAAGGTGTCCAACAAGGG
CCTGCCTAGCAGCATCGAGAAAACCATCAGCAAGGCCAAGGGCCAGCCAAGAGAACCCCAGGTGTAC
ACACTGCCTCCAAGCCAAGAGGAAATGACCAAGAACCAGGTGTCCCTGACCTGCCTGGTCAAGGGCT
TCTACCCTTCCGATATCGCCGTGGAATGGGAGAGCAATGGCCAGCCTGAGAACAACTACAAGACCAC
ACCTCCTGTGCTGGACAGCGACGGCTCATTCTTCCTGTACAGCAGACTGACCGTGGACAAGAGCAGA
TGGCAAGAGGGCAACGTGTTCAGCTGCAGCGTGATGCACGAGGCCCTGCACAACCACTACACCCAGA
AGTCTCTGAGCCTGAGCCTCGGCAAGGGCTCCTTCTGGGTGCTCGTTGTTGTTGGCGGCGTGCTGGC
CTGTTACAGCCTGCTGGTTACCGTGGCCTTCATCATCTTTTGGGTCCGAAGCAAGCGGAGCCGGCTG
CTGCACAGCGATTACATGAACATGACCCCTCGGAGGCCCGGACCAACCAGAAAGCACTACCAGCCTT
ACGCTCCTCCTAGAGACTTCGCCGCCTACCGGTCC*AGAGTGAAGTTCAGCAGATCCGCCGATGCTCC*
*CGCCTATCAGCAGGGACAGAACCAGCTGTACAACGAGCTGAACCTGGGGAGAAGAGAAGAGTACGAC*
*GTGCTGGATAAGCGGAGAGGCAGAGATCCTGAGATGGGCGGCAAGCCCAGACGGAAGAATCCTCAAG*
*AGGGCCTGTATAATGAGCTGCAGAAAGACAAGATGGCCGAGGCCTACAGCGAGATCGGAATGAAGGG*
*CGAGCGCAGAAGAGGCAAGGGACACGATGGACTGTACCAGGACTGAGCACCGCCACCAAGGATACC*
*TATGACGCACTGCACATGCAGGCCCTGCCACCTAGA*AGATCTGGCTCTGGCGAAGGCAGAGGCTCTC
TGCTGACATGTGGCGACGTGGAAGAGAATCCTGGACCTATGCCTCCCCCAGACTGCTGTTCTTCCT
GCTGTTCCTGACCCCTATGGAAGTGCGGCCCGAGGAACCCCTGGTCGTGAAAGTGGAAGAGGGCGAC
AACGCCGTGCTGCAGTGTCTGAAGGGCACCTCCGATGGCCCTACCCAGCAGCTGACCTGGTCCAGAG
AGAGCCCCCTGAAGCCCTTCCTGAAGCTGTCTCTGGGCCTGCCTGGCCTGGGCATCCATATGAGGCC
ACTGGCCATCTGGCTGTTCATCTTCAACGTGTCCCAGCAGATGGGAGGCTTCTACCTGTGCCAGCCT
GGCCCACCTTCTGAGAAGGCTTGGCAGCCTGGCTGGACCGTGAACGTGGAAGGATCTGGCGAGCTGT
TCCGGTGGAACGTGTCCGATCTGGGCGGCCTGGGATGCGGCCTGAAGAACAGATCTAGCGAGGGCCC
CAGCAGCCCCAGCGGCAAACTGATGAGCCCCAAGCTGTACGTGTGGGCCAAGGACAGACCCGAGATT
TGGGAGGGCGAGCCCCCTTGCCTGCCCCCTAGAGATAGCCTGAACCAGAGCCTGAGCCAGGACCTGA
CAATGGCCCCTGGCAGCACACTGTGGCTGAGCTGTGGCGTGCCACCCGACTCTGTGTCTAGAGGCCC
TCTGAGCTGGACCCACGTGCACCCTAAGGGCCCTAAGAGCCTGCTGTCCCTGGAACTGAAGGACGAC
AGGCCCGCCAGAGATATGTGGGTCATGGAAACCGGCCTGCTGCTGCCTAGAGCCACAGCCCAGGATG
CCGGCAAGTACTACTGCCACAGAGGCAACCTGACCATGAGCTTCCACCTGGAAATCACCGCCAGACC
CGTGCTGTGGCACTGGCTGCTGAGAACCGGCGGATGGAAAGTGTCCGCCGTGACTCTGGCCTACCTG
ATCTTCTGCCTGTGCTCCCTCGTGGGCATCCTGCATCTGCAGAGGGCTCTGGTGCTGCGGCGGAAGC
GGAAGAGAATGACCGACCCTACCCGGCGGTTCTAA Amino acid sequence:
MDWIWRILFLVGAATGAHSCTVALPGGYVRVCGGGGSCTVALPGGYVRVCGGGGSCTVALPGGYVRV
CEFESKYGPPCPSCPAPEFEGGPSVFLFPPKPKDTLMISRTPEVTCVVVDVSQEDPEVQFNWYVDGV
EVHNAKTKPREEQFQSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFLYSRLTVDKSR
WQEGNVFSCSVMHEALHNHYTQKSLSLSLGKGSFWVLVVVGGVLACYSLLVTVAFIIFWVRSKRSRL
LHSDYMNMTPRRPGPTRKHYQPYAPPRDFAAYRS*RVKFSRSADAPAYQQGQNQLYNELNLGRREEYD*
*VLDKRRGRDPEMGGKPRRKNPQEGLYNELQKDKMAEAYSEIGMKGERRRGKGHDGLYQGLSTATKDT*
*YDALHMQALPPR*RSGSGEGRGSLLTCGDVEENPGPMPPPRLLFFLLFLTPMEVRPEEPLVVKVEEGD
NAVLQCLKGTSDGPTQQLTWSRESPLKPFLKLSLGLPGLGIHMRPLAIWLFIFNVSQQMGGFYLCQP
GPPSEKAWQPGWTVNVEGSGELFRWNVSDLGGLGCGLKNRSSEGPSSPSGKLMSPKLYVWAKDRPEI
WEGEPPCLPPRDSLNQSLSQDLTMAPGSTLWLSCGVPPDSVSRGPLSWTHVHPKGPKSLLSLELKDD
RPARDMWVMETGLLLPRATAQDAGKYYCHRGNLTMSFHLEITARPVLWHWLLRTGGWKVSAVTLAYL
IFCLCSLVGILHLQRALVLRRKRKRMTDPTRRF*

FIG. 7A

<u>GRP78 scFv-CAR Component Sequences</u>

Leader: CD8α Leader Peptide
MALPVTALLL PLALLLHAARP

GRP78 L21 scFv sequence:
EVQLVESGGG VVQPGRSLRL SCAASGFTFS SYGMHWVRQA PGKGLEWVAV ISYDGSNKYY
ADSVKGRFTI SRDNSKNTLY LQMNSLRAED TAVYYCARKI NNTKEVWGQG TLVTVSSGGG
GSGGGGSGGS ALQSVLTQPP SASGTPGQRV TISCSGSSSN LGSNYVYWYQ QLPGTAPKLL
IYRNNHRPSG VPDRFSGSKS GTSASLAISG LRSEDEADYY CATWDDSLNP LVVFGGGTKL
TVLGAAAHHH HHHGAAEQKL ISEEDLNGAA

*GRP78 L2 scFv sequence:*
*EVQLVESGGG VVQPGRSLRL SCAASGFTFS SYGMHWVRQA PGKGLEWVAV ISYDGSNKYY*
*ADSVKGRFTI SRDNSKNTLY LQMNSLRAED TAVYYCARKI NSTKEVWGQG TLVTVSSGGG*
*GSGGGGSGGS ALQSVLTQPP SASGTPGQRV TISCSGSSSN LGSNYVYWYQ QLPGTAPKLL*
*IYRNNHRPSG VPDRFSGSKS GTSASLAISG LRSEDEADYY CAAWDDSLNP LVVFGGGTKL*
*TVLGAAAHHH HHHGAAEQKL ISEEDLNGAA*

GRP78 H19 scFv sequence:
EVQLVESGGG VVQPGRSLRL SCAASGFTFS SYGMHWVRQA PGKGLEWVAV ISYDGSNKYY
ADSVKGRFTI SRDNSKNTLY LQMNSLRAED TAVYYCARKI NSTKEVWGQG TLVTVSSGGG
GSGGGGSGGS ALQSVLTQPP SASGTPGQRV TISCSGSSSN LGSNYVYWYQ QLPGTAPKLL
IYRNNQRPSG VPDRFSGSKS GTSASLAISG LRSEDEADYY CAAWDDSLNP LVVFGGGTKL
TVLGAAAHHH HHHGAAEQKL ISEEDLNGAA

*CD8α Hinge/Transmembrane domain:*
*TTTPAPRPPT PAPTIASQPL SLRPEACRPA AGGAVHTRGL DFACDIYIWA PLAGTCGVLL*
*LSLVITLYC*

<u>Extra amino acids from CD8α cytoplasmic domain:</u>
*NHRNRRRVCK CPRPVV*

<u>41BB Costim/Endodomain:</u>
KRGRKKLLYI FKQPFMRPVQ TTQEEDGCSC RFPEEEEGGC EL

<u>*CD3ζ Endodomain*</u>
*RVKFSRSADA PAYQQGQNQL YNELNLGRRE EYDVLDKRRG RDPEMGGKPR RKNPQEGLYN*
*ELQKDKMAEA YSEIGMKGER RRGKGHDGLY QGLSTATKDT YDALHMQALP PR*

<u>E2A Ribosomal Skip:</u>
GGPQCTNYAL LKLAGDVESN PG

<u>Q8 sequence:</u>
MGLVRRGARA GPRMPRGWTA LCLLSLLPSG FMAELPTQGT FSNVSTNVSP AKPTTTPAPR
PPTPAPTIAS QPLSLRPEAC RPAAGGAVHT RGLDFACDIY IWAPLAGTCG VLLLSLVITL
YCNHRNRRRV CKCPRPVV*

FIG. 7B

GRP78 L21 scFv.CD8αHTM.41BB Costim.CD3ζ.E2A.Q8

Nucleotide sequence:

ATGGCCTTACCAGTGACCGCCTTGCTCCTGCCGCTGGCCTTGCTGCTCCACGCCGCCAGGCCGGAA
GTGCAGCTGGTGGAAAGCGGCGGCGGCGTGGTGCAGCCGGGCCGCAGCCTGCGCCTGAGCTGCGCG
GCGAGCGGCTTTACCTTTAGCAGCTATGGCATGCATTGGGTGCGCCAGGCGCCGGGCAAAGGCCTG
GAATGGGTGGCGGTGATTAGCTATGATGGCAGCAACAAATATTATGCGGATAGCGTGAAAGGCCGC
TTTACCATTAGCCGCGATAACAGCAAAAACACCCTGTATCTGCAGATGAACAGCCTGCGCGCGGAA
GATACCGCGGTGTATTATTGCGCGCGCAAAATTAACAACACCAAAGAAGTGTGGGGCCAGGGCACC
CTGGTGACCGTGAGCAGCGGCGGCGGCGGCAGCGGCGGCGGCGGCAGCGGCGGCAGCGCGCTGCAG
AGCGTGCTGACCCAGCCGCCGAGCGCGAGCGGCACCCCGGGCCAGCGCGTGACCATTAGCTGCAGC
GGCAGCAGCAGCAACCTGGGCAGCAACTATGTGTATTGGTATCAGCAGCTGCCGGGCACCGCGCCG
AAACTGCTGATTTATCGCAACAACCATCGCCCGAGCGGCGTGCCGGATCGCTTTAGCGGCAGCAAA
AGCGGCACCAGCGCGAGCCTGGCGATTAGCGGCCTGCGCAGCGAAGATGAAGCGGATTATTATTGC
GCGACCTGGGATGATAGCCTGAACCCGCTGGTGGTGTTTGGCGGCGGCACCAAACTGACCGTGCTG
GGCGCGGCGGCGCATCATCATCATCATCATGGCGCGGCGGAACAGAAACTGATTAGCGAAGAAGAT
CTGAACGGCGCGGCG_ACCACGACGCCAGCGCCGCGACCACCAACACCGGCGCCCACCATCGCGTCG_
_CAGCCCCTGTCCCTGCGCCCAGAGGCGTGCCGGCCAGCGGCGGGGGGCGCAGTGCACACGAGGGGG_
_CTGGACTTCGCCTGTGATATCTACATCTGGGCGCCCTTGGCCGGGACTTGTGGGGTCCTTCTCCTG_
_TCACTGGTTATCACCCTTTACTGC_<u>AACCATCGCAACCGCCGCCGCGTGTGCAAATGCCCGCGCCCG</u>
<u>GTGGTG</u><span style="text-decoration: underline wavy;">AAACGGGGCAGAAAGAAACTCCTGTATATATTCAAACAACCATTTATGAGACCAGTACAA</span>
<span style="text-decoration: underline wavy;">ACTACTCAAGAGGAAGATGGCTGTAGCTGCCGATTTCCAGAAGAAGAAGAAGGAGGATGTGAACTG</span>
_AGAGTGAAGTTCAGCAGGAGCGCAGACGCCCCCGCGTACCAGCAGGGCCAGAACCAGCTCTATAAC_
_GAGCTCAATCTAGGACGAAGAGAGGAGTACGATGTTTTGGACAAGAGACGTGGCCGGGACCCTGAG_
_ATGGGGGGAAAGCCGAGAAGGAAGAACCCTCAGGAAGGCCTGTACAATGAACTGCAGAAAGATAAG_
_ATGGCGGAGGCCTACAGTGAGATTGGGATGAAAGGCGAGCGCCGGAGGGGCAAGGGGCACGATGGC_
_CTTTACCAGGGTCTCAGTACAGCCACCAAGGACACCTACGACGCCCTTCACATGCAGGCCCTGCCC_
_CCTCGC_GGCGGACCGCAGTGCACCAACTACGCTCTGCTGAAACTGGCTGGCGACGTGGAAAGCAAT
CCCGGC<span style="text-decoration: underline dotted;">CCT</span>ATGGGACTCGTGCGCAGAGGCGCTAGAGCCGGCCCTAGAATGCCTAGAGGATGGACC
GCCCTGTGCCTGCTGTCTCTGCTGCCTAGCGGCTTCATGGCCGAGCTGCCTACTCAGGGCACCTTC
AGCAACGTGTCCACCAATGTGTCCCCAGCCAAGCCCACCACAACCCCTGCTCCTAGACCTCCTACC
CCAGCCCCTACCATTGCCTCCCAGCCACTGTCTCTGAGGCCCGAGGCTTGTAGACCTGCTGCAGGC
GGAGCCGTGCACACCAGAGGACTGGATTTCGCCTGCGACATCTATATCTGGGCCCCTCTGGCCGGC
ACCTGTGGCGTGCTGCTGCTGTCACTCGTGATCACCCTGTACTGCAACCACCGGAACCGGCGGAGA
GTGTGCAAGTGCCCTAGACCCGTCGTGTGA Amino acid sequence:

MALPVTALLLPLALLLHAARPEVQLVESGGGVVQPGRSLRLSCAASGFTFSSYGMHWVRQAPGKGL
EWVAVISYDGSNKYYADSVKGRFTISRDNSKNTLYLQMNSLRAEDTAVYYCARKINNTKEVWGQGT
LVTVSSGGGGSGGGGSGGSALQSVLTQPPSASGTPGQRVTISCSGSSSNLGSNYVYWYQQLPGTAP
KLLIYRNNHRPSGVPDRFSGSKSGTSASLAISGLRSEDEADYYCATWDDSLNPLVVFGGGTKLTVL
GAAAHHHHHHGAAEQKLISEEDLNGAA_TTTPAPRPPTPAPTIASQPLSLRPEACRPAAGGAVHTRG_
_LDFACDIYIWAPLAGTCGVLLLSLVITLYC_<u>NHRNRRRVCKCPRPVV</u><span style="text-decoration: underline wavy;">KRGRKKLLYIFKQPFMRPVQ</span>
<span style="text-decoration: underline wavy;">TTQEEDGCSCRFPEEEEGGCEL</span>_RVKFSRSADAPAYQQGQNQLYNELNLGRREEYDVLDKRRGRDPE_
_MGGKPRRKNPQEGLYNELQKDKMAEAYSEIGMKGERRRGKGHDGLYQGLSTATKDTYDALHMQALP_
_PR_GGPQCTNYALLKLAGDVESNPGPMGLVRRGARAGPRMPRGWTALCLLSLLPSGFMAELPTQGTF
SNVSTNVSPAKPTTTPAPRPPTPAPTIASQPLSLRPEACRPAAGGAVHTRGLDFACDIYIWAPLAG
TCGVLLLSLVITLYCNHRNRRRVCKCPRPVV*

FIG. 7C

GRP78 L2 scFv.CD8αHTM.41BB Costim.CD3ζ.E2A.Q8

Nucleotide sequence:

ATGGCCTTACCAGTGACCGCCTTGCTCCTGCCGCTGGCCTTGCTGCTCCACGCCGCCAGGCCG*GAA*
*GTGCAGCTGGTGGAAAGCGGCGGCGGCGTGGTGCAGCCGGGCCGCAGCCTGCGCCTGAGCTGCGCG*
*GCGAGCGGCTTTACCTTTAGCAGCTATGGCATGCATTGGGTGCGCCAGGCGCCGGGCAAAGGCCTG*
*GAATGGGTGGCGGTGATTAGCTATGATGGCAGCAACAAATATTATGCGGATAGCGTGAAAGGCCGC*
*TTTACCATTAGCCGCGATAACAGCAAAAACACCCTGTATCTGCAGATGAACAGCCTGCGCGCGGAA*
*GATACCGCGGTGTATTATTGCGCGCGCAAAATTAACAGCACCAAAGAAGTGTGGGGCCAGGGCACC*
*CTGGTGACCGTGAGCAGCGGCGGCGGCGGCAGCGGCGGCGGCGGCAGCGGCGGCAGCGCGCTGCAG*
*AGCGTGCTGACCCAGCCGCCGAGCGCGAGCGGCACCCCGGGCCAGCGCGTGACCATTAGCTGCAGC*
*GGCAGCAGCAGCAACCTGGGCAGCAACTATGTGTATTGGTATCAGCAGCTGCCGGGCACCGCGCCG*
*AAACTGCTGATTTATCGCAACAACCATCGCCCGAGCGGCGTGCCGGATCGCTTTAGCGGCAGCAAA*
*AGCGGCACCAGCGCGAGCCTGGCGATTAGCGGCCTGCGCAGCGAAGATGAAGCGGATTATTATTGC*
*GCGGCGTGGGATGATAGCCTGAACCCGCTGGTGGTGTTTGGCGGCGGCACCAAACTGACCGTGCTG*
*GGCGCGGCGGCGCATCATCATCATCATCATGGCGCGGCGGAACAGAAACTGATTAGCGAAGAAGAT*
*CTGAACGGCGCGGCG*ACCACGACGCCAGCGCCGCGACCACCAACACCGGCGCCCACCATCGCGTCG
CAGCCCCTGTCCCTGCGCCCAGAGGCGTGCCGGCCAGCGGCGGGGGGCGCAGTGCACACGAGGGGG
CTGGACTTCGCCTGTGATATCTACATCTGGGCGCCCTTGGCCGGGACTTGTGGGTCCTTCTCCTG
TCACTGGTTATCACCCTTTACTGCAACCATCGCAACCGCCGCCGCGTGTGCAAATGCCCGCGCCCG
GTGGTG~~AAACGGGGCAGAAAGAAACTCCTGTATATATTCAAACAACCATTTATGAGACCAGTACAA~~
~~ACTACTCAAGAGGAAGATGGCTGTAGCTGCCGATTTCCAGAAGAAGAAGAAGGAGGATGTGAACTG~~
*AGAGTGAAGTTCAGCAGGAGCGCAGACGCCCCCGCGTACCAGCAGGGCCAGAACCAGCTCTATAAC*
*GAGCTCAATCTAGGACGAAGAGAGGAGTACGATGTTTTGGACAAGAGACGTGGCCGGGACCCTGAG*
*ATGGGGGGAAAGCCGAGAAGGAAGAACCCTCAGGAAGGCCTGTACAATGAACTGCAGAAAGATAAG*
*ATGGCGGAGGCCTACAGTGAGATTGGGATGAAAGGCGAGCGCCGGAGGGGCAAGGGGCACGATGGC*
*CTTTACCAGGGTCTCAGTACAGCCACCAAGGACACCTACGACGCCCTTCACATGCAGGCCCTGCCC*
*CCTCGC*GGCGGACCGCAGTGCACCAACTACGCTCTGCTGAAACTGGCTGGCGACGTGGAAAGCAAT
CCCGGC~~CCT~~ATGGGACTCGTGCGCAGAGGCGCTAGAGCCGGCCCTAGAATGCCTAGAGGATGGACC
GCCCTGTGCCTGCTGTCTCTGCTGCCTAGCGGCTTCATGGCCGAGCTGCCTACTCAGGGCACCTTC
AGCAACGTGTCCACCAATGTGTCCCCAGCCAAGCCCACCACAACCCCTGCTCCTAGACCTCCTACC
CCAGCCCCTACCATTGCCTCCCAGCCACTGTCTCTGAGGCCCGAGGCTTGTAGACCTGCTGCAGGC
GGAGCCGTGCACACCAGAGGACTGGATTTCGCCTGCGACATCTATATCTGGGCCCCTCTGGCCGGC
ACCTGTGGCGTGCTGCTGCTGTCACTCGTGATCACCCTGTACTGCAACCACCGGAACCGGCGGAGA
GTGTGCAAGTGCCCTAGACCCGTCGTGTGA

Amino acid sequence:

MALPVTALLLPLALLLHAARP*EVQLVESGGGVVQPGRSLRLSCAASGFTFSSYGMHWVRQAPGKGL*
*EWVAVISYDGSNKYYADSVKGRFTISRDNSKNTLYLQMNSLRAEDTAVYYCARKINSTKEVWGQGT*
*LVTVSSGGGGSGGGGSGGGSALQSVLTQPPSASGTPGQRVTISCSGSSSNLGSNYVYWYQQLPGTAP*
*KLLIYRNNHRPSGVPDRFSGSKSGTSASLAISGLRSEDEADYYCAAWDDSLNPLVVFGGGTKLTVL*
*GAAAHHHHHHGAAEQKLISEEDLNGAA*TTTPAPRPPTPAPTIASQPLSLRPEACRPAAGGAVHTRG
LDFACDIYIWAPLAGTCGVLLLSLVITLYCNHRNRRRVCKCPRPVV~~KRGRKKLLYIFKQPFMRPVQ~~
~~TTQEEDGCSCRFPEEEEGGCEL~~*RVKFSRSADAPAYQQGQNQLYNELNLGRREEYDVLDKRRGRDPE*
*MGGKPRRKNPQEGLYNELQKDKMAEAYSEIGMKGERRRGKGHDGLYQGLSTATKDTYDALHMQALP*
*PR*GGPQCTNYALLKLAGDVESNPGPMGLVRRGARAGPRMPRGWTALCLLSLLPSGFMAELPTQGTF
SNVSTNVSPAKPTTTPAPRPPTPAPTIASQPLSLRPEACRPAAGGAVHTRGLDFACDIYIWAPLAG
TCGVLLLSLVITLYCNHRNRRRVCKCPRPVV*

FIG. 7D

GRP78 H19 scFv.CD8αHTM.41BB Costim.CD3ζ.E2A.Q8

Nucleotide Sequence:

ATGGCCTTACCAGTGACCGCCTTGCTCCTGCCGCTGGCCTTGCTGCTCCACGCCGCCAGGCCGGAGG
TGCAGCTGGTGGAGTCTGGGGGAGGCGTGGTCCAGCCTGGGAGGTCCCTGAGACTCTCCTGTGCAGC
CTCTGGATTCACCTTCAGTAGCTATGGCATGCACTGGGTCCGCCAGGCTCCAGGCAAGGGGCTGGAG
TGGGTGGCAGTTATATCATATGATGGAAGTAATAAATACTATGCAGACTCCGTGAAGGGCCGATTCA
CCATCTCCAGAGACAATTCCAAGAACACGCTGTATCTGCAAATGAACAGCCTGAGAGCTGAGGACAC
GGCCGTGTATTACTGTGCAAGAAAGATTAATAGTACGAAGGAGGTGTGGGGCCAAGGTACCCTGGTC
ACCGTCTCGAGTGGTGGAGGCGGTTCAGGCGGAGGTGGCTCTGGCGGTAGTGCACTTCAGTCTGTGC
TGACTCAGCCACCCTCAGCGTCTGGGACCCCCGGGCAGAGGGTCACCATCTCTTGTTCTGGAAGCAG
CTCCAACATCGGAAGTAATTATGTATACTGGTACCAGCAGCTCCCAGGAACGGCCCCCAAACTCCTC
ATCTATAGGAATAATCAGCGGCCCTCAGGGGTCCCTGACCGATTCTCTGGCTCCAAGTCTGGCACCT
CAGCCTCCCTGGCCATCAGTGGGCTCCGGTCCGAGGATGAGGCTGATTATTACTGTGCAGCATGGGA
TGACAGCCTGAATCCTCTTGTTGTATTCGGCGGAGGGACCAAGCTGACCGTCCTAGGTGCGGCCGCA
CATCATCATCACCATCACGGGGCCGCAGAACAAAAACTCATCTCAGAAGAGGATCTGAATGGGGCCG
*CAACCACGACGCCAGCGCCGCGACCACCAACACCGGCGCCCACCATCGCGTCGCAGCCCCTGTCCCT*
*GCGCCCAGAGGCGTGCCGGCCAGCGGCGGGGGGCGCAGTGCACACGAGGGGGCTGGACTTCGCCTGT*
*GATATCTACATCTGGGCGCCCTTGGCCGGGACTTGTGGGGTCCTTCTCCTGTCACTGGTTATCACCC*
*TTTACTGC*AACCATCGCAACCGCCGCCGCGTGTGCAAATGCCCGCGCCCGGTGGTGAAACGGGGCAG
AAAGAAACTCCTGTATATATTCAAACAACCATTTATGAGACCAGTACAAACTACTCAAGAGGAAGAT
GGCTGTAGCTGCCGATTTCCAGAAGAAGAAGAAGGAGGATGTGAACTG*AGAGTGAAGTTCAGCAGGA*
*GCGCAGACGCCCCCGCGTACCAGCAGGGCCAGAACCAGCTCTATAACGAGCTCAATCTAGGACGAAG*
*AGAGGAGTACGATGTTTTGGACAAGAGACGTGGCCGGGACCCTGAGATGGGGGGAAAGCCGAGAAGG*
*AAGAACCCTCAGGAAGGCCTGTACAATGAACTGCAGAAAGATAAGATGGCGGAGGCCTACAGTGAGA*
*TTGGGATGAAAGGCGAGCGCCGGAGGGGCAAGGGGCACGATGGCCTTTACCAGGGTCTCAGTACAGC*
*CACCAAGGACACCTACGACGCCCTTCACATGCAGGCCCTGCCCCCTCGC*GGCGGACCGCAGTGCACC
AACTACGCTCTGCTGAAACTGGCTGGCGACGTGGAAAGCAATCCCGGC⬚⬚⬚ATGGGACTCGTGCGCA
GAGGCGCTAGAGCCGGCCCTAGAATGCCTAGAGGATGGACCGCCCTGTGCCTGCTGTCTCTGCTGCC
TAGCGGCTTCATGGCCGAGCTGCCTACTCAGGGCACCTTCAGCAACGTGTCCACCAATGTGTCCCCA
GCCAAGCCCACCACAACCCCTGCTCCTAGACCTCCTACCCCAGCCCCTACCATTGCCTCCCAGCCAC
TGTCTCTGAGGCCCGAGGCTTGTAGACCTGCTGCAGGCGGAGCCGTGCACACCAGAGGACTGGATTT
CGCCTGCGACATCTATATCTGGGCCCCTCTGGCCGGCACCTGTGGCGTGCTGCTGCTGTCACTCGTG
ATCACCCTGTACTGCAACCACCGGAACCGGCGGAGAGTGTGCAAGTGCCCTAGACCCGTCGTGTGA

Amino acid sequence:

MALPVTALLLPLALLLHAARP*EVQLVESGGGVVQPGRSLRLSCAASGFTFSSYGMHWVRQAPGKGLE*
*WVAVISYDGSNKYYADSVKGRFTISRDNSKNTLYLQMNSLRAEDTAVYYCARKINSTKEVWGQGTLV*
*TVSSGGGGSGGGGSGGSALQSVLTQPPSASGTPGQRVTISCSGSSSNIGSNYVYWYQQLPGTAPKLL*
*IYRNNQRPSGVPDRFSGSKSGTSASLAISGLRSEDEADYYCAAWDDSLNPLVVFGGGTKLTVLGAAA*
*HHHHHHGAAEQKLISEEDLNGAA*TTTPAPRPPTPAPTIASQPLSLRPEACRPAAGGAVHTRGLDFAC
DIYIWAPLAGTCGVLLLSLVITLYCNHRNRRRVCKCPRPVVKRGRKKLLYIFKQPFMRPVQTTQEED
GCSCRFPEEEEGGCEL*RVKFSRSADAPAYQQGQNQLYNELNLGRREEYDVLDKRRGRDPEMGGKPRR*
*KNPQEGLYNELQKDKMAEAYSEIGMKGERRRGKGHDGLYQGLSTATKDTYDALHMQALPPR*GGPQCT
NYALLKLAGDVESNPGPMGLVRRGARAGPRMPRGWTALCLLSLLPSGFMAELPTQGTFSNVSTNVSP
AKPTTTPAPRPPTPAPTIASQPLSLRPEACRPAAGGAVHTRGLDFACDIYIWAPLAGTCGVLLLSLV
ITLYCNHRNRRRVCKCPRPVV*

FIG. 8A

CAR Component Sequences mutIgG4 Hinge (amino acid sequence)
ESKYGPPCPSCPAPEFEGGPSVFLFPPKPKDTLMISRTPEVTCVVVDVSQEDPEVQFNWYVDGVEVHN
AKTKPREEQFQSTYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYSRLTVDKSRWQEGNV
FSCSVMHEALHNHYTQKSLSLSLGK mutIgG4 Hinge (nucleotide sequence)
GAGTCTAAGTACGGCCCTCCTTGTCCTAGCTGCCCCGCTCCTGAATTTGAAGGCGGCCCTTCCGTGTT
CCTGTTTCCTCCAAAGCCTAAGGACACCCTGATGATCAGCAGAACCCCTGAAGTGACCTGCGTGGTGG
TGGACGTGTCCCAAGAGGATCCTGAGGTGCAGTTCAATTGGTACGTGGACGGCGTGGAAGTGCACAAC
GCCAAGACCAAGCCTAGAGAGGAACAGTTCCAGAGCACCTACAGAGTGGTGTCCGTGCTGACAGTGCT
GCACCAGGATTGGCTGAACGGCAAAGAGTACAAGTGCAAGGTGTCCAACAAGGGCCTGCCTAGCAGCA
TCGAGAAAACCATCAGCAAGGCCAAGGGCCAGCCAAGAGAACCCCAGGTGTACACACTGCCTCCAAGC
CAAGAGGAAATGACCAAGAACCAGGTGTCCCTGACCTGCCTGGTCAAGGGCTTCTACCCTTCCGATAT
CGCCGTGGAATGGGAGAGCAATGGCCAGCCTGAGAACAACTACAAGACCACACCTCCTGTGCTGGACA
GCGACGGCTCATTCTTCCTGTACAGCAGACTGACCGTGGACAAGAGCAGATGGCAAGAGGGCAACGTG
TTCAGCTGCAGCGTGATGCACGAGGCCCTGCACAACCACTACACCCAGAAGTCTCTGAGCCTGAGCCT
CGGCAAG 41BB Costim/Endodomain (amino acid sequence)
KRGRKKLLYIFKQPFMRPVQTTQEEDGCSCRFPEEEEGGCEL 41BB Costim/Endodomain (nucleotide sequence)
AAACGGGGCAGAAAGAAACTCCTGTATATATTCAAACAACCATTTATGAGACCAGTACAAACTACTCA
AGAGGAAGATGGCTGTAGCTGCCGATTTCCAGAAGAAGAAGAAGGAGGATGTGAACTG CD8a Hinge/Transmembrane domain (amino acid sequence)
TTTPAPRPPTPAPTIASQPLSLRPEACRPAAGGAVHTRGLDFACDIYIWAPLAGTCGVLLLSLVITLY
C CD8a Hinge/Transmembrane domain (nucleotide sequence)
ACCACGACGCCAGCGCCGCGACCACCAACACCGGCGCCCACCATCGCGTCGCAGCCCCTGTCCCTGCG
CCCAGAGGCGTGCCGGCCAGCGGCGGGGGGCGCAGTGCACACGAGGGGGCTGGACTTCGCCTGTGATA
TCTACATCTGGGCGCCCTTGGCCGGGACTTGTGGGGTCCTTCTCCTGTCACTGGTTATCACCCTTTAC
TGC Extra amino acids from CD8a cytoplasmic domain (amino acid sequence)
NHRNRRRVCKCPRPVV Extra amino acids from CD8a cytoplasmic domain (nucleotide sequence)
AACCATCGCAACCGCCGCCGCGTGTGCAAATGCCCGCGCCCGGTGGTG OX40 (amino acid sequences)
RDQRLPPDAHKPPGGGSFRTPIQEEQADAHSTLAKI OX40 (nucleotide sequences)
AGGGACCAGAGGCTGCCCCCCGATGCCCACAAGCCCCCTGGGGGAGGCAGTTTCCGGACCCCCATCCA
AGAGGAGCAGGCCGACGCCCACTCCACCCTGGCCAAGATC

FIG. 8B

IgG1-derived hinge-CH3 spacer (amino acid sequences)
EPKSCDKTHTCPGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK

IgG1-derived hinge-CH3 spacer (nucleotide sequences)
GAACCGAAAAGCTGCGATAAAACCCATACCTGCCCGGGCCAGCCGCGCGAACCGCAGGTG
TATACCCTGCCGCCGAGCCGCGATGAACTGACCAAAAACCAGGTGAGCCTGACCTGCCTG
GTGAAAGGCTTTTATCCGAGCGATATTGCGGTGGAATGGGAAAGCAACGGCCAGCCGGAA
AACAACTATAAAACCACCCCGCCGGTGCTGGATAGCGATGGCAGCTTTTTTCTGTATAGC
AAACTGACCGTGGATAAAAGCCGCTGGCAGCAGGGCAACGTGTTTAGCTGCAGCGTGATG
CATGAAGCGCTGCATAACCATTATACCCAGAAAAGCCTGAGCCTGAGCCCGGGCAAA

IgG1-derived hinge-CH2CH3 spacer (amino acid sequences)
EPKSCDKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK

IgG1-derived hinge-CH2CH3 spacer CH3 (nucleotide sequences)
GAACCGAAAAGCTGCGATAAAACCCATACCTGCCCGCCGTGCCCGGCGCCGGAACTGCTG
GGCGGCCCGAGCGTGTTTCTGTTTCCGCCGAAACCGAAAGATACCCTGATGATTAGCCGC
ACCCCGGAAGTGACCTGCGTGGTGGTGGATGTGAGCCATGAAGATCCGGAAGTGAAATTT
AACTGGTATGTGGATGGCGTGGAAGTGCATAACGCGAAAACCAAACCGCGCGAAGAACAG
TATAACAGCACCTATCGCGTGGTGAGCGTGCTGACCGTGCTGCATCAGGATTGGCTGAAC
GGCAAAGAATATAAATGCAAAGTGAGCAACAAAGCGCTGCCGGCGCCGATTGAAAAAACC
ATTAGCAAAGCGAAAGGCCAGCCGCGCGAACCGCAGGTGTATACCCTGCCGCCGAGCCGC
GATGAACTGACCAAAAACCAGGTGAGCCTGACCTGCCTGGTGAAAGGCTTTTATCCGAGC
GATATTGCGGTGGAATGGGAAAGCAACGGCCAGCCGGAAAACAACTATAAAACCACCCCG
CCGGTGCTGGATAGCGATGGCAGCTTTTTTCTGTATAGCAAACTGACCGTGGATAAAAGC
CGCTGGCAGCAGGGCAACGTGTTTAGCTGCAGCGTGATGCATGAAGCGCTGCATAACCAT
TATACCCAGAAAAGCCTGAGCCTGAGCCCGGGCAAA

FIG. 8C

IgG1-derived modified hinge-CH2CH3 spacer (amino acid sequences)

EPKSPDKTHTCPPCPAPPVAGPSVFLFPPKPKDTLMISRTPEVTCVVVDVSHEDPEVKFNWYVDG
VEVHNAKTKPREEQYQSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGK

IgG1-derived modified hinge-CH2CH3 spacer CH3 (nucleotide sequences)

GAACCGAAAAGCCCGGATAAAACCCATACCTGCCCGCCGTGCCCGGCGCCGCCGGTGGCGGGCCC
GAGCGTGTTTCTGTTTCCGCCGAAACCGAAAGATACCCTGATGATTAGCCGCACCCCGGAAGTGA
CCTGCGTGGTGGTGGATGTGAGCCATGAAGATCCGGAAGTGAAATTTAACTGGTATGTGGATGGC
GTGGAAGTGCATAACGCGAAAACCAAACCGCGCGAAGAACAGTATCAGAGCACCTATCGCGTGGT
GAGCGTGCTGACCGTGCTGCATCAGGATTGGCTGAACGGCAAAGAATATAAATGCAAAGTGAGCA
ACAAAGCGCTGCCGGCGCCGATTGAAAAAACCATTAGCAAAGCGAAAGGCCAGCCGCGCGAACCG
CAGGTGTATACCCTGCCGCCGAGCCGCGATGAACTGACCAAAAACCAGGTGAGCCTGACCTGCCT
GGTGAAAGGCTTTTATCCGAGCGATATTGCGGTGGAATGGGAAAGCAACGGCCAGCCGGAAAACA
ACTATAAAACCACCCCGCCGGTGCTGGATAGCGATGGCAGCTTTTTTCTGTATAGCAAACTGACC
GTGGATAAAAGCCGCTGGCAGCAGGGCAACGTGTTTAGCTGCAGCGTGATGCATGAAGCGCTGCA
TAACCATTATACCCAGAAAAGCCTGAGCCTGAGCCCGGGCAAA

FIG. 9A

| Primary AML | Diagnosis | Recurrent Molecular Findings | Source (BM/PB) |
|---|---|---|---|
| AML 1 | AML, FAB, M2 | None identified | BM |
| AML 9 | AML (FAB M1) | N.D. | BM |
| AML 2 | AML (FAB M4) | NUP98-NSD1 | PB |
| AML 3 | AML (FAB M5) | NUP98-NSD1 | PB |
| AML 11 | AML (FAB M4) | NUP98-NSD1 | BM |
| AML 14 | AML (FAB M5) | NPM1c | BM |
| AML 8 | AML, relapse | NUP98 NSD1 | BM |
| AML10 | AML, relapse | KMT2A-MLLT4 | BM |
| AML12 | AML, relapse | KAT6A-CREBBP | BM |
| AML 13 | AML, relapse | KMT2A-MLLT3 | BM |
| AML 6 | Therapy-related AML | KMT2A-MLLT3 | BM |
| AML 5 | Therapy-related AML | KMT2A-MLLT3 | BM |
| AML 4 | Therapy-related AML | KMT2A-MLLT3, FLT3-ITD | PB |
| AML 7 | Therapy-related AML | KMT2A-MLLT3 | BM |

FIG. 9B

| AML-PDX | ID | Diagnosis | Molecular Findings | Source (BM/PB) |
|---|---|---|---|---|
| AML-PDX 1 | FWV75 | AML with myelodysplasia related changes | DEK-NUP214 | BM>PDX |
| AML-PDX 2 | GWK6C | AML (without maturation, FAB M2) | NPM1-MLF1, FLT3 ITD | BM>PDX |
| AML-PDX 3 | 8KG5 | Therapy-related AML | KMT2A-MLLT10 | BM>PDX |
| AML-PDX 4 | NPxP4 | Therapy-related AML, relapse | KMT2A-MLLT3 | BM>PDX |
| AML-PDX 5 | GQHGJ | MPAL, relapse | CBL, EZH2, TP53, ETV6 | BM>PDX |

Isotype Control de novo AML

Relapsed AML

Therapy-related AML

GRP78

Isotype Control

AML
PDX

1

2

3

4

5

GRP78 ⟶

FIG. 11
MILE-BloodSpot
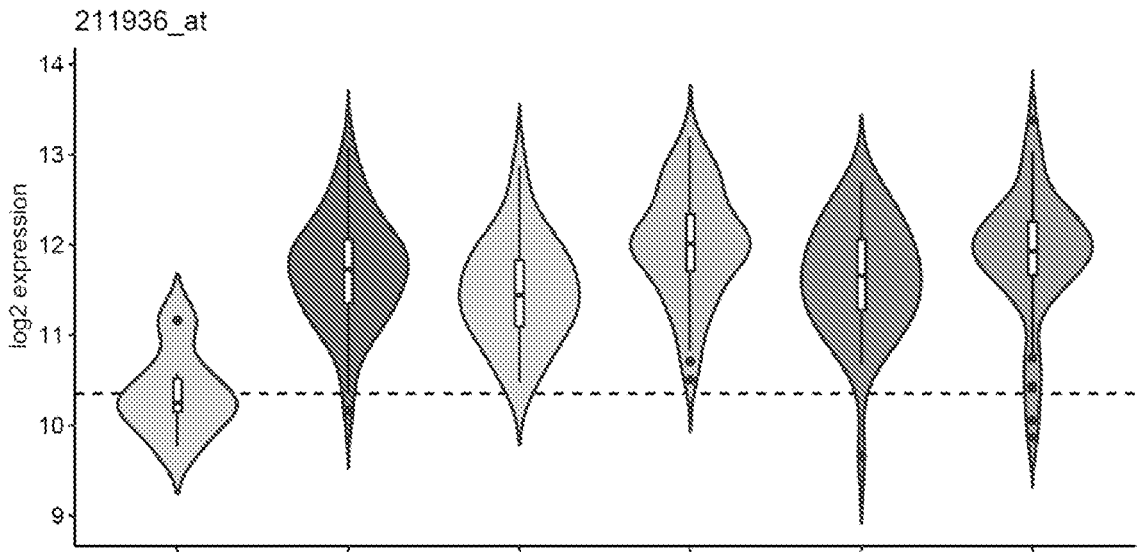
211936_at
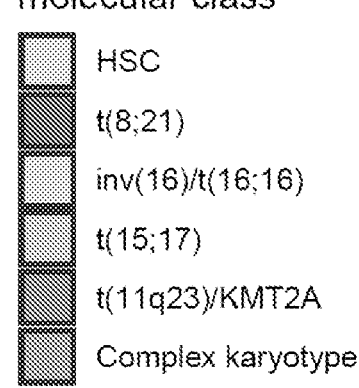
molecular class
HSC
t(8;21)
inv(16)/t(16;16)
t(15;17)
t(11q23)/KMT2A
Complex karyotype

FIG. 13A
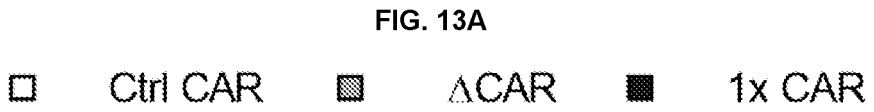
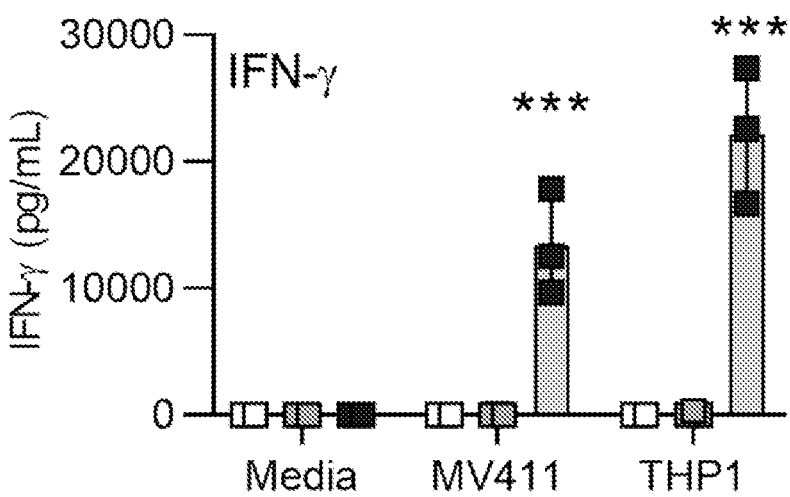
FIG. 13B
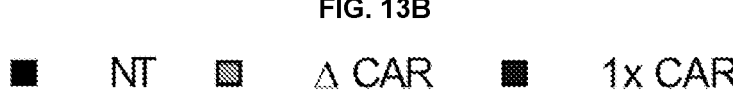
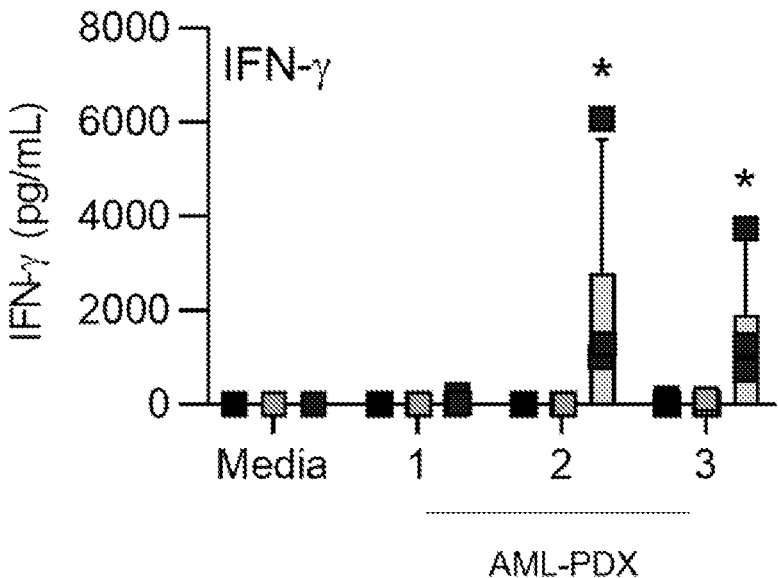

Fresh tumor re-challenge

CAR T-cell

MOLM13 ffluc

Lysis (%)

SEQUENCE LISTING

```
<160> NUMBER OF SEQ ID NOS: 92

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Thr Val Ala Leu Pro Gly Gly Tyr Val Arg Val Cys
1               5                   10

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgtactgtgg cccttcctgg tggatacgtt agagtgtgc                          39

<210> SEQ ID NO 3
<211> LENGTH: 19
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 3

Met Asp Trp Ile Trp Arg Ile Leu Phe Leu Val Gly Ala Ala Thr Gly
1               5                   10                  15

Ala His Ser

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atggactgga tttggcggat cctgtttctc gtgggagccg ccacaggcgc ccattct          57

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser
1               5

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtggcggcg gaagc                                                        15

<210> SEQ ID NO 7
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95
```

-continued

```
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 8
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gagtctaagt acggccctcc ttgtcctagc tgccccgctc ctgaatttga aggcggccct      60
tccgtgttcc tgtttcctcc aaagcctaag gacaccctga tgatcagcag aaccccctgaa    120 gtgacctgcg tggtggtgga cgtgtcccaa gaggatcctg aggtgcagtt caattggtac     180
gtggacggcg tggaagtgca caacgccaag accaagccta gagaggaaca gttccagagc     240
acctacagag tggtgtccgt gctgacagtg ctgcaccagg attggctgaa cggcaaagag     300
tacaagtgca aggtgtccaa caagggcctg cctagcagca tcgagaaaac catcagcaag     360
gccaagggcc agccaagaga accccaggtg tacacactgc ctccaagcca gaggaaatg      420 accaagaacc aggtgtccct gacctgcctg gtcaagggct ctacccttc cgatatcgcc      480 gtggaatggg agagcaatgg ccagcctgag aacaactaca gaccacacc tcctgtgctg      540 gacagcgacg gctcattctt cctgtacagc agactgaccg tggacaagag cagatggcaa     600
gagggcaacg tgttcagctg cagcgtgatg cacgaggccc tgcacaacca ctacacccag     660
aagtctctga gcctgagcct cggcaag                                          687

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

```
<210> SEQ ID NO 10
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttctgggtgc tcgttgttgt tggcggcgtg ctggcctgtt acagcctgct ggttaccgtg        60
gccttcatca tcttttgggt c                                                  81

<210> SEQ ID NO 11
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
cgaagcaagc ggagccggct gctgcacagc gattacatga acatgacccc tcggaggccc        60
ggaccaacca gaaagcacta ccagccttac gctcctccta gagacttcgc cgcctaccgg       120
tcc                                                                     123

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

-continued

```
Arg Arg Gly Lys Gly His Asp Gly Leu Tyr Gln Gly Leu Ser Thr Ala
              85                  90                  95

Thr Lys Asp Thr Tyr Asp Ala Leu His Met Gln Ala Leu Pro Pro Arg
              100                 105                 110

<210> SEQ ID NO 14
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
agagtgaagt tcagcagatc cgccgatgct cccgcctatc agcagggaca gaaccagctg        60
tacaacgagc tgaacctggg gagaagagaa gagtacgacg tgctggataa gcggagaggc       120
agagatcctg agatgggcgg caagcccaga cggaagaatc ctcaagaggg cctgtataat       180
gagctgcaga aagacaagat ggccgaggcc tacagcgaga tcggaatgaa gggcgagcgc       240
agaagaggca agggacacga tggactgtac cagggactga gcaccgccac caaggatacc       300
tatgacgcac tgcacatgca ggccctgcca cctaga                                 336

<210> SEQ ID NO 15
<211> LENGTH: 18
<212> TYPE: PRT
<213> ORGANISM: Thosea asigna virus

<400> SEQUENCE: 15

Glu Gly Arg Gly Ser Leu Leu Thr Cys Gly Asp Val Glu Glu Asn Pro
1               5                   10                  15

Gly Pro

<210> SEQ ID NO 16
<211> LENGTH: 54
<212> TYPE: DNA
<213> ORGANISM: Thosea asigna virus

<400> SEQUENCE: 16
gaaggcagag gctctctgct gacatgtggc gacgtggaag agaatcctgg acct              54

<210> SEQ ID NO 17
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
              20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
     50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
```

```
                 85                   90                   95
Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
            130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
                180                 185                 190

Gly Ser Thr Leu Trp Leu Ser Cys Gly Val Pro Pro Asp Ser Val Ser
                195                 200                 205

Arg Gly Pro Leu Ser Trp Thr His Val His Pro Lys Gly Pro Lys Ser
            210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
                325                 330
```

```
<210> SEQ ID NO 18
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atgcctcccc ccagactgct gttcttcctg ctgttcctga cccctatgga agtgcggccc       60
gaggaacccc tggtcgtgaa agtggaagag ggcgacaacg ccgtgctgca gtgtctgaag      120
ggcacctccg atggccctac ccagcagctg acctggtcca gagagagccc cctgaagccc      180
ttcctgaagc tgtctctggg cctgcctggc ctgggcatcc atatgaggcc actggccatc      240
tggctgttca tcttcaacgt gtcccagcag atgggaggct ctacctgtg ccagcctggc       300 ccaccttctg agaaggcttg gcagcctggc tggaccgtga acgtggaagg atctggcgag      360
ctgttccggt ggaacgtgtc cgatctgggc ggcctgggat cgggcctgaa gaacagatct      420
agcgagggcc ccagcagccc cagcggcaaa ctgatgagcc ccaagctgta cgtgtgggcc      480
aaggacagac ccgagatttg ggagggcgag cccccttgcc tgcccccctag agatagcctg      540 aaccagagct tgagccagga cctgacaatg gcccctggca gcacactgtg gctgagctgt      600
ggcgtgccac ccgactctgt gtctagaggc cctctgagct ggacccacgt gcaccctaag      660
```

```
ggccctaaga gcctgctgtc cctggaactg aaggacgaca ggcccgccag agatatgtgg      720
gtcatggaaa ccggcctgct gctgcctaga gccacagccc aggatgccgg caagtactac      780
tgccacagag gcaacctgac catgagcttc cacctggaaa tcaccgccag acccgtgctg      840
tggcactggc tgctgagaac cggcggatgg aaagtgtccg ccgtgactct ggcctacctg      900
atcttctgcc tgtgctccct cgtgggcatc ctgcatctgc agagggctct ggtgctgcgg      960
cggaagcgga agagaatgac cgaccctacc cggcggttct aa                         1002
```

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 19

Arg Ser Gly Ser Gly
1               5

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 20
agatctggct ctggc                                                       15

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 21

Met Asp Trp Ile Trp Arg Ile Leu Phe Leu Val Gly Ala Ala Thr Gly
1               5                   10                  15

Ala His Ser Cys Thr Val Ala Leu Pro Gly Gly Tyr Val Arg Val Cys
            20                  25                  30

<210> SEQ ID NO 22
<211> LENGTH: 96
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 22
atggactgga tttggcggat cctgtttctc gtgggagccg ccacaggcgc ccattcttgt      60
actgtggccc ttcctggtgg atacgttaga gtgtgc                                96

<210> SEQ ID NO 23
<211> LENGTH: 50
<212> TYPE: PRT
<213> ORGANISM: Artificial Sequence
<220> FEATURE:
<223> OTHER INFORMATION: Description of Artificial Sequence: Synthetic -continued

```
        polypeptide

<400> SEQUENCE: 23

Met Asp Trp Ile Trp Arg Ile Leu Phe Leu Val Gly Ala Ala Thr Gly
1               5                   10                  15

Ala His Ser Cys Thr Val Ala Leu Pro Gly Gly Tyr Val Arg Val Cys
            20                  25                  30

Gly Gly Gly Gly Ser Cys Thr Val Ala Leu Pro Gly Gly Tyr Val Arg
        35                  40                  45

Val Cys
    50

<210> SEQ ID NO 24
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atggactgga tttggcggat cctgtttctc gtgggagccg ccacaggcgc ccattcttgt      60
actgtggccc ttcctggtgg atacgttaga gtgtgcggtg gcggcggaag ctgtactgtg     120
gcccttcctg gtggatacgt tagagtgtgc                                      150

<210> SEQ ID NO 25
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Trp Ile Trp Arg Ile Leu Phe Leu Val Gly Ala Ala Thr Gly
1               5                   10                  15

Ala His Ser Cys Thr Val Ala Leu Pro Gly Gly Tyr Val Arg Val Cys
            20                  25                  30

Gly Gly Gly Gly Ser Cys Thr Val Ala Leu Pro Gly Gly Tyr Val Arg
        35                  40                  45

Val Cys Gly Gly Gly Gly Ser Cys Thr Val Ala Leu Pro Gly Gly Tyr
    50                  55                  60

Val Arg Val Cys
65

<210> SEQ ID NO 26
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atggactgga tttggcggat cctgtttctc gtgggagccg ccacaggcgc ccattcttgt      60
actgtggccc ttcctggtgg atacgttaga gtgtgcggtg gcggcggaag ctgtactgtg     120
gcccttcctg gtggatacgt tagagtgtgc ggtggcggcg gaagctgtac tgtggccctt     180
cctggtggat acgttagagt gtgc                                            204
```

US 12,655,192 B2

77

78

-continued

```
<210> SEQ ID NO 27
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser Arg Val Lys Phe Ser Arg Ser
            35                  40                  45

Ala Asp Ala Pro Ala Tyr Gln Gln Gly Gln Asn Gln Leu Tyr Asn Glu
        50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Arg Arg Lys Asn Pro Gln
                85                  90                  95

Glu Gly Leu Tyr Asn Glu Leu Gln Lys Asp Lys Met Ala Glu Ala Tyr
            100                 105                 110

Ser Glu Ile Gly Met Lys Gly Glu Arg Arg Arg Gly Lys Gly His Asp
        115                 120                 125

Gly Leu Tyr Gln Gly Leu Ser Thr Ala Thr Lys Asp Thr Tyr Asp Ala
    130                 135                 140

Leu His Met Gln Ala Leu Pro Pro Arg
145                 150

<210> SEQ ID NO 28
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
cgaagcaagc ggagccggct gctgcacagc gattacatga acatgacccc tcggaggccc      60
ggaccaacca gaaagcacta ccagccttac gctcctccta gagacttcgc cgcctaccgg     120
tccagagtga agttcagcag atccgccgat gctcccgcct atcagcaggg acagaaccag     180
ctgtacaacg agctgaacct ggggagaaga gaagagtacg acgtgctgga taagcggaga     240
ggcagagatc ctgagatggg cggcaagccc agacggaaga tcctcaaga gggcctgtat      300 aatgagctgc agaaagacaa gatggccgag gcctacagcg agatcggaat gaagggcgag     360
cgcagaagag gcaagggaca cgatggactg taccagggac tgagcaccgc caccaaggat     420
acctatgacg cactgcacat gcaggccctg ccacctaga                            459

<210> SEQ ID NO 29
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Asp Trp Ile Trp Arg Ile Leu Phe Leu Val Gly Ala Ala Thr Gly
```

-continued

```
1               5               10              15

Ala His Ser Cys Thr Val Ala Leu Pro Gly Gly Tyr Val Arg Val Cys
            20              25              30

Glu Phe Glu Ser Lys Tyr Gly Pro Pro Cys Pro Ser Cys Pro Ala Pro
            35              40              45

Glu Phe Glu Gly Gly Pro Ser Val Phe Leu Phe Pro Pro Lys Pro Lys
    50              55              60

Asp Thr Leu Met Ile Ser Arg Thr Pro Glu Val Thr Cys Val Val Val
65              70              75              80

Asp Val Ser Gln Glu Asp Pro Glu Val Gln Phe Asn Trp Tyr Val Asp
            85              90              95

Gly Val Glu Val His Asn Ala Lys Thr Lys Pro Arg Glu Glu Gln Phe
            100             105             110

Gln Ser Thr Tyr Arg Val Val Ser Val Leu Thr Val Leu His Gln Asp
            115             120             125

Trp Leu Asn Gly Lys Glu Tyr Lys Cys Lys Val Ser Asn Lys Gly Leu
    130             135             140

Pro Ser Ser Ile Glu Lys Thr Ile Ser Lys Ala Lys Gly Gln Pro Arg
145             150             155             160

Glu Pro Gln Val Tyr Thr Leu Pro Pro Ser Gln Glu Glu Met Thr Lys
            165             170             175

Asn Gln Val Ser Leu Thr Cys Leu Val Lys Gly Phe Tyr Pro Ser Asp
            180             185             190

Ile Ala Val Glu Trp Glu Ser Asn Gly Gln Pro Glu Asn Asn Tyr Lys
            195             200             205

Thr Thr Pro Pro Val Leu Asp Ser Asp Gly Ser Phe Phe Leu Tyr Ser
    210             215             220

Arg Leu Thr Val Asp Lys Ser Arg Trp Gln Glu Gly Asn Val Phe Ser
225             230             235             240

Cys Ser Val Met His Glu Ala Leu His Asn His Tyr Thr Gln Lys Ser
            245             250             255

Leu Ser Leu Ser Leu Gly Lys Gly Ser Phe Trp Val Leu Val Val Val
            260             265             270

Gly Gly Val Leu Ala Cys Tyr Ser Leu Leu Val Thr Val Ala Phe Ile
            275             280             285

Ile Phe Trp Val Arg Ser Lys Arg Ser Arg Leu Leu His Ser Asp Tyr
    290             295             300

Met Asn Met Thr Pro Arg Arg Pro Gly Pro Thr Arg Lys His Tyr Gln
305             310             315             320

Pro Tyr Ala Pro Pro Arg Asp Phe Ala Ala Tyr Arg Ser Arg Val Lys
            325             330             335

Phe Ser Arg Ser Ala Asp Ala Pro Ala Tyr Gln Gln Gly Gln Asn Gln
            340             345             350

Leu Tyr Asn Glu Leu Asn Leu Gly Arg Arg Glu Glu Tyr Asp Val Leu
            355             360             365

Asp Lys Arg Arg Gly Arg Asp Pro Glu Met Gly Gly Lys Pro Arg Arg
    370             375             380

Lys Asn Pro Gln Glu Gly Leu Tyr Asn Glu Leu Gln Lys Asp Lys Met
385             390             395             400

Ala Glu Ala Tyr Ser Glu Ile Gly Met Lys Gly Glu Arg Arg Arg Gly
            405             410             415

Lys Gly His Asp Gly Leu Tyr Gln Gly Leu Ser Thr Ala Thr Lys Asp
            420             425             430
```

Thr Tyr Asp Ala Leu His Met Gln Ala Leu Pro Pro Arg
        435                 440                 445

<210> SEQ ID NO 30
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atggactgga tttggcggat cctgtttctc gtgggagccg ccacaggcgc ccattcttgt      60
actgtggccc ttcctggtgg atacgttaga gtgtgcgaat tcgagtctaa gtacggccct     120
ccttgtccta gctgccccgc tcctgaattt gaaggcggcc cttccgtgtt cctgtttcct     180
ccaaagccta aggacaccct gatgatcagc agaacccctg aagtgacctg cgtggtggtg     240
gacgtgtccc aagaggatcc tgaggtgcag ttcaattggt acgtggacgg cgtggaagtg     300
cacaacgcca agaccaagcc tagagaggaa cagttccaga gcacctacag agtggtgtcc     360
gtgctgacag tgctgcacca ggattggctg aacggcaaag agtacaagtg caaggtgtcc     420
aacaagggcc tgcctagcag catcgagaaa accatcagca aggccaaggg ccagccaaga     480
gaaccccagg tgtacacact gcctccaagc aagaggaaa tgaccaagaa ccaggtgtcc     540
ctgacctgcc tggtcaaggg cttctaccct tccgatatcg ccgtggaatg ggagagcaat     600
ggccagcctg agaacaacta caagaccaca cctcctgtgc tggacagcga cggctcattc     660
ttcctgtaca gcagactgac cgtggacaag agcagatggc aagagggcaa cgtgttcagc     720
tgcagcgtga tgcacgaggc cctgcacaac cactacaccc agaagtctct gagcctgagc     780
ctcggcaagg gctccttctg ggtgctcgtt gttgttggcg gcgtgctggc ctgttacagc     840
ctgctggtta ccgtggcctt catcatcttt tgggtccgaa gcaagcggag ccggctgctg     900
cacagcgatt acatgaacat gaccccctcgg aggcccggac caaccagaaa gcactaccag     960
ccttacgctc ctcctagaga cttcgccgcc taccggtcca gagtgaagtt cagcagatcc    1020
gccgatgctc ccgcctatca gcagggacag aaccagctgt acaacgagct gaacctgggg    1080
agaagagaag agtacgacgt gctggataag cggagaggca gagatcctga gatgggcggc    1140
aagcccagac ggaagaatcc tcaagagggc ctgtataatg agctgcagaa agacaagatg    1200
gccgaggcct acagcgagat cggaatgaag ggcgagcgca agaggcaa gggacacgat    1260 ggactgtacc agggactgag caccgccacc aaggatacct atgacgcact gcacatgcag    1320
gccctgccac ctaga                                                    1335

<210> SEQ ID NO 31
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Asp Trp Ile Trp Arg Ile Leu Phe Leu Val Gly Ala Ala Thr Gly
1               5                   10                  15

Ala His Ser Cys Thr Val Ala Leu Pro Gly Gly Tyr Val Arg Val Cys
                20                  25                  30

Gly Gly Gly Gly Ser Cys Thr Val Ala Leu Pro Gly Gly Tyr Val Arg

```
              35                    40                    45
Val Cys Glu Phe Glu Ser Lys Tyr Gly Pro Pro Cys Pro Ser Cys Pro
  50                    55                    60

Ala Pro Glu Phe Glu Gly Gly Pro Ser Val Phe Leu Phe Pro Pro Lys
65                    70                    75                    80

Pro Lys Asp Thr Leu Met Ile Ser Arg Thr Pro Glu Val Thr Cys Val
                  85                    90                    95

Val Val Asp Val Ser Gln Glu Asp Pro Glu Val Gln Phe Asn Trp Tyr
                 100                   105                   110

Val Asp Gly Val Glu Val His Asn Ala Lys Thr Lys Pro Arg Glu Glu
                 115                   120                   125

Gln Phe Gln Ser Thr Tyr Arg Val Val Ser Val Leu Thr Val Leu His
     130                   135                   140

Gln Asp Trp Leu Asn Gly Lys Glu Tyr Lys Cys Lys Val Ser Asn Lys
145                   150                   155                   160

Gly Leu Pro Ser Ser Ile Glu Lys Thr Ile Ser Lys Ala Lys Gly Gln
                 165                   170                   175

Pro Arg Glu Pro Gln Val Tyr Thr Leu Pro Pro Ser Gln Glu Glu Met
                 180                   185                   190

Thr Lys Asn Gln Val Ser Leu Thr Cys Leu Val Lys Gly Phe Tyr Pro
                 195                   200                   205

Ser Asp Ile Ala Val Glu Trp Glu Ser Asn Gly Gln Pro Glu Asn Asn
     210                   215                   220

Tyr Lys Thr Thr Pro Pro Val Leu Asp Ser Asp Gly Ser Phe Phe Leu
225                   230                   235                   240

Tyr Ser Arg Leu Thr Val Asp Lys Ser Arg Trp Gln Glu Gly Asn Val
                 245                   250                   255

Phe Ser Cys Ser Val Met His Glu Ala Leu His Asn His Tyr Thr Gln
                 260                   265                   270

Lys Ser Leu Ser Leu Ser Leu Gly Lys Gly Ser Phe Trp Val Leu Val
                 275                   280                   285

Val Val Gly Gly Val Leu Ala Cys Tyr Ser Leu Leu Val Thr Val Ala
     290                   295                   300

Phe Ile Ile Phe Trp Val Arg Ser Lys Arg Ser Arg Leu Leu His Ser
305                   310                   315                   320

Asp Tyr Met Asn Met Thr Pro Arg Arg Pro Gly Pro Thr Arg Lys His
                 325                   330                   335

Tyr Gln Pro Tyr Ala Pro Pro Arg Asp Phe Ala Ala Tyr Arg Ser Arg
                 340                   345                   350

Val Lys Phe Ser Arg Ser Ala Asp Ala Pro Ala Tyr Gln Gln Gly Gln
                 355                   360                   365

Asn Gln Leu Tyr Asn Glu Leu Asn Leu Gly Arg Arg Glu Glu Tyr Asp
     370                   375                   380

Val Leu Asp Lys Arg Arg Gly Arg Asp Pro Glu Met Gly Gly Lys Pro
385                   390                   395                   400

Arg Arg Lys Asn Pro Gln Glu Gly Leu Tyr Asn Glu Leu Gln Lys Asp
                 405                   410                   415

Lys Met Ala Glu Ala Tyr Ser Glu Ile Gly Met Lys Gly Glu Arg Arg
                 420                   425                   430

Arg Gly Lys Gly His Asp Gly Leu Tyr Gln Gly Leu Ser Thr Ala Thr
                 435                   440                   445

Lys Asp Thr Tyr Asp Ala Leu His Met Gln Ala Leu Pro Pro Arg
     450                   455                   460
```

-continued

```
<210> SEQ ID NO 32
<211> LENGTH: 1389
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggactgga tttggcggat cctgtttctc gtgggagccg ccacaggcgc ccattcttgt      60
actgtggccc ttcctggtgg atacgttaga gtgtgcggtg gcggcggaag ctgtactgtg     120
gcccttcctg gtggatacgt tagagtgtgc gaattcgagt ctaagtacgg ccctccttgt     180
cctagctgcc ccgctcctga atttgaaggc ggccttccg tgttcctgtt tcctccaaag      240
cctaaggaca ccctgatgat cagcagaacc cctgaagtga cctgcgtggt ggtggacgtg     300
tcccaagagg atcctgaggt gcagttcaat tggtacgtgg acggcgtgga agtgcacaac     360
gccaagacca gcctagaga ggaacagttc cagagcacct acagagtggt gtccgtgctg      420
acagtgctgc accaggattg gctgaacggc aaagagtaca agtgcaaggt gtccaacaag     480
ggcctgccta gcagcatcga gaaaaccatc agcaaggcca agggccagcc aagagaaccc     540
caggtgtaca cactgcctcc aagccaagag gaaatgacca agaaccaggt gtccctgacc     600
tgcctggtca agggcttcta cccttccgat atcgccgtgg aatgggagag caatggccag     660
cctgagaaca actacaagac cacacctcct gtgctggaca gcgacggctc attcttcctg     720
tacagcagac tgaccgtgga caagagcaga tggcaagagg gcaacgtgtt cagctgcagc     780
gtgatgcacg aggccctgca caaccactac acccagaagt ctctgagcct gagcctcggc     840
aagggctcct ctgggtgct cgttgttgtt ggcggcgtgc tggcctgtta cagcctgctg      900
gttaccgtgg ccttcatcat cttttgggtc cgaagcaagc ggagccggct gctgcacagc     960
gattacatga acatgacccc tcggaggccc ggaccaacca gaaagcacta ccagccttac    1020
gctcctccta gagacttcgc cgcctaccgg tccagagtga agttcagcag atccgccgat    1080
gctcccgcct atcagcaggg acagaaccag ctgtacaacg agctgaacct ggggagaaga    1140
gaagagtacg acgtgctgga taagcggaga ggcagagatc ctgagatggg cggcaagccc    1200
agacggaaga atcctcaaga gggcctgtat aatgagctgc agaaagacaa gatggccgag    1260
gcctacagcg agatcggaat gaagggcgag cgcagaagag gcaagggaca cgatggactg    1320
taccagggac tgagcaccgc caccaaggat acctatgacg cactgcacat gcaggccctg    1380
ccacctaga                                                           1389

<210> SEQ ID NO 33
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Asp Trp Ile Trp Arg Ile Leu Phe Leu Val Gly Ala Ala Thr Gly
1               5                   10                  15

Ala His Ser Cys Thr Val Ala Leu Pro Gly Gly Tyr Val Arg Val Cys
                20                  25                  30

Gly Gly Gly Gly Ser Cys Thr Val Ala Leu Pro Gly Gly Tyr Val Arg
        35                  40                  45
```

-continued

```
Val Cys Gly Gly Gly Gly Ser Cys Thr Val Ala Leu Pro Gly Gly Tyr
    50                  55                  60

Val Arg Val Cys Glu Phe Glu Ser Lys Tyr Gly Pro Pro Cys Pro Ser
65                  70                  75                  80

Cys Pro Ala Pro Glu Phe Glu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser Gln Glu Asp Pro Glu Val Gln Phe Asn
            115                 120                 125

Trp Tyr Val Asp Gly Val Glu Val His Asn Ala Lys Thr Lys Pro Arg
        130                 135                 140

Glu Glu Gln Phe Gln Ser Thr Tyr Arg Val Val Ser Val Leu Thr Val
145                 150                 155                 160

Leu His Gln Asp Trp Leu Asn Gly Lys Glu Tyr Lys Cys Lys Val Ser
            165                 170                 175

Asn Lys Gly Leu Pro Ser Ser Ile Glu Lys Thr Ile Ser Lys Ala Lys
            180                 185                 190

Gly Gln Pro Arg Glu Pro Gln Val Tyr Thr Leu Pro Pro Ser Gln Glu
            195                 200                 205

Glu Met Thr Lys Asn Gln Val Ser Leu Thr Cys Leu Val Lys Gly Phe
        210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
            245                 250                 255

Phe Leu Tyr Ser Arg Leu Thr Val Asp Lys Ser Arg Trp Gln Glu Gly
            260                 265                 270

Asn Val Phe Ser Cys Ser Val Met His Glu Ala Leu His Asn His Tyr
            275                 280                 285

Thr Gln Lys Ser Leu Ser Leu Ser Leu Gly Lys Gly Ser Phe Trp Val
        290                 295                 300

Leu Val Val Val Gly Gly Val Leu Ala Cys Tyr Ser Leu Leu Val Thr
305                 310                 315                 320

Val Ala Phe Ile Ile Phe Trp Val Arg Ser Lys Arg Ser Arg Leu Leu
            325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
            355                 360                 365

Ser Arg Val Lys Phe Ser Arg Ser Ala Asp Ala Pro Ala Tyr Gln Gln
        370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
            405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
        450                 455                 460
```

```
Ala Thr Lys Asp Thr Tyr Asp Ala Leu His Met Gln Ala Leu Pro Pro
465                 470                 475                 480

Arg

<210> SEQ ID NO 34
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggactgga tttggcggat cctgtttctc gtgggagccg ccacaggcgc ccattcttgt      60
actgtggccc ttcctggtgg atacgttaga gtgtgcggtg gcggcggaag ctgtactgtg     120
gcccttcctg gtggatacgt tagagtgtgc ggtggcggcg gaagctgtac tgtggccctt     180
cctggtggat acgttagagt gtgcgaattc gagtctaagt acggccctcc ttgtcctagc     240
tgccccgctc ctgaatttga aggcggccct tccgtgttcc tgtttcctcc aaagcctaag     300
gacaccctga tgatcagcag aacccctgaa gtgacctgcg tggtggtgga cgtgtcccaa     360
gaggatcctg aggtgcagtt caattggtac gtggacggcg tggaagtgca caacgccaag     420
accaagccta gagaggaaca gttccagagc acctacagag tggtgtccgt gctgacagtg     480
ctgcaccagg attggctgaa cggcaaagag tacaagtgca aggtgtccaa caagggcctg     540
cctagcagca tcgagaaaac catcagcaag gccaagggcc agccaagaga accccaggtg     600
tacacactgc ctccaagcca agaggaaatg accaagaacc aggtgtccct gacctgcctg     660
gtcaagggct ctacccttc cgatatcgcc gtggaatggg agagcaatgg ccagcctgag     720
aacaactaca gaccacacc tcctgtgctg gacagcgacg gctcattctt cctgtacagc     780
agactgaccg tggacaagag cagatggcaa gagggcaacg tgttcagctg cagcgtgatg     840
cacgaggccc tgcacaacca ctacacccag aagtctctga gcctgagcct cggcaagggc     900
tccttctggg tgctcgttgt tgttggcggc gtgctggcct gttacagcct gctggttacc     960
gtggccttca tcatcttttg ggtccgaagc aagcggagcc ggctgctgca cagcgattac    1020
atgaacatga cccctcggag gcccggacca accagaaagc actaccagcc ttacgctcct    1080
cctagagact tcgccgccta ccggtccaga gtgaagttca gcagatccgc cgatgctccc    1140
gcctatcagc agggacagaa ccagctgtac aacgagctga acctggggag aagagaagag    1200
tacgacgtgc tggataagcg gagaggcaga gatcctgaga tgggcggcaa gcccagacgg    1260
aagaatcctc aagagggcct gtataatgag ctgcagaaag acaagatggc cgaggcctac    1320
agcgagatcg gaatgaaggg cgagcgcaga gaggcaagg acacgatgg actgtaccag    1380 ggactgagca ccgccaccaa ggataccat gacgcactgc acatgcaggc cctgccacct    1440
aga                                                                   1443

<210> SEQ ID NO 35
<211> LENGTH: 801
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Asp Trp Ile Trp Arg Ile Leu Phe Leu Val Gly Ala Ala Thr Gly
1               5                   10                  15
```

-continued

```
Ala His Ser Cys Thr Val Ala Leu Pro Gly Gly Tyr Val Arg Val Cys
            20                  25                  30

Glu Phe Glu Ser Lys Tyr Gly Pro Pro Cys Pro Ser Cys Pro Ala Pro
            35                  40                  45

Glu Phe Glu Gly Gly Pro Ser Val Phe Leu Phe Pro Pro Lys Pro Lys
    50                  55                  60

Asp Thr Leu Met Ile Ser Arg Thr Pro Glu Val Thr Cys Val Val Val
65                  70                  75                  80

Asp Val Ser Gln Glu Asp Pro Glu Val Gln Phe Asn Trp Tyr Val Asp
                85                  90                  95

Gly Val Glu Val His Asn Ala Lys Thr Lys Pro Arg Glu Glu Gln Phe
            100                 105                 110

Gln Ser Thr Tyr Arg Val Val Ser Val Leu Thr Val Leu His Gln Asp
            115                 120                 125

Trp Leu Asn Gly Lys Glu Tyr Lys Cys Lys Val Ser Asn Lys Gly Leu
    130                 135                 140

Pro Ser Ser Ile Glu Lys Thr Ile Ser Lys Ala Lys Gly Gln Pro Arg
145                 150                 155                 160

Glu Pro Gln Val Tyr Thr Leu Pro Pro Ser Gln Glu Glu Met Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
            195                 200                 205

Thr Thr Pro Pro Val Leu Asp Ser Asp Gly Ser Phe Phe Leu Tyr Ser
    210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Leu Gly Lys Gly Ser Phe Trp Val Leu Val Val Val
            260                 265                 270

Gly Gly Val Leu Ala Cys Tyr Ser Leu Leu Val Thr Val Ala Phe Ile
            275                 280                 285

Ile Phe Trp Val Arg Ser Lys Arg Ser Arg Leu Leu His Ser Asp Tyr
    290                 295                 300

Met Asn Met Thr Pro Arg Arg Pro Gly Pro Thr Arg Lys His Tyr Gln
305                 310                 315                 320

Pro Tyr Ala Pro Pro Arg Asp Phe Ala Ala Tyr Arg Ser Arg Val Lys
                325                 330                 335

Phe Ser Arg Ser Ala Asp Ala Pro Ala Tyr Gln Gln Gly Gln Asn Gln
            340                 345                 350

Leu Tyr Asn Glu Leu Asn Leu Gly Arg Arg Glu Glu Tyr Asp Val Leu
            355                 360                 365

Asp Lys Arg Arg Gly Arg Asp Pro Glu Met Gly Gly Lys Pro Arg Arg
    370                 375                 380

Lys Asn Pro Gln Glu Gly Leu Tyr Asn Glu Leu Gln Lys Asp Lys Met
385                 390                 395                 400

Ala Glu Ala Tyr Ser Glu Ile Gly Met Lys Gly Glu Arg Arg Arg Gly
                405                 410                 415

Lys Gly His Asp Gly Leu Tyr Gln Gly Leu Ser Thr Ala Thr Lys Asp
            420                 425                 430
```

-continued

```
Thr Tyr Asp Ala Leu His Met Gln Ala Leu Pro Pro Arg Arg Ser Gly
        435             440             445

Ser Gly Glu Gly Arg Gly Ser Leu Leu Thr Cys Gly Asp Val Glu Glu
    450             455             460

Asn Pro Gly Pro Met Pro Pro Arg Leu Leu Phe Phe Leu Leu Phe
465             470             475             480

Leu Thr Pro Met Glu Val Arg Pro Glu Glu Pro Leu Val Val Lys Val
            485             490             495

Glu Glu Gly Asp Asn Ala Val Leu Gln Cys Leu Lys Gly Thr Ser Asp
            500             505             510

Gly Pro Thr Gln Gln Leu Thr Trp Ser Arg Glu Ser Pro Leu Lys Pro
        515             520             525

Phe Leu Lys Leu Ser Leu Gly Leu Pro Gly Leu Gly Ile His Met Arg
        530             535             540

Pro Leu Ala Ile Trp Leu Phe Ile Phe Asn Val Ser Gln Gln Met Gly
545             550             555             560

Gly Phe Tyr Leu Cys Gln Pro Gly Pro Pro Ser Glu Lys Ala Trp Gln
            565             570             575

Pro Gly Trp Thr Val Asn Val Glu Gly Ser Gly Glu Leu Phe Arg Trp
            580             585             590

Asn Val Ser Asp Leu Gly Gly Leu Gly Cys Gly Leu Lys Asn Arg Ser
        595             600             605

Ser Glu Gly Pro Ser Ser Pro Ser Gly Lys Leu Met Ser Pro Lys Leu
        610             615             620

Tyr Val Trp Ala Lys Asp Arg Pro Glu Ile Trp Glu Gly Glu Pro Pro
625             630             635             640

Cys Leu Pro Pro Arg Asp Ser Leu Asn Gln Ser Leu Ser Gln Asp Leu
            645             650             655

Thr Met Ala Pro Gly Ser Thr Leu Trp Leu Ser Cys Gly Val Pro Pro
            660             665             670

Asp Ser Val Ser Arg Gly Pro Leu Ser Trp Thr His Val His Pro Lys
        675             680             685

Gly Pro Lys Ser Leu Leu Ser Leu Glu Leu Lys Asp Asp Arg Pro Ala
        690             695             700

Arg Asp Met Trp Val Met Glu Thr Gly Leu Leu Leu Pro Arg Ala Thr
705             710             715             720

Ala Gln Asp Ala Gly Lys Tyr Tyr Cys His Arg Gly Asn Leu Thr Met
            725             730             735

Ser Phe His Leu Glu Ile Thr Ala Arg Pro Val Leu Trp His Trp Leu
        740             745             750

Leu Arg Thr Gly Gly Trp Lys Val Ser Ala Val Thr Leu Ala Tyr Leu
        755             760             765

Ile Phe Cys Leu Cys Ser Leu Val Gly Ile Leu His Leu Gln Arg Ala
        770             775             780

Leu Val Leu Arg Arg Lys Arg Lys Arg Met Thr Asp Pro Thr Arg Arg
785             790             795             800

Phe
```

<210> SEQ ID NO 36
<211> LENGTH: 2406
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 36
atggactgga tttggcggat cctgtttctc gtgggagccg ccacaggcgc ccattcttgt        60
actgtggccc ttcctggtgg atacgttaga gtgtgcgaat tcgagtctaa gtacggccct       120
ccttgtccta gctgccccgc tcctgaattt gaaggcggcc cttccgtgtt cctgtttcct       180
ccaaagccta aggacaccct gatgatcagc agaacccctg aagtgacctg cgtggtggtg       240
gacgtgtccc aagaggatcc tgaggtgcag ttcaattggt acgtggacgg cgtggaagtg       300
cacaacgcca gaccaagcc tagagaggaa cagttccaga gcacctacag agtggtgtcc        360
gtgctgacag tgctgcacca ggattggctg aacggcaaag agtacaagtg caaggtgtcc       420
aacaagggcc tgcctagcag catcgagaaa accatcagca aggccaaggg ccagccaaga       480
gaaccccagg tgtacacact gcctccaagc caagaggaaa tgaccaagaa ccaggtgtcc       540
ctgacctgcc tggtcaaggg cttctaccct tccgatatcg ccgtggaatg ggagagcaat       600
ggccagcctg agaacaacta caagaccaca cctcctgtgc tggacagcga cggctcattc       660
ttcctgtaca gcagactgac cgtggacaag agcagatggc aagagggcaa cgtgttcagc       720
tgcagcgtga tgcacgaggc cctgcacaac cactacaccc agaagtctct gagcctgagc       780
ctcggcaagg gctccttctg ggtgctcgtt gttgttggcg gcgtgctggc ctgttacagc       840
ctgctggtta ccgtggcctt catcatcttt tgggtccgaa gcaagcggag ccggctgctg       900
cacagcgatt acatgaacat gacccctcgg aggcccggac caaccagaaa gcactaccag       960
ccttacgctc ctcctagaga cttcgccgcc taccggtcca gagtgaagtt cagcagatcc      1020
gccgatgctc ccgcctatca gcagggacag aaccagctgt acaacgagct gaacctgggg      1080
agaagagaag agtacgacgt gctggataag cggagaggca gagatcctga gatgggcggc      1140
aagcccagac ggaagaatcc tcaagagggc ctgtataatg agctgcagaa agacaagatg      1200
gccgaggcct acagcgagat cggaatgaag ggcgagcgca gaagaggcaa gggacacgat      1260
ggactgtacc agggactgag caccgccacc aaggatacct atgacgcact gcacatgcag      1320
gccctgccac ctagaagatc tggctctggc gaaggcagag ctctctgct gacatgtggc        1380 gacgtggaag agaatcctgg acctatgcct ccccccagac tgctgttctt cctgctgttc      1440 ctgacccta tggaagtgcg gcccgaggaa cccctggtcg tgaaagtgga agagggcgac        1500
aacgccgtgc tgcagtgtct gaagggcacc tccgatggcc ctacccagca gctgacctgg      1560
tccagagaga gccccctgaa gcccttcctg aagctgtctc tgggcctgcc tggcctgggc      1620
atccatatga ggccactggc catctggctg ttcatcttca cgtgtcccca gcagatggga      1680
ggcttctacc tgtgccagcc tggcccacct tctgagaagg cttggcagcc tggctggacc      1740
gtgaacgtgg aaggatctgg cgagctgttc cggtggaacg tgtccgatct gggcggcctg      1800
ggatgcggcc tgaagaacag atctagcgag ggccccagca gccccagcgg caaactgatg      1860
agccccaagc tgtacgtgtg ggccaaggac agacccgaga tttgggaggg cgagccccct      1920
tgcctgcccc ctagagatag cctgaaccag agcctgagcc aggacctgac aatggcccct      1980
ggcagcacac tgtggctgag ctgtggcgtg ccacccgact ctgtgtctag aggccctctg      2040
agctggaccc acgtgcaccc taagggccct aagagcctgc tgtccctgga actgaaggac      2100
gacaggcccg ccagagatat gtgggtcatg gaaaccggcc tgctgctgcc tagagccaca      2160
gcccaggatg ccggcaagta ctactgccac agaggcaacc tgaccatgag cttccacctg      2220
gaaatcaccg ccagacccgt gctgtggcac tggctgctga gaaccggcgg atggaaagtg      2280
```

-continued tccgccgtga ctctggccta cctgatcttc tgcctgtgct ccctcgtggg catcctgcat    2340
ctgcagaggg ctctggtgct gcggcggaag cggaagagaa tgaccgaccc tacccggcgg    2400
ttctaa                                                               2406

<210> SEQ ID NO 37
<211> LENGTH: 819
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Asp Trp Ile Trp Arg Ile Leu Phe Leu Val Gly Ala Ala Thr Gly
1               5                   10                  15

Ala His Ser Cys Thr Val Ala Leu Pro Gly Gly Tyr Val Arg Val Cys
                20                  25                  30

Gly Gly Gly Gly Ser Cys Thr Val Ala Leu Pro Gly Gly Tyr Val Arg
            35                  40                  45

Val Cys Glu Phe Glu Ser Lys Tyr Gly Pro Pro Cys Pro Ser Cys Pro
        50                  55                  60

Ala Pro Glu Phe Glu Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
                100                 105                 110

Val Asp Gly Val Glu Val His Asn Ala Lys Thr Lys Pro Arg Glu Glu
            115                 120                 125

Gln Phe Gln Ser Thr Tyr Arg Val Val Ser Val Leu Thr Val Leu His
        130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
                180                 185                 190

Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
        210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly Lys Gly Ser Phe Trp Val Leu Val
        275                 280                 285

Val Val Gly Gly Val Leu Ala Cys Tyr Ser Leu Leu Val Thr Val Ala
        290                 295                 300

Phe Ile Ile Phe Trp Val Arg Ser Lys Arg Ser Arg Leu Leu His Ser
305                 310                 315                 320

Asp Tyr Met Asn Met Thr Pro Arg Arg Pro Gly Pro Thr Arg Lys His
                325                 330                 335

```
Tyr Gln Pro Tyr Ala Pro Pro Arg Asp Phe Ala Ala Tyr Arg Ser Arg
            340             345             350

Val Lys Phe Ser Arg Ser Ala Asp Ala Pro Ala Tyr Gln Gln Gly Gln
            355             360             365

Asn Gln Leu Tyr Asn Glu Leu Asn Leu Gly Arg Arg Glu Glu Tyr Asp
    370             375             380

Val Leu Asp Lys Arg Arg Gly Arg Asp Pro Glu Met Gly Gly Lys Pro
385             390             395             400

Arg Arg Lys Asn Pro Gln Glu Gly Leu Tyr Asn Glu Leu Gln Lys Asp
                405             410             415

Lys Met Ala Glu Ala Tyr Ser Glu Ile Gly Met Lys Gly Glu Arg Arg
            420             425             430

Arg Gly Lys Gly His Asp Gly Leu Tyr Gln Gly Leu Ser Thr Ala Thr
            435             440             445

Lys Asp Thr Tyr Asp Ala Leu His Met Gln Ala Leu Pro Pro Arg Arg
    450             455             460

Ser Gly Ser Gly Glu Gly Arg Gly Ser Leu Leu Thr Cys Gly Asp Val
465             470             475             480

Glu Glu Asn Pro Gly Pro Met Pro Pro Pro Arg Leu Leu Phe Phe Leu
                485             490             495

Leu Phe Leu Thr Pro Met Glu Val Arg Pro Glu Glu Pro Leu Val Val
            500             505             510

Lys Val Glu Glu Gly Asp Asn Ala Val Leu Gln Cys Leu Lys Gly Thr
            515             520             525

Ser Asp Gly Pro Thr Gln Gln Leu Thr Trp Ser Arg Glu Ser Pro Leu
    530             535             540

Lys Pro Phe Leu Lys Leu Ser Leu Gly Leu Pro Gly Leu Gly Ile His
545             550             555             560

Met Arg Pro Leu Ala Ile Trp Leu Phe Ile Phe Asn Val Ser Gln Gln
            565             570             575

Met Gly Gly Phe Tyr Leu Cys Gln Pro Gly Pro Pro Ser Glu Lys Ala
            580             585             590

Trp Gln Pro Gly Trp Thr Val Asn Val Glu Gly Ser Gly Glu Leu Phe
            595             600             605

Arg Trp Asn Val Ser Asp Leu Gly Gly Leu Gly Cys Gly Leu Lys Asn
    610             615             620

Arg Ser Ser Glu Gly Pro Ser Ser Pro Ser Gly Lys Leu Met Ser Pro
625             630             635             640

Lys Leu Tyr Val Trp Ala Lys Asp Arg Pro Glu Ile Trp Glu Gly Glu
            645             650             655

Pro Pro Cys Leu Pro Pro Arg Asp Ser Leu Asn Gln Ser Leu Ser Gln
            660             665             670

Asp Leu Thr Met Ala Pro Gly Ser Thr Leu Trp Leu Ser Cys Gly Val
    675             680             685

Pro Pro Asp Ser Val Ser Arg Gly Pro Leu Ser Trp Thr His Val His
    690             695             700

Pro Lys Gly Pro Lys Ser Leu Leu Ser Leu Glu Leu Lys Asp Asp Arg
705             710             715             720

Pro Ala Arg Asp Met Trp Val Met Glu Thr Gly Leu Leu Leu Pro Arg
            725             730             735

Ala Thr Ala Gln Asp Ala Gly Lys Tyr Tyr Cys His Arg Gly Asn Leu
            740             745             750
```

-continued

```
Thr Met Ser Phe His Leu Glu Ile Thr Ala Arg Pro Val Leu Trp His
        755                 760                 765

Trp Leu Leu Arg Thr Gly Gly Trp Lys Val Ser Ala Val Thr Leu Ala
    770                 775                 780

Tyr Leu Ile Phe Cys Leu Cys Ser Leu Val Gly Ile Leu His Leu Gln
785                 790                 795                 800

Arg Ala Leu Val Leu Arg Arg Lys Arg Lys Arg Met Thr Asp Pro Thr
                805                 810                 815

Arg Arg Phe
```

```
<210> SEQ ID NO 38
<211> LENGTH: 2460
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggactgga tttggcggat cctgtttctc gtgggagccg ccacaggcgc ccattcttgt      60
actgtggccc ttcctggtgg atacgttaga gtgtgcggtg gcggcggaag ctgtactgtg     120
gcccttcctg gtggatacgt tagagtgtgc gaattcgagt ctaagtacgg ccctccttgt     180
cctagctgcc ccgctcctga atttgaaggc ggcccttccg tgttcctgtt tcctccaaag     240
cctaaggaca ccctgatgat cagcagaacc cctgaagtga cctgcgtggt ggtggacgtg     300
tcccaagagg atcctgaggt gcagttcaat tggtacgtgg acggcgtgga agtgcacaac     360
gccaagacca gcctagaga ggaacagttc cagagcacct acagagtggt gtccgtgctg     420
acagtgctgc accaggattg gctgaacggc aaagagtaca agtgcaaggt gtccaacaag     480
ggcctgccta gcagcatcga gaaaaccatc agcaaggcca agggccagcc aagagaaccc     540
caggtgtaca cactgcctcc aagccaagag gaaatgacca gaaccaggt gtccctgacc     600 tgcctggtca agggcttcta cccttccgat atcgccgtgg aatgggagag caatggccag     660
cctgagaaca actacaagac cacacctcct gtgctggaca cgacggctc attcttcctg     720 tacagcagac tgaccgtgga caagagcaga tggcaagagg caacgtgtt cagctgcagc     780 gtgatgcacg aggccctgca caaccactac acccagaagt ctctgagcct gagcctcggc     840
aagggctcct ctgggtgct cgttgttgtt ggcggcgtgc tggcctgtta cagcctgctg     900
gttaccgtgg ccttcatcat ctttttgggtc cgaagcaagc ggagccggct gctgcacagc     960
gattacatga acatgacccc tcggaggccc ggaccaacca gaaagcacta ccagccttac    1020
gctcctccta gagacttcgc cgcctaccgg tccagagtga agttcagcag atccgccgat    1080
gctcccgcct atcagcaggg acagaaccag ctgtacaacg agctgaacct ggggagaaga    1140
gaagagtacg acgtgctgga taagcggaga ggcagagatc ctgagatggg cggcaagccc    1200
agacggaaga atcctcaaga gggcctgtat aatgagctgc agaaagacaa gatggccgag    1260
gcctacagcg agatcggaat gaagggcgag cgcagaagag gcaagggaca cgatggactg    1320
taccagggac tgagcaccgc caccaaggat acctatgacg cactgcacat gcaggccctg    1380
ccacctagaa gatctggctc tggcgaaggc agaggctctc tgctgacatg tggcgacgtg    1440
gaagagaatc ctggacctat gcctccccc agactgctgt tcttcctgct gttcctgacc    1500
cctatggaag tgcggcccga ggaacccctg gtcgtgaaag tggaagaggg cgacaacgcc    1560
gtgctgcagt gtctgaaggg cacctccgat ggccctaccc agcagctgac ctggtccaga    1620
```

```
gagagccccc tgaagccctt cctgaagctg tctctgggcc tgcctggcct gggcatccat    1680
atgaggccac tggccatctg gctgttcatc ttcaacgtgt cccagcagat gggaggcttc    1740
tacctgtgcc agcctggccc accttctgag aaggcttggc agcctggctg gaccgtgaac    1800
gtggaaggat ctggcgagct gttccggtgg aacgtgtccg atctgggcgg cctgggatgc    1860
ggcctgaaga acagatctag cgagggcccc agcagcccca gcggcaaact gatgagcccc    1920
aagctgtacg tgtgggccaa ggacagaccc gagatttggg agggcgagcc cccttgcctg    1980 cccccctagag atagcctgaa ccagagcctg agccaggacc tgacaatggc ccctggcagc    2040
acactgtggc tgagctgtgg cgtgccaccc gactctgtgt ctagaggccc tctgagctgg    2100
acccacgtgc accctaaggg ccctaagagc ctgctgtccc tggaactgaa ggacgacagg    2160
cccgccagag atatgtgggt catggaaacc ggcctgctgc tgcctagagc cacagcccag    2220
gatgccggca agtactactg ccacagaggc aacctgacca tgagcttcca cctggaaatc    2280
accgccagac ccgtgctgtg gcactggctg ctgagaaccg gcggatggaa agtgtccgcc    2340
gtgactctgg cctacctgat cttctgcctg tgctccctcg tgggcatcct gcatctgcag    2400
agggctctgg tgctgcggcg gaagcggaag agaatgaccg accctacccg gcggttctaa    2460
```

```
<210> SEQ ID NO 39
<211> LENGTH: 837
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Asp Trp Ile Trp Arg Ile Leu Phe Leu Val Gly Ala Ala Thr Gly
1               5                   10                  15

Ala His Ser Cys Thr Val Ala Leu Pro Gly Gly Tyr Val Arg Val Cys
            20                  25                  30

Gly Gly Gly Gly Ser Cys Thr Val Ala Leu Pro Gly Gly Tyr Val Arg
        35                  40                  45

Val Cys Gly Gly Gly Gly Ser Cys Thr Val Ala Leu Pro Gly Gly Tyr
    50                  55                  60

Val Arg Val Cys Glu Phe Glu Ser Lys Tyr Gly Pro Pro Cys Pro Ser
65                  70                  75                  80

Cys Pro Ala Pro Glu Phe Glu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser Gln Glu Asp Pro Glu Val Gln Phe Asn
            115                 120                 125

Trp Tyr Val Asp Gly Val Glu Val His Asn Ala Lys Thr Lys Pro Arg
        130                 135                 140

Glu Glu Gln Phe Gln Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Gly Leu Pro Ser Ser Ile Glu Lys Thr Ile Ser Lys Ala Lys
            180                 185                 190

Gly Gln Pro Arg Glu Pro Gln Val Tyr Thr Leu Pro Pro Ser Gln Glu
            195                 200                 205

Glu Met Thr Lys Asn Gln Val Ser Leu Thr Cys Leu Val Lys Gly Phe
```

-continued

```
        210                 215                 220
Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Arg Leu Thr Val Asp Lys Ser Arg Trp Gln Glu Gly
                260                 265                 270

Asn Val Phe Ser Cys Ser Val Met His Glu Ala Leu His Asn His Tyr
                275                 280                 285

Thr Gln Lys Ser Leu Ser Leu Ser Leu Gly Lys Gly Ser Phe Trp Val
        290                 295                 300

Leu Val Val Val Gly Gly Val Leu Ala Cys Tyr Ser Leu Leu Val Thr
305                 310                 315                 320

Val Ala Phe Ile Ile Phe Trp Val Arg Ser Lys Arg Ser Arg Leu Leu
                325                 330                 335

His Ser Asp Tyr Met Asn Met Thr Pro Arg Arg Pro Gly Pro Thr Arg
                340                 345                 350

Lys His Tyr Gln Pro Tyr Ala Pro Pro Arg Asp Phe Ala Ala Tyr Arg
                355                 360                 365

Ser Arg Val Lys Phe Ser Arg Ser Ala Asp Ala Pro Ala Tyr Gln Gln
        370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
                420                 425                 430

Lys Asp Lys Met Ala Glu Ala Tyr Ser Glu Ile Gly Met Lys Gly Glu
                435                 440                 445

Arg Arg Arg Gly Lys Gly His Asp Gly Leu Tyr Gln Gly Leu Ser Thr
        450                 455                 460

Ala Thr Lys Asp Thr Tyr Asp Ala Leu His Met Gln Ala Leu Pro Pro
465                 470                 475                 480

Arg Arg Ser Gly Ser Gly Glu Gly Arg Gly Ser Leu Leu Thr Cys Gly
                485                 490                 495

Asp Val Glu Glu Asn Pro Gly Pro Met Pro Pro Arg Leu Leu Phe
                500                 505                 510

Phe Leu Leu Phe Leu Thr Pro Met Glu Val Arg Pro Glu Glu Pro Leu
                515                 520                 525

Val Val Lys Val Glu Glu Gly Asp Asn Ala Val Leu Gln Cys Leu Lys
        530                 535                 540

Gly Thr Ser Asp Gly Pro Thr Gln Gln Leu Thr Trp Ser Arg Glu Ser
545                 550                 555                 560

Pro Leu Lys Pro Phe Leu Lys Leu Ser Leu Gly Leu Pro Gly Leu Gly
                565                 570                 575

Ile His Met Arg Pro Leu Ala Ile Trp Leu Phe Ile Phe Asn Val Ser
                580                 585                 590

Gln Gln Met Gly Gly Phe Tyr Leu Cys Gln Pro Gly Pro Pro Ser Glu
                595                 600                 605

Lys Ala Trp Gln Pro Gly Trp Thr Val Asn Val Glu Gly Ser Gly Glu
                610                 615                 620

Leu Phe Arg Trp Asn Val Ser Asp Leu Gly Gly Leu Gly Cys Gly Leu
625                 630                 635                 640
```

-continued

```
Lys Asn Arg Ser Ser Glu Gly Pro Ser Ser Pro Ser Gly Lys Leu Met
            645                 650                 655

Ser Pro Lys Leu Tyr Val Trp Ala Lys Asp Arg Pro Glu Ile Trp Glu
            660                 665                 670

Gly Glu Pro Pro Cys Leu Pro Pro Arg Asp Ser Leu Asn Gln Ser Leu
            675                 680                 685

Ser Gln Asp Leu Thr Met Ala Pro Gly Ser Thr Leu Trp Leu Ser Cys
            690                 695                 700

Gly Val Pro Pro Asp Ser Val Ser Arg Gly Pro Leu Ser Trp Thr His
705                 710                 715                 720

Val His Pro Lys Gly Pro Lys Ser Leu Leu Ser Leu Glu Leu Lys Asp
            725                 730                 735

Asp Arg Pro Ala Arg Asp Met Trp Val Met Glu Thr Gly Leu Leu Leu
            740                 745                 750

Pro Arg Ala Thr Ala Gln Asp Ala Gly Lys Tyr Tyr Cys His Arg Gly
            755                 760                 765

Asn Leu Thr Met Ser Phe His Leu Glu Ile Thr Ala Arg Pro Val Leu
            770                 775                 780

Trp His Trp Leu Leu Arg Thr Gly Gly Trp Lys Val Ser Ala Val Thr
785                 790                 795                 800

Leu Ala Tyr Leu Ile Phe Cys Leu Cys Ser Leu Val Gly Ile Leu His
            805                 810                 815

Leu Gln Arg Ala Leu Val Leu Arg Arg Lys Arg Lys Arg Met Thr Asp
            820                 825                 830

Pro Thr Arg Arg Phe
            835

<210> SEQ ID NO 40
<211> LENGTH: 2514
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atggactgga tttggcggat cctgtttctc gtgggagccg ccacaggcgc ccattcttgt      60
actgtggccc ttcctggtgg atacgttaga gtgtgcggtg gcggcggaag ctgtactgtg     120
gcccttcctg gtggatacgt tagagtgtgc ggtggcggcg gaagctgtac tgtggccctt     180
cctggtggat acgttagagt gtgcgaattc gagtctaagt acggccctcc ttgtcctagc     240
tgccccgctc ctgaatttga aggcggccct tccgtgttcc tgtttcctcc aaagcctaag     300
gacaccctga tgatcagcag aacccctgaa gtgacctgcg tggtggtgga cgtgtcccaa     360
gaggatcctg aggtgcagtt caattggtac gtggacggcg tggaagtgca caacgccaag     420
accaagccta gagaggaaca gttccagagc acctacagag tggtgtccgt gctgacagtg     480
ctgcaccagg attggctgaa cggcaaagag tacaagtgca aggtgtccaa caagggcctg     540
cctagcagca tcgagaaaac catcagcaag gccaagggcc agccaagaga accccaggtg     600
tacacactgc ctccaagcca agaggaaatg accaagaacc aggtgtccct gacctgcctg     660
gtcaagggct ctaccccttc cgatatcgcc gtggaatggg agagcaatgg ccagcctgag     720
aacaactaca gaccacacc tcctgtgctg gacagcgacg gctcattctt cctgtacagc     780
agactgaccg tggacaagag cagatggcaa gagggcaacg tgttcagctg cagcgtgatg     840
```

-continued

```
cacgaggccc tgcacaacca ctacacccag aagtctctga gcctgagcct cggcaagggc    900
tccttctggg tgctcgttgt tgttggcggc gtgctggcct gttacagcct gctggttacc    960
gtggccttca tcatcttttg ggtccgaagc aagcggagcc ggctgctgca cagcgattac   1020
atgaacatga cccctcggag gcccggacca accagaaagc actaccagcc ttacgctcct   1080
cctagagact tcgccgccta ccggtccaga gtgaagttca gcagatccgc cgatgctccc   1140
gcctatcagc agggacagaa ccagctgtac aacgagctga acctggggag aagagaagag   1200
tacgacgtgc tggataagcg gagaggcaga gatcctgaga tgggcggcaa gcccagacgg   1260
aagaatcctc aagagggcct gtataatgag ctgcagaaag acaagatggc cgaggcctac   1320
agcgagatcg gaatgaaggg cgagcgcaga agaggcaagg acacgatgg actgtaccag   1380 ggactgagca ccgccaccaa ggatacctat gacgcactgc acatgcaggc cctgccacct   1440
agaagatctg gctctggcga aggcagaggc tctctgctga catgtggcga cgtggaagag   1500
aatcctggac ctatgcctcc ccccagactg ctgttcttcc tgctgttcct gaccccctatg   1560 gaagtgcggc ccgaggaacc cctggtcgtg aaagtgaag agggcgacaa cgccgtgctg   1620
cagtgtctga agggcacctc cgatggccct acccagcagc tgacctggtc cagagagagc   1680
cccctgaagc ccttcctgaa gctgtctctg ggcctgcctg cctgggcat ccatatgagg   1740 ccactggcca tctggctgtt catcttcaac gtgtcccagc agatgggagg cttctacctg   1800
tgccagcctg cccaccttc tgagaaggct tggcagcctg ctggaccgt gaacgtggaa   1860 ggatctggcg agctgttccg gtggaacgtg tccgatctgg cggcctggg atgcggcctg   1920 aagaacagat ctagcgaggg ccccagcagc cccagcggca aactgatgag ccccaagctg   1980
tacgtgtggg ccaaggacag acccgagatt tgggagggcg agccccctg cctgcccct   2040 agagatagcc tgaaccagag cctgagccag gacctgacaa tggcccctgg cagcacactg   2100
tggctgagct gtggcgtgcc acccgactct gtgtctagag ccctctgag ctggacccac   2160 gtgcaccta agggccctaa gagcctgctg tccctggaac tgaaggacga caggcccgcc   2220
agagatatgt gggtcatgga aaccggcctg ctgctgccta gagccacagc ccaggatgcc   2280
ggcaagtact actgccacag aggcaacctg accatgagct tccacctgga aatcaccgcc   2340
agacccgtgc tgtggcactg gctgctgaga accggcggat ggaaagtgtc cgccgtgact   2400
ctggcctacc tgatcttctg cctgtgctcc ctcgtgggca tcctgcatct gcagagggct   2460
ctggtgctgc ggcggaagcg gaagagaatg accgacccta cccggcggtt ctaa        2514
```

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 42
<211> LENGTH: 63
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 42
atggccttac cagtgaccgc cttgctcctg ccgctggcct tgctgctcca cgccgccagg      60
ccg                                                                      63

<210> SEQ ID NO 43
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Asn Asn Thr Lys Glu Val Trp Gly Gln Gly Thr Leu
            100                 105                 110

Val Thr Val Ser Ser Gly Gly Gly Gly Ser Gly Gly Gly Gly Ser Gly
            115                 120                 125

Gly Ser Ala Leu Gln Ser Val Leu Thr Gln Pro Pro Ser Ala Ser Gly
        130                 135                 140

Thr Pro Gly Gln Arg Val Thr Ile Ser Cys Ser Gly Ser Ser Ser Asn
145                 150                 155                 160

Leu Gly Ser Asn Tyr Val Tyr Trp Tyr Gln Gln Leu Pro Gly Thr Ala
                165                 170                 175

Pro Lys Leu Leu Ile Tyr Arg Asn Asn His Arg Pro Ser Gly Val Pro
            180                 185                 190

Asp Arg Phe Ser Gly Ser Lys Ser Gly Thr Ser Ala Ser Leu Ala Ile
            195                 200                 205

Ser Gly Leu Arg Ser Glu Asp Glu Ala Asp Tyr Tyr Cys Ala Thr Trp
    210                 215                 220

Asp Asp Ser Leu Asn Pro Leu Val Val Phe Gly Gly Gly Thr Lys Leu
225                 230                 235                 240

Thr Val Leu Gly Ala Ala Ala His His His His His His Gly Ala Ala
                245                 250                 255

Glu Gln Lys Leu Ile Ser Glu Glu Asp Leu Asn Gly Ala Ala
            260                 265                 270

<210> SEQ ID NO 44
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 44

```
gaagtgcagc tggtggaaag cggcggcggc gtggtgcagc cgggccgcag cctgcgcctg      60
agctgcgcgg cgagcggctt tacctttagc agctatggca tgcattgggt gcgccaggcg     120
ccgggcaaag gcctggaatg ggtggcggtg attagctatg atggcagcaa caaatattat     180
gcggatagcg tgaaaggccg ctttaccatt agccgcgata acagcaaaaa caccctgtat     240
ctgcagatga acagcctgcg cgcggaagat accgcggtgt attattgcgc gcgcaaaatt     300
aacaacacca agaagtgtg gggccagggc accctggtga ccgtgagcag cggcggcggc      360
ggcagcggcg cggcggcag cggcggcagc gcgctgcaga gcgtgctgac ccagccgccg     420
agcgcgagcg gcaccccggg ccagcgcgtg accattagct gcagcggcag cagcagcaac     480
ctgggcagca actatgtgta ttggtatcag cagctgccgg gcaccgcgcc gaaactgctg     540
atttatcgca caaccatcg cccgagcggc gtgccggatc gctttagcgg cagcaaaagc     600
ggcaccagcg cgagcctggc gattagcggc ctgcgcagcg aagatgaagc ggattattat     660
tgcgcgacct gggatgatag cctgaacccg ctggtggtgt ttggcggcgg caccaaactg     720
accgtgctgg cgcggcggc gcatcatcat catcatcatg cgcggcggga acagaaactg      780
attagcgaag aagatctgaa cggcgcggcg                                      810
```

```
<210> SEQ ID NO 45
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 45

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Asn Ser Thr Lys Glu Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Ser Ala Leu Gln Ser Val Leu Thr Gln Pro Pro Ser Ala Ser Gly
    130                 135                 140

Thr Pro Gly Gln Arg Val Thr Ile Ser Cys Ser Gly Ser Ser Ser Asn
145                 150                 155                 160

Leu Gly Ser Asn Tyr Val Tyr Trp Tyr Gln Gln Leu Pro Gly Thr Ala
                165                 170                 175

Pro Lys Leu Leu Ile Tyr Arg Asn Asn His Arg Pro Ser Gly Val Pro
            180                 185                 190

Asp Arg Phe Ser Gly Ser Lys Ser Gly Thr Ser Ala Ser Leu Ala Ile
```

```
                195                   200                   205
Ser Gly Leu Arg Ser Glu Asp Glu Ala Asp Tyr Tyr Cys Ala Ala Trp
    210                   215                   220

Asp Asp Ser Leu Asn Pro Leu Val Val Phe Gly Gly Gly Thr Lys Leu
225                   230                   235                   240

Thr Val Leu Gly Ala Ala Ala His His His His His His Gly Ala Ala
                245                   250                   255

Glu Gln Lys Leu Ile Ser Glu Glu Asp Leu Asn Gly Ala Ala
                260                   265                   270
```

<210> SEQ ID NO 46
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
gaagtgcagc tggtggaaag cggcggcggc gtggtgcagc cgggccgcag cctgcgcctg      60
agctgcgcgg cgagcggctt tacctttagc agctatggca tgcattgggt cgcgccaggcg    120 ccgggcaaag gcctggaatg ggtggcggtg attagctatg atggcagcaa caaatattat     180
gcggatagcg tgaaaggccg ctttaccatt agccgcgata acagcaaaaa caccctgtat     240
ctgcagatga acagcctgcg cgcggaagat accgcggtgt attattgcgc gcgcaaaatt     300
aacagcacca agaagtgtg tgggccaggg caccctggtga ccgtgagcag cggcggcggc     360
ggcagcggcg cggcggcag cggcggcagc gcgctgcaga gcgtgctgac ccagccgccg     420
agcgcgagcg gcaccccggg ccagcgcgtg accattagct gcagcggcag cagcagcaac     480
ctgggcagca actatgtgta ttggtatcag cagctgccgg gcaccgcgcc gaaactgctg     540
atttatcgca caaccatcg cccgagcggc gtgccggatc gctttagcgg cagcaaaagc      600
ggcaccagcg cgagcctggc gattagcggc ctgcgcagcg aagatgaagc ggattattat     660
tgcgcggcgt gggatgatag cctgaacccg ctggtggtgt ttggcggcgg caccaaactg     720
accgtgctgg cgcggcggc gcatcatcat catcatcatg cgcggcgga acagaaactg       780 attagcgaag aagatctgaa cggcgcggcg                                      810
```

<210> SEQ ID NO 47
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Arg Lys Ile Asn Ser Thr Lys Glu Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Ser Ala Leu Gln Ser Val Leu Thr Gln Pro Pro Ser Ala Ser Gly
    130                 135                 140

Thr Pro Gly Gln Arg Val Thr Ile Ser Cys Ser Gly Ser Ser Ser Asn
145                 150                 155                 160

Ile Gly Ser Asn Tyr Val Tyr Trp Tyr Gln Gln Leu Pro Gly Thr Ala
                165                 170                 175

Pro Lys Leu Leu Ile Tyr Arg Asn Asn Gln Arg Pro Ser Gly Val Pro
            180                 185                 190

Asp Arg Phe Ser Gly Ser Lys Ser Gly Thr Ser Ala Ser Leu Ala Ile
            195                 200                 205

Ser Gly Leu Arg Ser Glu Asp Glu Ala Asp Tyr Tyr Cys Ala Ala Trp
    210                 215                 220

Asp Asp Ser Leu Asn Pro Leu Val Val Phe Gly Gly Gly Thr Lys Leu
225                 230                 235                 240

Thr Val Leu Gly Ala Ala Ala His His His His His His Gly Ala Ala
            245                 250                 255

Glu Gln Lys Leu Ile Ser Glu Glu Asp Leu Asn Gly Ala Ala
            260                 265                 270
```

```
<210> SEQ ID NO 48
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gaggtgcagc tggtggagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggccgtgt attactgtgc aagaaagatt     300
aatagtacga aggaggtgtg gggccaaggt accctggtca ccgtctcgag tggtggaggc     360
ggttcaggcg gaggtggctc tggcggtagt gcacttcagt ctgtgctgac tcagccaccc     420
tcagcgtctg gaccccccgg gcagagggtc accatctctt gttctggaag cagctccaac     480
atcggaagta attatgtata ctggtaccag cagctcccag gaacggcccc caaactcctc     540
atctatagga ataatcagcg gccctcaggg gtccctgacc gattctctgg ctccaagtct     600
ggcacctcag cctccctggc catcagtggg ctccggtccg aggatgaggc tgattattac     660
tgtgcagcat gggatgacag cctgaatcct cttgttgtat cggcggagg gaccaagctg      720 accgtcctag gtgcggccgc acatcatcat caccatcacg ggccgcagaa caaaaactc      780 atctcagaag aggatctgaa tggggccgca                                      810
```

```
<210> SEQ ID NO 49
<211> LENGTH: 69
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 49

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 50
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
accacgacgc cagcgccgcg accaccaaca ccggcgccca ccatcgcgtc gcagcccctg       60
tccctgcgcc cagaggcgtg ccggccagcg gcggggggcg cagtgcacac gagggggctg      120
gacttcgcct gtgatatcta catctgggcg cccttggccg ggacttgtgg ggtccttctc      180
ctgtcactgg ttatcaccct ttactgc                                          207

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn His Arg Asn Arg Arg Arg Val Cys Lys Cys Pro Arg Pro Val Val
1               5                   10                  15

<210> SEQ ID NO 52
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aaccatcgca accgccgccg cgtgtgcaaa tgcccgcgcc cggtggtg                     48

<210> SEQ ID NO 53
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53
```

-continued

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

```
<210> SEQ ID NO 54
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126
```

```
<210> SEQ ID NO 55
<211> LENGTH: 22
<212> TYPE: PRT
<213> ORGANISM: Equine rhinitis A virus

<400> SEQUENCE: 55

Gly Gly Pro Gln Cys Thr Asn Tyr Ala Leu Leu Lys Leu Ala Gly Asp
1               5                   10                  15

Val Glu Ser Asn Pro Gly
            20
```

```
<210> SEQ ID NO 56
<211> LENGTH: 66
<212> TYPE: DNA
<213> ORGANISM: Equine rhinitis A virus

<400> SEQUENCE: 56
ggcggaccgc agtgcaccaa ctacgctctg ctgaaactgg ctggcgacgt ggaaagcaat      60
cccggc                                                                66
```

```
<210> SEQ ID NO 57
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gly Leu Val Arg Arg Gly Ala Arg Ala Gly Pro Arg Met Pro Arg
1               5                   10                  15

Gly Trp Thr Ala Leu Cys Leu Leu Ser Leu Leu Pro Ser Gly Phe Met
            20                  25                  30

Ala Glu Leu Pro Thr Gln Gly Thr Phe Ser Asn Val Ser Thr Asn Val
        35                  40                  45

Ser Pro Ala Lys Pro Thr Thr Thr Pro Ala Pro Arg Pro Pro Thr Pro
        50                  55                  60

Ala Pro Thr Ile Ala Ser Gln Pro Leu Ser Leu Arg Pro Glu Ala Cys
65                  70                  75                  80

Arg Pro Ala Ala Gly Gly Ala Val His Thr Arg Gly Leu Asp Phe Ala
```

```
                        85                    90                    95

Cys Asp Ile Tyr Ile Trp Ala Pro Leu Ala Gly Thr Cys Gly Val Leu
                100                   105                   110

Leu Leu Ser Leu Val Ile Thr Leu Tyr Cys Asn His Arg Asn Arg Arg
        115                   120                   125

Arg Val Cys Lys Cys Pro Arg Pro Val Val
    130                   135
```

<210> SEQ ID NO 58
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
atgggactcg tgcgcagagg cgctagagcc ggccctagaa tgcctagagg atggaccgcc      60
ctgtgcctgc tgtctctgct gcctagcggc ttcatggccg agctgcctac tcagggcacc     120
ttcagcaacg tgtccaccaa tgtgtcccca gccaagccca ccacaacccc tgctcctaga     180
cctcctaccc cagcccctac cattgcctcc cagccactgt ctctgaggcc cgaggcttgt     240
agacctgctg caggcggagc cgtgcacacc agaggactgg atttcgcctg cgacatctat     300
atctgggccc tctctggccgg cacctgtggc gtgctgctgc tgtcactcgt gatcaccctg     360
tactgcaacc accggaaccg gcggagagtg tgcaagtgcc ctagacccgt cgtgtga       417
```

<210> SEQ ID NO 59
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Met Ala Leu Pro Val Thr Ala Leu Leu Leu Pro Leu Ala Leu Leu Leu
1                   5                   10                  15

His Ala Ala Arg Pro Glu Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Lys Ile Asn Asn Thr Lys Glu Val Trp
        115                 120                 125

Gly Gln Gly Thr Leu Val Thr Val Ser Ser Gly Gly Gly Gly Ser Gly
    130                 135                 140

Gly Gly Gly Ser Gly Gly Ser Ala Leu Gln Ser Val Leu Thr Gln Pro
145                 150                 155                 160

Pro Ser Ala Ser Gly Thr Pro Gly Gln Arg Val Thr Ile Ser Cys Ser
                165                 170                 175
```

```
Gly Ser Ser Ser Asn Leu Gly Ser Asn Tyr Val Tyr Trp Tyr Gln Gln
            180                 185                 190

Leu Pro Gly Thr Ala Pro Lys Leu Leu Ile Tyr Arg Asn Asn His Arg
            195                 200                 205

Pro Ser Gly Val Pro Asp Arg Phe Ser Gly Ser Lys Ser Gly Thr Ser
            210                 215                 220

Ala Ser Leu Ala Ile Ser Gly Leu Arg Ser Glu Asp Glu Ala Asp Tyr
225                 230                 235                 240

Tyr Cys Ala Thr Trp Asp Asp Ser Leu Asn Pro Leu Val Val Phe Gly
                245                 250                 255

Gly Gly Thr Lys Leu Thr Val Leu Gly Ala Ala Ala His His His His
            260                 265                 270

His His Gly Ala Ala Glu Gln Lys Leu Ile Ser Glu Glu Asp Leu Asn
            275                 280                 285

Gly Ala Ala Thr Thr Thr Pro Ala Pro Arg Pro Pro Thr Pro Ala Pro
            290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
                325                 330                 335

Ile Tyr Ile Trp Ala Pro Leu Ala Gly Thr Cys Gly Val Leu Leu Leu
                340                 345                 350

Ser Leu Val Ile Thr Leu Tyr Cys Asn His Arg Asn Arg Arg Arg Val
            355                 360                 365

Cys Lys Cys Pro Arg Pro Val Val Lys Arg Gly Arg Lys Lys Leu Leu
            370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Ala Pro Ala Tyr Gln
            420                 425                 430

Gln Gly Gln Asn Gln Leu Tyr Asn Glu Leu Asn Leu Gly Arg Arg Glu
            435                 440                 445

Glu Tyr Asp Val Leu Asp Lys Arg Arg Gly Arg Asp Pro Glu Met Gly
            450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
            515                 520                 525

Pro Arg
    530
```

<210> SEQ ID NO 60
<211> LENGTH: 1590
<212> TYPE: DNA
<213> ORGANISM: Artificial Sequence
<220> FEATURE:
<223> OTHER INFORMATION: Description of Artificial Sequence: Synthetic
     polynucleotide

```
<400> SEQUENCE: 60
atggccttac cagtgaccgc cttgctcctg ccgctggcct tgctgctcca cgccgccagg      60
ccggaagtgc agctggtgga aagcggcggc ggcgtggtgc agccgggccg cagcctgcgc     120
ctgagctgcg cggcgagcgg ctttaccttt agcagctatg gcatgcattg ggtgcgccag     180
gcgccgggca aaggcctgga atgggtggcg gtgattagct atgatggcag caacaaatat     240
tatgcggata gcgtgaaagg ccgctttacc attagccgcg ataacagcaa aaacaccctg     300
tatctgcaga tgaacagcct gcgcgcggaa gataccgcgg tgtattattg cgcgcgcaaa     360
attaacaaca ccaaagaagt gtggggccag ggcaccctgg tgaccgtgag cagcggcggc     420
ggcggcagcg gcggcggcgg cagcggcggc agcgcgctgc agagcgtgct gacccagccg     480
ccgagcgcga gcggcacccc gggccagcgc gtgaccatta gctgcagcgg cagcagcagc     540
aacctgggca gcaactatgt gtattggtat cagcagctgc cgggcaccgc gccgaaactg     600
ctgatttatc gcaacaacca tcgcccgagc ggcgtgccgg atcgctttag cggcagcaaa     660
agcggcacca gcgcgagcct ggcgattagc ggcctgcgca gcgaagatga agcggattat     720
tattgcgcga cctgggatga tagcctgaac ccgctggtgg tgtttggcgg cggcaccaaa     780
ctgaccgtgc tgggcgcggc ggcgcatcat catcatcatc atggcgcggc ggaacagaaa     840
ctgattagcg aagaagatct gaacggcgcg gcgaccacga cgccagcgcc gcgaccacca     900 acaccgcgc ccaccatcgc gtcgcagccc ctgtccctgc gcccagaggc gtgccggcca     960
gcggcggggg gcgcagtgca cacgagggg ctggacttcg cctgtgatat ctacatctgg    1020
gcgcccttgg ccgggacttg tggggtcctt ctcctgtcac tggttatcac cctttactgc    1080
aaccatcgca accgccgccg cgtgtgcaaa tgcccgcgcc cggtggtgaa acggggcaga    1140
aagaaactcc tgtatatatt caaacaacca tttatgagac cagtacaaac tactcaagag    1200
gaagatggct gtagctgccg atttccagaa gaagaagaag gaggatgtga actgagagtg    1260
aagttcagca ggagcgcaga cgcccccgcg taccagcagg gccagaacca gctctataac    1320
gagctcaatc taggacgaag agaggagtac gatgttttgg acaagagacg tggccgggac    1380
cctgagatgg ggggaaagcc gagaaggaag aaccctcagg aaggcctgta caatgaactg    1440
cagaaagata agatggcgga ggcctacagt gagattggga tgaaaggcga gcgccggagg    1500
ggcaaggggc acgatggcct ttaccagggt ctcagtacag ccaccaagga cacctacgac    1560
gcccttcaca tgcaggccct gccccctcgc                                      1590

<210> SEQ ID NO 61
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60
```

-continued

```
Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Lys Ile Asn Ser Thr Lys Glu Val Trp
            115                 120                 125

Gly Gln Gly Thr Leu Val Thr Val Ser Ser Gly Gly Gly Ser Gly
        130                 135                 140

Gly Gly Gly Ser Gly Gly Ser Ala Leu Gln Ser Val Leu Thr Gln Pro
145                 150                 155                 160

Pro Ser Ala Ser Gly Thr Pro Gly Gln Arg Val Thr Ile Ser Cys Ser
                165                 170                 175

Gly Ser Ser Ser Asn Leu Gly Ser Asn Tyr Val Tyr Trp Tyr Gln Gln
            180                 185                 190

Leu Pro Gly Thr Ala Pro Lys Leu Leu Ile Tyr Arg Asn Asn His Arg
        195                 200                 205

Pro Ser Gly Val Pro Asp Arg Phe Ser Gly Ser Lys Ser Gly Thr Ser
    210                 215                 220

Ala Ser Leu Ala Ile Ser Gly Leu Arg Ser Glu Asp Glu Ala Asp Tyr
225                 230                 235                 240

Tyr Cys Ala Ala Trp Asp Asp Ser Leu Asn Pro Leu Val Val Phe Gly
                245                 250                 255

Gly Gly Thr Lys Leu Thr Val Leu Gly Ala Ala Ala His His His His
            260                 265                 270

His His Gly Ala Ala Glu Gln Lys Leu Ile Ser Glu Glu Asp Leu Asn
        275                 280                 285

Gly Ala Ala Thr Thr Thr Pro Ala Pro Arg Pro Pro Thr Pro Ala Pro
    290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
            325                 330                 335

Ile Tyr Ile Trp Ala Pro Leu Ala Gly Thr Cys Gly Val Leu Leu Leu
        340                 345                 350

Ser Leu Val Ile Thr Leu Tyr Cys Asn His Arg Asn Arg Arg Arg Val
        355                 360                 365

Cys Lys Cys Pro Arg Pro Val Val Lys Arg Gly Arg Lys Lys Leu Leu
    370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Gly Gly Cys
            405                 410                 415

Glu Leu Arg Val Lys Phe Ser Arg Ser Ala Asp Ala Pro Ala Tyr Gln
            420                 425                 430

Gln Gly Gln Asn Gln Leu Tyr Asn Glu Leu Asn Leu Gly Arg Arg Glu
        435                 440                 445

Glu Tyr Asp Val Leu Asp Lys Arg Arg Gly Arg Asp Pro Glu Met Gly
    450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
```

-continued

```
              485              490              495
Glu Arg Arg Arg Gly Lys Gly His Asp Gly Leu Tyr Gln Gly Leu Ser
            500              505              510

Thr Ala Thr Lys Asp Thr Tyr Asp Ala Leu His Met Gln Ala Leu Pro
        515              520              525

Pro Arg
    530

<210> SEQ ID NO 62
<211> LENGTH: 1590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atggccttac cagtgaccgc cttgctcctg ccgctggcct tgctgctcca cgccgccagg        60
ccggaagtgc agctggtgga aagcggcggc ggcgtggtgc agccgggccg cagcctgcgc       120
ctgagctgcg cggcgagcgg ctttaccttt agcagctatg cgatgcattg ggtgcgccag       180
gcgccgggca aaggcctgga atgggtggcg gtgattagct atgatggcag caacaaatat       240
tatgcggata gcgtgaaagg ccgctttacc attagccgcg ataacagcaa aaacaccctg       300
tatctgcaga tgaacagcct gcgcgcggaa gataccgcgg tgtattattg cgcgcgcaaa       360
attaacagca ccaaagaagt gtggggccag ggcaccctgg tgaccgtgag cagcggcggc       420
ggcggcagcg gcggcggcgg cagcggcggc agcgcgctgc agagcgtgct gacccagccg       480
ccgagcgcga gcggcacccc gggccagcgc gtgaccatta gctgcagcgg cagcagcagc       540
aacctgggca gcaactatgt gtattggtat cagcagctgc cgggcaccgc gccgaaactg       600
ctgatttatc gcaacaacca tcgcccgagc ggcgtgccgg atcgctttag cggcagcaaa       660
agcggcacca cgcgcgagcct ggcgattagc ggcctgcgca cgaagatga agcggattat       720 tattgcgcgg cgtgggatga tagcctgaac ccgctggtgg tgtttggcgg cggcaccaaa       780
ctgaccgtgc tgggcgcggc ggcgcatcat catcatcatc atggcgcggc ggaacagaaa       840
ctgattagcg aagaagatct gaacggcgcg gcgaccacga cgccagcgcc gcgaccacca       900
acaccggcgc ccaccatcgc gtcgcagccc ctgtccctgc gcccagaggc gtgccggcca       960
gcggcggggg gcgcagtgca cacgaggggg ctggacttcg cctgtgatat ctacatctgg      1020
gcgcccttgg ccgggacttg tggggtcctt ctcctgtcac tggttatcac cctttactgc      1080
aaccatcgca accgccgccg cgtgtgcaaa tgcccgcgcc cggtggtgaa acggggcaga      1140
aagaaactcc tgtatatatt caaacaacca tttatgagac cagtacaaac tactcaagag      1200
gaagatggct gtagctgccg atttccagaa gaagaagaag gaggatgtga actgagagtg      1260
aagttcagca ggagcgcaga cgcccccgcg taccagcagg gccagaacca gctctataac      1320
gagctcaatc taggacgaag agaggagtac gatgttttgg acaagagacg tggccgggac      1380
cctgagatgg ggggaaagcc gagaaggaag aaccctcagg aaggcctgta caatgaactg      1440
cagaaagata gatgccggga ggcctacagt gagattggga tgaaaggcga cgcgcggagg      1500
ggcaaggggc acgatggcct ttaccagggt ctcagtacag ccaccaagga cacctacgac      1560
gcccttcaca tgcaggccct gccccctcgc                                        1590

<210> SEQ ID NO 63
<211> LENGTH: 530
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Lys Ile Asn Ser Thr Lys Glu Val Trp
            115                 120                 125

Gly Gln Gly Thr Leu Val Thr Val Ser Ser Gly Gly Gly Gly Ser Gly
    130                 135                 140

Gly Gly Gly Ser Gly Gly Ser Ala Leu Gln Ser Val Leu Thr Gln Pro
145                 150                 155                 160

Pro Ser Ala Ser Gly Thr Pro Gly Gln Arg Val Thr Ile Ser Cys Ser
            165                 170                 175

Gly Ser Ser Ser Asn Ile Gly Ser Asn Tyr Val Tyr Trp Tyr Gln Gln
            180                 185                 190

Leu Pro Gly Thr Ala Pro Lys Leu Leu Ile Tyr Arg Asn Asn Gln Arg
            195                 200                 205

Pro Ser Gly Val Pro Asp Arg Phe Ser Gly Ser Lys Ser Gly Thr Ser
    210                 215                 220

Ala Ser Leu Ala Ile Ser Gly Leu Arg Ser Glu Asp Glu Ala Asp Tyr
225                 230                 235                 240

Tyr Cys Ala Ala Trp Asp Asp Ser Leu Asn Pro Leu Val Val Phe Gly
            245                 250                 255

Gly Gly Thr Lys Leu Thr Val Leu Gly Ala Ala Ala His His His His
            260                 265                 270

His His Gly Ala Ala Glu Gln Lys Leu Ile Ser Glu Glu Asp Leu Asn
            275                 280                 285

Gly Ala Ala Thr Thr Thr Pro Ala Pro Arg Pro Pro Thr Pro Ala Pro
    290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
            325                 330                 335

Ile Tyr Ile Trp Ala Pro Leu Ala Gly Thr Cys Gly Val Leu Leu Leu
            340                 345                 350

Ser Leu Val Ile Thr Leu Tyr Cys Asn His Arg Asn Arg Arg Arg Val
            355                 360                 365

Cys Lys Cys Pro Arg Pro Val Val Lys Arg Gly Arg Lys Lys Leu Leu
    370                 375                 380
```

-continued

```
Tyr Ile Phe Lys Gln Pro Phe Met Arg Pro Val Gln Thr Thr Gln Glu
385             390             395             400

Glu Asp Gly Cys Ser Cys Arg Phe Pro Glu Glu Glu Glu Gly Gly Cys
            405             410             415

Glu Leu Arg Val Lys Phe Ser Arg Ser Ala Asp Ala Pro Ala Tyr Gln
            420             425             430

Gln Gly Gln Asn Gln Leu Tyr Asn Glu Leu Asn Leu Gly Arg Arg Glu
            435             440             445

Glu Tyr Asp Val Leu Asp Lys Arg Arg Gly Arg Asp Pro Glu Met Gly
        450             455             460

Gly Lys Pro Arg Arg Lys Asn Pro Gln Glu Gly Leu Tyr Asn Glu Leu
465             470             475             480

Gln Lys Asp Lys Met Ala Glu Ala Tyr Ser Glu Ile Gly Met Lys Gly
            485             490             495

Glu Arg Arg Arg Gly Lys Gly His Asp Gly Leu Tyr Gln Gly Leu Ser
            500             505             510

Thr Ala Thr Lys Asp Thr Tyr Asp Ala Leu His Met Gln Ala Leu Pro
            515             520             525

Pro Arg
    530
```

```
<210> SEQ ID NO 64
<211> LENGTH: 1590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggccttac cagtgaccgc cttgctcctg ccgctggcct tgctgctcca cgccgccagg        60
ccggaggtgc agctggtgga gtctgggggga ggcgtggtcc agcctgggag gtccctgaga       120
ctctcctgtg cagcctctgg attcaccttc agtagctatg gcatgcactg ggtccgccag       180
gctccaggca aggggctgga gtgggtggca gttatatcat atgatggaag taataaatac       240
tatgcagact ccgtgaaggg ccgattcacc atctccagag acaattccaa gaacacgctg       300
tatctgcaaa tgaacagcct gagagctgag gacacggccg tgtattactg tgcaagaaag       360
attaatagta cgaaggaggt gtggggccaa ggtaccctgg tcaccgtctc gagtggtgga       420
ggcggttcag gcggaggtgg ctctggcggt agtgcacttc agtctgtgct gactcagcca       480
ccctcagcgt ctgggacccc cgggcagagg gtcaccatct cttgttctgg aagcagctcc       540
aacatcggaa gtaattatgt atactggtac cagcagctcc caggaacggc ccccaaactc       600
ctcatctata ggaataatca gcggccctca ggggtccctg accgattctc tggctccaag       660
tctggcacct cagcctccct ggccatcagt gggctccggt ccgaggatga ggctgattat       720
tactgtgcag catgggatga cagcctgaat cctcttgttg tattcggcgg agggaccaag       780
ctgaccgtcc taggtgcggc cgcacatcat catcaccatc acggggccgc agaacaaaaa       840
ctcatctcag aagaggatct gaatggggcc gcaaccacga cgccagcgcc gcgaccacca       900
acaccggcgc ccaccatcgc gtcgcagccc ctgtccctgc cccagaggc gtgccggcca        960 gcggcggggg gcgcagtgca cacgaggggg ctggacttcg cctgtgatat ctacatctgg      1020
gcgcccttgg ccgggacttg tggggtcctt ctcctgtcac tggttatcac cctttactgc      1080
aaccatcgca accgccgccg cgtgtgcaaa tgcccgcgcc cggtggtgaa acggggcaga      1140
```

-continued

```
aagaaactcc tgtatatatt caaacaacca tttatgagac cagtacaaac tactcaagag      1200
gaagatggct gtagctgccg atttccagaa gaagaagaag gaggatgtga actgagagtg      1260
aagttcagca ggagcgcaga cgcccccgcg taccagcagg gccagaacca gctctataac      1320
gagctcaatc taggacgaag agaggagtac gatgttttgg acaagagacg tggccgggac      1380
cctgagatgg ggggaaagcc gagaaggaag aaccctcagg aaggcctgta caatgaactg      1440
cagaaagata agatggcgga ggcctacagt gagattggga tgaaaggcga cgccggagg      1500 ggcaagggc acgatggcct ttaccagggt ctcagtacag ccaccaagga cacctacgac      1560
gcccttcaca tgcaggccct gccccctcgc                                      1590
```

<210> SEQ ID NO 65
<211> LENGTH: 691
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Lys Ile Asn Asn Thr Lys Glu Val Trp
        115                 120                 125

Gly Gln Gly Thr Leu Val Thr Val Ser Ser Gly Gly Gly Gly Ser Gly
    130                 135                 140

Gly Gly Gly Ser Gly Gly Ser Ala Leu Gln Ser Val Leu Thr Gln Pro
145                 150                 155                 160

Pro Ser Ala Ser Gly Thr Pro Gly Gln Arg Val Thr Ile Ser Cys Ser
                165                 170                 175

Gly Ser Ser Asn Leu Gly Ser Asn Tyr Val Tyr Trp Tyr Gln Gln
            180                 185                 190

Leu Pro Gly Thr Ala Pro Lys Leu Leu Ile Tyr Arg Asn Asn His Arg
        195                 200                 205

Pro Ser Gly Val Pro Asp Arg Phe Ser Gly Ser Lys Ser Gly Thr Ser
    210                 215                 220

Ala Ser Leu Ala Ile Ser Gly Leu Arg Ser Glu Asp Glu Ala Asp Tyr
225                 230                 235                 240

Tyr Cys Ala Thr Trp Asp Asp Ser Leu Asn Pro Leu Val Val Phe Gly
                245                 250                 255

Gly Gly Thr Lys Leu Thr Val Leu Gly Ala Ala Ala His His His His
            260                 265                 270
```

```
His His Gly Ala Ala Glu Gln Lys Leu Ile Ser Glu Glu Asp Leu Asn
        275                 280                 285

Gly Ala Ala Thr Thr Thr Pro Ala Pro Arg Pro Pro Thr Pro Ala Pro
        290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
                325                 330                 335

Ile Tyr Ile Trp Ala Pro Leu Ala Gly Thr Cys Gly Val Leu Leu Leu
            340                 345                 350

Ser Leu Val Ile Thr Leu Tyr Cys Asn His Arg Asn Arg Arg Arg Val
            355                 360                 365

Cys Lys Cys Pro Arg Pro Val Val Lys Arg Gly Arg Lys Lys Leu Leu
        370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Ala Pro Ala Tyr Gln
            420                 425                 430

Gln Gly Gln Asn Gln Leu Tyr Asn Glu Leu Asn Leu Gly Arg Arg Glu
        435                 440                 445

Glu Tyr Asp Val Leu Asp Lys Arg Arg Gly Arg Asp Pro Glu Met Gly
    450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
            485                 490                 495

Glu Arg Arg Arg Gly Lys Gly His Asp Gly Leu Tyr Gln Gly Leu Ser
        500                 505                 510

Thr Ala Thr Lys Asp Thr Tyr Asp Ala Leu His Met Gln Ala Leu Pro
        515                 520                 525

Pro Arg Gly Gly Pro Gln Cys Thr Asn Tyr Ala Leu Leu Lys Leu Ala
        530                 535                 540

Gly Asp Val Glu Ser Asn Pro Gly Pro Met Gly Leu Val Arg Arg Gly
545                 550                 555                 560

Ala Arg Ala Gly Pro Arg Met Pro Arg Gly Trp Thr Ala Leu Cys Leu
                565                 570                 575

Leu Ser Leu Leu Pro Ser Gly Phe Met Ala Glu Leu Pro Thr Gln Gly
            580                 585                 590

Thr Phe Ser Asn Val Ser Thr Asn Val Ser Pro Ala Lys Pro Thr Thr
            595                 600                 605

Thr Pro Ala Pro Arg Pro Pro Thr Pro Ala Pro Thr Ile Ala Ser Gln
        610                 615                 620

Pro Leu Ser Leu Arg Pro Glu Ala Cys Arg Pro Ala Ala Gly Gly Ala
625                 630                 635                 640

Val His Thr Arg Gly Leu Asp Phe Ala Cys Asp Ile Tyr Ile Trp Ala
                645                 650                 655

Pro Leu Ala Gly Thr Cys Gly Val Leu Leu Leu Ser Leu Val Ile Thr
                660                 665                 670

Leu Tyr Cys Asn His Arg Asn Arg Arg Arg Val Cys Lys Cys Pro Arg
        675                 680                 685

Pro Val Val
```

690

<210> SEQ ID NO 66
<211> LENGTH: 2076
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
atggccttac cagtgaccgc cttgctcctg ccgctggcct tgctgctcca cgccgccagg       60
ccggaagtgc agctggtgga aagcggcggc ggcgtggtgc agccgggccg cagcctgcgc      120
ctgagctgcg cggcgagcgg ctttaccttt agcagctatg gcatgcattg ggtgcgccag      180
gcgccgggca aaggcctgga atgggtggcg gtgattagct atgatggcag caacaaatat      240
tatgcggata gcgtgaaagg ccgctttacc attagccgcg ataacagcaa aaacaccctg      300
tatctgcaga tgaacagcct gcgcgcggaa gataccgcgg tgtattattg cgcgcgcaaa      360
attaacaaca ccaaagaagt gtggggccag ggcacccTGG tgaccgtgag cagcggcggc      420
ggcggcagcg gcggcggcgg cagcggcggc agcgcgctgc agagcgtgct gacccagccg      480
ccgagcgcga gcggcacccc gggccagcgc gtgaccatta gctgcagcgg cagcagcagc      540
aacctgggca gcaactatgt gtattggtat cagcagctgc cgggcaccgc gccgaaactg      600
ctgatttatc gcaacaacca tcgcccgagc ggcgtgccgg atcgctttag cggcagcaaa      660
agcggcacca cgcgcgagcct ggcgattagc ggcctgcgca gcgaagatga agcggattat      720
tattgcgcga cctgggatga tagcctgaac ccgctggtgg tgtttggcgg cggcaccaaa      780
ctgaccgtgc tgggcgcggc ggcgcatcat catcatcatc atggcgcggc ggaacagaaa      840
ctgattagcg aagaagatct gaacggcgcg gcgaccacga cgccagcgcc gcgaccacca      900
acaccggcgc ccaccatcgc gtcgcagccc ctgtccctgc gcccagaggc gtgccggcca      960
gcggcggggg gcgcagtgca cacgagggggg ctggacttcg cctgtgatat ctacatctgg     1020
gcgcccttgg ccgggacttg tggggtcctt ctcctgtcac tggttatcac cctttactgc     1080
aaccatcgca accgccgccg cgtgtgcaaa tgcccgcgcc cggtggtgaa acggggcaga     1140
aagaaactcc tgtatatatt caaacaacca tttatgagac cagtacaaac tactcaagag     1200
gaagatggct gtagctgccg atttccagaa gaagaagaag gaggatgtga actgagagtg     1260
aagttcagca ggagcgcaga cgcccccgcg taccagcagg gccagaacca gctctataac     1320
gagctcaatc taggacgaag agaggagtac gatgttttgg acaagagacg tggccgggac     1380
cctgagatgg ggggaaagcc gagaaggaag aaccctcagg aaggcctgta caatgaactg     1440
cagaaagata gatggcgga ggcctacagt gagattggga tgaaaggcga cgccggagg      1500 ggcaaggggc acgatggcct ttaccagggt ctcagtacag ccaccaagga cacctacgac     1560
gcccttcaca tgcaggccct gccccctcgc ggcggaccgc agtgcaccaa ctacgctctg     1620
ctgaaactgg ctggcgacgt ggaaagcaat cccggcccta tgggactcgt gcgcagaggc     1680
gctagagccg ccctagaat gcctagagga tggaccgccc tgtgcctgct gtctctgctg     1740
cctagcggct tcatggccga gctgcctact cagggcacct tcagcaacgt gtccaccaat     1800
gtgtccccag ccaagcccac cacaacccct gctcctagac ctcctacccc agccccctacc     1860 attgcctccc agccactgtc tctgaggccc gaggcttgta gacctgctgc aggcggagcc     1920
gtgcacacca gaggactgga tttcgcctgc gacatctata tctgggcccc tctggccggc     1980

-continued

--- acctgtggcg tgctgctgct gtcactcgtg atcaccctgt actgcaacca ccggaaccgg    2040
cggagagtgt gcaagtgccc tagacccgtc gtgtga    2076

<210> SEQ ID NO 67
<211> LENGTH: 691
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 67

Met Ala Leu Pro Val Thr Ala Leu Leu Leu Pro Leu Ala Leu Leu Leu
1           5                10                15

His Ala Ala Arg Pro Glu Val Gln Leu Val Glu Ser Gly Gly Gly Val
          20                25                30

Val Gln Pro Gly Arg Ser Leu Arg Leu Ser Cys Ala Ala Ser Gly Phe
          35                40                45

Thr Phe Ser Ser Tyr Gly Met His Trp Val Arg Gln Ala Pro Gly Lys
          50                55                60

Gly Leu Glu Trp Val Ala Val Ile Ser Tyr Asp Gly Ser Asn Lys Tyr
65                70                75                80

Tyr Ala Asp Ser Val Lys Gly Arg Phe Thr Ile Ser Arg Asp Asn Ser
          85                90                95

Lys Asn Thr Leu Tyr Leu Gln Met Asn Ser Leu Arg Ala Glu Asp Thr
          100               105               110

Ala Val Tyr Tyr Cys Ala Arg Lys Ile Asn Ser Thr Lys Glu Val Trp
          115               120               125

Gly Gln Gly Thr Leu Val Thr Val Ser Ser Gly Gly Gly Gly Ser Gly
          130               135               140

Gly Gly Gly Ser Gly Gly Ser Ala Leu Gln Ser Val Leu Thr Gln Pro
145                150                155                160

Pro Ser Ala Ser Gly Thr Pro Gly Gln Arg Val Thr Ile Ser Cys Ser
          165               170               175

Gly Ser Ser Ser Asn Leu Gly Ser Asn Tyr Val Tyr Trp Tyr Gln Gln
          180               185               190

Leu Pro Gly Thr Ala Pro Lys Leu Leu Ile Tyr Arg Asn Asn His Arg
          195               200               205

Pro Ser Gly Val Pro Asp Arg Phe Ser Gly Ser Lys Ser Gly Thr Ser
          210               215               220

Ala Ser Leu Ala Ile Ser Gly Leu Arg Ser Glu Asp Glu Ala Asp Tyr
225                230                235                240

Tyr Cys Ala Ala Trp Asp Asp Ser Leu Asn Pro Leu Val Val Phe Gly
               245               250               255

Gly Gly Thr Lys Leu Thr Val Leu Gly Ala Ala Ala His His His His
          260               265               270

His His Gly Ala Ala Glu Gln Lys Leu Ile Ser Glu Glu Asp Leu Asn
          275               280               285

Gly Ala Ala Thr Thr Thr Pro Ala Pro Arg Pro Pro Thr Pro Ala Pro
          290               295               300

Thr Ile Ala Ser Gln Pro Leu Ser Leu Arg Pro Glu Ala Cys Arg Pro
305                310                315                320

Ala Ala Gly Gly Ala Val His Thr Arg Gly Leu Asp Phe Ala Cys Asp
          325               330               335

Ile Tyr Ile Trp Ala Pro Leu Ala Gly Thr Cys Gly Val Leu Leu Leu

-continued

```
              340               345               350

Ser Leu Val Ile Thr Leu Tyr Cys Asn His Arg Asn Arg Arg Val
        355               360               365

Cys Lys Cys Pro Arg Pro Val Val Lys Arg Gly Arg Lys Lys Leu Leu
    370               375               380

Tyr Ile Phe Lys Gln Pro Phe Met Arg Pro Val Gln Thr Thr Gln Glu
385               390               395               400

Glu Asp Gly Cys Ser Cys Arg Phe Pro Glu Glu Glu Glu Gly Gly Cys
                405               410               415

Glu Leu Arg Val Lys Phe Ser Arg Ser Ala Asp Ala Pro Ala Tyr Gln
            420               425               430

Gln Gly Gln Asn Gln Leu Tyr Asn Glu Leu Asn Leu Gly Arg Arg Glu
        435               440               445

Glu Tyr Asp Val Leu Asp Lys Arg Arg Gly Arg Asp Pro Glu Met Gly
    450               455               460

Gly Lys Pro Arg Arg Lys Asn Pro Gln Glu Gly Leu Tyr Asn Glu Leu
465               470               475               480

Gln Lys Asp Lys Met Ala Glu Ala Tyr Ser Glu Ile Gly Met Lys Gly
                485               490               495

Glu Arg Arg Arg Gly Lys Gly His Asp Gly Leu Tyr Gln Gly Leu Ser
            500               505               510

Thr Ala Thr Lys Asp Thr Tyr Asp Ala Leu His Met Gln Ala Leu Pro
        515               520               525

Pro Arg Gly Gly Pro Gln Cys Thr Asn Tyr Ala Leu Leu Lys Leu Ala
    530               535               540

Gly Asp Val Glu Ser Asn Pro Gly Pro Met Gly Leu Val Arg Arg Gly
545               550               555               560

Ala Arg Ala Gly Pro Arg Met Pro Arg Gly Trp Thr Ala Leu Cys Leu
                565               570               575

Leu Ser Leu Leu Pro Ser Gly Phe Met Ala Glu Leu Pro Thr Gln Gly
            580               585               590

Thr Phe Ser Asn Val Ser Thr Asn Val Ser Pro Ala Lys Pro Thr Thr
        595               600               605

Thr Pro Ala Pro Arg Pro Pro Thr Pro Ala Pro Thr Ile Ala Ser Gln
    610               615               620

Pro Leu Ser Leu Arg Pro Glu Ala Cys Arg Pro Ala Ala Gly Gly Ala
625               630               635               640

Val His Thr Arg Gly Leu Asp Phe Ala Cys Asp Ile Tyr Ile Trp Ala
            645               650               655

Pro Leu Ala Gly Thr Cys Gly Val Leu Leu Leu Ser Leu Val Ile Thr
            660               665               670

Leu Tyr Cys Asn His Arg Asn Arg Arg Val Cys Lys Cys Pro Arg
            675               680               685

Pro Val Val
    690
```

<210> SEQ ID NO 68
<211> LENGTH: 2076
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
atggccttac cagtgaccgc cttgctcctg ccgctggcct tgctgctcca cgccgccagg        60
ccggaagtgc agctggtgga aagcggcggc ggcgtggtgc agccgggccg cagcctgcgc       120
ctgagctgcg cggcgagcgg ctttaccttt agcagctatg catgcattg ggtgcgccag        180 gcgccgggca aaggcctgga atgggtggcg gtgattagct atgatggcag caacaaatat       240
tatgcggata gcgtgaaagg ccgctttacc attagccgcg ataacagcaa aaacaccctg       300
tatctgcaga tgaacagcct gcgcgcgaa gataccgcgg tgtattattg cgcgcgcaaa        360
attaacagca ccaaagaagt gtggggccag ggcaccctgg tgaccgtgag cagcggcggc       420
ggcggcagcg gcggcggcgg cagcggcggc agcgcgctgc agagcgtgct gacccagccg       480
ccgagcgcga gcggcacccc gggccagcgc gtgaccatta gctgcagcgg cagcagcagc       540
aacctgggca gcaactatgt gtattggtat cagcagctgc cgggcaccgc gccgaaactg       600
ctgatttatc gcaacaacca tcgcccgagc ggcgtgccgg atcgctttag cggcagcaaa       660
agcggcacca cgcgcgagcct ggcgattagc ggcctgcgca cgaagatga agcggattat      720 tattgcgcgg cgtgggatga tagcctgaac ccgctggtgg tgtttggcgg cggcaccaaa       780
ctgaccgtgc tgggcgcggc ggcgcatcat catcatcatc atggcgcggc ggaacagaaa       840
ctgattagcg aagaagatct gaacggcgcg cgcaccacga cgccagcgcc gcgaccacca       900
acaccggcgc ccaccatcgc gtcgcagccc ctgtccctgc gcccagaggc gtgccggcca       960
gcggcggggg cgcagtgca cacgaggggg ctggacttcg cctgtgatat ctacatctgg      1020
gcgcccttgg ccgggacttg tggggtcctt ctcctgtcac tggttatcac cctttactgc     1080
aaccatcgca accgccgccg cgtgtgcaaa tgcccgcgcc cggtggtgaa acggggcaga      1140
aagaaactcc tgtatatatt caaacaacca tttatgagac cagtacaaac tactcaagag     1200
gaagatggct gtagctgccg atttccagaa gaagaagaag gaggatgtga actgagagtg     1260
aagttcagca ggagcgcaga cgcccccgcg taccagcagg gccagaacca gctctataac     1320
gagctcaatc taggacgaag agaggagtac gatgttttgg acaagagacg tggccgggac     1380
cctgagatgg ggggaaagcc gagaaggaag aaccctcagg aaggcctgta caatgaactg     1440
cagaaagata gatgcggga ggcctacagt gagattggga tgaaaggcga cgccggagg      1500 ggcaagggc acgatggcct ttaccagggt ctcagtacag ccaccaagga cacctacgac     1560
gcccttcaca tgcaggccct gcccctcgc ggcggaccgc agtgcaccaa ctacgctctg     1620
ctgaaactgg ctggcgacgt ggaaagcaat cccggcccta tgggactcgt gcgcagaggc    1680
gctagagccg ccctagaat gcctagagga tggaccgccc tgtgcctgct gtctctgctg     1740
cctagcggct tcatggccga gctgcctact cagggcacct tcagcaacgt gtccaccaat     1800
gtgtccccag ccaagcccac cacaaccccc gctcctagac ctcctacccc agccctacc      1860 attgcctccc agccactgtc tctgaggccc gaggcttgta gacctgctgc aggcggagcc    1920
gtgcacacca gaggactgga tttcgcctgc gacatctata tctgggcccc tctggccggc    1980
acctgtggcg tgctgctgct gtcactcgtg atcaccctgt actgcaacca ccggaaccgg    2040
cggagagtgt gcaagtgccc tagacccgtc gtgtga                               2076
```

<210> SEQ ID NO 69
<211> LENGTH: 691
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 69

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Lys Ile Asn Ser Thr Lys Glu Val Trp
            115                 120                 125

Gly Gln Gly Thr Leu Val Thr Val Ser Ser Gly Gly Gly Gly Ser Gly
        130                 135                 140

Gly Gly Gly Ser Gly Gly Ser Ala Leu Gln Ser Val Leu Thr Gln Pro
145                 150                 155                 160

Pro Ser Ala Ser Gly Thr Pro Gly Gln Arg Val Thr Ile Ser Cys Ser
                165                 170                 175

Gly Ser Ser Ser Asn Ile Gly Ser Asn Tyr Val Tyr Trp Tyr Gln Gln
            180                 185                 190

Leu Pro Gly Thr Ala Pro Lys Leu Leu Ile Tyr Arg Asn Asn Gln Arg
        195                 200                 205

Pro Ser Gly Val Pro Asp Arg Phe Ser Gly Ser Lys Ser Gly Thr Ser
        210                 215                 220

Ala Ser Leu Ala Ile Ser Gly Leu Arg Ser Glu Asp Glu Ala Asp Tyr
225                 230                 235                 240

Tyr Cys Ala Ala Trp Asp Asp Ser Leu Asn Pro Leu Val Val Phe Gly
                245                 250                 255

Gly Gly Thr Lys Leu Thr Val Leu Gly Ala Ala Ala His His His His
            260                 265                 270

His His Gly Ala Ala Glu Gln Lys Leu Ile Ser Glu Glu Asp Leu Asn
        275                 280                 285

Gly Ala Ala Thr Thr Thr Pro Ala Pro Arg Pro Pro Thr Pro Ala Pro
        290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
                325                 330                 335

Ile Tyr Ile Trp Ala Pro Leu Ala Gly Thr Cys Gly Val Leu Leu Leu
            340                 345                 350

Ser Leu Val Ile Thr Leu Tyr Cys Asn His Arg Asn Arg Arg Arg Val
            355                 360                 365

Cys Lys Cys Pro Arg Pro Val Val Lys Arg Gly Arg Lys Lys Leu Leu
        370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415
```

```
Glu Leu Arg Val Lys Phe Ser Arg Ser Ala Asp Ala Pro Ala Tyr Gln
            420                 425                 430

Gln Gly Gln Asn Gln Leu Tyr Asn Glu Leu Asn Leu Gly Arg Arg Glu
            435                 440                 445

Glu Tyr Asp Val Leu Asp Lys Arg Arg Gly Arg Asp Pro Glu Met Gly
    450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
            515                 520                 525

Pro Arg Gly Gly Pro Gln Cys Thr Asn Tyr Ala Leu Leu Lys Leu Ala
    530                 535                 540

Gly Asp Val Glu Ser Asn Pro Gly Pro Met Gly Leu Val Arg Arg Gly
545                 550                 555                 560

Ala Arg Ala Gly Pro Arg Met Pro Arg Gly Trp Thr Ala Leu Cys Leu
                565                 570                 575

Leu Ser Leu Leu Pro Ser Gly Phe Met Ala Glu Leu Pro Thr Gln Gly
            580                 585                 590

Thr Phe Ser Asn Val Ser Thr Asn Val Ser Pro Ala Lys Pro Thr Thr
            595                 600                 605

Thr Pro Ala Pro Arg Pro Pro Thr Pro Ala Pro Thr Ile Ala Ser Gln
    610                 615                 620

Pro Leu Ser Leu Arg Pro Glu Ala Cys Arg Pro Ala Ala Gly Gly Ala
625                 630                 635                 640

Val His Thr Arg Gly Leu Asp Phe Ala Cys Asp Ile Tyr Ile Trp Ala
                645                 650                 655

Pro Leu Ala Gly Thr Cys Gly Val Leu Leu Leu Ser Leu Val Ile Thr
                660                 665                 670

Leu Tyr Cys Asn His Arg Asn Arg Arg Val Cys Lys Cys Pro Arg
            675                 680                 685

Pro Val Val
    690
```

```
<210> SEQ ID NO 70
<211> LENGTH: 2076
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atggccttac cagtgaccgc cttgctcctg ccgctggcct tgctgctcca cgccgccagg        60
ccggaggtgc agctggtgga gtctggggga ggcgtggtcc agcctgggag gtccctgaga       120
ctctcctgtg cagcctctgg attcaccttc agtagctatg catgcactg ggtccgccag        180 gctccaggca aggggctgga gtgggtggca gttatatcat atgatggaag taataaatac       240
tatgcagact ccgtgaaggg ccgattcacc atctccagag acaattccaa gaacacgctg       300
tatctgcaaa tgaacagcct gagagctgag gacacggccg tgtattactg tgcaagaaag       360
attaatagta cgaaggaggt gtggggccaa ggtaccctgg tcaccgtctc gagtggtgga       420
```

-continued

```
ggcggttcag gcggaggtgg ctctggcggt agtgcacttc agtctgtgct gactcagcca      480
ccctcagcgt ctgggacccc cgggcagagg gtcaccatct cttgttctgg aagcagctcc      540
aacatcggaa gtaattatgt atactggtac cagcagctcc caggaacggc ccccaaactc      600
ctcatctata ggaataatca gcggccctca ggggtccctg accgattctc tggctccaag      660
tctggcacct cagcctccct ggccatcagt gggctccggt ccgaggatga ggctgattat      720
tactgtgcag catgggatga cagcctgaat cctcttgttg tattcggcgg agggaccaag      780
ctgaccgtcc taggtgcggc cgcacatcat catcaccatc acggggccgc agaacaaaaa      840
ctcatctcag aagaggatct gaatggggcc gcaaccacga cgccagcgcc gcgaccacca      900
acaccggcgc ccaccatcgc gtcgcagccc ctgtccctgc gcccagaggc gtgccggcca      960
gcggcggggg gcgcagtgca cacgagggggg ctggacttcg cctgtgatat ctacatctgg      1020
gcgcccttgg ccgggacttg tggggtcctt ctcctgtcac tggttatcac cctttactgc      1080
aaccatcgca accgccgccg cgtgtgcaaa tgcccgcgcc cggtggtgaa acggggcaga      1140
aagaaactcc tgtatatatt caaacaacca tttatgagac cagtacaaac tactcaagag      1200
gaagatggct gtagctgccg atttccagaa gaagaagaag gaggatgtga actgagagtg      1260
aagttcagca ggagcgcaga cgcccccgcg taccagcagg gccagaacca gctctataac      1320
gagctcaatc taggacgaag agaggagtac gatgttttgg acaagagacg tggccgggac      1380
cctgagatgg ggggaaagcc gagaaggaag aaccctcagg aaggcctgta caatgaactg      1440
cagaaagata agatggcgga ggcctacagt gagattggga tgaaaggcga gcgccggagg      1500 ggcaagggg c acgatggcct ttaccagggt ctcagtacag ccaccaagga cacctacgac      1560
gcccttcaca tgcaggccct gccccctcgc ggcggaccgc agtgcaccaa ctacgctctg      1620
ctgaaactgg ctggcgacgt ggaaagcaat cccggcccta tgggactcgt gcgcagaggc      1680
gctagagccg ccctagaat g cctagagga tggaccgccc tgtgcctgct gtctctgctg      1740
cctagcggct tcatggccga gctgcctact cagggcacct tcagcaacgt gtccaccaat      1800
gtgtccccag ccaagcccac cacaacccct gctcctagac ctcctacccc agccccctacc      1860 attgcctccc agccactgtc tctgaggccc gaggcttgta gacctgctgc aggcggagcc      1920
gtgcacacca gaggactgga tttcgcctgc gacatctata tctgggcccc tctggccggc      1980
acctgtggcg tgctgctgct gtcactcgtg atcaccctgt actgcaacca ccggaaccgg      2040
cggagagtgt gcaagtgccc tagacccgtc gtgtga                               2076
```

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (1)..(1)
<223> OTHER INFORMATION: Biotin-Ahx
<400> SEQUENCE: 71

Xaa Cys Thr Val Ala Leu Pro Gly Gly Tyr Val Arg Val Cys
1               5                    10

<210> SEQ ID NO 72
<211> LENGTH: 19
<212> TYPE: PRT

<213> ORGANISM: Thosea asigna virus

<400> SEQUENCE: 72

Ala Glu Gly Arg Gly Ser Leu Leu Thr Cys Gly Asp Val Glu Glu Asn
1               5                   10                  15

Pro Gly Pro

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 74
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60

<210> SEQ ID NO 75
<211> LENGTH: 19
<212> TYPE: PRT
<213> ORGANISM: Amphimedon sp.

<400> SEQUENCE: 75

Leu Leu Cys Phe Leu Leu Leu Leu Leu Ser Gly Asp Val Glu Leu Asn
1               5                   10                  15

Pro Gly Pro

<210> SEQ ID NO 76
<211> LENGTH: 20
<212> TYPE: PRT
<213> ORGANISM: Amphimedon sp.

<400> SEQUENCE: 76

His His Phe Met Phe Leu Leu Leu Leu Leu Ala Gly Asp Ile Glu Leu
1               5                   10                  15

Asn Pro Gly Pro
            20

<210> SEQ ID NO 77
<211> LENGTH: 20

```
<212> TYPE: PRT
<213> ORGANISM: Saccoglossus kowalevskii

<400> SEQUENCE: 77

Trp Phe Leu Val Leu Leu Ser Phe Ile Leu Ser Gly Asp Ile Glu Val
1               5                   10                  15

Asn Pro Gly Pro
            20

<210> SEQ ID NO 78
<211> LENGTH: 20
<212> TYPE: PRT
<213> ORGANISM: Branchiostoma floridae

<400> SEQUENCE: 78

Lys Asn Cys Ala Met Tyr Met Leu Leu Leu Ser Gly Asp Val Glu Thr
1               5                   10                  15

Asn Pro Gly Pro
            20

<210> SEQ ID NO 79
<211> LENGTH: 20
<212> TYPE: PRT
<213> ORGANISM: Branchiostoma floridae

<400> SEQUENCE: 79

Met Val Ile Ser Gln Leu Met Leu Lys Leu Ala Gly Asp Val Glu Glu
1               5                   10                  15

Asn Pro Gly Pro
            20

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 80

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 81
<211> LENGTH: 23
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 81

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 82
<211> LENGTH: 8
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 82

Asp Xaa Glu Xaa Asn Pro Gly Pro
1               5

<210> SEQ ID NO 83
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 84
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
agggaccaga ggctgccccc cgatgcccac aagccccctg ggggaggcag tttccggacc      60
cccatccaag aggagcaggc cgacgcccac tccaccctgg ccaagatc                  108

<210> SEQ ID NO 85
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Pro Lys Ser Cys Asp Lys Thr His Thr Cys Pro Gly Gln Pro Arg
1               5                   10                  15

Glu Pro Gln Val Tyr Thr Leu Pro Pro Ser Arg Asp Glu Leu Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Lys Leu Thr Val Asp Lys Ser Arg Trp Gln Gln Gly Asn Val Phe Ser
                85                  90                  95
```

```
Cys Ser Val Met His Glu Ala Leu His Asn His Tyr Thr Gln Lys Ser
            100                 105                 110

Leu Ser Leu Ser Pro Gly Lys
        115

<210> SEQ ID NO 86
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gaaccgaaaa gctgcgataa aacccatacc tgcccgggcc agccgcgcga accgcaggtg      60
tataccctgc cgccgagccg cgatgaactg accaaaaacc aggtgagcct gacctgcctg     120
gtgaaaggct tttatccgag cgatattgcg gtggaatggg aaagcaacgg ccagccggaa     180
aacaactata aaaccacccc gccggtgctg gatagcgatg cagctttttt tctgtatagc     240
aaactgaccg tggataaaag ccgctggcag cagggcaacg tgtttagctg cagcgtgatg     300
catgaagcgc tgcataacca ttatacccag aaaagcctga gcctgagccc gggcaaa       357

<210> SEQ ID NO 87
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205
```

```
Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 88
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gaaccgaaaa gctgcgataa aacccatacc tgcccgccgt gcccggcgcc ggaactgctg      60
ggcggcccga gcgtgtttct gtttccgccg aaaccgaaag ataccctgat gattagccgc     120
accccggaag tgacctgcgt ggtggtggat gtgagccatg aagatccgga agtgaaattt     180
aactggtatg tggatggcgt ggaagtgcat aacgcgaaaa ccaaaccgcg cgaagaacag     240
tataacagca cctatcgcgt ggtgagcgtg ctgaccgtgc tgcatcagga ttggctgaac     300
ggcaaagaat ataaatgcaa agtgagcaac aaagcgctgc cggcgccgat tgaaaaaacc     360
attagcaaag cgaaaggcca gccgcgcgaa ccgcaggtgt ataccctgcc gccgagccgc     420
gatgaactga ccaaaaacca ggtgagcctg acctgcctgg tgaaaggctt ttatccgagc     480
gatattgcgg tggaatggga aagcaacggc agccggaaa acaactataa aaccaccccg     540
ccggtgctgg atagcgatgg cagcttttt ctgtatagca aactgaccgt ggataaaagc     600
cgctggcagc agggcaacgt gtttagctgc agcgtgatgc atgaagcgct gcataaccat     660
tatacccaga aaagcctgag cctgagcccg ggcaaa                              696

<210> SEQ ID NO 89
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Pro Lys Ser Pro Asp Lys Thr His Thr Cys Pro Pro Cys Pro Ala
1                 5                  10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Gln Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140
```

```
Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225                 230
```

<210> SEQ ID NO 90
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
gaaccgaaaa gcccggataa aacccatacc tgcccgccgt gcccggcgcc gccggtggcg     60
ggcccgagcg tgtttctgtt tccgccgaaa ccgaaagata ccctgatgat tagccgcacc    120
ccggaagtga cctgcgtggt ggtggatgtg agccatgaag atccggaagt gaaatttaac    180
tggtatgtgg atggcgtgga agtgcataac gcgaaaacca aaccgcgcga agaacagtat    240
cagagcacct atcgcgtggt gagcgtgctg accgtgctgc atcaggattg gctgaacggc    300
aaagaatata aatgcaaagt gagcaacaaa gcgctgccgg cgccgattga aaaaaccatt    360
agcaaagcga aaggccagcc gcgcgaaccg caggtgtata ccctgccgcc gagccgcgat    420
gaactgacca aaaaccaggt gagcctgacc tgcctggtga aaggctttta tccgagcgat    480
attgcggtgg aatgggaaag caacggccag ccggaaaaca actataaaac caccccgccg    540
gtgctggata gcgatggcag cttttttctg tatagcaaac tgaccgtgga taaaagccgc    600
tggcagcagg gcaacgtgtt tagctgcagc gtgatgcatg aagcgctgca taaccattat    660
acccagaaaa gcctgagcct gagcccgggc aaa                                  693
```

<210> SEQ ID NO 91
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240 cggagggggca aggggcacga tggcctttac caggtctca gtacagccac caaggacacc    300
tacgacgccc ttcacatgca ggccctgccc cctcgc                              336
```

<210> SEQ ID NO 92

-continued

```
<211> LENGTH: 4
<212> TYPE: PRT
<213> ORGANISM: Unknown
<220> FEATURE:
<223> OTHER INFORMATION: Description of Unknown:
      "KDEL" motif peptide

<400> SEQUENCE: 92

Lys Asp Glu Leu
1
```

GRP78 TARGETED ADOPTIVE CELL THERAPY

CROSS-REFERENCE TO RELATED APPLICATIONS

This application is a U.S. National Phase of International Patent Application No. PCT/US2021/028830, filed on Apr. 23, 2021, which published as WO 2021/216994 A1 on Oct. 28, 2021, and claims priority to U.S. Provisional Application No. 63/015,119, filed Apr. 24, 2020, the disclosure of both of which is herein incorporated by reference in their entireties.

SEQUENCE LISTING

The instant application contains a Sequence Listing which has been submitted electronically in ASCII format and is hereby incorporated by reference in its entirety. Said ASCII copy, created on Apr. 19, 2021, is named 243734_000145_SL.txt and is 146,607 bytes in size.

FIELD OF THE INVENTION

The application relates to chimeric antigen receptors (CARs) specific for glucose-regulated-protein 78 (GRP78). The application further relates to polynucleotides and recombinant vectors encoding the CARs, as well as to isolated host cells and methods for preparing isolated host cells that express the CARs. The application further relates to pharmaceutical compositions comprising the CAR modified cells and to methods for treating a tumor using the CAR modified cells.

BACKGROUND

Adoptive immunotherapy using CAR modified T cells (CAR T cells) allows these cells to directly recognize and kill antigen-expressing tumor cells in a manner independent of human leukocyte antigen (HLA). Treatment with chimeric antigen receptor (CAR) T cells offers a promising approach to enhance survival of cancer patients without the overlapping toxicities observed with conventional chemotherapy. However, this therapeutic approach is highly dependent upon molecular design of the CAR.

It is ideal to develop CAR T cells that can recognize a target that is cancer specific, essential for a malignant phenotype, and expressed in a broad range of cancers and, thus, effective in the treatment of multiple cancers. Members of the unfolded protein response (UPR) fulfill these characteristics because the UPR regulates hallmarks of cancer including the ability of cancer cells to resist cell death, sustain proliferation, and metastasize. Intracellular Glucose-regulated-protein 78 (GRP78; NCBI gene ID is 27201) is a key UPR regulator, which normally resides in the endoplasmic reticulum (ER). GRP78 is overexpressed and translocated to the cell surface in a broad range of solid tumors and hematological malignancies in response to elevated ER stress, but not in normal tissues [4, 5, 18, 19]. ER stress is driven by a multitude of cellular processes in tumor cells. The UPR, reactive oxygen species, and antioxidant enzyme dysregulation are some of the critical factors leading to highly elevated ER stress in tumor cells [11-15]. Therefore, GRP78 is an attractive target for CAR T cell therapy as a pan-cancer target.

Thus, there is a need to develop CAR T cells targeting GRP78 that are clinically effective in targeting a broad range of malignancies. The present invention provides a solution to address this problem.

SUMMARY OF THE INVENTION

The present invention discloses, in various aspects, chimeric antigen receptors (CARs) specific for glucose-regulated-protein 78 (GRP78), as well as related polynucleotides, vectors, and cell compositions comprising the same. Further disclosed are compositions (e.g., pharmaceutical compositions) comprising the polypeptides, polynucleotides, vectors, or cell compositions, and methods of using such compositions in treating a cancer in a subject.

In one aspect, provided herein is a polynucleotide encoding a chimeric antigen receptor (CAR) comprising
   a) an extracellular target-binding domain comprising one or more glucose-regulated-protein 78 (GRP78)-binding moieties,
   b) a transmembrane domain; and
   c) a cytoplasmic domain comprising a signaling domain.

In some embodiments, the GRP78-binding moiety comprises a GRP78-binding peptide. In some embodiments, the GRP78-binding peptide comprises the amino acid sequence SEQ ID NO: 1, or a variant thereof. In some embodiments, the nucleotide sequence encoding the GRP78-binding peptide comprises the sequence SEQ ID NO: 2, or a nucleotide sequence having at least 80% sequence identity thereof.

In some embodiments, the extracellular target-binding domain comprises one, two or three GRP78-binding moieties. In some embodiments, when more than one GRP78-binding moiety is used, each GRP78-binding moiety is linked via a linker sequence. In some embodiments, the linker sequence comprises the amino acid sequence SEQ ID NO: 5. In some embodiments, the nucleotide encoding the linker sequence comprises SEQ ID NO: 6. In some embodiments, the extracellular target-binding domain comprises one GRP78-binding moiety.

In some embodiments, the extracellular target-binding domain further comprises a leader sequence. In some embodiments, the leader sequence is derived from human immunoglobulin (IgG) heavy chain variable region or CD8α. In some embodiments, the IgG-derived leader sequence comprises the amino acid sequence of SEQ ID NO: 3, or an amino acid sequence having at least 80% sequence identity thereof. In some embodiments, the nucleotide sequence encoding the IgG-derived leader sequence comprises the sequence of SEQ ID NO: 4, or a nucleotide sequence having at least 80% sequence identity thereof. In some embodiments, the CD8α-derived leader sequence comprises the amino acid sequence of SEQ ID NO: 41, or an amino acid sequence having at least 80% sequence identity thereof. In some embodiments, the nucleotide sequence encoding the CD8α-derived leader sequence comprises the sequence of SEQ ID NO: 42, or a nucleotide sequence having at least 80% sequence identity thereof.

In some embodiments, the transmembrane domain is derived from CD28, CD8α, CD8, CD4, CD3ζ, CD40, CD134 (OX-40), or CD7. In some embodiments, the transmembrane domain is derived from CD28. In some embodiments, the CD28 transmembrane domain comprises the amino acid sequence SEQ ID NO: 9, or an amino acid sequence having at least 80% sequence identity thereof. In some embodiments, the nucleotide sequence encoding the CD28 transmembrane domain comprises the sequence SEQ ID NO: 10, or a nucleotide sequence having at least 80% sequence identity thereof.

In some embodiments, the extracellular target binding domain further comprises a hinge domain between the GRP78-binding moiety and the transmembrane domain. In some embodiments, the hinge domain is derived from a mutated IgG4 hinge, CD8α, CD28, a chimeric mouse IgG4/CD8α hinge, an IgG1-derived hinge-CH3 spacer, an IgG1-derived hinge-CH2-CH3 spacer, or an IgG1-derived modified hinge-CH2-CH3 spacer.

In some embodiments, the hinge domain is derived from a mutated IgG4 hinge. In some embodiments, the mutated IgG4 hinge domain comprises the amino acid sequence of SEQ ID NO: 7, or an amino acid sequence having at least 80% sequence identity thereof. In some embodiments, the nucleotide sequence encoding the mutated IgG4 hinge domain comprises the sequence of SEQ ID NO: 8, or a nucleotide sequence having at least 80% sequence identity thereof.

In some embodiments, the hinge domain is derived from an IgG1-derived hinge-CH3 spacer. In some embodiments, the IgG1-derived hinge-CH3 spacer comprises the amino acid sequence of SEQ ID NO: 85, or an amino acid sequence having at least 80% sequence identity thereof. In some embodiments, the nucleotide sequence encoding the IgG1-derived hinge-CH3 spacer comprises the sequence of SEQ ID NO: 86, or a nucleotide sequence having at least 80% sequence identity thereof.

In some embodiments, the hinge domain is derived from an IgG1-derived hinge-CH2-CH3 spacer. In some embodiments, the IgG1-derived hinge-CH2-CH3 spacer comprises the amino acid sequence of SEQ ID NO: 87, or an amino acid sequence having at least 80% sequence identity thereof. In some embodiments, the nucleotide sequence encoding the IgG1-derived hinge-CH2-CH3 spacer comprises the sequence of SEQ ID NO: 88, or a nucleotide sequence having at least 80% sequence identity thereof.

In some embodiments, the hinge domain is derived from an IgG1-derived modified hinge-CH2-CH3 spacer. In some embodiments, the IgG1-derived modified hinge-CH2-CH3 spacer comprises the amino acid sequence of SEQ ID NO: 89, or an amino acid sequence having at least 80% sequence identity thereof. In some embodiments, the nucleotide sequence encoding the IgG1-derived modified hinge-CH2-CH3 spacer comprises the sequence of SEQ ID NO: 90, or a nucleotide sequence having at least 80% sequence identity thereof.

In some embodiments, the polynucleotide encodes additional amino acids between the GRP78-binding moiety and the hinge domain. In some embodiments, the polynucleotide encodes the amino acids EF between the GRP78-binding moiety and the hinge domain. In some embodiments, the polynucleotide comprises the nucleotides GAATTC between the GRP78-binding moiety and the hinge domain.

In some embodiments, the polynucleotide encodes additional amino acids between the hinge domain and the transmembrane domain. In some embodiments, the polynucleotide encodes the amino acids GS between the hinge domain and the transmembrane domain. In some embodiments, the polynucleotide comprises the nucleotides GGCTCC between the GRP78-binding moiety and the hinge domain.

In some embodiments, the signaling domain is derived from CD3ζ, DAP10, DAP12, Fc ε receptor I γ chain (FCER1G), CD3δ, CD3ε, CD3γ, CD226, or CD79A. In some embodiments, the signaling domain is derived from CD3ζ. In some embodiments, the CD3ζ signaling domain comprises the amino acid sequence SEQ ID NO: 13, or an amino acid sequence having at least 80% sequence identity thereof. In some embodiments, the nucleotide sequence encoding the CD3ζ signaling domain comprises the sequence SEQ ID NO: 14 or SEQ ID NO: 91, or a nucleotide sequence having at least 80% sequence identity thereof.

In some embodiments, the cytoplasmic domain further comprises one or more costimulatory domains. In some embodiments, the one or more costimulatory domains are derived from CD28, CD27, CD40, CD134, CD226, CD79A, ICOS, 41BB, OX40 or MyD88, or any combination thereof. In some embodiments, the cytoplasmic domain comprises a CD28 costimulatory domain. In some embodiments, the CD28 costimulatory domain comprises the amino acid sequence of SEQ ID NO: 11, or an amino acid sequence having at least 80% sequence identity thereof.

In some embodiments, the nucleotide sequence encoding the CD28 costimulatory domain comprises the sequence of SEQ ID NO: 12, or a nucleotide sequence having at least 80% sequence identity thereof. In some embodiments, the cytoplasmic domain comprises a 41BB costimulatory domain.

In some embodiments, the 41BB costimulatory domain comprises the amino acid sequence of SEQ ID NO: 53, or an amino acid sequence having at least 80% sequence identity thereof. In some embodiments, the nucleotide sequence encoding the 41BB costimulatory domain comprises the sequence of SEQ ID NO: 54, or a nucleotide sequence having at least 80% sequence identity thereof.

In some embodiments, the cytoplasmic domain comprises an OX40 costimulatory domain. In some embodiments, the OX40 costimulatory domain comprises the amino acid sequence of SEQ ID NO: 83, or an amino acid sequence having at least 80% sequence identity thereof. In some embodiments, the nucleotide sequence encoding the OX40 costimulatory domain comprises the sequence of SEQ ID NO: 84, or a nucleotide sequence having at least 80% sequence identity thereof.

In some embodiments, the CAR comprises the amino acid sequence of any one of SEQ ID NOs: 29, 31, or 33, or an amino acid sequence having at least 80% sequence identity thereof. In some embodiments, the nucleotide sequence encoding the CAR comprises the sequence of any one of SEQ ID NOs: 30, 32, or 34, or a nucleotide sequence having at least 80% sequence identity thereof.

In some embodiments, the polynucleotide further encodes at least one additional polypeptide. In some embodiments, the at least one polypeptide is a transduced host cell selection marker, an in vivo tracking marker, a cytokine, or a safety switch gene.

In some embodiments, the transduced host cell selection marker is a truncated CD19 (tCD19) polypeptide. In some embodiments, the tCD19 comprises the amino acid sequence SEQ ID NO: 17, or an amino acid sequence having at least 80% sequence identity thereof. In some embodiments, the nucleotide sequence encoding the tCD19 comprises the nucleotide sequence SEQ ID NO: 18, or a nucleotide sequence having at least 80% sequence identity thereof. In some embodiments, the transduced host cell selection marker is a Q8 polypeptide. In some embodiments, the Q8 polypeptide comprises the amino acid sequence SEQ ID NO: 57, or an amino acid sequence having at least 80% sequence identity thereof. In some embodiments, the nucleotide sequence encoding the Q8 polypeptide comprises the nucleotide sequence SEQ ID NO: 58, or a nucleotide sequence having at least 80% sequence identity thereof.

5

In some embodiments, the sequence encoding the CAR is operably linked to the sequence encoding at least an additional polypeptide sequence via a sequence encoding a self-cleaving peptide and/or an internal ribosomal entry site (IRES). In some embodiments, the self-cleaving peptide is a 2A peptide. In some embodiments, the 2A peptide is T2A, P2A, E2A, or F2A peptide. In some embodiments, the 2A peptide is a T2A peptide. In some embodiments, the T2A peptide comprises the amino acid sequence SEQ ID NO: 15, or an amino acid sequence having at least 80% sequence identity thereof. In some embodiments, the sequence encoding the T2A peptide comprises the nucleotide sequence SEQ ID NO: 16, or a nucleotide sequence having at least 80% sequence identity thereof. In some embodiments, the 2A peptide is an E2A peptide. In some embodiments, the E2A peptide comprises the amino acid sequence SEQ ID NO: 55, or an amino acid sequence having at least 80% sequence identity thereof. In some embodiments, the sequence encoding the E2A peptide comprises the nucleotide sequence SEQ ID NO: 56, or a nucleotide sequence having at least 80% sequence identity thereof.

In some embodiments, the polynucleotide encodes additional amino acids between the CAR and the sequence encoding a self-cleaving peptide and/or an internal ribosomal entry site (IRES). In some embodiments, the polynucleotide encodes the additional amino acids SEQ ID NO: 19 between the CAR and the sequence encoding a self-cleaving peptide and/or an internal ribosomal entry site (IRES).

In some embodiments, the polynucleotide comprises the nucleotide sequence SEQ ID NO: 20 between the CAR and the sequence encoding a self-cleaving peptide and/or an internal ribosomal entry site (IRES).

In some embodiments, the polynucleotide encodes the amino acid sequence of any one of SEQ ID NOs: 35, 37, or 39, or an amino acid sequence having at least 80% sequence identity thereof.

In some embodiments, the polynucleotide comprises the nucleotide sequence of any one of SEQ ID NOs: 36, 38, or 40, or a nucleotide sequence having at least 80% sequence identity thereof.

In various embodiments, the polynucleotide is a DNA molecule.

In various embodiments, the polynucleotide is an RNA molecule.

In one aspect, provided herein is a chimeric antigen receptor (CAR) encoded by a polynucleotide described herein.

In one aspect, provided herein is a recombinant vector comprising a polynucleotide described herein.

In some embodiments, the vector is a viral vector.

In some embodiments, the viral vector is a retroviral vector, a lentiviral vector, an adenoviral vector, an adeno-associated virus vector, an alphaviral vector, a herpes virus vector, a baculoviral vector, or a vaccinia virus vector.

In some embodiments, the viral vector is a retroviral vector. In some embodiments, the vector is a non-viral vector.

In some embodiments, the non-viral vector is a minicircle plasmid, a Sleeping Beauty transposon, a piggyBac transposon, or a single or double stranded DNA molecule that is used as a template for homology directed repair (HDR) based gene editing.

In one aspect, provided herein is an isolated host cell comprising the polynucleotide described herein or the recombinant vector described herein.

In one aspect, provided herein is an isolated host cell comprising a chimeric antigen receptor (CAR) encoded by the polynucleotide described herein. In some embodiments, the host cell is an immune cell. In some embodiments, the host cell is a T cell, a natural killer (NK) cell, a mesenchymal stem cell (MSC), or a macrophage. In some embodiments, the host cell is a T cell.

In some embodiments, the host cell is a CD8+ T cell, a CD4+ T cell, a cytotoxic T cell, an αβ T cell receptor (TCR) T cell, an invariant natural killer T (iNKT) cell, a γδ T cell, a memory T cell, a memory stem T cell (TSCM), a naïve T cell, an effector T cell, a T-helper cell, or a regulatory T cell (Treg). In some embodiments, the host cell is a natural killer (NK) cell. In some embodiments, the host cell has been activated and/or expanded ex vivo. In some embodiments, the host cell is an allogeneic cell. In some embodiments, the host cell is an autologous cell.

In some embodiments, the host cell is isolated from a subject having a cancer, wherein one or more cells of the cancer express GRP78. In some embodiments, the cancer is a solid tumor, brain tumor or a hematologic malignancy. In some embodiments, the hematologic malignancy is acute myeloid leukemia (AML), acute lymphoblastic leukemia (ALL), B-cell acute lymphoblastic leukemia (B-ALL), T cell acute lymphoblastic leukemia (T-ALL), or lymphoma. In some embodiments, the solid tumor is Ewings sarcoma, lung adenocarcinoma, osteosarcoma, breast cancer, or prostate cancer. In some embodiments, the brain tumor is glioblastoma or neuroblastoma. In some embodiments, the host cell is derived from a blood, marrow, tissue, or a tumor sample.

In one aspect, provided herein is a pharmaceutical composition comprising the host cell described herein and a pharmaceutically acceptable carrier and/or excipient.

In one aspect, provided herein is a method of generating the isolated host cell described herein, said method comprising genetically modifying the host cell with the polynucleotide described herein or the recombinant vector described herein.

In some embodiments, the genetic modifying step is conducted via viral gene delivery. In some embodiments, the genetic modifying step is conducted via non-viral gene delivery. In some embodiments, the genetic modification is conducted ex vivo. In some embodiments, the method further comprises activation and/or expansion of the host cell ex vivo before, after and/or during said genetic modification.

In one aspect, provided herein is a method for killing a cancer cell expressing GRP78, said method comprising contacting said cell with the host cell(s) described herein or the pharmaceutical composition described herein.

In one aspect, provided herein is a method for treating a cancer in a subject in need thereof, wherein one or more cells of the tumor express GRP78, said method comprising administering to the subject a therapeutically effective amount of the host cell(s) described herein or the pharmaceutical composition described herein. In some embodiments, the cancer is a solid tumor, brain tumor or a hematologic malignancy.

In some embodiments, the hematologic malignancy is acute myeloid leukemia (AML), acute lymphoblastic leukemia (ALL), B-cell acute lymphoblastic leukemia (B-ALL), T cell acute lymphoblastic leukemia (T-ALL), or lymphoma. In some embodiments, the solid tumor is Ewings sarcoma, lung adenocarcinoma, osteosarcoma, breast cancer, or prostate cancer. In some embodiments, the brain tumor is glioblastoma or neuroblastoma.

In some embodiments, the method comprises:

a) isolating T cells, NK cells, mesenchymal stem cells or macrophages from the subject;

b) genetically modifying said T cells, NK cells, mesenchymal stem cells, or macrophages ex vivo with the polynucleotide described herein or the vector described herein;

c) optionally, expanding and/or activating said T cells, NK cells, mesenchymal stem cells, or macrophages before, after or during step (b); and d) introducing the genetically modified T cells, NK cells, mesenchymal stem cells, or macrophages into the subject.

In various embodiments, the subject is human.

These and other aspects of the present invention will be apparent to those of ordinary skill in the art in the following description, claims and drawings.

BRIEF DESCRIPTION OF THE DRAWINGS

FIG. 1A provides flow cytometric analysis comparing cell surface GRP78 expression on AML cells to normal T cells. FIG. 1A discloses SEQ ID NO: 71. FIG. 1D shows MFI for the expression. FIG. 1E discloses SEQ ID NO: 71.

FIG. 2A demonstrates efficiency of GRP78 CAR transduction in activated PBMCs on days 5-7 post transduction. FIG. 2B provides FACS analysis of immunophenotype of GRP78 CAR transduced cells on day 7 post transduction. FIGS. 2C-2D and 2H provide data from experiments where MOLM13, see FIGS. 2C-2D, or MDA-MD468, see FIG. 2H, cells were co-cultured with GRP78 CARs, control CAR or non-transduced cells for 24 hours at a 2:1 E:T ratio and the levels of IFNγ and IL-2 were measured using an ELISA. FIG. 2E provides results from a luciferase based cytotoxicity assay showing the efficacy of GRP78 CARs against MOLM13 cells at 3 different effector: target (E:T) ratios. FIG. 2F provides results from a 24-hour MTS based cytotoxicity assay using solid tumor cell lines LM7, A673, MDA-MB468 co-cultured with GRP78 CARs at a 2:1 (E:T) ratio. FIG. 2G provides results from an experiment where MOLM13 cells were co-cultured with three different GRP78 scFv CAR T cells at a 2:1 (E:T) ratio and IFNγ levels were measured in culture supernatants using ELISA. FIG. 2I provides cytotoxicity data measured using flow cytometry based CFSE assay following 24 hours of co-culture of MOLM13 cells with GRP78 scFv CAR T cells or control CAR.

FIGS. 3A-3D demonstrate that binding of cell surface GRP78 is insufficient to induce tumor cell death and that expansion of GRP78-CAR T cells was comparable to expansion of non-transduced (NT) T cells. FIG. 3A provides results from an experiment where T cells were transduced with control CAR or GRP78-binding peptide CARs and the expansion was measured for 7 days post transduction. There was no statistically significant difference between the different groups of CAR transduced cells compared to the non-transduced group. FIG. 3B provides results from an experiment where MOLM13 cells were co-cultured for 24 hours with a control CAR, GRP78.1×-CAR or GRP78-ΔCAR lacking the CD28 costimulatory and CD3ζ domains. Cytotoxicity was measured using a luciferase cytotoxicity assay. FIG. 3C shows flow cytometric analysis of GRP78-ΔCAR where control CAR- and NT T cells were used for isotype controls. FIG. 3D provides results from an experiment where T cells were transduced with control or GRP78-binding peptide CARs and the total cell viability was measured from day 2 to day 9 post transduction using trypan blue. FIG. 3E shows the results from a colony-forming unit (CFU) assay.

FIGS. 4A-4G demonstrate that GRP78-binding peptide CAR shows potent antitumor activity in vivo. FIG. 4A provides a schematic showing in vivo experimental design. FIG. 4B provides results from an experiment where MDA-MB468 cells ($0.5×10^6$) were injected orthotopically into the mammary fat pads of NSG mice. The tumors were measured twice weekly using bioluminescent imaging with the IVIS imager. FIG. 4D provides results from an experiment where NSG mice were injected with MOLM13 ($5×10^3$) (AML) cells intravenously through the tail vein (i.v.) and on day 7 received a single i.v. dose of $1×10^7$ T cells. IVIS imaging was performed twice weekly (N=10, p<0.0001, t-test). FIG. 4F provides results from an experiment where $1×10^6$ A673 (Ewings sarcoma) cells were injected subcutaneously (s.c.) into the flanks of NSG mice. The tumors were measured twice weekly using caliper measurements. FIGS. 4C, 4E, and 4G provide data demonstrating that mice treated with the 1×peptide CAR showed a statistically significant improvement in overall survival compared to mice treated with the ΔCAR (control) across all the tumor models tested. In all the models, CART cells were injected at a dose of $10×10^6$ cells per mouse after 7 days of tumor injection. The Log-rank (Mantel-COX) test was used to perform statistical analyses of survival between groups.

FIGS. 5A and 5B provide images from luminescence imaging of NSG mice injected with MOLM13 cells. FIGS. 5C and 5D provide results from an experiment where MOLM13 ($5×10^3$) cells were injected intravenously through the tail vein and tumor progression was measured using bioluminescence imaging. FIGS. 5E and 5F provide results from an experiment where NSG mice were injected with A673 cells subcutaneously. The tumor growth was measured using calipers twice a week. In the experiments corresponding to FIGS. 5C and 5E, the mice were treated with $3×10^6$ CART cells that were injected 7 days post tumor injection. FIGS. 5D and 5F provide survival data demonstrating that mice treated with 1× and 2× peptide CARs showed statistically significant improvement in overall survival compared to the control CAR. The statistical analysis was performed using the Log-rank (Mantel-COX) test.

FIGS. 6A-6D provide amino acid and nucleotide sequences for exemplary GRP78-binding peptide CAR constructs of the disclosure (SEQ ID NOs 3, 1, 5, 7, 9, 11, 13, 15, 17, 36, 35, 38, 37, 40, and 39, respectively, in order of appearance).

FIGS. 7A-7D provide amino acid and nucleotide sequences for exemplary GRP78 scFv CAR constructs of the disclosure (SEQ ID NOs 41, 43, 45, 47, 49, 51, 53, 13, 55, 57, 66, 65, 68, 67, 70, 69, respectively, in order of appearance).

FIGS. 8A-8C provide amino acid and nucleotide sequences for exemplary CAR components (SEQ ID NOs 7, 8, 53, 54, 49-52, 83-90, respectively, in order of appearance).

FIGS. 9A-9B show a description of acute myeloid leukemia (AML) samples. Description of primary acute myeloid leukemia (AML) samples (FIG. 9A) and AML-PDX samples (FIG. 9B). BM-Bone Marrow; PB— Peripheral Blood; N.D.—Not Determined.

FIG. 10A shows flow cytometric analysis of 14 primary AML samples showing cell surface GRP78 expression (de novo N=6, relapsed N=4, therapy related N=4). Flow cytometric analysis of five AML-PDX samples showing percentage of cell surface GRP78+ cells is displayed in FIG. 10B. Violin plots of gene expression analysis by RNA seq comparing HSPA5 expression on normal cord blood CD34+ cells to the TARGET (N=159) are displayed in FIG. 10C. Normal control HPCs to the TCGA (N=244) dataset AML samples are displayed in FIG. 10D. Statistical analysis: TARGET and TCGA datasets, normal controls (CD34+ cells/HPCs) vs AML; T-test with pairwise comparisons was used, p-value<0.05.

FIG. 11 displays exemplary GRP78 gene expression data. Violin plots of GRP78 (HSPA5) gene expression were generated by microarray analysis of AML samples present in the MILE study as compared to normal HSCs (N=252, HSCs vs AML; T-test with pairwise comparisons, p<0.0001).

FIGS. 12A-12B show expression and immunophenotype of GRP78-CAR T cells. Western blot analysis of T cells transduced with a control CAR (Ctrl CAR), GRP78.1x-CAR (1xCAR), GRP78.2x-CAR (2xCAR) or GRP78.3x-CAR (3xCAR) (FIG. 12A). Flow cytometric analysis of CD4: CD8 ratio for NT and CAR T cells (FIG. 12B).

FIGS. 13A-13D demonstrate GRP78-CAR T cells target AML cells expressing cell surface GRP78 in vitro. FIG. 13A and FIG. 13B show determination of IFN-γ secretion by enzyme-linked immunosorbent assay (ELISA) in co-culture assays with MV-4-11 (GRP78.1x-CAR vs Δ-CAR; IFN-γ N=3, T-test was used with pairwise comparisons, p<0.05) or THP-1 (GRP78.1x-CAR vs Δ-CAR; IFN-γ N=3, p<0.0001). For data displayed in FIG. 13B, three AML PDX samples were co-cultured with GRP78.1x-CAR, Δ-CAR or NT T cells for 24 hours at a 1:1 E:T ratio and IFN-γ secretion was determined (N=3, GRP78.1xCAR vs Δ-CAR, two-factor ANOVA, *p<0.05). FIG. 13C provides data corresponding to a luciferase-based cytotoxicity assay of GRP78-CAR T cells or control effector T cells (NT T cells, Control CAR or Δ-CAR) or Control CAR T cells against MV-4-11 and THP-1 AML cell lines at a 2:1 E:T ratio (GRP78.1x-CAR vs Δ-CAR; N=3, T-test was used with pairwise comparisons, p<0.005). A multiplex analysis of cytokine production by GRP78-CAR T cells or control effector T cells (NT T cells or Δ-CAR) against MV-4-11 cells at a 1:1 E:T ratio is shown in FIG. 13D. Supernatant for ELISA was collected 24 hours after stimulation (N=3, T-test, p<0.05).

FIG. 14A displays a schematic for an exemplary serial stimulation assay using MOLM13 ffluc cells. FIG. 14B and FIG. 14C show data generated by a serial stimulation assay using effector T cells (GRP78.1x-CAR, control CAR, ΔCAR or NT T cells) and MOLM13 cells. Fresh MOLM13 cells were added every 72 hours (N=3). FIG. 14B shows data corresponding to a Luciferase-based cytotoxicity assay (N=3). FIG. 14C shows data corresponding to a multiplex analysis of cytokine production by GRP78-CAR T cells or control effector T cells (NT T cells or ΔCAR) against MOLM13 cells at a 1:1 E:T ratio. Supernatant for ELISA was collected 24-72 hours after stimulation (N=3, T-test, p<0.0001).

DETAILED DESCRIPTION

Figure 1A:
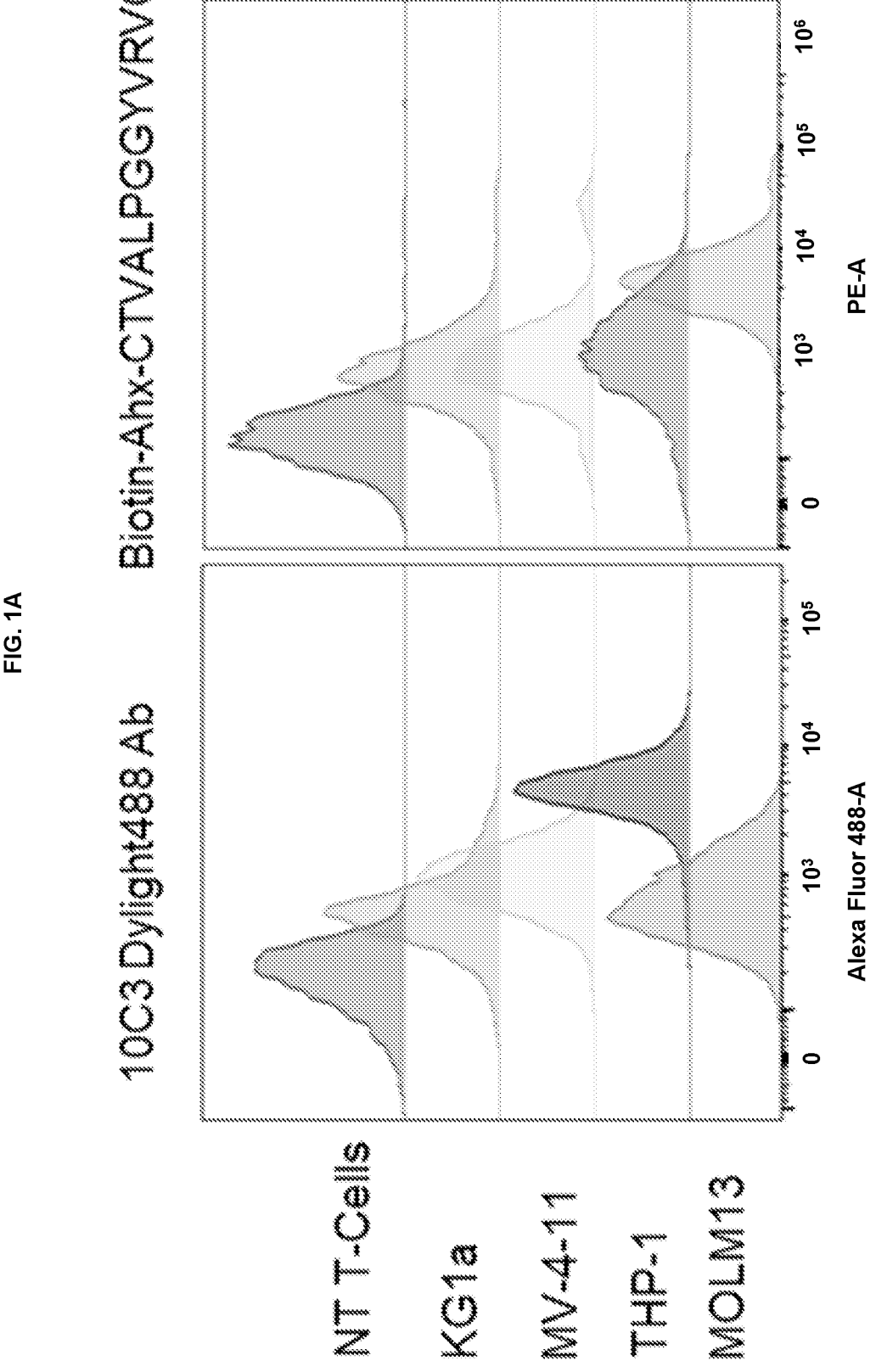
FIGS. 1A-IG demonstrate elevated cell surface GRP78 expression in cancer and design of the GRP78-binding peptide CAR.
Figure 1B:
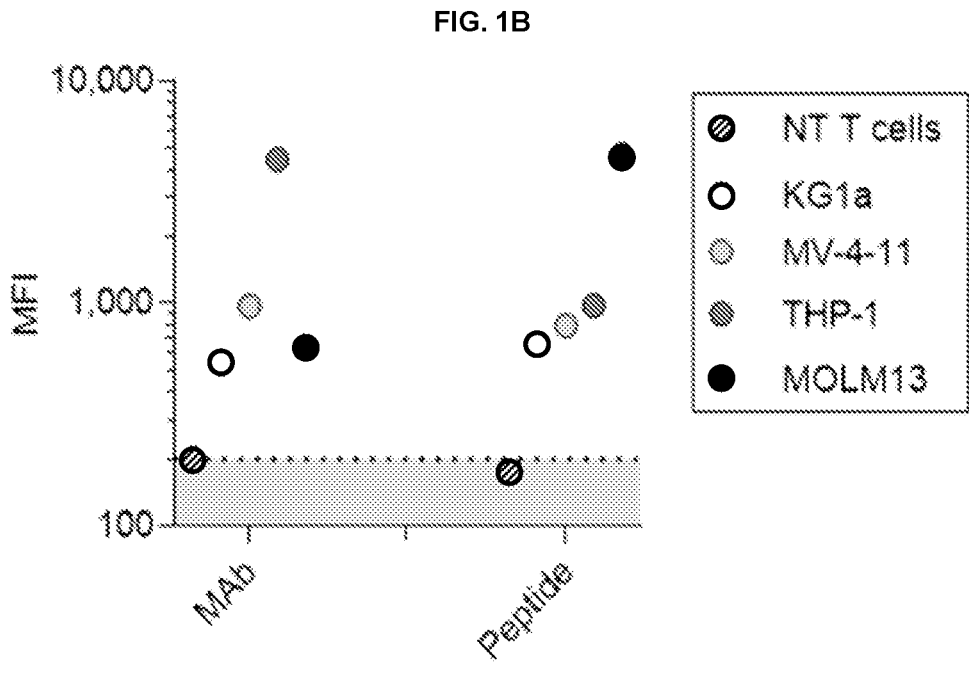
FIG. 1B provides a plot of Mean Fluorescence Intensity (MFI) of mAb compared with peptide staining in AIL cell lines.
Figure 1C:
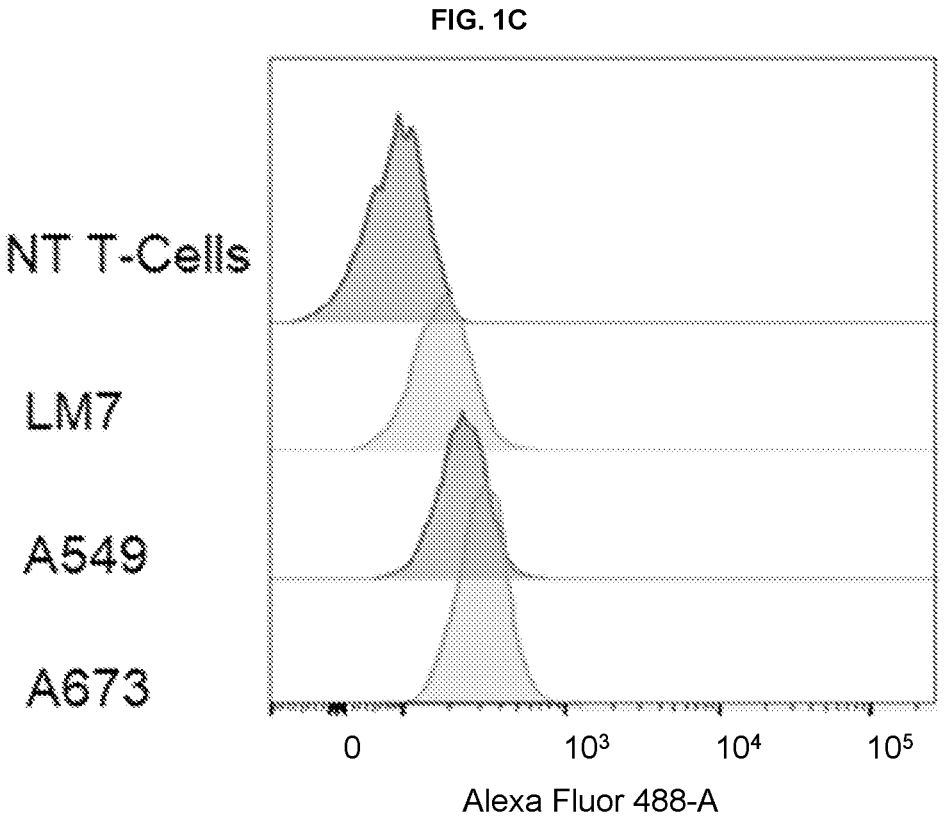
FIGS. 1C-1D provide results from a flow cytometry analysis of cell surface GRP78 expression on solid tumor cell lines (LM7, A549, A673) using the anti-KDEL (10C3) antibody.
Figure 1D:
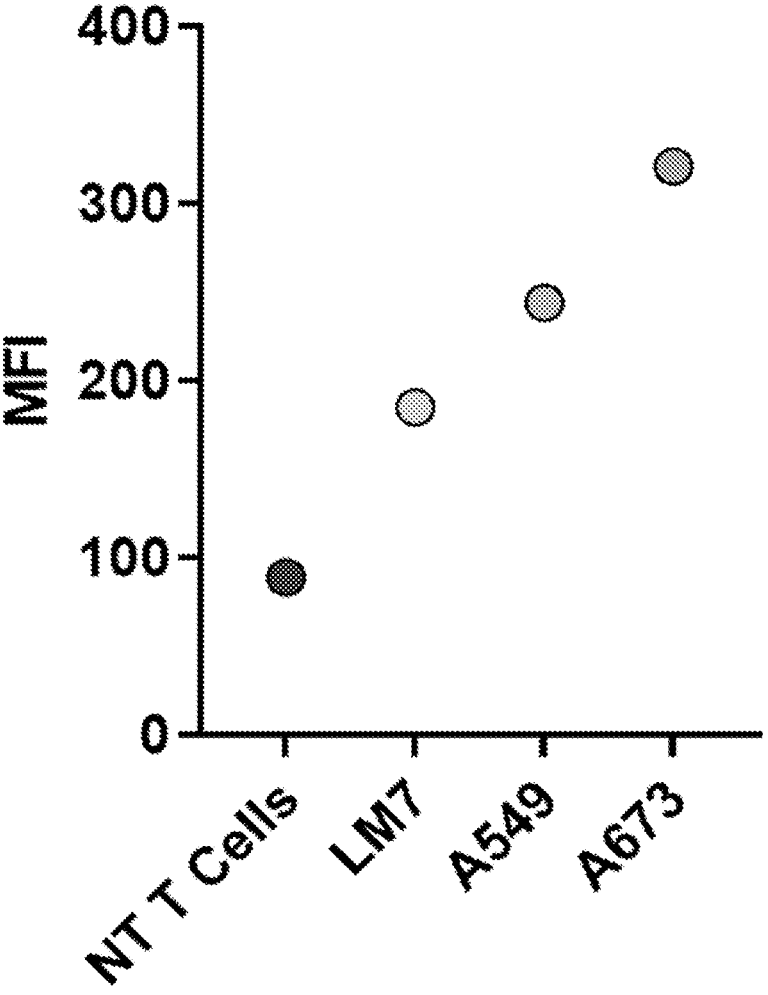

The present invention provides, among other things, chimeric antigen receptors (CARs) targeting cell surface GRP78 (GRP78-CAR). In some embodiments, the GRP78-CAR comprises one or more peptides as a target-binding domain.

Glucose-regulated-protein 78 (GRP78) is a central regulator of endoplasmic reticulum (ER) homeostasis involved in the unfolded protein response. Not wishing to be limited to any proposed model, GRP78 is confined to the intracellular space in healthy tissues and is highly expressed at the cell surface of cancer cells (e.g., acute myeloid leukemia (AML) cells) [16-17].

As detailed in the Examples section below, exemplary GRP78-CAR constructs were designed encoding one or more GRP78-specific peptides as the antigen recognition domain, and GRP78-CAR T cells were successfully generated by retroviral transduction of primary human T cells. As demonstrated in the Examples section below, the GRP78-CAR T cells had potent antitumor activity in vitro and in vivo. The GRP78-CAR specifically targeted tumor cells that express GRP78 on their cell surface with no apparent toxicity to normal tissue. The GRP78-CAR can be safe in immunocompetent model systems. In vivo studies have shown that GRP78-CAR T cells can successfully inhibit tumor growth and extend overall survival in several tumor types. The data provided herein support that GRP78-CAR modified cells are effective in inhibiting growth of or killing a broad range of malignancies, including as non-limiting examples hematological malignancies (e.g., AML) and solid tumors (e.g., Ewing sarcoma). Not wishing to be bound to any particular theory of operation, since GRP78 is retained in the cytoplasm in healthy cells, there may be a reduced risk for "on target/off cancer" toxicity of the GRP78-CAR T cells.

Definitions

The term "chimeric antigen receptor" or "CAR" as used herein is defined as a cell-surface receptor comprising an extracellular target-binding domain, a transmembrane domain and a cytoplasmic domain, comprising a lymphocyte activation domain and optionally at least one co-stimulatory signaling domain, all in a combination that is not naturally found together on a single protein. This particularly includes receptors wherein the extracellular domain and the cytoplasmic domain are not naturally found together on a single receptor protein. The chimeric antigen receptors of the present invention are intended primarily for use with lymphocyte such as T cells and natural killer (NK) cells.

The terms "T cell" and "T lymphocyte" are interchangeable and used synonymously herein. As used herein, T cell includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "NKT cells", which refer to a specialized population of T cells that express a semi-invariant αβ T cell receptor, but also express a variety of molecular markers that are typically associated with NK cells, such as NK1.1. NKT cells include NK1.1+ and NK1.1−, as well as CD4+, CD4−, CD8+ and CD8−cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation and were found to be an important source of IL-17 and to induce robust CD8+ cytotoxic T cell response. Also included are "regulatory T cells" or "Tregs" refers to T cells that suppress an abnormal or excessive immune response and play a role in immune tolerance. Tregs cells are typically transcription factor Foxp3-positive CD4+ T cells and can also include transcription factor Foxp3-negative regulatory T cells that are IL-10-producing CD4+ T cells.

The terms "natural killer cell" and "NK cell" are used interchangeably and used synonymously herein. As used herein, NK cell refers to a differentiated lymphocyte with a CD 16+CD56+ and/or CD57+ TCR− phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

As used herein, the term "antigen" refers to any agent (e.g., protein, peptide, polysaccharide, glycoprotein, glycolipid, nucleic acid, portions thereof, or combinations thereof) molecule capable of being bound by a T cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample or might be a macromolecule besides a polypeptide. Such a biological sample can include, but is not limited to a tissue sample, a tumor sample, a cell or a fluid with other biological components, organisms, subunits of proteins/antigens, killed or inactivated whole cells or lysates.

The term "antigen-binding domain" or "antigen-binding moiety" refers to a target-specific binding element that may be any ligand that binds to the antigen of interest or a polypeptide or fragment thereof, wherein the ligand is either naturally derived or synthetic. Examples of antigen-binding domains include, but are not limited to, antibodies; polypeptides derived from antibodies, such as, for example, single chain variable fragments (scFv), Fab, Fab', F(ab')2, and Fv fragments; polypeptides derived from T cell receptors, such as, for example, TCR variable domains; secreted factors (e.g., cytokines, growth factors) that can be artificially fused to signaling domains (e.g., "zytokines"); and any ligand or receptor fragment (e.g., CD27, NKG2D) that binds to the antigen of interest. Combinatorial libraries could also be used to identify peptides binding with high affinity to the therapeutic target.

Terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLO-PACK Gold Cells, can be used as host cells for vector replication and/or expression. Additionally, bacterial cells such as E. coli LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12. In certain embodiments, the host cell is autologous. In certain embodiments, the host cell is allogenic.

Host cells of the present disclosure include immune cells (e.g., T cells and natural killer cells) that contain the DNA or RNA sequences encoding the CAR and express the CAR on the cell surface. Host cells may be used for enhancing immune cell activity (e.g., effector function), treatment of tumors, and treatment of autoimmune disease.

The terms "activation" or "stimulation" means to induce a change in their biologic state by which the cells (e.g., T cells and NK cells) express activation markers, produce cytokines, proliferate and/or become cytotoxic to target cells. All these changes can be produced by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or NK cell proliferation and/or upregulation or downregulation of key molecules.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "tumor" refers to a benign or malignant abnormal growth of tissue. The term "tumor" includes cancer.

The term "effector function" refers to a specialized function of a cell. Effector function of a T cell, for example, may be cytolytic activity or helper activity including the secretion of cytokines.

As used herein, the term "safety switch" refers to any mechanism that is capable of removing or inhibiting the effect of CAR from a system (e.g., a culture or a subject).

The term "site-specific nuclease" as used herein refers to a nuclease capable of specifically recognizing and cleaving a nucleic acid (DNA or RNA) sequence.

The terms "genetically modified" or "genetically engineered" refers to the addition of extra genetic material in the form of DNA or RNA into a cell.

The term "tumor killing activity" as used herein refers to the ability of an immune cell to inhibit tumor growth and/or to kill the tumor cells (e.g., cancer cells).

The terms "expand" or "expansion" when used in relation to an immune cell refer to the ability of the immune cell to undergo cellular proliferation (i.e., to increase the number of cells). The terms used herein encompass both in vivo and in vitro immune cell expansion.

The terms "persist" or "persistence" when used in relation to an immune cell refer to the ability of the immune cell (and/or its progenies) to be maintained in a recipient (e.g., a subject) for a period of time. The terms used herein encompass both in vivo and in vitro immune cell persistence.

As used herein, the term "variant", "derivative" or "derived from" in the context of proteins or polypeptides (e.g., CARs or domains thereof) refer to: (a) a polypeptide that has at least 40%, 45%, 50%, 55%, 60%, 65%, 70%, 75%, 80%, 85%, 90%, 95%, 98% or 99% sequence identity to the polypeptide it is a variant or derivative of, (b) a polypeptide encoded by a nucleotide sequence that has at least 40%, 45%, 50%, 55%, 60%, 65%, 70%, 75%, 80%, 85%, 90%, 95%, 98% or 99% sequence identity to a nucleotide sequence encoding the polypeptide it is a variant or derivative of; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to the polypeptide it is a variant or derivative of; (d) a polypeptide encoded by nucleic acids can hybridize under high, moderate or typical stringency hybridization conditions to nucleic acids encoding the polypeptide it is a variant or derivative of, (e) a polypeptide encoded by a nucleotide sequence that can hybridize under high, moderate or typical stringency hybridization conditions to a nucleotide sequence encoding a fragment of the polypeptide, it is a variant or derivative of, of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of the polypeptide it is a variant or derivative of. The terms also encompass a fusion protein or polypeptide comprising the polypeptide it is a variant or derivative of. For example, a variant of a GRP78-binding peptide disclosed herein may include a fusion protein or polypeptide that comprises the GRP78-binding peptide and one or more additional polypeptides.

Percent sequence identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wisconsin). Information regarding hybridization conditions (e.g., high, moderate, and typical stringency conditions) have been described, see, e.g., U.S. Patent Application Publication No. US 2005/0048549 (e.g., paragraphs 72-73).

The variant or derivative of a protein or polypeptide may be a functional variant or derivative of the referenced protein or polypeptide. The term "functional variant" or "functional derivative" as used herein refers to a polypeptide or protein, or a polynucleotide encoding the polypeptide or protein, that retains at least one function of the referenced polypeptide or protein. The functional variant or derivative of a polypeptide or protein may retain one, two, three, four, five, or more functions of the referenced protein or polypeptide. For example, a functional variant or derivative of a GRP78-binding peptide may retain its ability to bind to GRP78.

The terms "vector", "cloning vector," "recombinant vector," and "expression vector" mean the vehicle by which a DNA or RNA sequence (e.g., a foreign gene) can be introduced into a host cell, so as to genetically modify the host and promote expression (e.g., transcription and translation) of the introduced sequence. Vectors include plasmids, synthesized RNA and DNA molecules, phages, viruses, etc. In certain embodiments, the vector is a viral vector such as, but not limited to, viral vector is an adenoviral, adeno-associated, alphaviral, herpes, lentiviral, retroviral, or vaccinia vector.

As used herein, the term "operably linked," or "operatively linked," and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

The terms "enhance" or "promote," or "increase," or "expand," or "improve" refer generally to the ability of a composition contemplated herein to produce, elicit, or cause a greater physiological response (i.e., downstream effects)

compared to the response caused by either vehicle or a control molecule/composition. A measurable physiological response may include an increase in immune cell expansion, activation, effector function, persistence, and/or an increase in tumor cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

The terms "decrease" or "lower," or "lessen," or "reduce," or "abate" refer generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof, or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The term "pharmaceutical composition," as used herein, represents a composition comprising polynucleotides, vectors, peptides, compositions, or host cells described herein formulated for administration to a subject for treatment, abatement, or prevention of a disease.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid, the term may also refer to the nucleic acid sequence including the portion coding for any amino acids added as an artifact of cloning, including any amino acids coded for by linkers.

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art. If aspects of the disclosure are described as "comprising" a feature, or versions thereof (e.g., comprise), embodiments also are contemplated "consisting of" or "consisting essentially of" the feature.

The practice of the present disclosure employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al.

eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ. Additional techniques are explained, e.g., in U.S. Pat. No. 7,912,698 and U.S. Patent Appl. Pub. Nos. 2011/0202322 and 2011/0307437.

The technology illustratively described herein suitably may be practiced in the absence of any element(s) not specifically disclosed herein.

The terms and expressions which have been employed are used as terms of description and not of limitation, and use of such terms and expressions do not exclude any equivalents of the features shown and described or portions thereof, and various modifications are possible within the scope of the technology claimed.

Chimeric Antigen Receptors (CARs)

The present disclosure provides, among other things, CARs that specifically bind GRP78.

In one aspect, the present disclosure provides polynucleotides encoding a CAR of the present disclosure. The CAR may comprise a) an extracellular target-binding domain comprising one or more glucose-regulated-protein 78 (GRP78)-binding moieties, b) a transmembrane domain, and c) a cytoplasmic domain comprising a signaling domain.

In another aspect, the present disclosure provides CARs encoded by the polynucleotides. In some embodiments, the present disclosure provides CARs operatively linked to an additional polypeptide sequence encoded by the polynucleotides.

In certain embodiments, the polynucleotide is a DNA molecule or a derivative of a DNA molecule. In some embodiments, the polynucleotide is an RNA molecule or a derivative of an RNA molecule.

CAR constructs with only the target-binding domain together with the signaling domain are termed first-generation CARs. Second generation CARs usually comprise co-stimulatory polypeptides to boost the CAR-induced immune response. The most commonly used co-stimulating molecules include CD28 and 4-1BB, which may promote both T cell proliferation and cell survival. Third generation CARs typically include three signaling domains (e.g., CD3ζ, CD28, and 4-1BB), which may further improve lymphocyte cell survival and efficacy.

In some embodiments, the CAR is a first generation CAR. In certain embodiments, the CAR is a second generation CAR. In various embodiments, the CAR is a third generation CAR.

Extracellular Target-Binding Domain of the CAR

GRP78-Binding Moiety

In some embodiments, the extracellular target-binding domain of the present disclosure is specific for GRP78. GRP78 is also known as HSP70, binding immunoglobulin protein (BiP), heat shock 78 kDa protein 5 (HSPA5), or Byun1. In a specific embodiment, the GRP78-binding moiety is an anti-GRP78 single chain variable fragment (scFv). In certain embodiments, the GRP78-binding moiety is a GRP78-binding peptide.

In some embodiments, the GRP78-binding peptide comprises the amino acid sequence set forth in SEQ ID NO: 1, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 1. In certain embodiments, the nucleotide sequence that encodes the GRP78-binding peptide comprises the nucleotide sequence that encodes the amino acid sequence of SEQ ID NO: 1, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 1. In certain embodiments, the nucleotide sequence that encodes the GRP78-binding peptide comprises the nucleotide sequence set forth in SEQ ID NO: 2, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 2. In certain embodiments, the GRP78-binding peptide comprises the amino acid sequence set forth in SEQ ID NO: 1. In certain embodiments, the nucleotide sequence that encodes the GRP78-binding peptide comprises the nucleotide sequence set forth in SEQ ID NO: 2.

In various embodiments, the target-binding domain comprises more than one GRP78-binding moiety. In certain embodiments, the target-binding domain comprises 1, 2, 3, 4, 5, 6, 7, 8, 9, or 10 GRP78-binding moieties. In various embodiments, the target-binding domain comprises one GRP78-binding moiety. In certain embodiment, the target-binding domain comprises two GRP78-binding moieties. In some embodiments, the target-binding domain comprises three GRP78-binding moieties.

In certain embodiments, when more than one GRP78-binding moiety is used in the CAR, each GRP78-binding moiety is operably linked via a linker sequence. In various embodiments, the linker sequence is 1, 2, 3, 4, 5, 6, 7, 8, 9, 10, 11, 12, 13, 14, 15, 16, 17, 18, 19, 20, or more than 20 amino acids in length. In various embodiments, GRP78-binding moieties may be separated by linkers of non-equal lengths such that the length of each linker is independently selected. In various embodiments, the linkers are of equal length. In some embodiments, the linkers each comprise independently selected sequences. In various embodiments, the linkers all comprise the same amino acid sequence. It is contemplated that any amino acid linkers can be used to link the GRP78-binding moieties. The GRP78-binding moieties are attached via linker sequences in a manner that does not interfere with each GRP78-binding moiety binding to GRP78.

In some embodiments, the linker comprises the amino acid sequence set forth in SEQ ID NO: 5, or a variant thereof having at least 60%, or at least 80%, sequence identity with SEQ ID NO: 5. In certain embodiments, the nucleotide sequence that encodes the linker comprises the nucleotide sequence that encodes the amino acid sequence of SEQ ID NO: 5, or a variant thereof having at least 60%, or at least 80%, sequence identity with SEQ ID NO: 5. In certain embodiments, the linker comprises the nucleotide sequence set forth in SEQ ID NO: 6, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 6. In certain embodiments, the linker comprises the amino acid sequence set forth in SEQ ID NO: 5. In certain embodiments, the nucleotide sequence that encodes the linker comprises the nucleotide sequence set forth in SEQ ID NO: 6.

Leader Sequence

In various embodiments, the extracellular target-binding domain comprises a leader sequence. The leader sequence may be positioned at the N-terminus of the extracellular target-binding domain. The leader sequence may be optionally cleaved from the extracellular target-binding domain during cellular processing and localization of the CAR to the cellular membrane. Any of various leader sequences known to one of skill in the art may be used as the leader sequence. Non-limiting examples of peptides from which the leader sequence may be derived include FcεR, human immunoglobulin (IgG) heavy chain (HC) variable region, CD8α, or any of various other proteins secreted by T cells. In various embodiments, the leader sequence is compatible with the secretory pathway of a T cell. In certain embodiments, the leader sequence is derived from human immunoglobulin heavy chain (HC). In some embodiments, the leader sequence is derived from CD8α.

In certain embodiments the leader sequence comprises the amino acid sequence set forth in SEQ ID NO: 3, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 3. In certain embodiments, the nucleotide sequence that encodes the leader sequence comprises the nucleotide sequence that encodes the amino acid sequence of SEQ ID NO: 3, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 3. In certain embodiments, the nucleotide sequence that encodes the leader sequence comprises the nucleotide sequence set forth in SEQ ID NO: 4, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 4. In certain embodiments, the leader sequence comprises the amino acid sequence set forth in SEQ ID NO: 3. In certain embodiments, the nucleotide sequence that encodes the leader sequence comprises the nucleotide sequence set forth in SEQ ID NO: 4.

In certain embodiments the leader sequence comprises the amino acid sequence set forth in SEQ ID NO: 41, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 41. In certain embodiments, the nucleotide sequence that encodes the leader sequence comprises the nucleotide sequence that encodes the amino acid sequence of SEQ ID NO: 41, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 41. In certain embodiments, the nucleotide sequence that encodes the leader sequence comprises the nucleotide sequence set forth in SEQ ID NO: 42, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 42. In certain embodiments, the leader sequence comprises the amino acid sequence set forth in SEQ ID NO: 41. In certain embodiments, the nucleotide sequence that encodes the leader sequence comprises the nucleotide sequence set forth in SEQ ID NO: 42.

In various embodiments, the extracellular target-binding domain comprises an N-terminal leader sequence followed by a single GRP78-binding moiety (e.g., GRP78-binding peptide). In some embodiments, the extracellular target-binding domain comprises an N-terminal leader sequence followed by two GRP78-binding moieties (e.g., GRP78-binding peptide) each separated by a linker. In some embodiments, the extracellular target-binding domain comprises an N-terminal leader sequence followed by three GRP78-binding moieties (e.g., GRP78-binding peptide) each separated by a linker.

In some embodiments, the extracellular target-binding domain comprises the amino acid sequence set forth in SEQ ID NO: 21, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 21. In certain embodiments, the nucleotide sequence that encodes the extracellular target-binding domain comprises the nucleotide sequence that encodes the amino acid sequence of SEQ ID NO: 21, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 21. In certain embodiments, the nucleotide sequence that encodes the extracellular target-binding domain comprises the nucleotide sequence set forth in SEQ ID NO: 22, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 22. In certain embodiments, the extracellular target-binding domain comprises the amino acid sequence set forth in SEQ ID NO: 21. In certain embodiments, the nucleotide sequence that encodes the extracellular target-binding domain comprises the nucleotide sequence set forth in SEQ ID NO: 22.

In some embodiments, the extracellular target-binding domain comprises the amino acid sequence set forth in SEQ ID NO: 23, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 23. In certain embodiments, the nucleotide sequence that encodes the extracellular target-binding domain comprises the nucleotide sequence that encodes the amino acid sequence of SEQ ID NO: 23, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 23. In certain embodiments, the nucleotide sequence that encodes the extracellular target-binding domain comprises the nucleotide sequence set forth in SEQ ID NO: 24, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 24. In certain embodiments, the extracellular target-binding domain comprises the amino acid sequence set forth in SEQ ID NO: 23. In certain embodiments, the nucleotide sequence that encodes the extracellular target-binding domain comprises the nucleotide sequence set forth in SEQ ID NO: 24.

In some embodiments, the extracellular target-binding domain comprises the amino acid sequence set forth in SEQ ID NO: 25, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 25. In certain embodiments, the nucleotide sequence that encodes the extracellular target-binding domain comprises the nucleotide sequence that encodes the amino acid sequence of SEQ ID NO: 25, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 25. In certain embodiments, the nucleotide sequence that encodes the extracellular target-binding domain comprises the nucleotide sequence set forth in SEQ ID NO: 26, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 26. In certain embodiments, the extracellular target-binding domain comprises the amino acid sequence set forth in SEQ ID NO: 25. In certain embodiments, the nucleotide sequence that encodes the extracellular target-binding domain comprises the nucleotide sequence set forth in SEQ ID NO: 26.

Hinge Domain

In various embodiments, the extracellular target binding domain further comprises a hinge domain disposed between the GRP78-binding moiety and the transmembrane domain. The hinge domain may be derived from all or part of naturally occurring molecules, such as from all or part of the extracellular region of immunoglobulin IgG hinge, CD8, CD4, or CD28, or from all or part of an antibody constant region. Alternatively, the hinge domain may be a synthetic sequence that corresponds to a naturally occurring hinge domain sequence or may be an entirely synthetic hinge domain sequence. Suitable hinge domains include, but are not limited to those derived from a mutated IgG4 hinge, CD8α, CD28, a chimeric mIgG4/CD8α hinge, an IgG1-derived hinge-CH2-CH3 spacer, or an IgG1-derived hinge-CH3 spacer. The hinge may be mutated to prevent Fc receptor binding. In various embodiments, the hinge domain is derived from a mutated IgG4 hinge. In various embodiments, the hinge domain is derived from CD8α. In various embodiments, the hinge domain is derived from IgG1. In some embodiments, the hinge domain comprises an IgG1-derived hinge-CH3 spacer. In some embodiments, the hinge domain comprises an IgG1-derived hinge-CH2-CH3 spacer. In some embodiments, the hinge domain comprises a IgG1-derived modified hinge-CH2-CH3 spacer. The hinge domain can provide flexibility and accessibility between the GRP78-binding moiety and the transmembrane domain.

The hinge domain may comprise up to 300 amino acids, up to 400 amino acids, up to 500 amino acids, up to 600 amino acids, up to 700 amino acids, up to 800 amino acids, up to 900 amino acids, at least 10 amino acids, at least 20 amino acids, at least 30 amino acids, at least 50 amino acids, at least 100 amino acids, at least 150 amino acids, at least 200 amino acids, at least 250 amino acids, at least 300 amino acids, at least 350 amino acids, at least 400 amino acids, at least 450 amino acids, at least 500 amino acids, at least 550 amino acids, at least 600 amino acids, at least 650 amino acids, at least 700 amino acids, at least 750 amino acids, at least 800 amino acids, at least 850 amino acids, at least 900 amino acids, at least 950 amino acids, from 50 to 500 amino acids, from 150 to 450 amino acids, from 200 to 300 amino acids, from 200 to 250 amino acids, from 250 to 300 amino acids, from 200 to 400 amino acids, from 200 to 1000 amino acids, or from 220 to 1000 amino acids. In one embodiment, the hinge domain comprises about 229 amino acids. In one embodiment, the hinge domain comprises about 119 amino acids. In one embodiment, the hinge domain comprises about 232 amino acids. In one embodiment, the hinge domain comprises about 231 amino acids.

In some embodiments, the mutated IgG4 hinge domain comprises the amino acid sequence set forth in SEQ ID NO: 7, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 7. In certain embodiments, the nucleotide sequence that encodes the mutated IgG4 hinge domain comprises the nucleotide sequence that encodes the amino acid sequence of SEQ ID NO: 7, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 7. In certain embodiments, the nucleotide sequence that encodes the mutated IgG4 hinge domain comprises the nucleotide sequence set forth in SEQ ID NO: 8, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 8. In certain embodiments, the mutated IgG4 hinge domain comprises the amino acid sequence set forth in SEQ ID NO: 7. In certain embodiments, the nucleotide sequence that encodes the mutated IgG4 hinge domain comprises the nucleotide sequence set forth in SEQ ID NO: 8.

In some embodiments, the IgG1-derived hinge-CH3 spacer comprises the amino acid sequence set forth in SEQ ID NO: 85, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 85. In certain embodiments, the nucleotide sequence that encodes the IgG1-derived hinge-CH3 spacer comprises the nucleotide sequence that encodes the amino acid sequence of SEQ ID NO: 85, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 85. In certain embodiments, the nucleotide sequence that encodes the IgG1-derived hinge-CH3 spacer comprises the nucleotide sequence set forth in SEQ ID NO: 86, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 86. In certain embodiments, the IgG1-derived hinge-CH3 spacer comprises the amino acid sequence set forth in SEQ ID NO: 85. In certain embodiments, the nucleotide sequence that encodes the IgG1-derived hinge-CH3 spacer comprises the nucleotide sequence set forth in SEQ ID NO: 86.

In some embodiments, the IgG1-derived hinge-CH2-CH3 spacer comprises the amino acid sequence set forth in SEQ ID NO: 87, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 87. In certain embodiments, the nucleotide sequence that encodes the IgG1-derived hinge-CH2-CH3 spacer comprises the nucleotide sequence that encodes the amino acid sequence of SEQ ID NO: 87, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 87. In certain embodiments, the nucleotide sequence that encodes the IgG1-derived hinge-CH2-CH3 spacer comprises the nucleotide sequence set forth in SEQ ID NO: 88, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 88. In certain embodiments, the IgG1-derived hinge-CH2-CH3 spacer comprises the amino acid sequence set forth in SEQ ID NO: 87. In certain embodiments, the nucleotide sequence that encodes the IgG1-derived hinge-CH2-CH3 spacer comprises the nucleotide sequence set forth in SEQ ID NO: 88.

In some embodiments, IgG1-derived modified hinge-CH2-CH3 spacer comprises the amino acid sequence set forth in SEQ ID NO: 89, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 89. In certain embodiments, the nucleotide sequence that encodes the IgG1-derived modified hinge-CH2-CH3 spacer comprises the nucleotide sequence that encodes the amino acid sequence of SEQ ID NO: 89, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 89. In certain embodiments, the nucleotide sequence that encodes the IgG1-derived modified hinge-CH2-CH3 spacer comprises the nucleotide sequence set forth in SEQ ID NO: 90, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 90. In certain embodiments, the hinge derived from IgG1-derived modified hinge-CH2-CH3 spacer comprises the amino acid sequence set forth in SEQ ID NO: 89. In certain embodiments, the nucleotide sequence that encodes the IgG1-derived modified hinge-CH2-CH3 spacer comprises the nucleotide sequence set forth in SEQ ID NO: 90.

Other hinge domains suitable for use in the present invention may be derived from an immunoglobulin IgG hinge or functional fragment, including IgG1, IgG2, IgG3, IgG4, IgM1, IgM2, IgA1, IgA2, IgD, IgE or a chimera or variant thereof.

In certain embodiments, the CAR comprises a first sequence of additional amino acids between the GRP78-binding moiety and the hinge domain. In some embodiments, the CAR comprises a second sequence of additional amino acids between the hinge domain and the transmembrane domain. In various embodiments, the first sequence of additional amino acids comprises 1, 2, 3, 4, 5, 6, 7, 8, 9, 10, 11, 12, 13, 14, 15, or more than 15 amino acids. In some embodiments, the second sequence of additional amino acids comprises 1, 2, 3, 4, 5, 6, 7, 8, 9, 10, 11, 12, 13, 14, 15, or more than 15 amino acids.

In a specific embodiment, the first sequence of additional amino acids comprises the amino acid sequence EF. In some embodiments, the first sequence of additional amino acids is encoded by a sequence comprising the nucleotide sequence GAATTC. In various embodiments, the second sequence of additional amino acids comprises the amino acid sequence GS. In various embodiments, the second sequence of additional amino acids is encoded by a sequence comprising the nucleotide sequence GGCTCC.

Transmembrane Domain of the CAR

In certain embodiments, the transmembrane domain is derived from CD8α, CD28, CD8, CD4, CD3ζ, CD40, CD134 (OX-40), or CD7. In a specific embodiment, the transmembrane domain is derived from CD28. The transmembrane domain may be fused in frame or operably linked between the extracellular target-binding domain and the cytoplasmic domain.

In some instances, the transmembrane domain can be modified by amino acid substitution, deletions, or insertions to avoid binding of proteins naturally associated with the transmembrane domain. In certain embodiments, the transmembrane domain includes additional amino acids to allow for flexibility and/or optimal distance between the domains connected to the transmembrane domain.

The transmembrane domain may be derived from a natural or from a synthetic source. Where the source is natural, the domain may be derived from any membrane-bound or transmembrane protein. Non-limiting examples of transmembrane domains of particular use in this disclosure may be derived from (i.e. comprise at least the transmembrane region(s) of) the α, β or ζ chain of the T cell receptor, CD28, CD3ε, CD3ζ, CD45, CD4, CD5, CD7, CD8, CD8α, CD9, CD16, CD22, CD33, CD37, CD40, CD64, CD80, CD86, CD134 (OX-40), CD137, or CD154. Alternatively, the transmembrane domain may be synthetic, in which case the transmembrane domain will comprise predominantly hydrophobic residues such as leucine and valine. For example, a triplet of phenylalanine, tryptophan and/or valine can be found at each end of a synthetic transmembrane domain.

In some embodiments, it will be desirable to utilize the transmembrane domain of the ζ, η, or FcεR1γ chains which contain a cysteine residue capable of disulfide bonding, so that the resulting chimeric protein will be able to form disulfide linked dimers with itself, or with unmodified versions of the ζ, η, or FcεR1γ chains or related proteins. In some instances, the transmembrane domain will be selected or modified by amino acid substitution to avoid-binding of such domains to the transmembrane domains of the same or different surface membrane proteins to minimize interactions with other members of the receptor complex. In other cases, it will be desirable to employ the transmembrane domain of ζ, η or FcεR1γ and −β. MB1 (Igα), B29, or CD3-γ, ζ, or η, in order to retain physical association with other members of the receptor complex.

In some embodiments the CD28 transmembrane domain comprises the amino acid sequence set forth in SEQ ID NO: 9, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 9. In certain embodiments, the nucleotide sequence that encodes the CD28 transmembrane domain comprises the nucleotide sequence that encodes the amino acid sequence of SEQ ID NO: 9, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 9. In certain embodiments, the nucleotide sequence that encodes the CD28 transmembrane domain comprises the nucleotide sequence set forth in SEQ ID NO: 10, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 10. In certain embodiments, the CD28 transmembrane domain comprises the amino acid sequence set forth in SEQ ID NO: 9. In certain embodiments, the nucleotide sequence that encodes the CD28 transmembrane domain comprises the nucleotide sequence set forth in SEQ ID NO: 10.

Cytoplasmic Domain of the CAR

The cytoplasmic domain can comprise one or more signaling domains. The signaling domain may be derived from CD3ζ, DAP10, DAP12, Fcε receptor I γ chain (FCER1G), CD3δ, CD3ε, CD3γ, CD27, CD28, CD40, CD134, CD137, ICOS, MyD88, CD226, CD79A, or any combination thereof. In certain embodiments, the signaling domain is derived from CD3ζ.

The signaling domain may activate at least one of the normal effector functions of a cell expressing the CAR.

In various embodiments the CD3ζ signaling domain comprises the amino acid sequence set forth in SEQ ID NO: 13, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 13. In certain embodiments, the nucleotide sequence that encodes the CD3ζ signaling domain comprises the nucleotide sequence that encodes the amino acid sequence of SEQ ID NO: 13, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 13. In certain embodiments, the nucleotide sequence that encodes the CD3ζ signaling domain comprises the nucleotide sequence set forth in SEQ ID NO: 14 or 91, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 14 or 91. In certain embodiments, the CD3ζ signaling domain comprises the amino acid sequence set forth in SEQ ID NO: 13. In certain embodiments, the nucleotide sequence that encodes the CD3ζ signaling domain comprises the nucleotide sequence set forth in SEQ ID NO: 14 or 91.

In various embodiments, the cytoplasmic domain further comprises one or more costimulatory domains. Costimulatory domains can boost a CAR-induced immune response. Non-limiting examples of costimulatory domains include those derived from CD28, 4-1BB (CD137), CD27, CD40, CD134 (OX-40), BTLA, GITR, HVEM, CD30, CD226, CD79A, ICOS, or MyD88, or any combination thereof. In certain embodiments, the cytoplasmic domain comprises a CD28 costimulatory domain. In various embodiments, the cytoplasmic domain comprises a 4-1BB costimulatory domain. In some embodiments, the cytoplasmic domain comprises an OX40 costimulatory domain.

In various embodiments the CD28 costimulatory domain comprises the amino acid sequence set forth in SEQ ID NO: 11, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 11. In certain embodiments, the nucleotide sequence that encodes the CD28 costimulatory domain comprises the nucleotide sequence that encodes the amino acid sequence of SEQ ID NO: 11, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 11. In certain embodiments, the nucleotide sequence that encodes the CD28 costimulatory domain comprises the nucleotide sequence set forth in SEQ ID NO: 12, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 12. In certain embodiments, the CD28 costimulatory domain comprises the amino acid sequence set forth in SEQ ID NO: 11. In certain embodiments, the nucleotide sequence that encodes the CD28 costimulatory domain comprises the nucleotide sequence set forth in SEQ ID NO: 12.

In various embodiments the 4-1BB costimulatory domain comprises the amino acid sequence set forth in SEQ ID NO: 53, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 53. In certain embodiments, the nucleotide sequence that encodes the 4-1BB costimulatory domain comprises the nucleotide sequence that encodes the amino acid sequence of SEQ ID NO: 53, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 53. In certain embodiments, the nucleotide sequence that encodes the 4-1BB costimulatory domain comprises the nucleotide sequence set forth in SEQ ID NO: 54, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 54. In certain embodiments, the 4-1BB costimulatory domain comprises the amino acid sequence set forth in SEQ ID NO: 53. In certain embodiments, the nucleotide sequence that encodes the 4-1BB costimulatory domain comprises the nucleotide sequence set forth in SEQ ID NO: 54.

In various embodiments the OX40 costimulatory domain comprises the amino acid sequence set forth in SEQ ID NO: 83, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 83. In certain embodiments, the nucleotide sequence that encodes the OX40 costimulatory domain comprises the nucleotide sequence that encodes the amino acid sequence of SEQ ID NO: 83, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 83. In certain embodiments, the nucleotide sequence that encodes the OX40 costimulatory domain comprises the nucleotide sequence set forth in SEQ ID NO: 84, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 84. In certain embodiments, the OX40 costimulatory domain comprises the amino acid sequence set forth in SEQ ID NO: 83. In certain embodiments, the nucleotide sequence that encodes the OX40 costimulatory domain comprises the nucleotide sequence set forth in SEQ ID NO: 84.

In some embodiments, the cytoplasmic domain of the CAR is encoded by a nucleotide sequence comprising the nucleotides of SEQ ID NO: 28, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 28. In some embodiments, the cytoplasmic domain of the CAR comprises the amino acid sequence of SEQ ID NO: 27, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 27.

Non-Limiting Examples of CARs

In various embodiments the CAR of the present disclosure comprises one GRP78-binding peptide and optionally the amino acid sequence set forth in SEQ ID NO: 29, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 29. In certain embodiments, the nucleotide sequence that encodes the CAR comprises the nucleotide sequence that encodes the amino acid sequence of SEQ ID NO: 29, or a variant thereof having at least 50%, at least 55%, at least 60%, at least 65%, at least 70%, at least 75%, at least 80%, at least 85%, at least 86%, at least 87%, at least 88%, at least 93%, at least 94%, at least 95%, at least 96%, at least 97%, at least 98%, or at least 99%, sequence identity with SEQ ID NO:

29. In certain embodiments, the nucleotide sequence that encodes the CAR comprises the nucleotide sequence set forth in SEQ ID NO: 30, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 30. In certain embodiments, the CAR comprises the amino acid sequence set forth in SEQ ID NO: 29. In certain embodiments, the nucleotide sequence that encodes the CAR comprises the nucleotide sequence set forth in SEQ ID NO: 30.

In various embodiments the CAR of the present disclosure comprises two GRP78-binding peptides and optionally the amino acid sequence set forth in SEQ ID NO: 31, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 31. In certain embodiments, the nucleotide sequence that encodes the CAR comprises the nucleotide sequence that encodes the amino acid sequence of SEQ ID NO: 31, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 31. In certain embodiments, the nucleotide sequence that encodes the CAR comprises the nucleotide sequence set forth in SEQ ID NO: 32, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 32. In certain embodiments, the CAR comprises the amino acid sequence set forth in SEQ ID NO: 31. In certain embodiments, the nucleotide sequence that encodes the CAR comprises the nucleotide sequence set forth in SEQ ID NO: 32.

In various embodiments the CAR of the present disclosure comprises three GRP78-binding peptides and optionally the amino acid sequence set forth in SEQ ID NO: 33, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 33. In certain embodiments, the nucleotide sequence that encodes the CAR comprises the nucleotide sequence that encodes the amino acid sequence of SEQ ID NO: 33, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 33. In certain embodiments, the nucleotide sequence that encodes the CAR comprises the nucleotide sequence set forth in SEQ ID NO: 34, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 34. In certain embodiments, the CAR comprises the amino acid sequence set forth in SEQ ID NO: 33. In certain embodiments, the nucleotide sequence that encodes the CAR comprises the nucleotide sequence set forth in SEQ ID NO: 34.

Additional Genes

In addition to the CAR, the polynucleotide may further comprise at least one additional gene that encodes an additional peptide. Examples of additional genes can include a transduced host cell selection marker, an in vivo tracking marker, a cytokine, a safety switch gene, or some other functional gene. In certain embodiments, the functional additional gene can induce the expression of another molecule. In certain embodiments, the functional additional gene can increase the safety of the CAR. In various embodiments, the host cell selection marker is truncated CD19 (tCD19) polypeptide. The tCD19 can be used as a tag. Expression of tCD19 may also help determine transduction efficiency. In some embodiments, the host cell selection marker is a Q8 polypeptide. The Q8 can be used as a tag. Expression of Q8 may also help determine transduction efficiency.

In various embodiments the tCD19 comprises the amino acid sequence set forth in SEQ ID NO: 17, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 17. In certain embodiments, the nucleotide sequence that encodes the tCD19 comprises the nucleotide sequence that encodes the amino acid sequence of SEQ ID NO: 17, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 17. In certain embodiments, the nucleotide sequence that encodes the tCD19 comprises the nucleotide sequence set forth in SEQ ID NO: 18, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 18. In certain embodiments, the tCD19 comprises the amino acid sequence set forth in SEQ ID NO: 17. In certain embodiments, the nucleotide sequence that encodes the tCD19 comprises the nucleotide sequence set forth in SEQ ID NO: 18.

In various embodiments the Q8 polypeptide comprises the amino acid sequence set forth in SEQ ID NO: 57, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 57. In certain embodiments, the nucleotide sequence that encodes the Q8 polypeptide comprises the nucleotide sequence that encodes the amino acid sequence of SEQ ID NO: 57, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 57. In certain embodiments, the nucleotide sequence that encodes the Q8 polypeptide comprises the nucleotide sequence set forth in SEQ ID NO: 58, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 58. In certain embodiments, the Q8 polypeptide comprises the amino acid sequence set forth in SEQ ID NO: 57. In certain embodiments, the nucleotide sequence that encodes the Q8 polypeptide comprises the nucleotide sequence set forth in SEQ ID NO: 58.

Non-limiting examples of classes of additional genes that can be used to increase the effector function of cells expressing the CAR include (a) secretable cytokines (e.g., but not limited to, GM-CSF, IL-7, IL-12, IL-15, IL-18), (b) membrane bound cytokines (e.g., but not limited to, IL-15), (c) chimeric cytokine receptors (e.g., but not limited to, IL-2/IL-7, IL-4/IL-7), (d) constitutive active cytokine receptors (e.g., but not limited to, C7R), (e) dominant negative receptors (DNR; e.g., but not limited to TGFRII DNR), (f) ligands of costimulatory molecules (e.g., but not limited to, CD80, 4-1BBL), (g) nuclear factor of activated T cells (NFATs) (e.g., NFATc1, NFATc2, NFATc3, NFATc4, and NFAT5), (h) antibodies, including fragments thereof and bispecific antibodies (e.g., but not limited to, bispecific T cell engagers (BiTEs)), or (j) safety switches (e.g., CD20, truncated EGFR or HER2, inducible caspase 9 molecules).

In certain embodiments, the polynucleotide may comprise an additional gene that encodes GM-CSF. The expression of exogenous GM-CSF may further enhance the function of host cells expressing the CAR of the present disclosure.

In certain embodiments, the functional additional gene is a safety switch. A safety switch is a recombinant gene that will cause the host cell that the gene is expressed in to undergo programmed cell death or antibody mediated clearance at a desired time. Safety switches can function to increase the safety of the CAR. In another embodiment, the additional gene is an inducible safety switch. Non-limiting examples of safety switches include i) molecules that are expressed on the cell surface and can be targeted with a clinical grade monoclonal antibody including CD20, EGFR or a fragment thereof, HER2 or a fragment thereof, and ii) inducible safety switches (e.g., but not limited to inducible caspase 9 (see Straathof et al. (2005) *Blood.* 105(11): 4247-4254; US Publ. No. 2011/0286980, each of which are incorporated herein by reference in their entirety for all purposes)).

In certain aspects, genes encoding sequences of the present disclosure may be regulated by a safety switch. Safety switches can function to increase the safety of the CAR.

In some embodiments, the safety switch is a CD20 polypeptide. Expression of human CD20 on the cell surface presents an attractive strategy for a safety switch. The inventors and others have shown that cells that express CD20 can be rapidly eliminated with the FDA approved monoclonal antibody rituximab through complement-mediated cytotoxicity and antibody-dependent cell-mediated cytotoxicity (see e.g., Griffioen, M., et al. *Haematologica* 94, 1316-1320 (2009), which is incorporated herein by reference in its entirety for all purposes). Rituximab is an anti-CD20 monoclonal antibody that has been FDA approved for Chronic Lymphocytic Leukemia (CLL) and Non-Hodgkin's Lymphoma (NHL), among others (Storz, U. *MAbs* 6, 820-837 (2014), which is incorporated herein by reference in its entirety for all purposes). The CD20 safety switch is non-immunogenic and can function as a reporter/selection marker in addition to a safety switch (Bonifant, C. L., et al. *Mol Ther* 24, 1615-1626 (2016); van Loenen, M. M., et al. *Gene Ther* 20, 861-867 (2013); each of which is incorporated herein by reference in its entirety for all purposes).

In certain embodiments the polynucleotide comprises at least one additional gene (i.e., a second gene). In certain embodiments the polynucleotide comprises one second gene. In other embodiments, the polynucleotide comprises two additional genes (i.e., a third gene). In yet another embodiment, the polynucleotide comprises three additional genes (i.e., a fourth gene). In certain embodiments, the additional genes are separated from each other and a gene encoding the CAR. For example, they may be separated by 2A sequences and/or an internal ribosomal entry sites (IRES) as described below. In certain examples, the CAR can be encoded at any position of the polynucleotide chain.

In various embodiments, the CAR is operably linked to an additional polypeptide, optionally selected from one of the additional polypeptides described above. In various embodiments, the additional polypeptide is operably linked to the CAR via a self-cleaving peptide and/or an internal ribosomal entry site (IRES). The CAR may be N-terminal or C-terminal to the additional polypeptide. In some embodiments, the CAR is encoded upstream of the additional polypeptide. In some embodiments, the CAR is encoded downstream of the additional polypeptide. In various embodiments, the additional polypeptide is CD19.

In some embodiments, the self-cleaving peptide is a 2A peptide. Non-limiting examples of self-cleaving peptide sequences include *Thoseaasigna* virus 2A (T2A; AEGRGSLLTCGDVEENPGP (SEQ ID NO: 72), EGRGSLLTCGDVEENPGP (SEQ ID NO: 15), or GSGEGRGSLLTCGDVEENPGP (SEQ ID NO: 73)); the foot and mouth disease virus (FMDV) 2A sequence (F2A; GSGSRVTELLYRMKRAETYCPRPLLAIIPTEAR-HKQKIVA PVKQLLNFDLLKLAGDVESNPGP (SEQ ID NO: 74)), Sponge (*Amphimedon queenslandica*) 2A sequence (LLCFLLLLLSGDVELNPGP (SEQ ID NO: 75; or HHFMFLLLLLAGDIEL NPGP (SEQ ID NO: 76)); acorn worm 2A sequence (*Saccoglossus kowalevskii*) (WFLVLLSFILSGDIEVNPGP, (SEQ ID NO: 77)); amphioxus (*Branchiostoma floridae*) 2A sequence (KN-CAMYMLLLSGDVETNPGP (SEQ ID NO: 78); or MVISQLMLKL AGDVEENPGP (SEQ ID NO: 79)); porcine teschovirus-1 2A sequence (P2A; GSGATNFSLLKQAGDVEENPGP (SEQ ID NO: 80)); and equine rhinitis A virus 2A sequence (E2A; GSGQCTNYALLKLAGDVESNPGP (SEQ ID NO: 81), GGPQCTNYALLKLAGDVE SNPG (SEQ ID NO: 55)). In some embodiments, the separation sequence is a naturally occurring or synthetic sequence. In certain embodiments, the separation sequence includes the 2A consensus sequence D-X-E-X-NPGP (SEQ ID NO: 82), in which X is any amino acid residue. In certain embodiments, the self-cleaving peptide is a P2A peptide. In various embodiments, the 2A peptide is a T2A peptide. In some embodiments, the 2A peptide is an E2A peptide.

In various embodiments the T2A peptide comprises the amino acid sequence set forth in SEQ ID NO: 15, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 15. In certain embodiments, the nucleotide sequence that encodes the T2A peptide comprises the nucleotide sequence that encodes the amino acid sequence of SEQ ID NO: 15, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 15. In certain embodiments, the nucleotide sequence that encodes the T2A peptide comprises the nucleotide sequence set forth in SEQ ID NO: 16, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 16. In certain embodiments, the T2A peptide comprises the amino acid sequence set forth in SEQ ID NO: 15. In certain embodiments, the nucleotide sequence that encodes the T2A peptide comprises the nucleotide sequence set forth in SEQ ID NO: 16.

In various embodiments the E2A peptide comprises the amino acid sequence set forth in SEQ ID NO: 55, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 55. In certain embodiments, the nucleotide sequence that encodes the E2A peptide comprises the nucleotide sequence that encodes the amino acid sequence of SEQ ID NO: 55, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 55. In certain embodiments, the nucleotide sequence that encodes the E2A peptide comprises the nucleotide sequence set forth in SEQ ID NO: 56, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 56. In certain embodiments, the E2A peptide comprises the amino acid sequence set forth in SEQ ID NO: 55. In certain embodiments, the nucleotide sequence that encodes the E2A peptide comprises the nucleotide sequence set forth in SEQ ID NO: 56.

In some embodiments, an internal ribosome entry site (IRES) may be used to link the CAR to the additional polypeptide. IRES is an RNA element that allows for translation initiation in a cap-independent manner. IRES can link two coding sequences in one bicistronic vector and allow the translation of both encoded proteins in cells.

In various embodiments, the polynucleotide encodes a polypeptide comprising additional amino acids between the CAR and the self-cleaving peptide and/or IRES. In various embodiments, the additional amino acids comprise the amino acid sequence RSGSG (SEQ ID NO: 19). In some embodiments, the additional amino acids are encoded by a nucleotide sequence comprising SEQ ID NO: 20.

In some embodiments a polynucleotide of the present disclosure encodes an amino acid sequence set forth in SEQ ID NO: 35, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 35. In certain embodiments, a polynucleotide of the present disclosure comprises the nucleotide sequence that encodes the amino acid sequence of SEQ ID NO: 35, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 35. In certain embodiments, a polynucleotide of the present disclosure comprises the nucleotide sequence set forth in SEQ ID NO: 36, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 36. In certain embodiments, a polynucleotide of the present disclosure encodes the amino acid sequence set forth in SEQ ID NO: 35. In certain embodiments, a polynucleotide of the present disclosure comprises the nucleotide sequence set forth in SEQ ID NO: 36.

In some embodiments a polynucleotide of the present disclosure encodes the amino acid sequence set forth in SEQ ID NO: 37, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 37. In certain embodiments, a polynucleotide of the present disclosure comprises the nucleotide sequence that encodes the amino acid sequence of SEQ ID NO: 37, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 37. In certain embodiments, a polynucleotide of the present disclosure comprises the nucleotide sequence set forth in SEQ ID NO: 38, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 38. In certain embodiments, a polynucleotide of the present disclosure encodes the amino acid sequence set forth in SEQ ID NO: 37. In certain embodiments, a polynucleotide of the present disclosure comprises the nucleotide sequence set forth in SEQ ID NO: 38.

In various embodiments a polynucleotide of the present disclosure encodes the amino acid sequence set forth in SEQ ID NO: 39, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 39. In certain embodiments, a polynucleotide of the present disclosure comprises the nucleotide sequence that encodes the amino acid sequence of SEQ ID NO: 39, or a variant thereof having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 39. In certain embodiments, a polynucleotide of the present disclosure comprises the nucleotide sequence set forth in SEQ ID NO: 40, or a nucleotide sequence having at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity with SEQ ID NO: 40. In certain embodiments, a polynucleotide of the present disclosure encodes the amino acid sequence set forth in SEQ ID NO: 39. In certain embodiments, a polynucleotide of the present disclosure comprises the nucleotide sequence set forth in SEQ ID NO: 40.

Recombinant Vectors

In a further aspect, the present disclosure provides recombinant vectors comprising the polynucleotide described herein. Such recombinant vectors may comprise polynucleotides encoding the proteins disclosed herein. In certain embodiments, the polynucleotide is operatively linked to at least one regulatory element for expression of the CAR or the CAR operably linked to the additional polypeptide.

In certain embodiments, the vector is a viral vector. Non-limiting examples of viral vectors suitable for the invention include a retroviral vector, a lentiviral vector, an adenoviral vector, an adeno-associated virus vector, an alphaviral vector, a herpes virus vector, a baculoviral vector, and a vaccinia virus vector.

In some embodiments, the viral vector is a retroviral vector. In some embodiments, the viral vector is a lentiviral vector.

In some embodiments, the vector is a non-viral vector. Non-viral vectors suitable for use in this invention include but are not limited to minicircle plasmids, transposon systems (e.g. Sleeping Beauty, piggyBac), or single or double stranded DNA molecules that are used as templates for homology directed repair (HDR) based gene editing.

In certain embodiments, the polynucleotide is operably linked to at least a regulatory element. The regulatory element can be capable of mediating expression of the CAR in a host cell. Regulatory elements include, but are not limited to, promoters, enhancers, initiation sites, polyadenylation (polyA) tails, IRES elements, response elements, and termination signals. In certain embodiments, the regulatory element regulates CAR expression or the expression of a CAR operably linked to an additional polypeptide. In certain embodiments, the regulatory element increased the expression of the CAR or of the CAR operably linked to the additional polypeptide. In certain embodiments, the regulatory element increases expression of the CAR, or CAR operably linked to the additional polypeptide once the host cell is activated. In certain embodiments, the regulatory element decreases expression of the CAR or CAR operably linked to the additional polypeptide. In certain embodiments, the regulatory element decreases expression of the CAR or CAR operably linked to the additional polypeptide once the host cell is activated.

Isolated Host Cells

In another aspect, provided herein is an isolated host cell comprising the polynucleotide described above or the recombinant vector described above.

In a further aspect, provided herein is an isolated host cell comprising a CAR encoded by the polynucleotide described above.

In certain embodiments, the host cell is an immune cell. In some embodiments, the host cell is a T cell, a natural killer (NK) cell, a mesenchymal stem cell (MSC), or a macrophage. In various embodiments, the host cell is a T cell. T cells may include, but are not limited to, thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells memory T cells, NKT cells, and iNKT cells.

In some embodiments, the T cell is selected from a CD8+ T cell, a CD4+ T cell, a cytotoxic T cell, an αβ T cell receptor (TCR) T cell, a natural killer T (NKT) cell, an invariant natural killer T (iNKT) cell, a γδ T cell, a memory T cell, a memory stem T cell (TSCM, a naïve T cell, an effector T cell, a T-helper cell, and a regulatory T cell (Treg).

In various embodiments, the host cell is a natural killer (NK) cell. NK cell refers to a differentiated lymphocyte with a CD3− CD16+, CD3− CD56+, CD16+CD56+ and/or CD57+ TCR− phenotype.

In various embodiments, other host immune cells are selected, for example, but not limited to, macrophages. In various embodiments, the host immune cell is a dendritic cell, a Langerhans cell, or a B cell. In various embodiments, the host immune cell is a professional antigen-presenting cell (APC). In various embodiments, the host immune cell is a Non-professional APC.

In various embodiments, the host cell has been activated and/or expanded ex vivo.

In various embodiments, the host cell is an allogeneic cell. In various embodiments, the host cell is an autologous cell.

In certain embodiments, the host cell is isolated form a subject having a cancer. In certain embodiments, one or more cells of the cancer express GRP78. In some embodiments, the host cell is isolated from a subject having a tumor. In various embodiments, the cancer is a solid tumor, a brain tumor, or a hematologic malignancy. In certain embodiments, the hematologic malignancy is acute myeloid leukemia (AML), acute lymphoblastic leukemia (ALL), B-cell acute lymphoblastic leukemia (B-ALL), T cell acute lymphoblastic leukemia (T-ALL), or lymphoma. In some embodiments, the tumor can be found within, but not limited to, breast tissue, prostate tissue, bladder tissue, oral and/or dental tissue, head and/or neck tissue, stomach tissue, liver tissue, colorectal tissue, lung tissue, brain tissue, ovary, cervix, esophagus, skin, lymph nodes, and/or bone. In some embodiments, the tumor is a cancer. In some embodiments, the cancer can be, but not limited to, osteosarcoma, rhabdomyosarcoma, Ewing sarcoma and other Ewing sarcoma family of tumors, neuroblastoma, ganglioneuroblastoma, desmoplastic small round cell tumor, malignant peripheral nerve sheath tumor, synovial sarcoma, undifferentiated sarcoma, adrenocortical carcinoma, hepatoblastoma, Wilms tumor, rhabdoid tumor, high grade glioma (glioblastoma multiforme), medulloblastoma, astrocytoma, glioma, ependymoma, atypical teratoid rhabdoid tumor, meningioma, craniopharyngioma, primitive neuroectodermal tumor, diffuse intrinsic pontine glioma and other brain tumors, acute myeloid leukemia, acute lymphoblastic leukemia, multiple myeloma, lung cancer, mesothelioma, breast cancer, bladder cancer, gastric cancer, prostate cancer, colorectal cancer, endometrial cancer, cervical cancer, renal cancer, esophageal cancer, ovarian cancer, pancreatic cancer, hepatocellular carcinoma and other liver cancers, head and neck cancers, leiomyosarcoma, and melanoma. In some embodiments, the tumor is a solid tumor. In various embodiments, the solid tumor is Ewings sarcoma, lung adenocarcinoma, osteosarcoma, breast cancer, or prostate cancer. In certain embodiments, the brain tumor is glioblastoma or neuroblastoma.

In certain embodiments, the host cell is isolated from a subject having a tumor, wherein one or more cells of the tumor cells express GRP78. Non-limiting examples of tumors or cancer cells that express GRP78 include any of the above listed tumors or cancers.

In some embodiments, the host cell is derived from a blood, marrow, tissue, or a tumor sample.

In certain aspects, the present disclosure provides a method of generating an isolated host cell described herein. The method includes genetically modifying the host cell with the polynucleotide described herein or the recombinant vector described herein. In some embodiments, the genetic modifying step is conducted via viral gene delivery. In some embodiments, the genetic modifying step is conducted via non-viral gene delivery. In some embodiments, the genetically modifying step is conducted ex vivo. In some embodiments, the method further comprises activation and/or expansion of the host cell ex vivo before, after and/or during said genetic modification.

Isolation/Enrichment

The host cells may be autologous/autogeneic ("self") or non-autologous ("non-self," e.g., allogeneic, syngeneic or xenogeneic). In certain embodiments, the host cells are obtained from a mammalian subject. In other embodiments, the host cells are obtained from a primate subject. In certain embodiments, the host cells are obtained from a human subject.

Lymphocytes can be obtained from sources such as, but not limited to, peripheral blood mononuclear cells, bone marrow, lymph nodes tissue, cord blood, thymus issue, tissue from a site of infection, ascites, pleural effusion, spleen tissue, and tumors. Lymphocytes may also be generated by differentiation of stem cells. In certain embodiments, lymphocytes can be obtained from blood collected from a subject using techniques generally known to the skilled person, such as sedimentation, e.g., FICOLL™ separation.

In certain embodiments, cells from the circulating blood of a subject are obtained by apheresis. An apheresis device typically contains lymphocytes, including T cells, monocytes, granulocytes, B cells, other nucleated white blood cells, red blood cells, and platelets. In certain embodiments, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. A washing step may be accomplished by methods known to those in the art, such as, but not limited to, using a semiautomated flowthrough centrifuge (e.g., Cobe 2991 cell processor, or the Baxter CytoMate). After washing, the cells may be resuspended in a variety of biocompatible buffers, cell culture medias, or other saline solution with or without buffer.

In certain embodiments, host cells can be isolated from peripheral blood mononuclear cells (PBMCs) by lysing the red blood cells and depleting the monocytes. As an example, the cells can be sorted by centrifugation through a PERCOLL™ gradient. In certain embodiments, after isolation of PBMC, both cytotoxic and helper T lymphocytes can be sorted into naive, memory, and effector T cell subpopulations either before or after activation, expansion, and/or genetic modification.

In certain embodiments, T lymphocytes can be enriched. For example, a specific subpopulation of T lymphocytes, expressing one or more markers such as, but not limited to, CD3, CD4, CD8, CD14, CD15, CD16, CD19, CD27, CD28, CD34, CD36, CD45RA, CD45RO, CD56, CD62, CD62L, CD122, CD123, CD127, CD235a, CCR7, HLA-DR or a combination thereof using either positive or negative selection techniques. In certain embodiments, the T lymphocytes for use in the compositions of the disclosure do not express or do not substantially express one or more of the following markers: CD57, CD244, CD160, PD-1, CTLA4, TIM3, and LAG3.

In certain embodiments, NK cells can be enriched. For example, a specific subpopulation of T lymphocytes, expressing one or more markers such as, but not limited to, CD2, CD16, CD56, CD57, CD94, CD122 or a combination thereof using either positive or negative selection techniques.

Stimulation/Activation

In order to reach sufficient therapeutic doses of host cell compositions, host cells are often subjected to one or more rounds of stimulation/activation. In certain embodiments, a method of producing host cells for administration to a subject comprises stimulating the host cells to become activated in the presence of one or more stimulatory signals or agents (e.g., compound, small molecule, e.g., small organic molecule, nucleic acid, polypeptide, or a fragment, isoform, variant, analog, or derivative thereof). In certain embodiments, a method of producing host cells for administration to a subject comprises stimulating the host cells to become activated and to proliferate in the presence of one or more stimulatory signals or agents.

Host cells (e.g., T lymphocytes and NK cells) can be activated by inducing a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

T cells can be activated generally using methods as described, for example, in U.S. Pat. Nos. 6,352,694; 6,534, 055; 6,905,680; 6,692,964; 5,858,358; 6,887,466; 6,905, 681; 7,144,575; 7,067,318; 7,172,869; 7,232,566; 7,175, 843; 5,883,223; 6,905,874; 6,797,514; and 6,867,041, each of which is incorporated herein by reference in its entirety for all purposes.

In certain embodiments, the T cell based host cells can be activated by binding to an agent that activates CD3ζ.

In other embodiments, a CD2-binding agent may be used to provide a primary stimulation signal to the T cells. For example, and not by limitation, CD2 agents include, but are not limited to, CD2 ligands and anti-CD2 antibodies, e.g., the Tl 1.3 antibody in combination with the Tl 1.1 or Tl 1.2 antibody (Meuer, S. C. et al. (1984) Cell 36:897-906) and the 9.6 antibody (which recognizes the same epitope as TI 1.1) in combination with the 9-1 antibody (Yang, S. Y. et al. (1986) J. Immunol. 137:1097-1100). Other antibodies which bind to the same epitopes as any of the above described antibodies can also be used.

In certain embodiments, the host cells are activated by administering phorbol myristate acetate (PMA) and iono-mycine. In certain embodiments, the host cells are activated by administering an appropriate antigen that induces activation and then expansion. In certain embodiments, PMA, ionomycin, and/or appropriate antigen are administered with CD3 induce activation and/or expansion.

In general, the activating agents used in the present disclosure includes, but is not limited to, an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). The divalent antibody fragment may be an (Fab)2'-fragment, or a divalent single-chain Fv fragment while the monovalent antibody fragment may be selected from the group consisting of a Fab fragment, a Fv fragment, and a single-chain Fv fragment (scFv).

In certain embodiments, one or more binding sites of the CD3ζ agents may be a bivalent proteinaceous artificial binding molecule such as a dimeric lipocalin mutein (i.e., duocalin). In certain embodiments the receptor binding reagent may have a single second binding site, (i.e., mon-ovalent). Examples of monovalent agents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, and a single-chain Fv fragment (scFv), including a divalent single-chain Fv fragment.

The agent that specifically binds CD3 includes, but is not limited to, an anti-CD3– antibody, a divalent antibody fragment of an anti-CD3 antibody, a monovalent antibody fragment of an anti-CD3-antibody, and a proteinaceous CD3-binding molecule with antibody-like binding properties. A proteinaceous CD3-binding molecule with antibody-like binding properties can be an aptamer, a mutein based on a polypeptide of the lipocalin family, a glubody, a protein based on the ankyrin scaffold, a protein based on the crystalline scaffold, an adnectin, and an avimer. It also can be coupled to a bead.

In certain embodiments, the activating agent (e.g., CD3-binding agents) can be present in a concentration of about 0.1 to about 10 μg/ml. In certain embodiments, the activating agent (e.g., CD3-binding agents) can be present in a concentration of about 0.2 μg/ml to about 9 μg/ml, about 0.3 μg/ml to about 8 μg/ml, about 0.4 μg/ml to about 7 μg/ml, about 0.5 μg/ml to about 6 g/ml, about 0.6 μg/ml to about 5 μg/ml, about 0.7 μg/ml to about 4 μg/ml, about 0.8 μg/ml to about 3 μg/ml, or about 0.9 μg/ml to about 2 μg/ml. In certain embodiments, the activating agent (e.g., CD3-binding agents) is administered at a concentration of about 0.1 μg/ml, about 0.2 μg/ml, about 0.3 μg/ml, about 0.4 μg/ml, about 0.5 μg/ml, about 0.6 μg/ml, about 0.7 μg/ml, about 0.8 M, about 0.9 μg/ml, about 1 μg/ml, about 2 μg/ml, about 3 μg/ml, about 4 PM, about 5 μg/ml, about 6 μg/ml, about 7 μg/ml, about 8 μg/ml, about 9 μg/ml, or about 10 μg/ml. In certain embodiments, the CD3-binding agents can be present in a concentration of 1 μg/ml.

NK cells can be activated generally using methods as described, for example, in U.S. Pat. Nos. 7,803,376, 6,949, 520, 6,693,086, 8,834,900, 9,404,083, 9,464,274, 7,435,596, 8,026,097, 8,877,182; U.S. Patent Applications US2004/0058445, US2007/0160578, US2013/0011376, US2015/0118207, US2015/0037887; and PCT Patent Application WO2016/122147, each of which is incorporated herein by reference in its entirety for all purposes.

In certain embodiments, the NK based host cells can be activated by, for example and not limitation, inhibition of inhibitory receptors on NK cells (e.g., KIR2DL1, KIR2DL2/3, KIR2DL4, KIR2DL5A, KIR2DL5B, KIR3DL1, KIR3DL2, KIR3DL3, LILRB1, NKG2A, NKG2C, NKG2E or LTLRB5 receptor).

In certain embodiments, the NK based host cells can be activated by, for example and not limitation, feeder cells (e.g., native K562 cells or K562 cells that are genetically modified to express 4-1BBL and cytokines such as IL15 or IL21).

In other embodiments, interferons or macrophage-derived cytokines can be used to activate NK cells. For example and not limitation, such interferons include but are not limited to interferon alpha and interferon gamma, and such cytokines include but are not limited to IL-15, IL-2, IL-21.

In certain embodiments, the NK activating agent can be present in a concentration of about 0.1 to about 10 μg/ml. In certain embodiments, the NK activating agent can be present in a concentration of about 0.2 μg/ml to about 9 μg/ml, about 0.3 μg/ml to about 8 μg/ml, about 0.4 g/ml to about 7 μg/ml, about 0.5 μg/ml to about 6 μg/ml, about 0.6 μg/ml to about 5 μg/ml, about 0.7 μg/ml to about 4 μg/ml, about 0.8 μg/ml to about 3 μg/ml, or about 0.9 μg/ml to about 2 μg/ml. In certain embodiments, the NK activating agent is administered at a concentration of about 0.1 μg/ml, about 0.2 μg/ml, about 0.3 μg/ml, about 0.4 μg/ml, about 0.5 μg/ml, about 0.6 μg/ml, about 0.7 μg/ml, about 0.8 μg/ml, about 0.9 μg/ml, about 1 μg/ml, about 2 μg/ml, about 3 μg/ml, about 4 μg/ml, about 5 μg/ml, about 6 μg/ml, about 7 μg/ml, about 8 μg/ml, about 9 μg/ml, or about 10 μg/ml. In certain embodiments, the NK activating agent can be present in a concentration of 1 μg/ml.

In certain embodiments, the activating agent is attached to a solid support such as, but not limited to, a bead, an absorbent polymer present in culture plate or well or other matrices such as, but not limited to, Sepharose or glass; may be expressed (such as in native or recombinant forms) on cell surface of natural or recombinant cell line by means known to those skilled in the art.

Polynucleotide Transfer

The host cells can be genetically modified after stimulation/activation. In certain embodiments, the host cells are modified within 12 hours, 16 hours, 24 hours, 36 hours, or 48 hours of stimulation/activation. In certain embodiments, the cells are modified within 16 to 24 hours after stimulation/activation. In certain embodiments, the host cells are modified within 24 hours.

In order to genetically modify the host cell to express the CAR or other related molecule (e.g., TCR or bispecific antibody), the polynucleotide construct must be transferred into the host cell. Polynucleotide transfer may be via viral or non-viral gene methods. Suitable methods for polynucleotide delivery for use with the current methods include any method known by those of skill in the art, by which a polynucleotide can be introduced into an organelle, cell, tissue or organism.

In some embodiments, polynucleotides are transferred to the cell in a non-viral vector. Non-viral vectors suitable for use in this invention include but are not limited to minicircle plasmids, transposon systems (e.g. Sleeping Beauty, piggy-Bac), or single or double stranded DNA molecules that are used as templates for homology directed repair (HDR) based gene editing.

Nucleic acid vaccines can be used to transfer polynucleotides into the host cells. Such vaccines include, but are not limited to non-viral polynucleotide vectors, "naked" DNA and RNA, and viral vectors. Methods of genetically modifying cells with these vaccines, and for optimizing the expression of genes included in these vaccines are known to those of skill in the art.

In certain embodiments, the host cells can be genetically modified by methods ordinarily used by one of skill in the art. In certain embodiments, the host cells can be transduced via retroviral transduction. References describing retroviral transduction of genes are Anderson et al., U.S. Pat. No. 5,399,346; Mann et al., Cell 33:153 (1983); Temin et al., U.S. Pat. No. 4,650,764; Temin et al., U.S. Pat. No. 4,980,289; Markowitz et al., J. Virol. 62:1120 (1988); Temin et al., U.S. Pat. No. 5,124,263; International Patent Publication No. WO 95/07358, published Mar. 16, 1995, by Dougherty et al.; and Kuo et al., Blood 82:845 (1993), each of which is incorporated herein by reference in its entirety for all purposes.

One method of genetic modification includes ex vivo modification. Various methods are available for transfecting cells and tissues removed from a subject via ex vivo modification. For example, retroviral gene transfer in vitro can be used to genetically modified cells removed from the subject and the cell transferred back into the subject. See e.g., Wilson et al., Science, 244:1344-1346, 1989 and Nabel et al., Science, 244(4910):1342-1344, 1989, both of which are incorporated herein by reference in their entity for all purposes. In certain embodiments, the host cells may be removed from the subject and transfected ex vivo using the polynucleotides (e.g., expression vectors) of the disclosure. In certain embodiments, the host cells obtained from the subject can be transfected or transduced with the polynucleotides (e.g., expression vectors) of the disclosure and then administered back to the subject.

Another method of gene transfer includes injection. In certain embodiments, a cell or a polynucleotide or viral vector may be delivered to a cell, tissue, or organism via one or more injections (e.g., a needle injection). Non-limiting methods of injection include injection of a composition (e.g., a saline based composition). Polynucleotides can also be introduced by direct microinjection. Non-limiting sites of injection include, subcutaneous, intradermal, intramuscular, intranodal (allows for direct delivery of antigen to lymphoid tissues). intravenous, intraprotatic, intratumor, intralymphatic (allows direct administration of DCs) and intraperitoneal. It is understood that proper site of injection preparation is necessary (e.g., shaving of the site of injection to observe proper needle placement).

Electroporation is another method of polynucleotide delivery. See e.g., Potter et al., (1984) *Proc. Nat'l Acad. Sci. USA,* 81, 7161-7165 and Tur-Kaspa et al., (1986) *Mol. Cell Biol.,* 6, 716-718, both of which are incorporated herein in their entirety for all purposes. Electroporation involves the exposure of a suspension of cells and DNA to a high-voltage electric discharge. In certain embodiments, cell wall-degrading enzymes, such as pectin-degrading enzymes, can be employed to render the host cells more susceptible to genetic modification by electroporation than untreated cells. See e.g., U.S. Pat. No. 5,384,253, incorporated herein by reference in its entirety for all purposes.

In vivo electroporation involves a basic injection technique in which a vector is injected intradermally in a subject. Electrodes then apply electrical pulses to the intradermal site causing the cells localized there (e.g., resident dermal dendritic cells), to take up the vector. These tumor antigen-expressing dendritic cells activated by local inflammation can then migrate to lymph-nodes.

Methods of electroporation for use with this invention include, for example, Sardesai, N. Y., and Weiner, D. B., *Current Opinion in Immunotherapy* 23:421-9 (2011) and Ferraro, B. et al., *Human Vaccines* 7:120-127 (2011), both of which are hereby incorporated by reference herein in their entirety for all purposes.

Additional methods of polynucleotide transfer include liposome-mediated transfection (e.g., polynucleotide entrapped in a lipid complex suspended in an excess of aqueous solution. See e.g., Ghosh and Bachhawat, (1991) In: *Liver Diseases, Targeted Diagnosis and Therapy Using Specific Receptors and Ligands.* pp. 87-104). Also contemplated is a polynucleotide complexed with Lipofectamine, or Superfect); DEAE-dextran (e.g., a polynucleotide is delivered into a cell using DEAE-dextran followed by polyethylene glycol. See e.g., Gopal, T. V., *Mol Cell Biol.* 1985 May; 5(5):1188-90); calcium phosphate (e.g., polynucleotide is introduced to the cells using calcium phosphate precipitation. See e.g., Graham and van der Eb, (1973) *Virology,* 52, 456-467; Chen and Okayama, *Mol. Cell Biol.,* 7(8):2745-2752, 1987), and Rippe et al., *Mol. Cell Biol.,* 10:689-695, 1990); sonication loading (introduction of a polynucleotide by direct sonic loading. See e.g., Fechheimer et al., (1987) *Proc. Nat'l Acad Sci. USA,* 84, 8463-8467); microprojectile bombardment (e.g., one or more particles may be coated with at least one polynucleotide and delivered into cells by a propelling force. See e.g., U.S. Pat. Nos. 5,550,318; 5,538,880; 5,610,042; and PCT Application WO 94/09699; Klein et al., (1987) *Nature,* 327, 70-73, Yang et al., (1990) *Proc. Nat'l Acad Sci. USA,* 87, 9568-9572); and receptor-mediated transfection (e.g., selective uptake of macromolecules by receptor-mediated endocytosis that will be occurring in a target cell using cell type-specific distribution of various receptors. See e.g., Wu and Wu, (1987) *J. Biol. Chem.,* 262, 4429-4432; Wagner et al., *Proc. Natl. Acad Sci.* USA, 87(9):3410-3414, 1990; Perales et al., *Proc.*

*Natl. Acad Sci. USA,* 91:4086-4090, 1994; Myers, EPO 0273085; Wu and Wu, *Adv. Drug Delivery Rev.,* 12:159-167, 1993; Nicolau et al., (1987) *Methods Enzymol.,* 149, 157-176), each reference cited here is incorporated by reference in their entirety for all purposes.

In further embodiments, host cells are genetically modified using gene editing with homology-directed repair (HDR). Homology-directed repair (HDR) is a mechanism used by cells to repair double strand DNA breaks. In HDR, a donor polynucleotide with homology to the site of the double strand DNA break is used as a template to repair the cleaved DNA sequence, resulting in the transfer of genetic information from the donor polynucleotide to the DNA. As such, new nucleic acid material may be inserted or copied into a target DNA cleavage site. Double strand DNA breaks in host cells may be induced by a site-specific nuclease. Suitable site-specific nucleases for use in the present invention include, but are not limited to, RNA-guided endonuclease (e.g., CRISPR-associated (Cas) proteins), zinc finger nuclease, a TALEN nuclease, or mega-TALEN nuclease. For example, a site-specific nuclease (e.g., a Cas9+guide RNA) capable of inducing a double strand break in a target DNA sequence is introduced to a host cell, along with a donor polynucleotide encoding a CAR of the present disclosure and optionally an additional protein (e.g., TCR or bispecific antibody).

Expansion/Proliferation

After the host cells are activated and transduced, the cells are cultured to proliferate. T cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of T cells can include interleukins, such as IL-2, IL-7, IL-15, or IL-21 (see for example Cornish et al. 2006, Blood. 108(2):600-8, Bazdar and Sieg, 2007, Journal of Virology, 2007, 81(22): 12670-12674, Battalia et al, 2013, Immunology, 139(1):109-120, each of which is incorporated herein by reference in its entirety for all purposes). Other illustrative examples for agents that may be used for the expansion of T cells are agents that bind to CD8, CD45 or CD90, such as αCD8, αCD45 or αCD90 antibodies. Illustrative examples of T cell population including antigen-specific T cells, T helper cells, cytotoxic T cells, memory T cell (an illustrative example of memory T cells are CD62L+CD8+ specific central memory T cells) or regulatory T cells (an illustrative example of Treg are CD4+CD25+CD45RA+ Treg cells).

Additional agents that can be used to expand T lymphocytes includes methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety for all purposes.

In certain embodiments, the agent(s) used for expansion (e.g., IL-2) are administered at about 20 units/ml to about 200 units/ml. In certain embodiments, the agent(s) used for expansion (e.g., IL-2) are administered at about 25 units/ml to about 190 units/ml, about 30 units/ml to about 180 units/ml, about 35 units/ml to about 170 units/ml, about 40 units/ml to about 160 units/ml, about 45 units/ml to about 150 units/ml, about 50 units/ml to about 140 units/ml, about 55 units/ml to about 130 units/ml, about 60 units/ml to about 120 units/ml, about 65 units/ml to about 110 units/ml, about 70 units/ml to about 100 units/ml, about 75 units/ml to about 95 units/ml, or about 80 units/ml to about 90 units/ml. In certain embodiments, the agent(s) used for expansion (e.g., IL-2) are administered at about 20 units/ml, about 25 units/ml, about 30 units/ml, 35 units/ml, 40 units/ml, 45 units/ml, about 50 units/ml, about 55 units/ml, about 60 units/ml, about 65 units/ml, about 70 units/ml, about 75 units/ml, about 80 units/ml, about 85 units/ml, about 90 units/ml, about 95 units/ml, about 100 units/ml, about 105 units/ml, about 110 units/ml, about 115 units/ml, about 120 units/ml, about 125 units/ml, about 130 units/ml, about 135 units/ml, about 140 units/ml, about 145 units/ml, about 150 units/ml, about 155 units/ml, about 160 units/ml, about 165 units/ml, about 170 units/ml, about 175 units/ml, about 180 units/ml, about 185 units/ml, about 190 units/ml, about 195 units/ml, or about 200 units/ml. In certain embodiments, the agent(s) used for expansion (e.g., IL-2) are administered at about 5 mg/ml to about 10 ng/ml. In certain embodiments, the agent(s) used for expansion (e.g., IL-2) are administered at about 5.5 ng/ml to about 9.5 ng/ml, about 6 ng/ml to about 9 ng/ml, about 6.5 ng/ml to about 8.5 ng/ml, or about 7 ng/ml to about 8 ng/ml. In certain embodiments, the agent(s) used for expansion (e.g., IL-2) are administered at about 5 ng/ml, 6 ng/ml, 7 ng/ml, 8 ng/ml, 9, ng/ml, or 10 ng/ml.

After the host cells are activated and transduced, the cells are cultured to proliferate. NK cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of natural killer cells can include agents that bind to CD16 or CD56, such as for example αCD16 or αCD56 antibodies. In certain embodiments, the binding agent includes antibodies (see for example Hoshino et al, Blood. 1991 Dec. 15; 78(12):3232-40, which is incorporated herein by reference in its entirety for all purposes). Other agents that may be used for expansion of NK cells may be IL-15 (see for example Vitale et al. 2002. The Anatomical Record. 266:87-92, which is hereby incorporated by reference in its entirety for all purposes).

Conditions appropriate for T cell culture include appropriate media. Non-limiting examples of appropriate media include Minimal Essential Media (MEM), RPMI Media 1640, Lonza RPMI 1640, Advanced RPMI, Clicks, AIM-V, DMEM, a-MEM, F-12, TexMACS, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion.

Examples of other additives for host cell expansion include, but are not limited to, surfactant, plasmanate, pH buffers such as HEPES, and reducing agents such as N-acetyl-cysteine and 2-mercaptoethanol, Antibiotics (e.g., penicillin and streptomycin), are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In certain embodiments, host cells of the present disclosure may be modified such that the expression of an endogenous TCR, MHC molecule, or other immunogenic molecule is decreased or eliminated. When allogeneic cells are used, rejection of the therapeutic cells may be a concern as it may cause serious complications such as the graft-versus-host disease (GvHD). Although not wishing to be bound by theory, immunogenic molecules (e.g., endogenous TCRs and/or MHC molecules) are typically expressed on the cell surface and are involved in self vs non-self discrimination. Decreasing or eliminating the expression of such molecules may reduce or eliminate the ability of the therapeutic cells to cause GvHD.

In certain embodiments, expression of an endogenous TCR in the host cells is decreased or eliminated. In a particular embodiment, expression of an endogenous TCR (e.g., αβ TCR) in the host cells is decreased or eliminated. Expression of the endogenous TCR may be decreased or eliminated by disrupting the TRAC locus, TCR beta constant locus, and/or CD3 locus. In certain embodiments, expression of an endogenous TCR may be decreased or eliminated by disrupting one or more of the TRAC, TRBC1, TRBC2, CD3E, CD3G, and/or CD3D locus.

In certain embodiments, expression of one or more endogenous MHC molecules in the host cells is decreased or eliminated. Modified MHC molecule may be an MHC class I or class II molecule. In certain embodiments, expression of an endogenous MHC molecule may be decreased or eliminated by disrupting one or more of the MHC, β2M, TAP1, TAP2, CIITA, RFX5, RFXAP and/or RFXANK locus.

Expression of an endogenous TCR, an MHC molecule, and/or any other immunogenic molecule in the host cell can be disrupted using genome editing techniques such as Clustered regularly interspaced short palindromic repeats (CRISPR)/Cas, zinc finger nucleases (ZFNs), transcription activator-like effector nucleases (TALENs), and Meganucleases. These genome editing methods may disrupt a target gene by entirely knocking out all of its output or partially knocking down its expression. In a particular embodiment, expression of the endogenous TCR, an MHC molecule and/or any other immunogenic molecule in the host cell is disrupted using the CRISPR/Cas technique.

Pharmaceutical Compositions

In another aspect, the present disclosure provides for pharmaceutical compositions comprising the isolated host cells described above. Compositions of the present disclosure include, but are not limited to, pharmaceutical compositions.

In one aspect, the present disclosure provides a pharmaceutical composition comprising a polynucleotide or a recombinant vector encoding a CAR described herein, and a pharmaceutically accepted carrier and/or excipient.

In another aspect, the present disclosure provides pharmaceutical composition comprising the modified host cells comprising a CAR described herein and a pharmaceutically acceptable carrier and/or excipient.

Excipients included in the pharmaceutical composition will have different purposes depending, for example, on host cells used, the polynucleotide or recombinant vector used, the CAR used, and the mode of administration. Examples of generally used excipients include, without limitation: saline, buffered saline, dextrose, water, glycerol, ethanol, and combinations thereof, stabilizing agents, solubilizing agents and surfactants, buffers and preservatives, tonicity agents, bulking agents, and lubricating agents. Pharmaceutical compositions comprising isolated host cells will typically have been prepared and cultured in the absence of any non-human components, such as animal serum (e.g., bovine serum albumin).

Examples of pharmaceutical carriers include but are not limited to sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

Compositions comprising modified host cells disclosed herein may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions comprising modified host cells disclosed herein may comprise one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

In some embodiments, the compositions are formulated to be introduced into the subject by parenteral administration, e.g., intravascular (intravenous or intraarterial), intraperitoneal, intratumoral, intraventricular, intrapleural or intramuscular administration. The parenteral preparation can be enclosed in ampoules, disposable syringes or multiple dose vials made of glass or plastic. An injectable pharmaceutical composition is preferably sterile. In some embodiments, the composition is reconstituted from a lyophilized preparation prior to administration.

In some embodiments, the modified host cells may be mixed with substances that adhere to or penetrate the host cells prior to administration of the host cells. A non-limiting example of the substances is nanoparticles.

Therapeutic Methods

In one aspect, the present disclosure provides a method for killing a tumor or cancer cell expressing GRP78 comprising contacting the cell with the host cell(s), or the pharmaceutical composition(s) described herein.

In one aspect, the present disclosure provides a method for treating a tumor in a subject in need thereof. One or more cells of the tumor expresses GRP78. The method comprises administering to the subject a therapeutically effective amount of the modified host cell(s) comprising a CAR described herein or the pharmaceutical composition.

In various embodiments, the cancer is a solid tumor, a brain tumor, or a hematologic malignancy. In certain embodiments, the hematologic malignancy is AML, ALL, B-ALL, T-ALL, or lymphoma. Examples of tumors are, but not limited to, the soft tissue tumors (e.g., lymphomas), and tumors of the blood and blood-forming organs (e.g., leukemias), and solid tumors, which is one that grows in an anatomical site outside the bloodstream (e.g., carcinomas). Examples of cancer include, but are not limited to, carcinoma, lymphoma, blastoma, sarcoma (e.g., Ewing sarcoma and other Ewing sarcoma family of tumors, osteosarcoma or rhabdomyosarcoma), and leukemia or lymphoid malignancies. More particular examples of such cancers include squamous cell cancer (e.g., epithelial squamous cell cancer), adenosquamous cell carcinoma, lung cancer (e.g., including small-cell lung cancer, non-small cell lung cancer, adenocarcinoma of the lung, squamous carcinoma of the lung), cancer of the peritoneum, hepatocellular cancer, gastric or stomach cancer (e.g., including gastrointestinal cancer, pancreatic cancer), cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, primary or metastatic melanoma, multiple myeloma and B-cell lymphoma, non-Hodgkin's lymphoma, Hodgkin's lymphoma, brain (e.g., high grade glioma, diffuse pontine glioma, ependymoma, neuroblastoma, or glioblastoma), as well as head and neck cancer, and associated metastases. Additional examples of tumors can be found in The Merck Manual of Diagnosis and Therapy, 19th Edition, § on Hematology and Oncology, published by Merck Sharp & Dohme Corp., 2011 (ISBN 978-0-911910-19-3); The Merck Manual of Diagnosis and Therapy, 20th Edition, § on Hematology and Oncology, published by Merck Sharp & Dohme Corp., 2018 (ISBN 978-0-911-91042-1) (2018 digital online edition at internet website of Merck Manuals); and SEER Program Coding and Staging Manual 2016, each of which are incorporated by reference in their entirety for all purposes.

In various embodiments, the tumor is selected from osteosarcoma, rhabdomyosarcoma, Ewing sarcoma and other Ewing sarcoma family of tumors, neuroblastoma, ganglioneuroblastoma, desmoplastic small round cell tumor, malignant peripheral nerve sheath tumor, synovial sarcoma, undifferentiated sarcoma, adrenocortical carcinoma, hepatoblastoma, Wilms tumor, rhabdoid tumor, high grade glioma (glioblastoma multiforme), medulloblastoma, astrocytoma, glioma, ependymoma, atypical teratoid rhabdoid tumor, meningioma, craniopharyngioma, primitive neuroectodermal tumor, diffuse intrinsic pontine glioma and other brain tumors, acute myeloid leukemia, multiple myeloma, lung cancer, mesothelioma, breast cancer, bladder cancer, gastric cancer, prostate cancer, colorectal cancer, endometrial cancer, cervical cancer, renal cancer, esophageal cancer, ovarian cancer, pancreatic cancer, hepatocellular carcinoma and other liver cancers, head and neck cancers, leiomyosarcoma, and melanoma. In various embodiments, the tumor is a solid tumor. In various embodiments, the solid tumor is Ewings sarcoma, lung adenocarcinoma, osteosarcoma, breast cancer, or prostate cancer. In certain embodiments, the tumor is a brain tumor. In some embodiments, the brain tumor is glioblastoma or neuroblastoma.

In some embodiments, the therapeutic method of the present disclosure includes one or more of the following steps: a) isolating immune cells (e.g., T cells, iNKT cells, mesenchymal stem cells, macrophages, or NK cells) from the subject or donor; b) genetically modifying the immune cells (e.g., T cells, iNKT cells, mesenchymal stem cells, macrophages, or NK cells) ex vivo with the polynucleotide or the recombinant vector encoding a CAR described herein; c) optionally, expanding and/or activating the modified the immune cells (e.g., T cells, iNKT cells, mesenchymal stem cells, macrophages, or NK cells) before, after and/or during step b); and d) introducing a therapeutically effective amount of the modified immune cells (e.g., T cells, iNKT cells, mesenchymal stem cells, macrophages, or NK cells) into the subject. In some embodiments, the immune cell is an αβ TCR T cell, a γδ T cell, a macrophage, a mesenchymal stem cell, a NK cell, or an iNKT cell.

In some embodiments, the modified host cell is an autologous cell. In some embodiments, the modified host cell is an allogeneic cell. In cases where the host cell is isolated from a donor, the method may further include a method to prevent graft vs. host disease (GVHD) and host cell rejection.

In some embodiments, the modified host cells may also express a CD20 polypeptide as a safety switch. Accordingly, the method may further include administering an anti-CD20 antibody to the subject for removal of the isolated host cells. The anti-CD20 antibody is administered in an amount effective for sufficient removal of the isolated host cells from the subject. In some embodiments, the anti-CD20 antibody is administered in an amount effective for removal of more than 50% of the isolated host cells from the subject. For example, the anti-CD20 antibody may be administered in an amount effective for removal of more than 55%, more than 60%, more than 65%, more than 70%, more than 75%, more than 80%, more than 85%, more than 90%, more than 95%, more than 98%, more than 99%, or about 100% of the isolated host cells from the subject. The anti-CD20 antibody may be administered in an amount effective for removal of about 50% to about 70%, about 60% to about 80%, about 70% to about 90%, or about 80% to about 100% of the isolated host cells from the subject.

Non-limiting examples of anti-CD20 antibodies that can be used for removal of the isolated host cells include Rituximab, Ibritumomab tiuxetan, Tositumomab, Ofatumumab, Ocrelizumab, TRU-015, Veltuzumab, AME-133v, PRO131921, and Obinutuzumab. In some embodiments, the anti-CD20 antibody is Rituximab.

In some embodiments of any of the therapeutic methods described above, the composition is administered in a therapeutically effective amount. The dosages of the composition administered in the methods of the invention will vary widely, depending upon the subject's physical parameters, the frequency of administration, the manner of administration, the clearance rate, and the like. The initial dose may be larger and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve in vivo persistence of modified host cells. It is also contemplated that a variety of doses will be effective to improve in vivo effector function of modified host cells.

In some embodiments, composition comprising the modified host cells manufactured by the methods described herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of modified host cells will depend on the therapeutic use for which the composition is intended for.

Modified host cells may be administered multiple times at dosages listed above. The modified host cells may be allogeneic, syngeneic, xenogeneic, or autologous to the patient undergoing therapy.

The compositions and methods described in the present disclosure may be utilized in conjunction with other types of therapy for tumors, such as chemotherapy, surgery, radiation, gene therapy, and so forth.

It is also contemplated that when used to treat various diseases/disorders, the compositions and methods of the present disclosure can be utilized with other therapeutic methods/agents suitable for the same or similar diseases/disorders. Such other therapeutic methods/agents can be co-administered (simultaneously or sequentially) to generate additive or synergistic effects. Suitable therapeutically effective dosages for each agent may be lowered due to the additive action or synergy.

In some embodiments of any of the above therapeutic methods, the method further comprises administering to the subject one or more additional compounds selected from the group consisting of immuno-suppressives, biologicals, pro-biotics, prebiotics, and cytokines (e.g., GM-CSF, IFN or IL-2).

In some embodiments, the method described herein further comprises providing exogenous GM-CSF, in addition to the GM-CSF produced by the immune cells, to enhance the function of immune cells expressing a CAR of the present disclosure. Exogenous GM-CSF may be provided by, for example and not limitation, i) injection of the FDA-approved GM-CSF drug Sargramostin (Leukine™) or ii) the use of nonviral or viral vectors to express GM-CSF (e.g., FDA-approved GM-CSF expressing oncolytic virus talimogene laherparepvec [TVEC, Imlygic™]). These drugs could be given before, with, or after the administration (e.g., infusion) of the immune cells expressing a CAR of the present disclosure to patients.

As a non-limiting example, the invention can be combined with other therapies that block inflammation (e.g., via blockage of IL1, INFα/β, IL6, TNF, IL23, etc.).

The methods and compositions of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 4-1BB, OX40, etc.). The methods of the invention can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e). The methods of the invention can also be combined with other treatments such as midostaurin, enasidenib, or a combination thereof.

Therapeutic methods of the invention can be combined with additional immunotherapies and therapies. For example, when used for treating tumors, the compositions of the invention can be used in combination with conventional therapies, such as, e.g., surgery, radiotherapy, chemotherapy or combinations thereof, depending on type of the tumor, patient condition, other health issues, and a variety of factors. In certain aspects, other therapeutic agents useful for combination tumor therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the modified host cells of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present disclosure include, for example, aminoglutethimide, amsacrine, anastrozole, asparaginase, azacitidine, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, decitabine, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-tumor agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopi-dine, clopidogrel, abciximab; antimigratory agents; antise-cretory agents (breveldin); immunosuppressives (cy-closporine, tacrolimus (FK-506), sirolimus (rapamycin), azathioprine, mycophenolate mofetil); anti-angiogenic com-pounds (e.g., TNP-470, genistein, bevacizumab) and growth factor inhibitors (e.g., fibroblast growth factor (FGF) inhibi-tors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dac-tinomycin, eniposide, epirubicin, etoposide, idarubicin and mitoxantrone, topotecan, irinotecan), corticosteroids (corti-sone, dexamethasone, hydrocortisone, methylpednisolone, prednisone, and prenisolone); growth factor signal transduc-tion kinase inhibitors; mitochondrial dysfunction inducers and caspase activators; and chromatin disruptors.

In various embodiments of the methods described herein, the subject is a human. The subject may be a juvenile, a pediatric subject, or an adult, of any age or sex. In some embodiments, the subject is under the age of 18. In various embodiments, the subject is less than about 3 months, about 6 months, about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, or about 18 years of age. In some embodiments, the subject is about 19 years, about 20 years, about 25 years, about 30 years, about 35 years, about 40 years, abo 45 years, about 50 years, about 55 years, about 60 years, about 65 years, about 70 years, about 75 years, about 80 years, about 85 years, about 90 years, about 95 years, or about 100 years old.

EXAMPLES

The present invention is also described and demonstrated by way of the following examples. However, the use of these and other examples anywhere in the specification is illus-trative only and in no way limits the scope and meaning of the invention or of any exemplified term. Likewise, the invention is not limited to any particular preferred embodi-ments described here. Indeed, many modifications and varia-tions of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Materials and Methods

The following materials and methods were used in Examples 1-10, unless described otherwise in a specific Example.

Study Design

A second-generation GRP78 CAR using 1× (GRP78.1×-CAR), 2× (GRP78.2×-CAR) and 3× (GRP78.3×-CAR) repeats of a GRP78-binding peptide as the antigen recogni-tion domain. The CAR was developed with a mutIgG4 hinge, CD28 costimulatory domain and a CD3ζ signaling domain and the amino acid sequences for the GRP78.1×-CAR, GRP78.2×-CAR, and GRP78.3×-CAR comprise SEQ ID NO: 29, 31 and 33, respectively. The constructs were tested in vitro for cytokine release and cytotoxicity. Based on successful in vitro efficacy evaluation we subsequently tested the constructs in three separate in vivo xenograft models in immunodeficient mice.

Cell Lines and Culture Methods

The following cell lines used in the examples were procured from American Type Culture Collection (ATCC): KG1a, MV-4-11, THP-1, MOLM13 (acute myelogenous leukemia, AML), LM7 (osteosarcoma, OS), A549 (lung adenocarcinoma), A673 (Ewing's sarcoma), and MDA-MB-468 (triple negative breast carcinoma, TNBC). MOLM13 and MDA-MB-468 cells expressing firefly luciferase (ffluc) were generated by retroviral transduction as previously described [22-23]. Retroviral vectors were packaged using HEK 293T cells (ATCC) that were grown in IMDM (Thermo Scientific, Waltham, MA). Fourteen primary pedi-atric acute myeloid leukemia (AML) samples (initial diag-nosis, therapy-related or relapsed) were obtained as part of an IRB approved protocol. Five patient-derived xenograft (PDX) cell lines were established by intravenous (i.v.) injection of pediatric primary AML samples into NSG-S mice and subsequently propagated in vivo [33]. Additional details on the primary pediatric AML and PDX samples are provided in FIG. 9A and FIG. 9B. Cell lines were cultured in RPMI 1640 (ThermoFisher Scientific) or DMEM (GE Life Sciences) and grown in humidified incubators at 37° C. and 5% $CO_2$. All culture media was supplemented with 10% Fetal Bovine Serum (Thermo Scientific) and GlutaMAX (2 mmol/L; Invitrogen, Carlsbad, CA).

RNA-Seq Read Mapping, Gene Expression Summary and Batch Correction

RNA reads were mapped using a StrongARM pipeline, described previously [24]. Paired-end reads from RNA-seq were aligned to the following four database files using BWA: (i) the human GRCh37-lite reference sequence, (ii) RefSeq, (iii) a sequence file representing all possible com-binations of non-sequential pairs in RefSeq exons and, (iv) the AceView database flat file downloaded from UCSC representing transcripts constructed from human ESTs. Additionally, they were mapped to the human GRCh37-lite reference sequence using STAR. The mapping results from databases (ii)-(iv) were aligned to human reference genome coordinates. The final BAM file was constructed by select-ing the best of the five alignments.

Reads from aligned BAM files were assigned to genes and counted using HTSeq [25] with the GENCODE human release 19 gene annotation and Log 2 CPM (counts per million) values were generated. A cut-off of 10 counts was implemented to calculate the corresponding CPM, which was used as the threshold for expression. The number of samples in the smallest group among all groups being compared was first determined as N. For a gene to be considered as expressed, at least N=5 samples were required to have CPM values greater than the above-described expression threshold. Genes not meeting this cutoff value were excluded from downstream analysis. The detected batch effect due to data source of St. Jude vs. TARGET was corrected using the ComBat method available from the R package SVA26. Limma R package [26] was used for differential gene expression analysis.

Flow Cytometric Analysis

Anti-KDEL antibody for detection of cell surface GRP78 (Abcam, Clone-10C3; Cat. No. ab115638) and Streptavidin PE (BioLegend, San Diego, CA. Cat. No 405204 were used for flow cytometric analysis. A GRP78-binding peptide (CTVALPGGYVRVC (SEQ ID NO: 1)) with an N-terminal Biotin tag (Biotin-Ahx-CTVALPGGYVRVC (SEQ ID NO: 71)) was obtained from Genscript). The following antibod-ies purchased from BD Biosciences were used for flow cytometry: CD4, CD8, CCR7 FITC, CD45RA APC, CD19 APC, CD19 PE, CD8 APC-H7, CD4-KrO, TIM3 PE-Cy7, LAG3 PE, and PD1 BV605. Recombinant Human ErbB2/Her2 Fc Chimera Protein (R&D Systems, Cat. No 1129-ER) was used to detect HER2 CAR. Half a million Transduced and Non-Transduced T Cells were washed with 1×PBS and the cells were incubated with 3 μL of antibody and Fixable Live Dead aqua stain (Thermo Fisher Scientific, L34965) on ice and protected from light for 30 mins. Cells were washed with 1×PBS+2% FBS. FACS was carried out using FACS Canto II or Lyric (BD Biosciences). The analysis was performed using FlowJo 10.5.3 software (BD Biosciences, San Jose, CA).

Cytotoxicity Assays

To determine the cytotoxic potential of the CAR T cells, a luciferase-based assay was utilized for suspension cells and an MTS assay (3-(4,5-dimethylthiazol-2-yl)-5-(3-carboxymethoxyphenyl)-2-(4-sulfophenyl)-2H-tetrazolium) was used for adherent cells. Non-transduced (NT) or genetically modified CAR T cells were co-cultured with $5×10^5$ ffluc expressing target cells at a 1:1 Effector:Target (E:T) ratio in 96-well tissue culture plates overnight. In the luciferase-based assay, 100 μl of the cells (MOLM13ffluc) were incubated with D-Luciferin. Luminescence was measured on a Tecan Infinite® 200 (Life Sciences-Tecan) and analyzed using Magellan Software (Life Sciences-Tecan).

Adherent cell lines (LM7, A673, A549) were co-cultured in a similar fashion overnight, and were then incubated with the CellTiter 96® AQueous One Solution Cell Proliferation Assay (MTS), Promega (Cat. No. G3582). MTS assay was subsequently performed on Tecan Infinite® 200 following manufacturer's instructions.

Cytokine Evaluation by ELISA

Tumor cells were co-cultured with NT or genetically modified CAR T cells at a 2:1 (E:T) ratio. Following 24 hour of co-culture, the supernatants were collected and IFN-γ and IL-2 levels were assessed using ELISAs as per the manufacturer's protocols. The ELISA kits were obtained from R&D Systems.

Repeat Stimulation and Cytokine Multiplex Assay

Effector T cells ($5×10^5$ cells) were plated at a 1:1 effector to target (E:T) ratio with GRP78+ target cells expressing firefly luciferase (MOLM13.ffluc). Three days later, antitumor activity was determined by a luciferase-based assay and culture supernatants were collected. Afterwards, E:T ratio was adjusted back to 1:1 by adding fresh tumor cells. Harvested culture supernatants were then analyzed using a custom human Cytokine/Chemokine Multiplex assay containing analytes for GM-CSF, IFN-7, IL-10, IL-13, IL-2, IL-4, IL-5, IL-6 and TNF-α (EMD Millipore, Chicago, IL) as per manufacturer's instructions.

Colony Forming Unit (CFU) Assay

NT, GRP78.A or GRP78.2×-CAR T cells were co-cultured with CD34+ bone marrow cells (Lonza, Basel, Switzerland) at an E:T of 1:5 and 1:1 in for 4 hours and were then plated in the presence of MethoCult (Stem Cells, H4434) in a 6-well SmartDish® (Stemcell Technology, Vancouver, CA), and incubated for 12-14 days at 37° C. Plates were imaged using a Nikon C2 point-scanning confocal Microscope (Nikon, Tokyo, Japan) using a 4× objective. BFU-E (Burst Forming Unit—erythroid) and CFU colonies (Colony-forming unit—erythroid: CFU-E, Colony-forming unit—granulocyte, erythroid, macrophage, megakaryocyte: CFU-GEMM), and Colony-forming unit—granulocyte, macrophage+ CFU-GM) were enumerated.

In Vivo Studies

The in vivo studies were performed using NSG (NOD.Cg-Prkdc$^{scid}$/Il2rg$^{tm1Wj1}$/SzJ) mice obtained from an in-house breeding colony. The mice were injected with CAR T cells i.v. after 7 days of tumor injections. The mice were treated with either $3×10^6$ CAR T cells or $10×10^6$ CAR T cells given as a single dose through the tail vein.

For experiments using MOLM13 cells, $5×10^3$ MOLM13 ffluc cells were injected i.v. through the tail vein or $5×10^5$ MDA-MB-458 ffluc cells suspended in PBS:Matrigel mixture (1:1) were injected into the mammary fat pad. Tumor growth was monitored twice weekly by bioluminescence imaging using IVIS® system (IVIS, Xenogen Corp., Alameda, CA).

For experiments using A673 cells or MDA-MB-458 cells, $1×10^6$ A673 cells suspended in PBS:Matrigel mixture (1:1) were injected s.c. and tumor growth was monitored using caliper measurement twice a week. The Matrigel was purchased from Corning.

Statistical Analysis

Descriptive statistics were calculated for all outcomes. The one- or two-factor ANOVA test was used to examine overall differences in outcomes between multiple constructs. (Comparisons across multiple groups were performed by one- or two-factor ANOVA when appropriate.) The overall test was followed by pairwise comparisons using t-test when appropriate (i.e. overall test P<0.05). Generalized linear model was used to access the overall difference in outcomes with repeated measurements in order to account for intra subject correlation in each subject/donor. Log rank test was used to test difference between constructs of all survival outcomes.

Statistical analyses were conducted with SAS 9.4. A two-sided significance level of P<0.05 was used for all statistical tests, and adjustment for multiple testing was not performed due to small sample size and the exploratory nature of the analysis.

Example 1. GRP78 is Displayed on the Surface of Tumor Cells

Figure 1E:
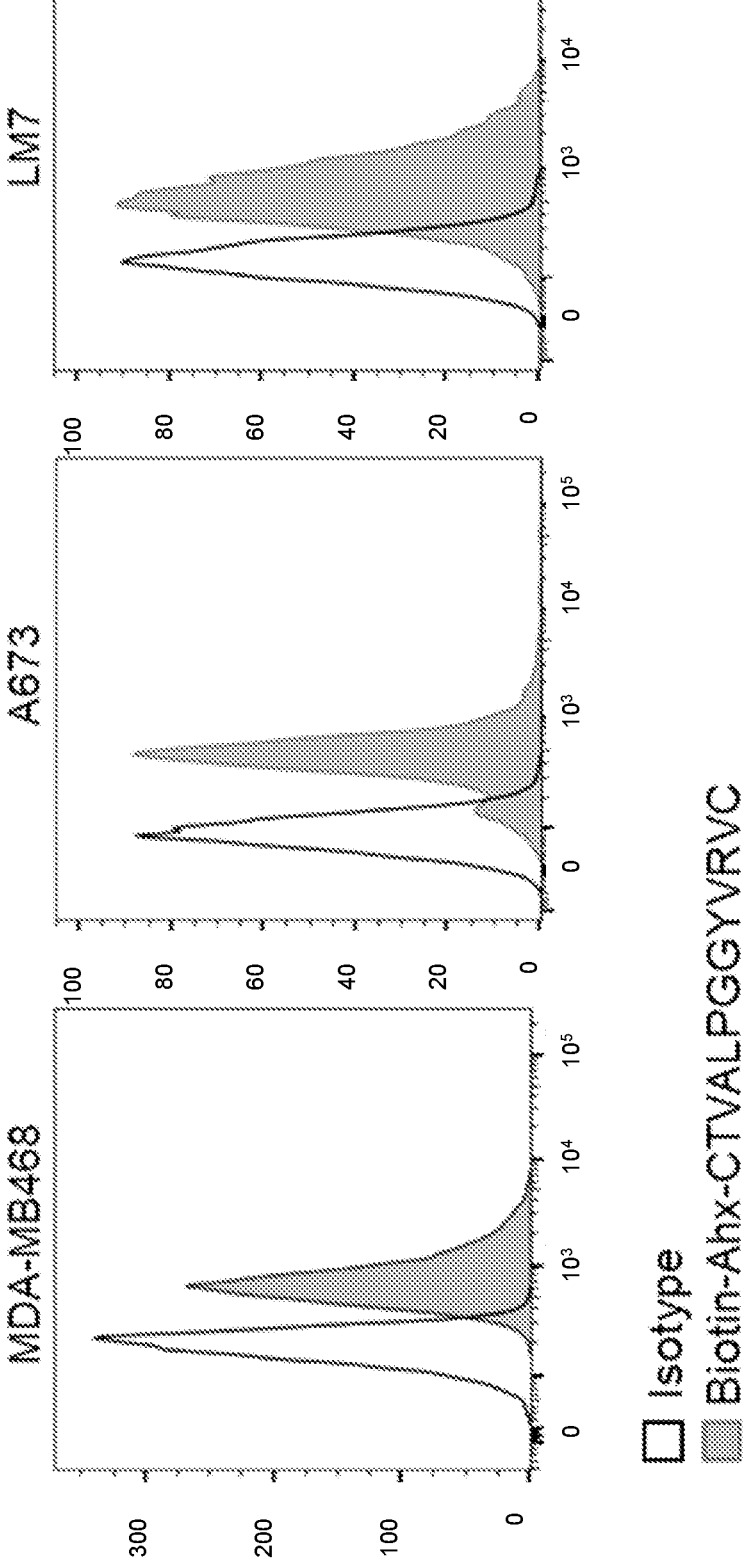
FIG. 1E provides plots of data demonstrating cell surface GRP78 expression on solid tumor cells.
Figure 1F:
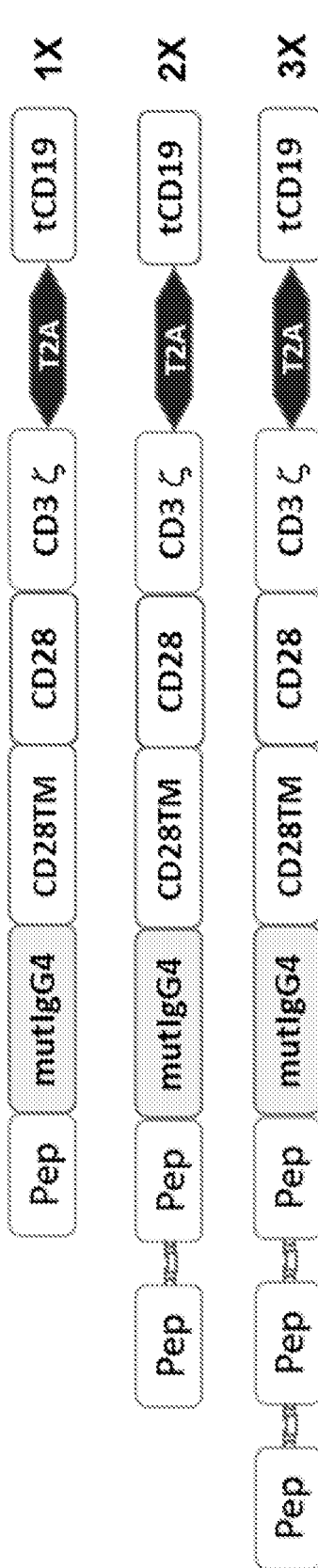
FIG. 1F provides a diagram illustrating generation of a peptide CAR against cell surface expressed GRP78. 1×CAR (GRP78.1×-CAR), top; 2×CAR (GRP78.2×-CAR), middle; 3×CAR (GRP78.3×-CAR), bottom.
Figure 1G:
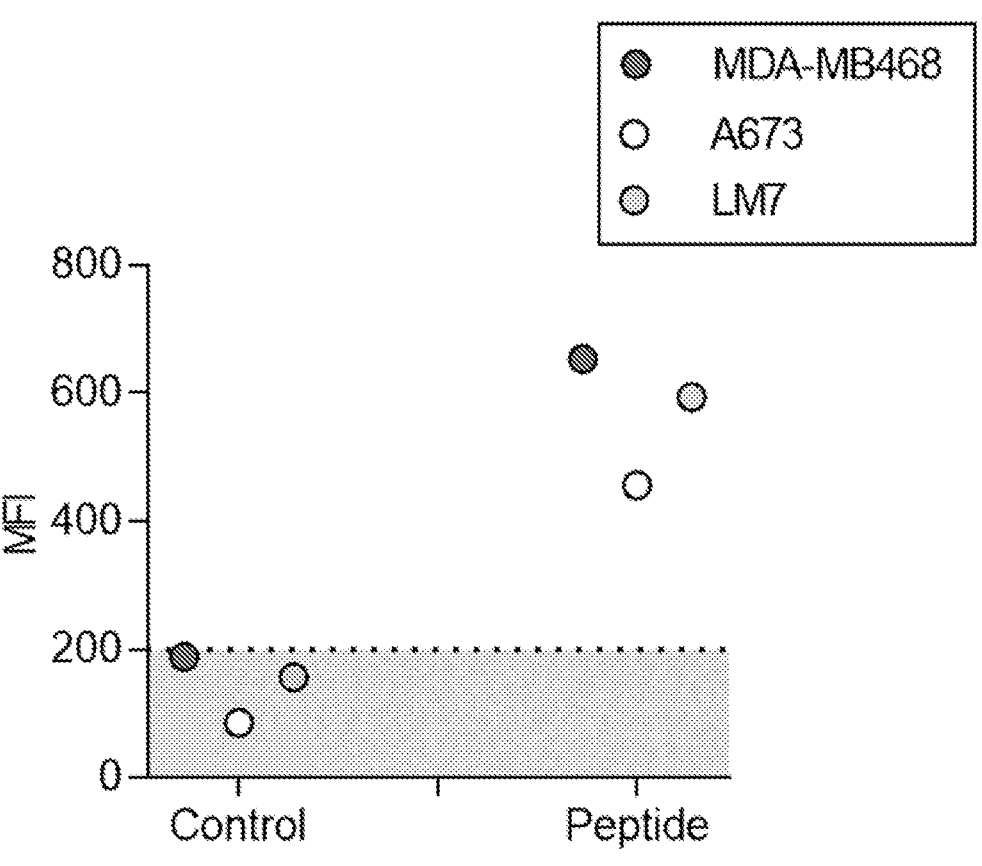
FIG. 1G provides a plot of MFI of peptide staining by flow cytometry.

The presence of GRP78 on the cell surface of tumor cells was assessed using a panel of acute myeloid leukemia (AML) cell lines including Kg1A, MV-4-11, THP-1, MOLM13 (FIGS. 1A and 1B) and a panel of solid tumor cell lines including A673 (Ewings sarcoma), A549 (lung adenocarcinoma), LM7 (osteosarcoma), MDA-MB-468 (triple negative breast cancer, TNBC) (FIGS. 1E and 1G). To detect GRP78, both a monoclonal antibody (mAb) that targets the KDEL endoplasmic reticulum (ER) retention sequence ("KDEL" disclosed as SEQ ID NO: 92) at the C-terminus of GRP78 and a biotin-conjugated GRP78-binding peptide (Biotin-Ahx-CTVALPGGYVRVC (SEQ ID NO: 71)) were used. All tumor cells lines evaluated showed increased expression of GRP78 as compared to normal T lymphocytes (MFI tumor cell lines range: 1257±572, MFI T cells: 230±46). The surface expression patterns on cell lines measured using either the antibody or the biotin-conjugated peptide were very similar (FIGS. 1A-1E, and 1G). These results confirmed that GRP78 is present and elevated on the surface of AML and solid tumor cell lines.

Example 2. Preparation of GRP78-CAR Constructs

Figure 2A:
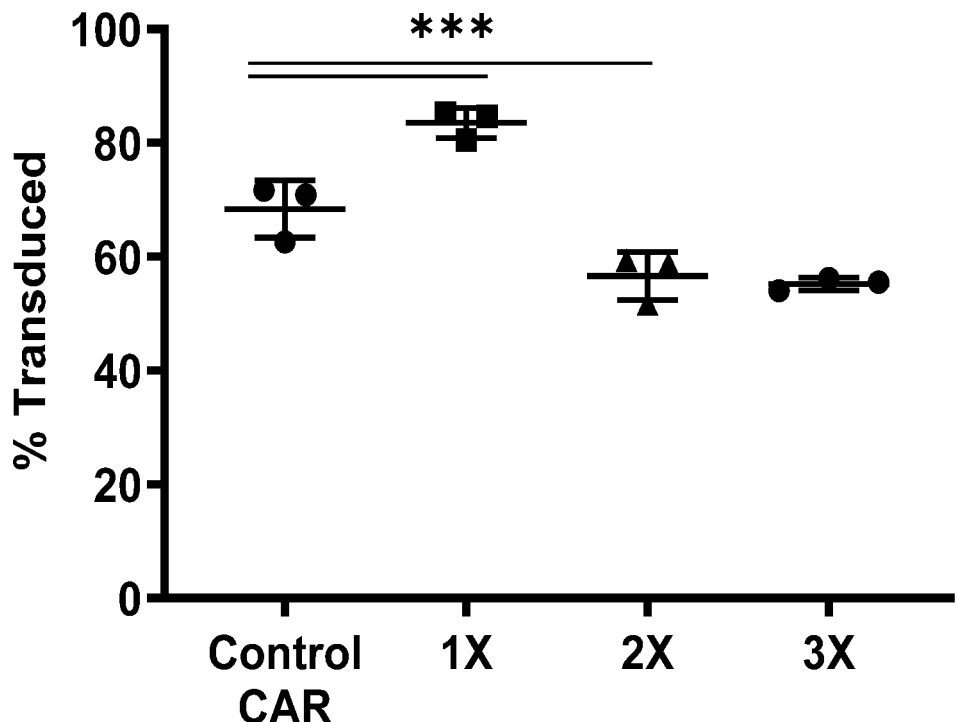
FIGS. 2A-2I demonstrate functional activity of GRP78-binding peptide CAR in vitro.
Figure 2B:
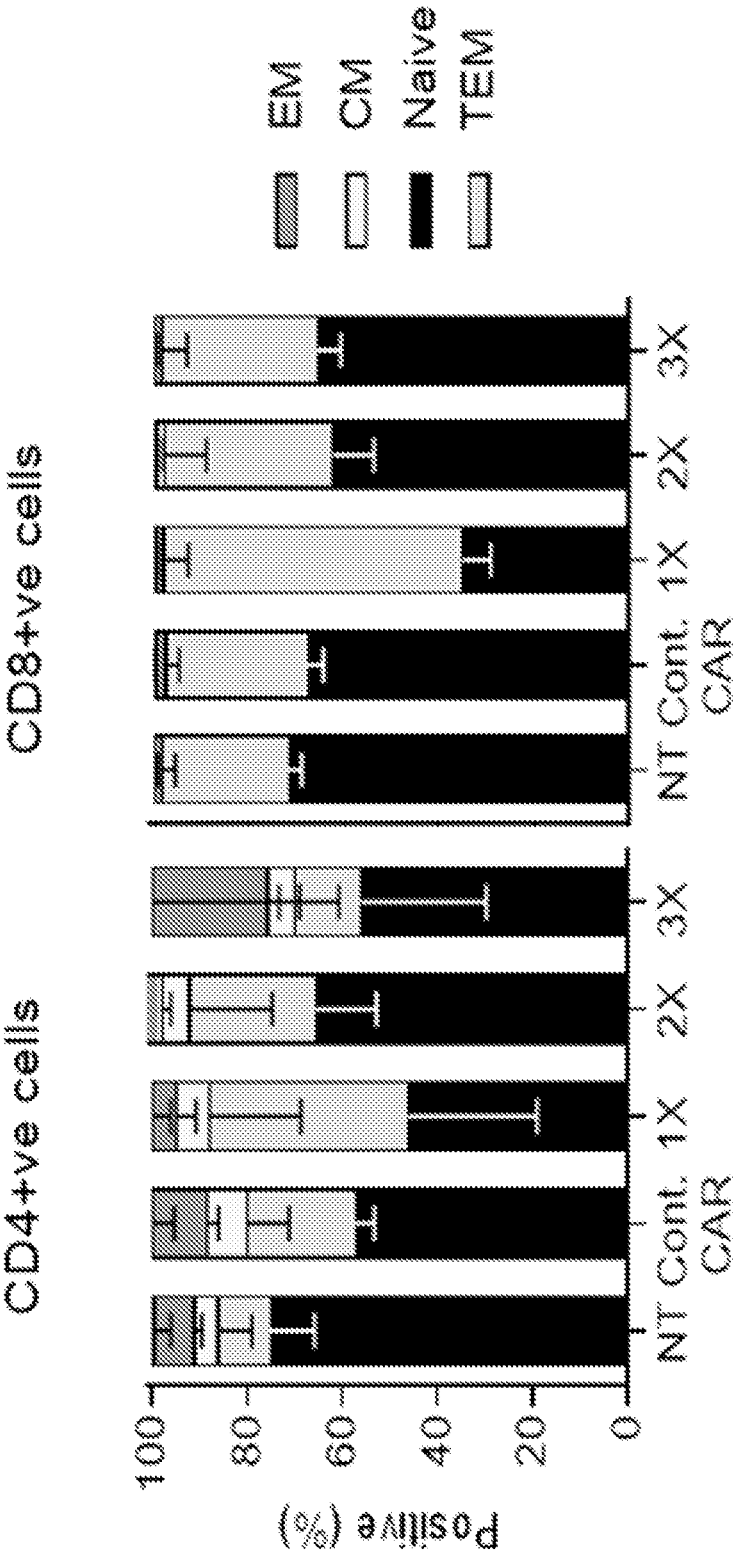
Figure 2C:
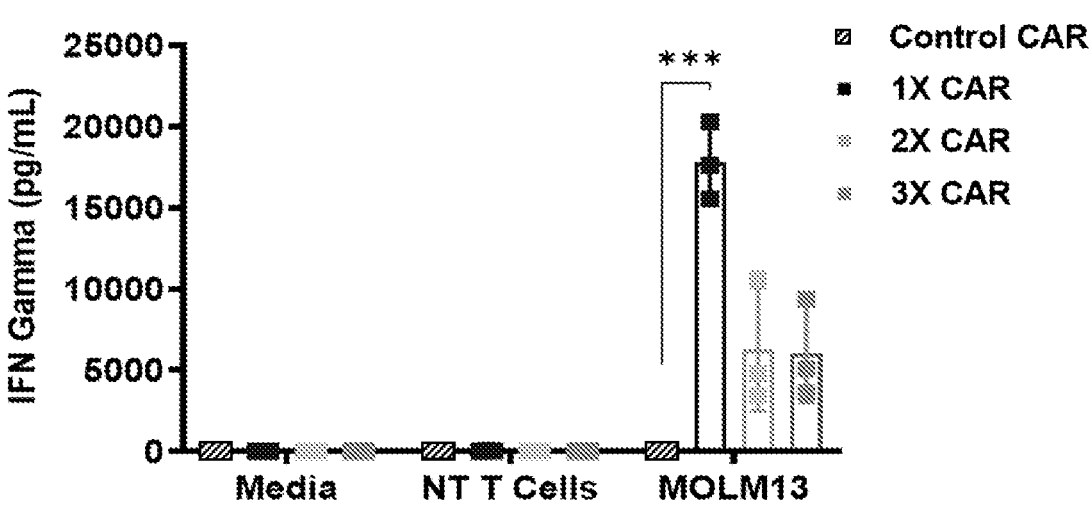
Figure 2D:
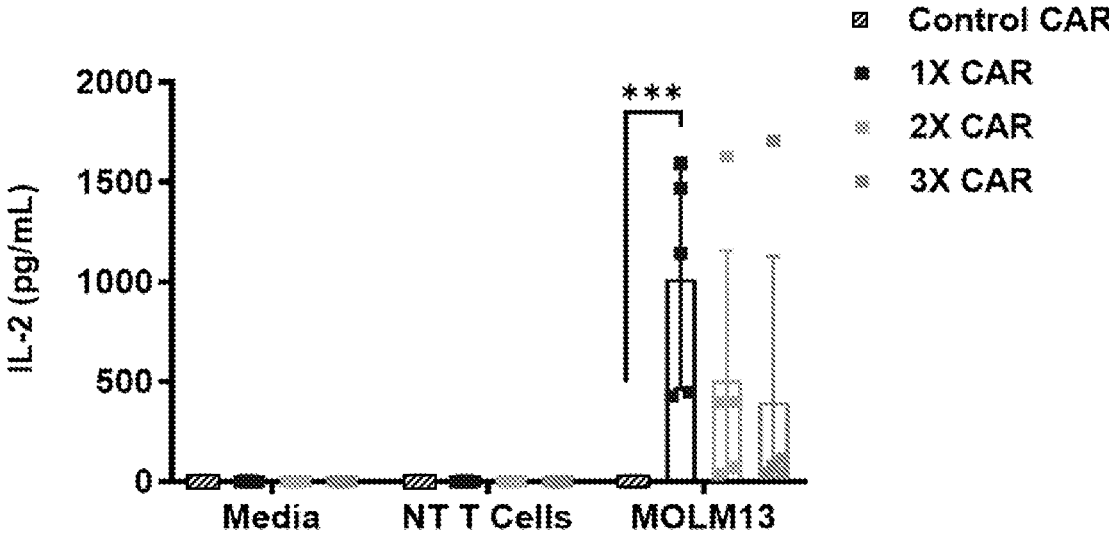
Figure 2E:
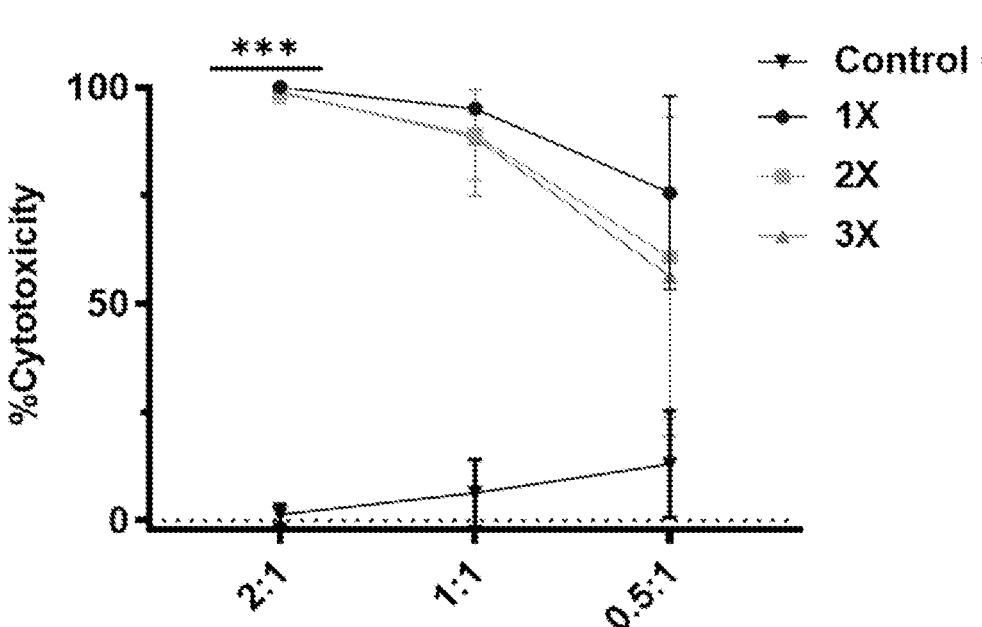
Figure 2F:
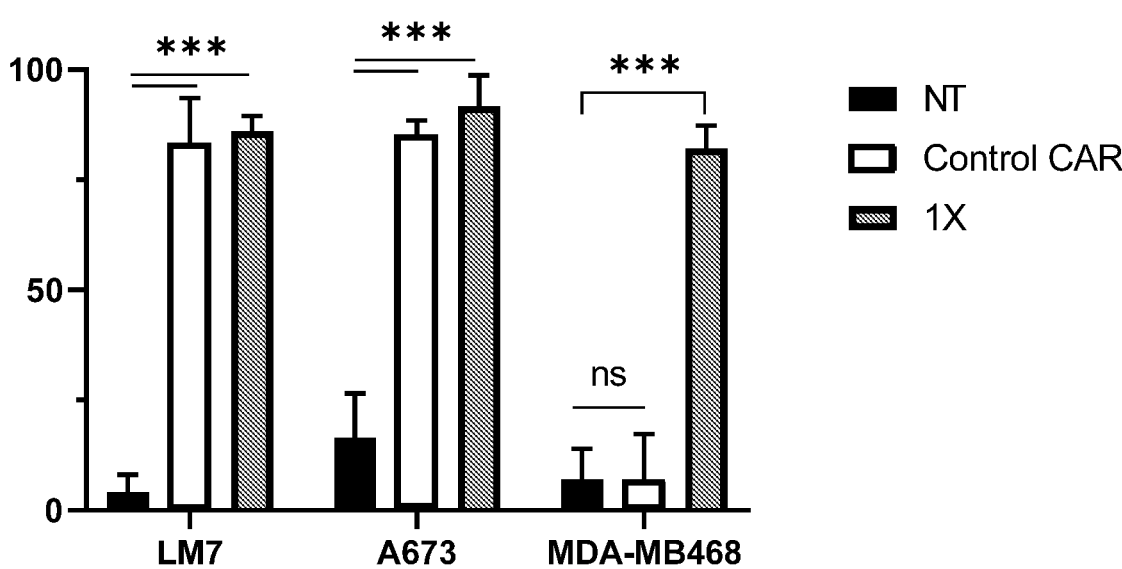
Figure 2G:
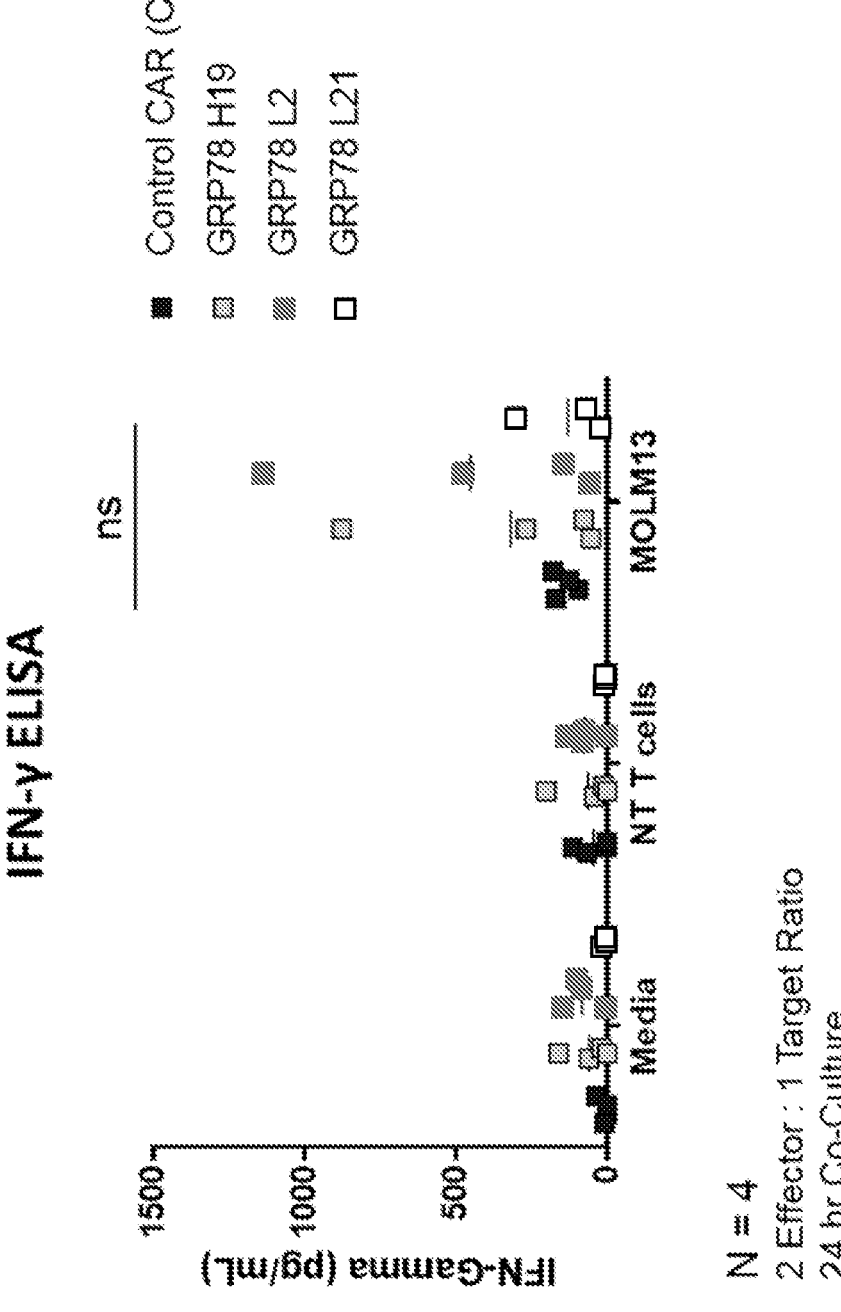
Figures 2H, 2I:
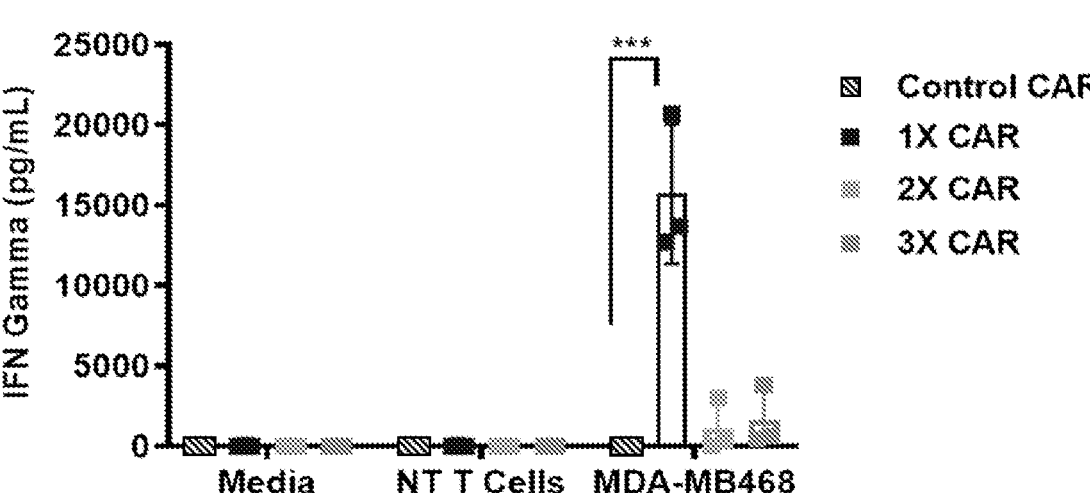

Because of the ability of the GRP78-binding peptide to bind GRP78 with a high degree of specificity and lack of activity of a GRP78-CAR using an scFv antigen as an antigen recognition domain, see FIGS. 2G and 2I, second generation GRP78-CAR constructs, see FIG. 1F, were prepared using the GRP78-binding peptide as an antigen binding domain. To investigate whether the number of peptide repeats used as the antigen binding domain influenced the ability the GRP78-CAR constructs to efficiently bind cell surface GRP78, three GRP78-CAR constructs comprising one (1×), two (2×), or three (3×) repeats of the GRP78-binding peptide (referred to as 1×GRP78-CAR (GRP78.1×-CAR), 2×GRP78-CAR (GRP78.2×-CAR), and 3×GRP78-CAR, respectively) were generated, see FIG. 1F.

The second generation GRP78-CAR constructs were subcloned into a pSFG retroviral vector. The constructs comprised an IgG heavy chain signal peptide, one (1×), two (2×), or three (3×) repeats of the 13-mer GRP78-binding peptide, a mutated IgG4 hinge [2-3] and CD28 transmembrane domain followed by a CD28 costimulatory and a CD3ζ activation domain. A truncated CD19 (tCD19) sequence separated by a T2A self-cleaving peptide was added to the retroviral vector as a surrogate marker for CAR transduction.

As a control, a GRP78-ΔCAR construct was generated by deleting the CD28 costimulatory and CD3ζ activation domains from GRP78.1×-CAR construct. The CD19 and FRP5 CARs used as controls have been previously reported [20-21]. The sequence of all cloned constructs was confirmed by sequencing performed by Hartwell Center DNA Sequencing Core at St. Jude Children's Research Hospital with Big Dye® Terminator (v3.1) Chemistry on Applied Biosystems 3730XL DNA Analyzers (Thermo Fisher Scientific, Waltham). RD114-pseudotyped retroviral particles were generated as described in Chow, K. K., et al. "T Cells Redirected to EphA2 for the Immunotherapy of Glioblastoma," Mol. Ther. 21, 629-637 (2013), the disclosure of which relating to formation of retroviral particles is incorporated herein in its entirety.

Example 3. Preparation of GRP78-CAR T Cells

GRP78-CAR T cells were prepared as follows. Human peripheral blood mononuclear cells (PBMCs) from healthy donors were obtained under a St. Jude Children's Research Hospital IRB approved protocol. PBMCs were stimulated on CD3 (1 μg/mL, Miltenyl Biotec, Bergisch Gladbach, Germany) and CD28 (1 μg/mL, Miltenyi Biotec, Germany) antibody-coated, non-tissue culture treated, 24-well plates (Corning). Human interleukin (IL) 7 (10 ng/mL, Peprotech, Rocky Hill, NJ) and IL-15 (5 ng/mL, Preprotech) were added to cultures on day 2, and on day 3 T cells were transduced with the retroviral particles comprising the GRP78-CAR constructs on RetroNectin (Takara Bio USA, Mountainview CA) coated plates in the presence IL-7 (10 ng/mL) and IL-15 (5 ng/mL). T cells were subsequently expanded with IL-7 and IL-15. Non-transduced (NT) T cells were activated with CD3/CD28 and expanded in parallel with IL7 and IL-15. Following expansion for 5-7 days transduced cells were analyzed for GRP78-CAR expression using flow cytometry and subsequently used for functional assays.

Figure 3A:
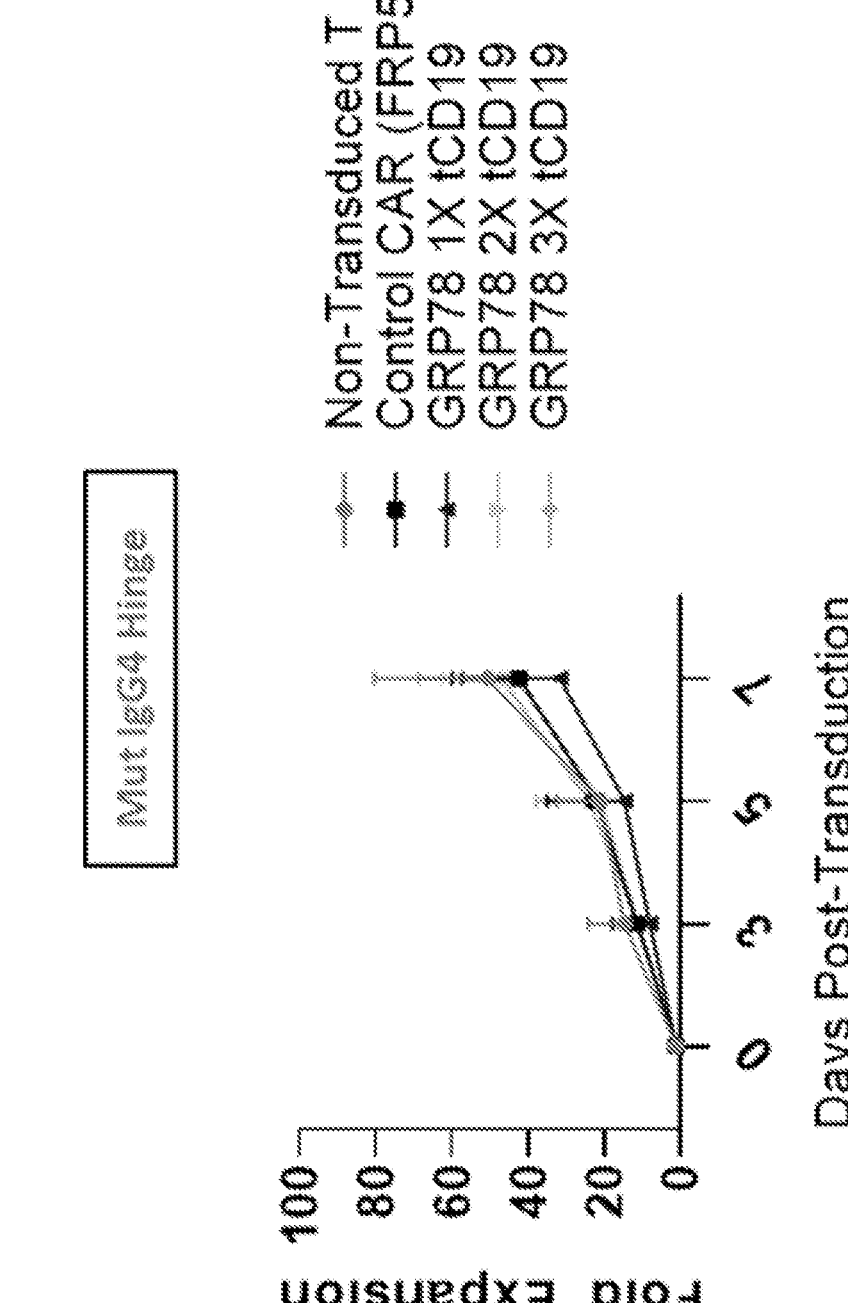
Figures 12A, 12B:
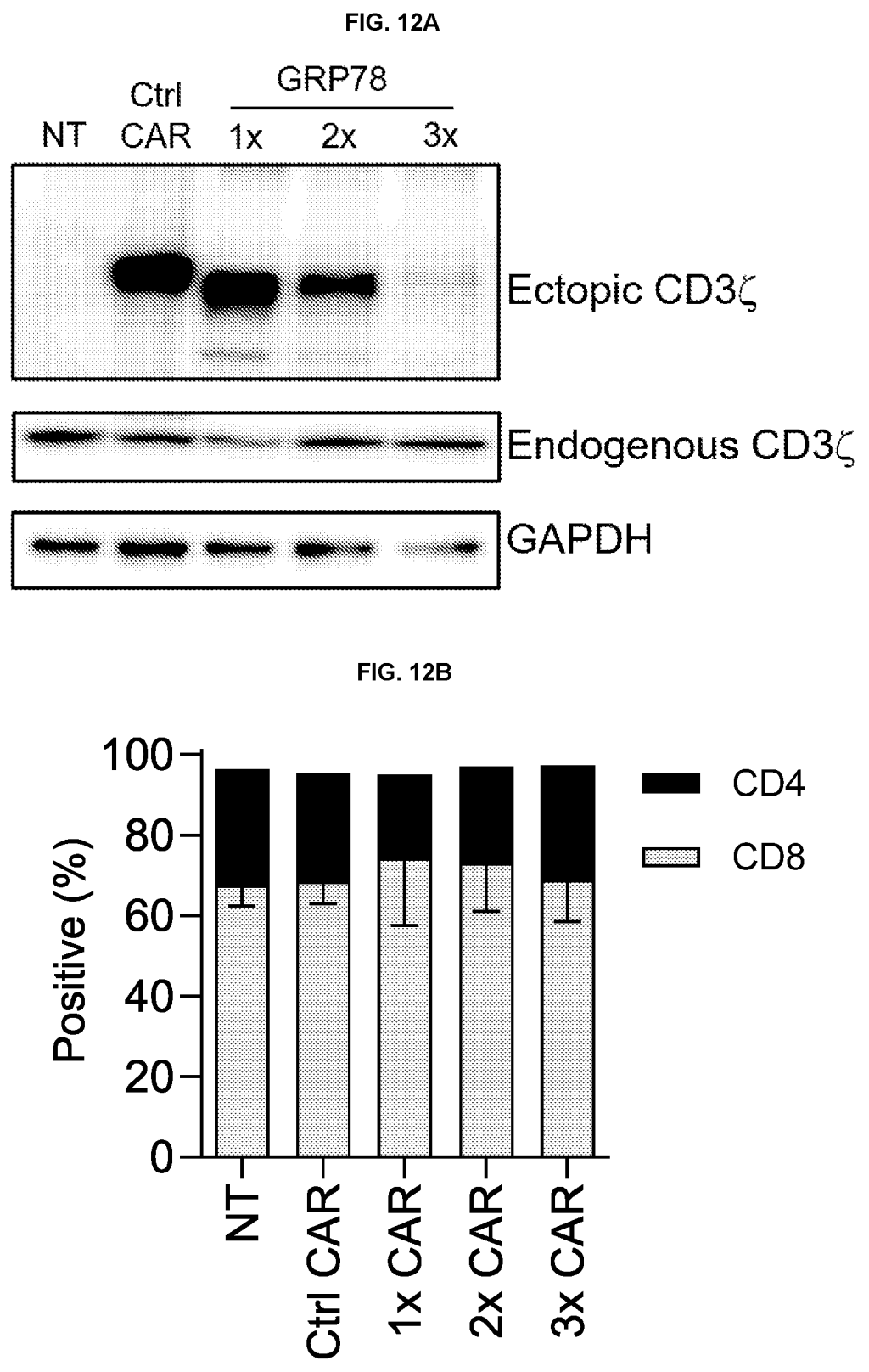

As shown in FIG. 2A, GRP78-CAR T cells were successfully generated using the respective GRP78-CAR constructs. Expression of GRP78-CARs in T-cells did not induce fratricide, and the median transduction efficiency was 82% (±5-8%, N=6). The GRP78.1×-CAR construct had the highest median transduction efficiency at 83% (±2%, N=6), see FIG. 2A. Higher levels of GRP78.1×-CARs were also confirmed by Western blot analysis (FIG. 12A). The 2×GRP78-CAR construct had a median transduction efficiency of 54% (±3%, N=6) and the 3×GRP78-CAR construct had a median transduction efficiency of 55% (±1%, N=6), see FIG. 2A. Expansion of all GRP78-CAR T cells was comparable to expansion of non-transduced cells (NT) (N=3 p=NS), see FIG. 3A. The viability of the CAR T cells was measured using trypan blue at different time points from days 2 to 9 post transduction, FIG. 3D. It was interesting to note that the viability of the 1× peptide CAR transduced cells was 15% lower than the 2×, 3× and FRP5 control CAR T cells. Not wishing to be bound by any theory, it is plausible that CAR transduction exerts some ER stress which allows for transient GRP78 elevation at the cell surface of CAR T cells resulting in low levels of fratricide in the 1× peptide CAR group. Immunophenotypic analysis revealed that all GRP78-CAR T cell populations had a CD4:CD8 ratio of ~1:2 (FIG. 12B), and CD4+ T cell subsets of all GRP78-CAR T cell populations and controls (NT, Control CAR) and CD8+ T cells of GRP78.2×- and GRP78.3×-CAR T cells displayed a predominantly naïve-like (CCR7+CD45 RA+) phenotype. Specifically, immunophenotypic analysis of GRP78-CAR T cells showed a predominance of naïve and terminal effector memory subsets on day 7 after transduction (N=5). CD4+GRP78-CAR T cell subsets for all constructs and CD8+GRP78-CAR T cells for the 2× and 3×GRP78-CAR constructs displayed a predominantly naïve phenotype CD4+, see FIG. 2B. The 1×GRP78-CAR (GRP78.1×-CAR) T cells showed a predominantly terminally differentiated effector memory phenotype (N=5), see FIG. 2B.

Example 4. Effector Function of GRP78-CAR T Cells In Vitro

To determine the effector function of the GRP78-CAR T cells in vitro the GRP78-CAR T cells were co-cultured in the presence of tumor cells (MOLM13, LM7, MDA-MB468) that express GRP78 on their cell surface (defined as being GRP78-positive) or normal cells (NT T cells) that do not express GRP78 on their cell surface (defined as being GRP78-negative). IFN-γ and IL2 production was measured after 18-24 hours of co-culture. T cells expressing CARs specific for HER2-, CD19-, or a non-functional GRP78 (GRP78-ΔCAR) and NT T cells served as negative controls. Only GRP78-CAR T cells co-cultured in the presence of GRP78-positive target cells secreted increased IFN-γ and IL-2 indicating antigen-dependent GRP78-CAR T cell activation; in contrast, control CAR T cells did not, see FIGS. 2C, 2D, and 2H. The 1×GRP78-CAR (GRP78.1×-CAR) construct induced statistically significantly increased IFN-γ and IL-2 secretion in comparison with the 2× and 3×GRP78-CAR constructs, see FIGS. 2C and 2D. These findings were confirmed in a luciferase-based cytotoxicity assay for MOLM13 suspension cells, see FIG. 2E, and in an MTS-based assay in a panel of cell surface GRP78+ solid tumors cell lines including A673, LM7, MDA-MB468, see FIG. 2F. GRP78-CAR T cells only killed GRP78+ target cells, thereby confirming specificity. Based on the results of the in vitro characterization assays, the 1×GRP78 CAR (GRP78.1×-CAR) construct was selected for further analyses.

Next, the above-described in vitro studies were extended to other GRP78+AML cell lines (MV-4-11, THP-1) and three AML PDX samples. GRP78.1×-CAR T cells produced significantly increased amounts of IFN-γ in the presence of MV-4-11 THP-1 AML cells and PDX samples (FIGS. 13A-13B) while GRP78.ΔCAR and Ctrl CAR T cells did not. In addition, MV-4-11 and THP-1 AML cells were recognized

Figures 13C, 13D:
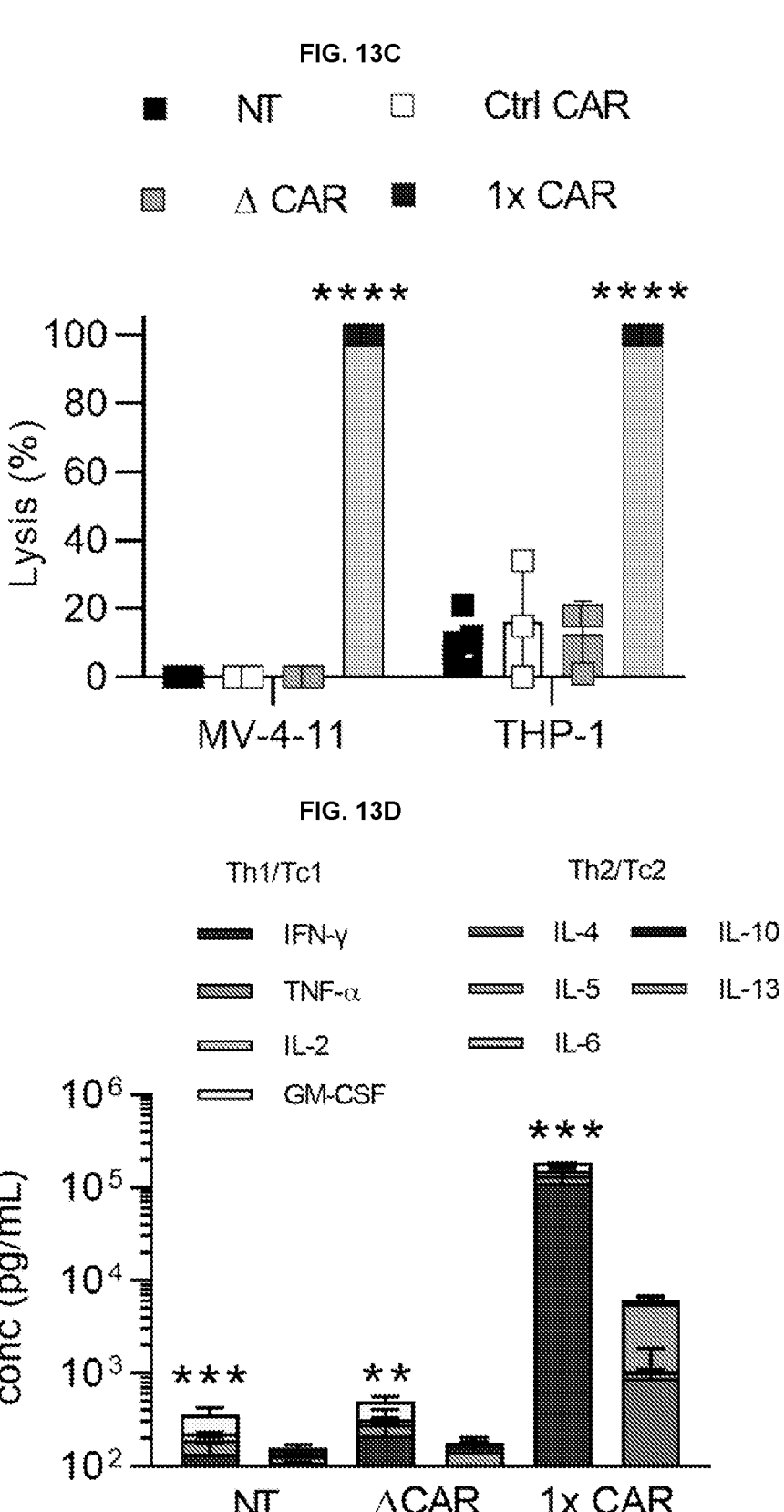

57 and killed by GRP78.1x-CAR T cells when evaluated in a luciferase-based cytotoxicity assay (FIG. 13C). To determine if GRP78.1x-CAR T cells secrete other cytokines than IFN-γ and IL-2, MV-4-11 were co-cultured with NT, GRP78. ΔCAR, or GRP78.1x-CAR T cells and determined the expression of Th1/Tc1 (IFN-γ, TNF-α, GMCSF, IL-2) and Th2/Tc2 (IL-4, IL-5, IL-6, IL10, IL13) cytokines. GRP78.1x-CAR T cells secreted significantly more Th1/Tc1 and Th2/Tc2 cytokines (FIG. 13D). Thus, GRP78-CAR T cells that produce cytokine and kill AML cells in an antigen-dependent manner were successfully generated.

Example 5. In Vitro Effector Function of CAR T Cells Expressing Anti-GRP78 CAR Comprising an scFv Antigen-Binding Domain GRP78-CARs comprising an scFv antigen-binding domain (scFv CAR constructs) were generated using scFvs derived from anti-GRP78 antibodies H19, L2, or L21. Each of the scFv CAR constructs comprised a CD8α leader, a GRP78 H19, GRP78 L2, or GRP78 L21 scFv as an antigen binding domain, a CD8α hinge/transmembrane domain followed by a 41BB costimulatory and a CD3ζ activation domain. A Q8 sequence separated by a self-cleaving E2A ribosomal skip peptide was added to the CAR constructs as a surrogate marker for CAR transduction.

To determine the effector function of CAR T cells expressing anti-GRP78 scFv CAR in vitro, T cells expressing GRP78 H19 CAR, GRP78 L2 CAR, or GRP78 L21 CAR were each individually co-cultured in the presence of GRP78-positive (MOLM13, LM7, MDA-MB468) or GRP78-negative target cells (NT T cells) and IFN-γ production was measured after 24 hours. The effector cell to target cell ratio was 2:1. T cells expressing the scFv CAR constructs demonstrated only moderate effector function (N=4, ns) in vitro and, therefore, unexpectedly showed effector function that was inferior to that of the GRP78 peptide CAR T cells, see FIGS. 2G, 2I.

Figure 3C:
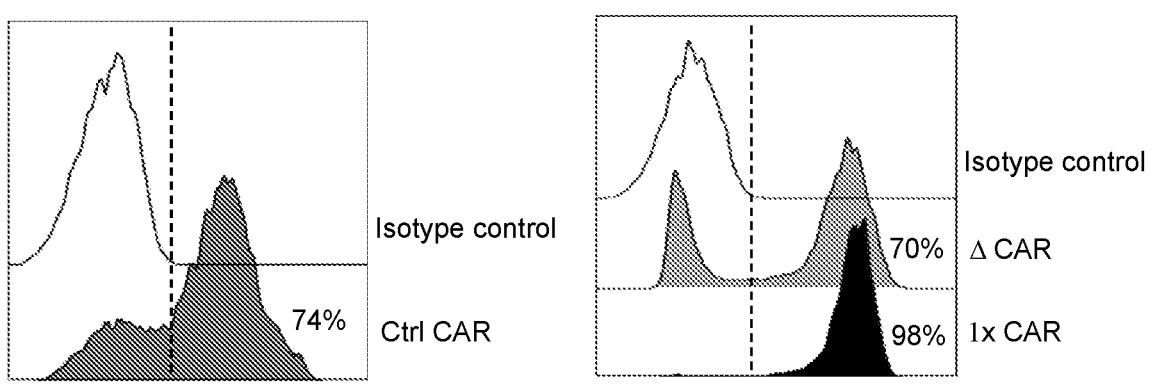
Figure 3D:
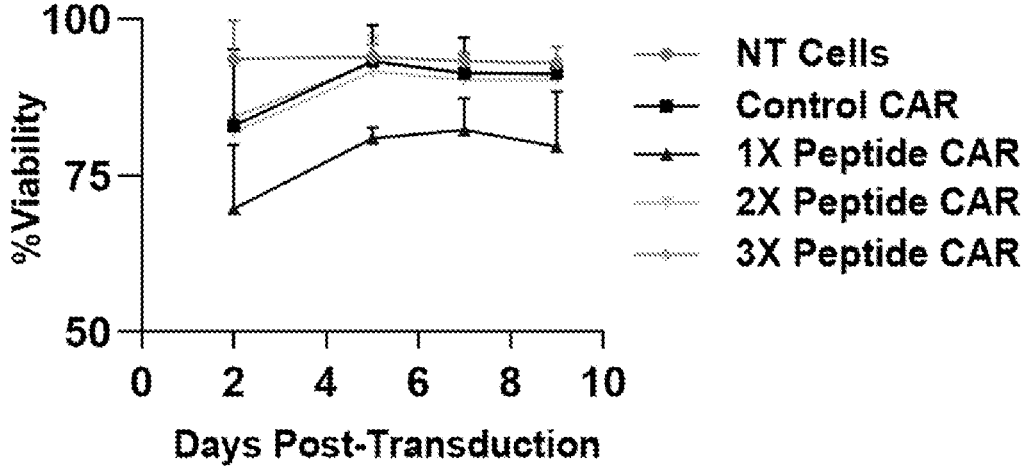

Example 6. Binding of Cell Surface GRP78 is not Sufficient to Induce Tumor Cell Death A control GRP78-ΔCAR construct, see upper panel of FIG. 3B, was prepared which comprises the GRP78-binding peptide for antigen recognition but lacks the CD28 costimulatory and the CD3ζ signaling domain. Flow cytometric analysis of GRP78-ΔCAR expression where control CAR- and NT T cells were used for isotype controls is shown in FIG. 3C. GRP78-ΔCAR T cells co-cultured with GRP78-positive MOLM13 cells, see bottom panel of FIG. 3B, did not exhibit any antitumor activity, confirming that binding of cell surface GRP78 is insufficient to induce tumor cell death, and that the cytotoxic potential of the GRP78-CAR is mediated by antigen-dependent CAR T cell activation.

Example 7. Evaluation of Myelotoxicity of GRP78-CAR T Cells

CFU assays were performed to evaluate the myelotoxic potential of GRP78-CAR T cells by coculturing them in the presence of bone marrow derived CD34+ myeloid progenitor cells. Burst forming unit-erythroid (BFU-E), colony-forming unit-granulocyte/macrophage (CFU-GM), and colony-forming unit-granulocyte/erythroid/macrophage/ megakaryocyte (CFU-GEMM) content was measured in the GRP78-CAR T cell treatment groups. GRP78-CAR T cells did not exhibit statistically significant myelotoxicity compared to the NT T cells or control GRP78-ΔCAR T cells, see FIG. 3E.

Example 8. Efficacy of CRP78-CAR T Cells in Xenograft Models

Figure 4A:
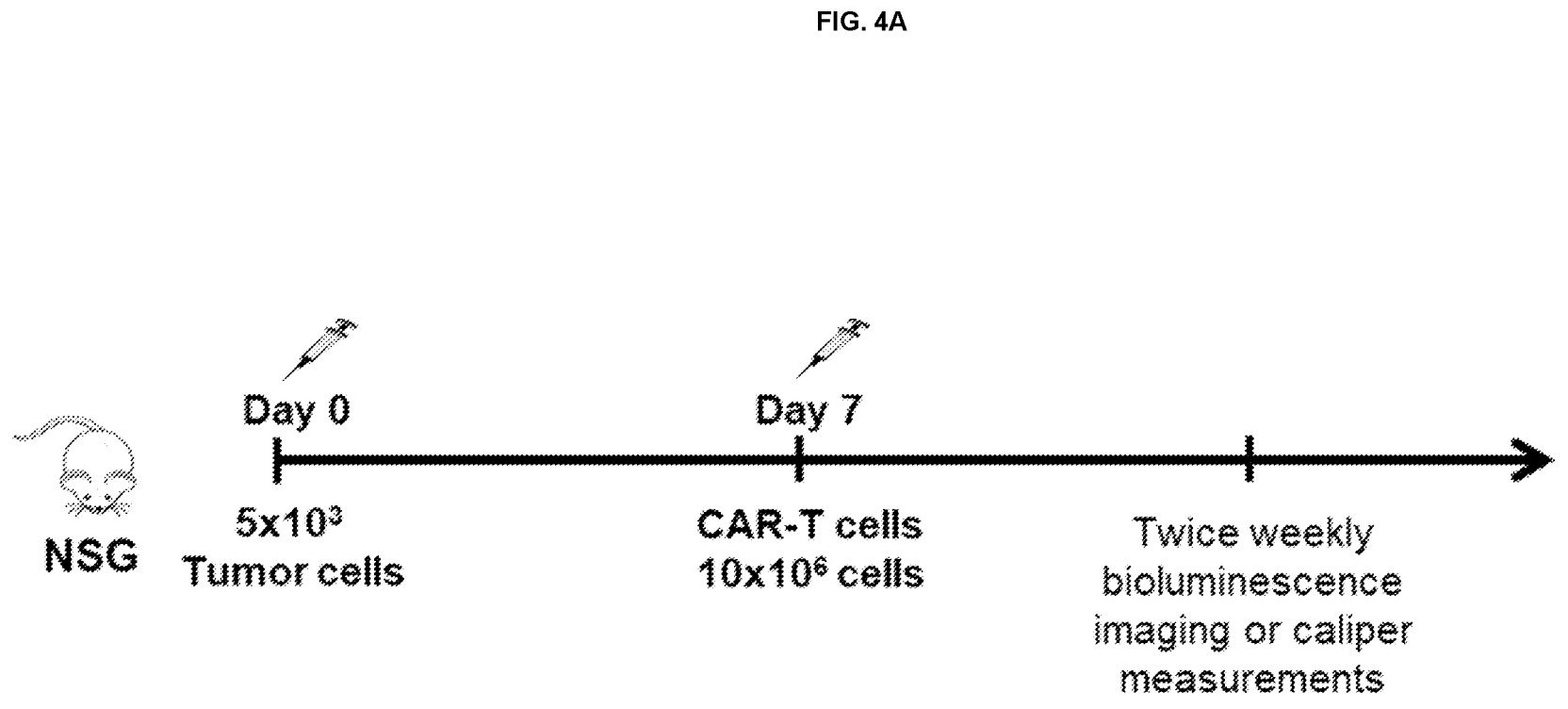
Figure 4B:
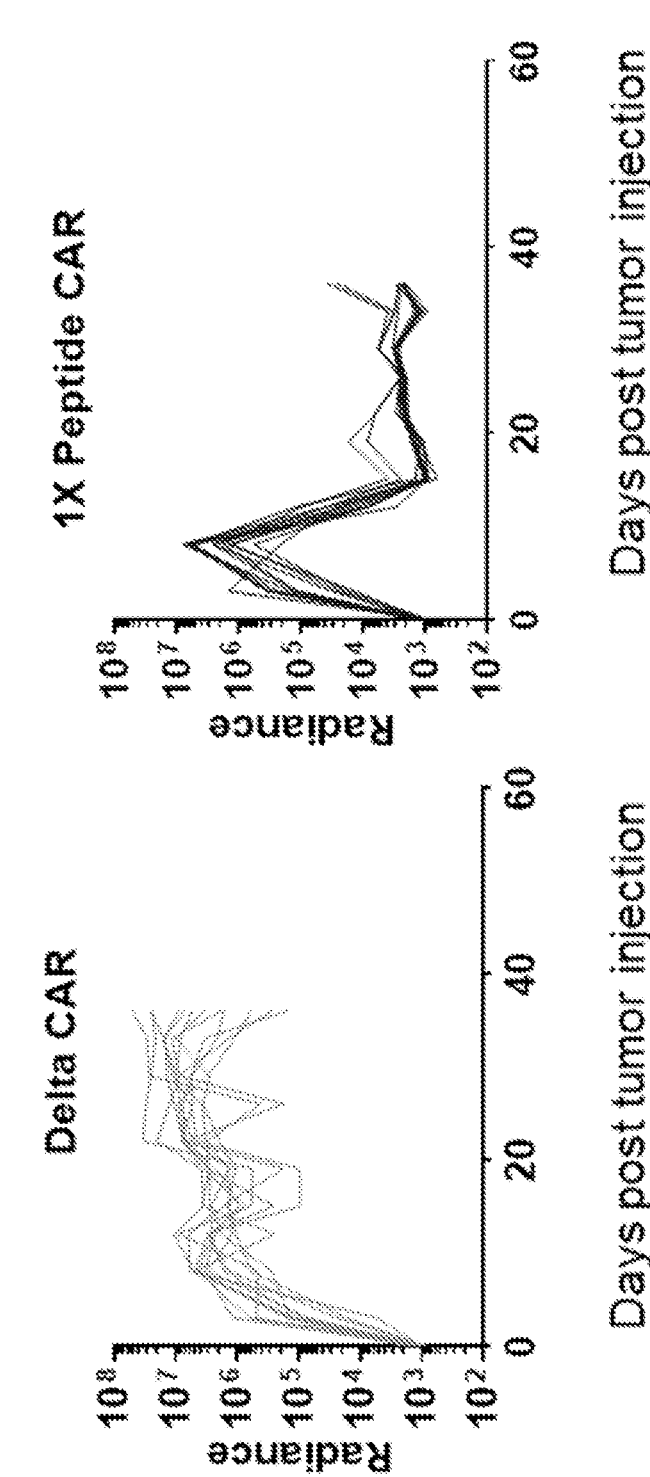

Elevated cell surface expression of GRP78 is seen in a broad range of tumor types and results in chemoresistance and poor prognosis [7-9] This elevated cell surface expression of GRP78 allows for targeting tumors using the GRP78-CAR. To test efficacy of the GRP78-CAR in other tumors the GRP78-CAR T cells were evaluated using in vivo AML and solid tumor xenograft models (MOLM13, A673, MDA-MB468). In these models, the animals received either subcutaneous or mammary fat pad injection of tumor cells. Seven days later, the animals were injected with CAR T cells. Tumor progression was measured using weekly bioluminescence imaging or caliper measurements, see FIG. 4A. In all three xenograft models (N=10 per group), a single intravenous dose of GRP78-CAR T cells induced tumor regression, which resulted in a significant (p<0.001) survival advantage in comparison to mice that had received control CAR T cells. T cells expressing GRP78-ΔCAR served as negative control CAR T cells.

Figure 4C:
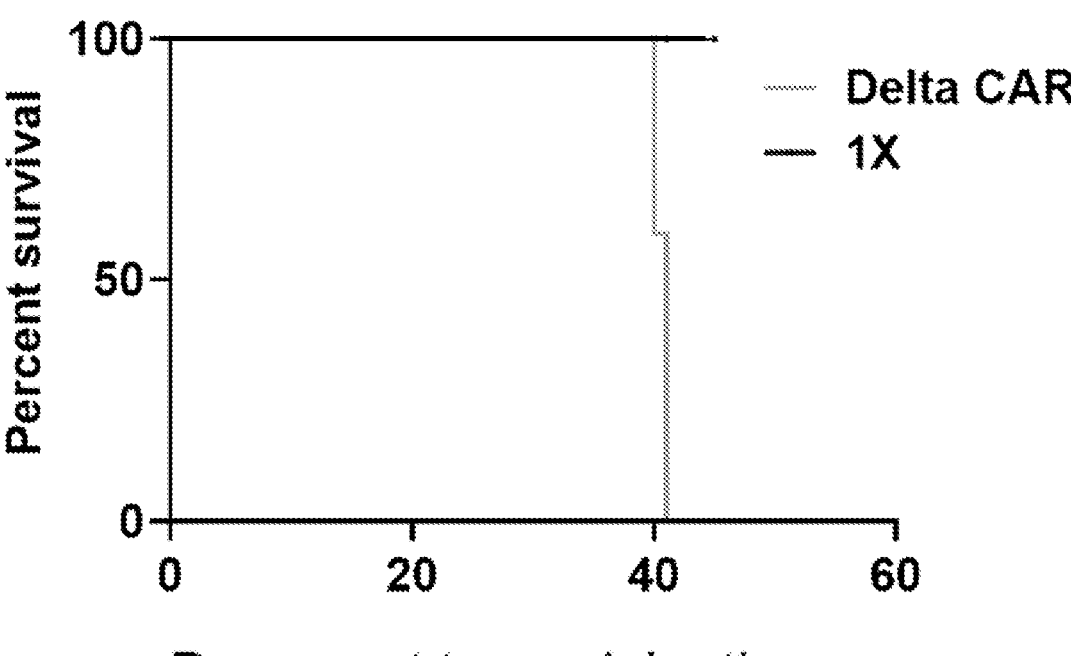
Figure 4D:
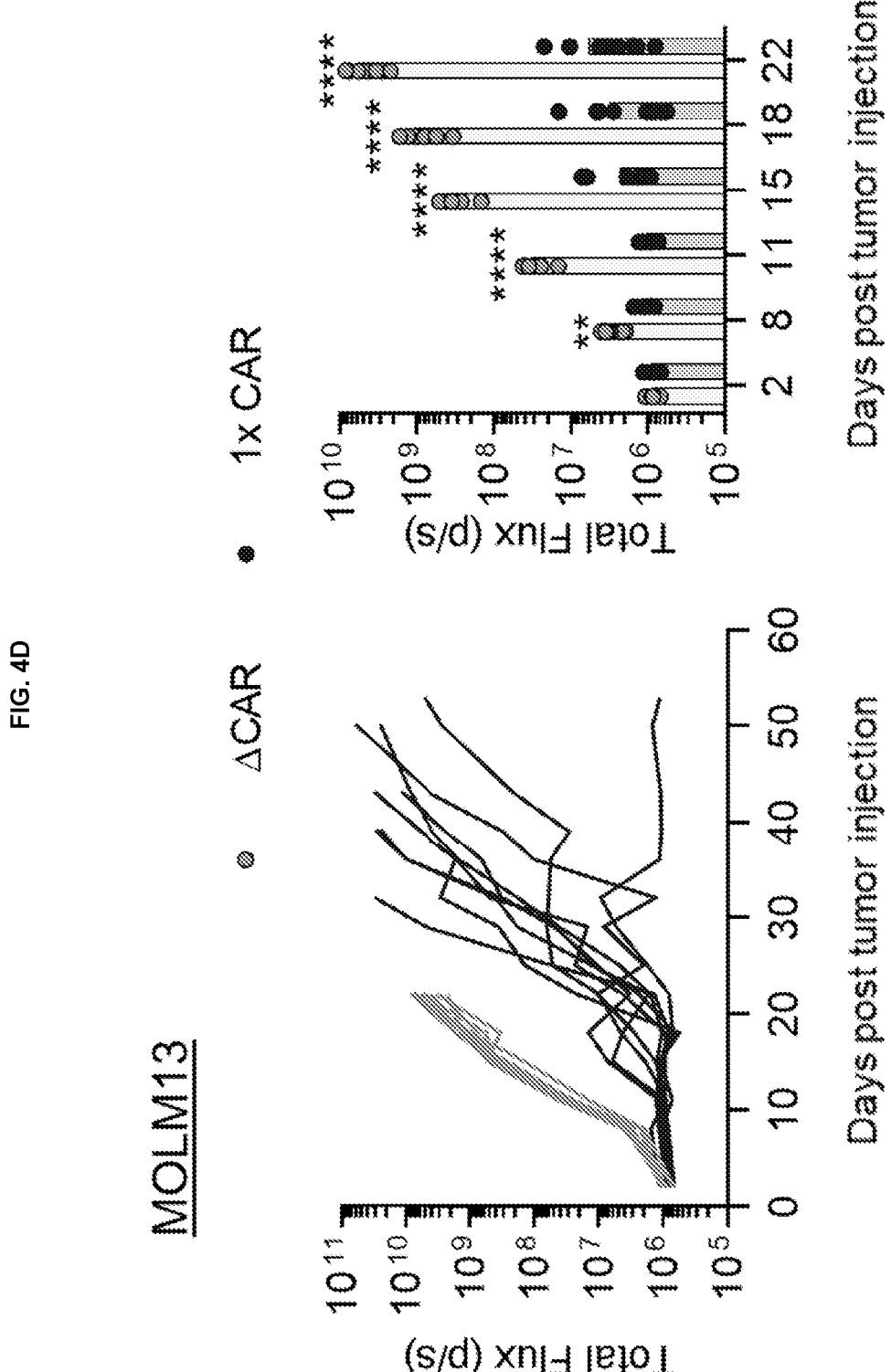
Figure 4E:
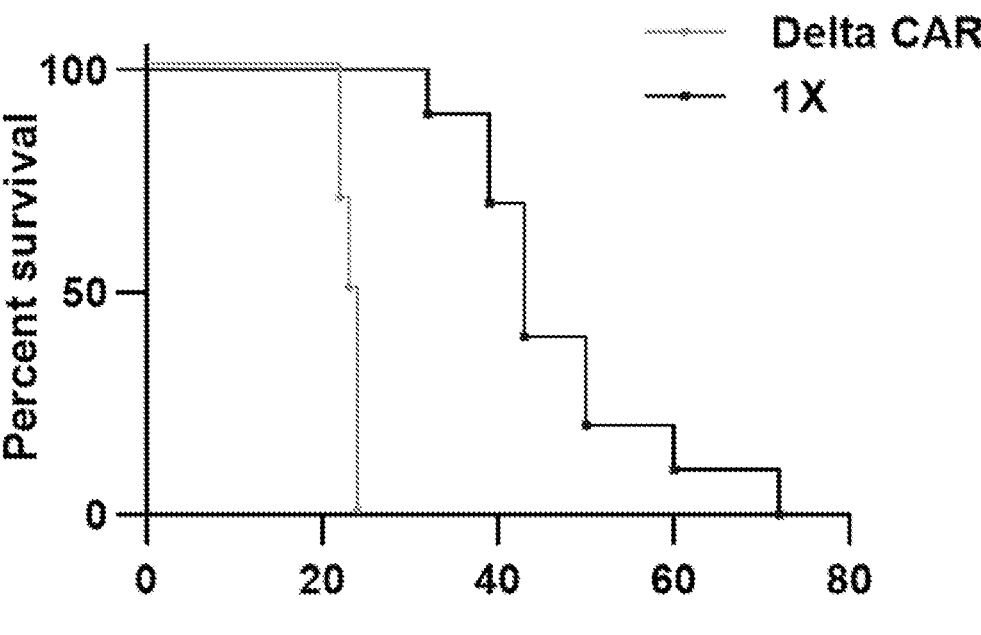
Figure 5A:
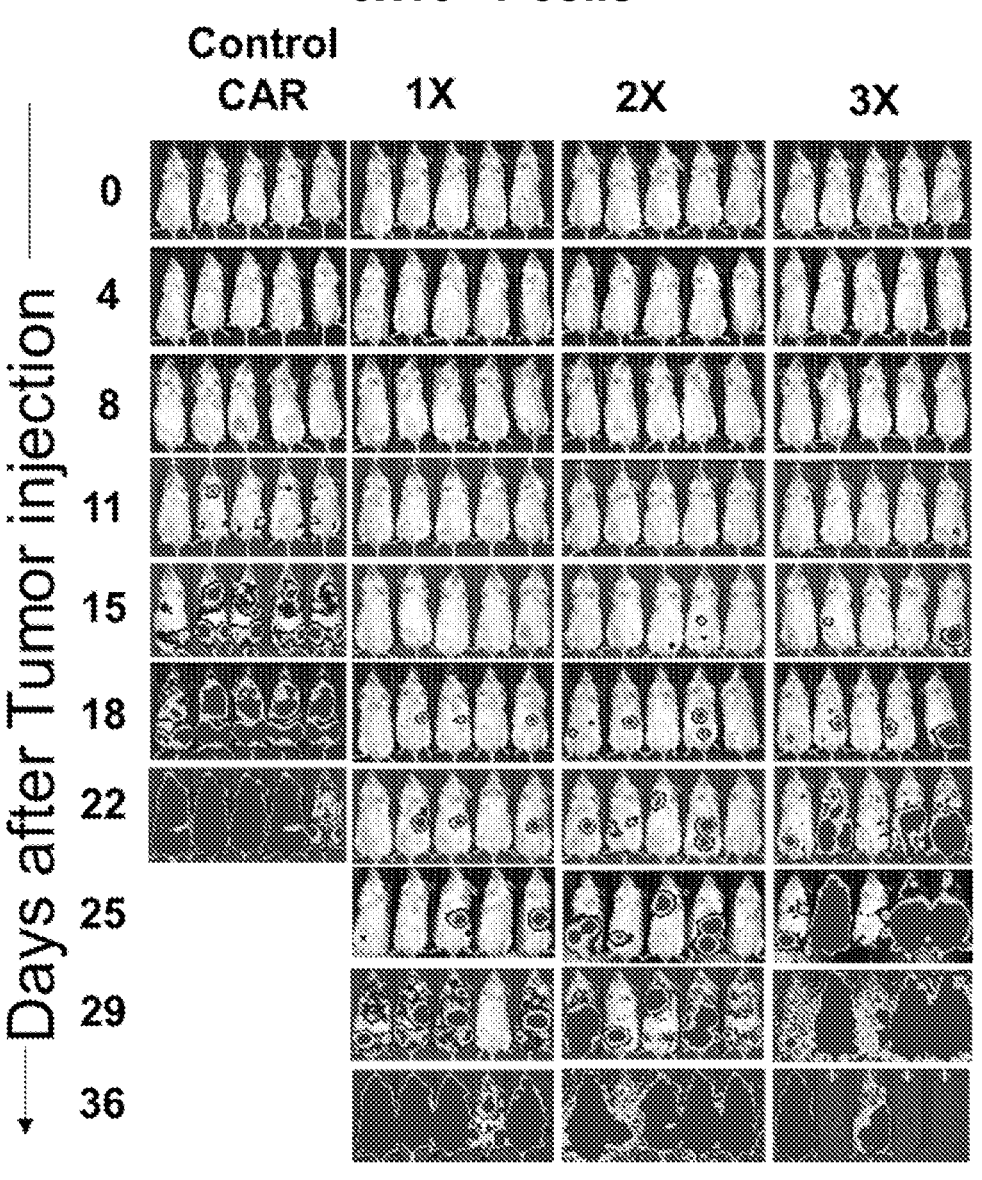
FIGS. 5A-5F demonstrate efficacy of the GRP78-CAR T cells as effector cells in vivo targeting acute myeloid leukemia (AML) and solid tumor models.
Figure 5B:
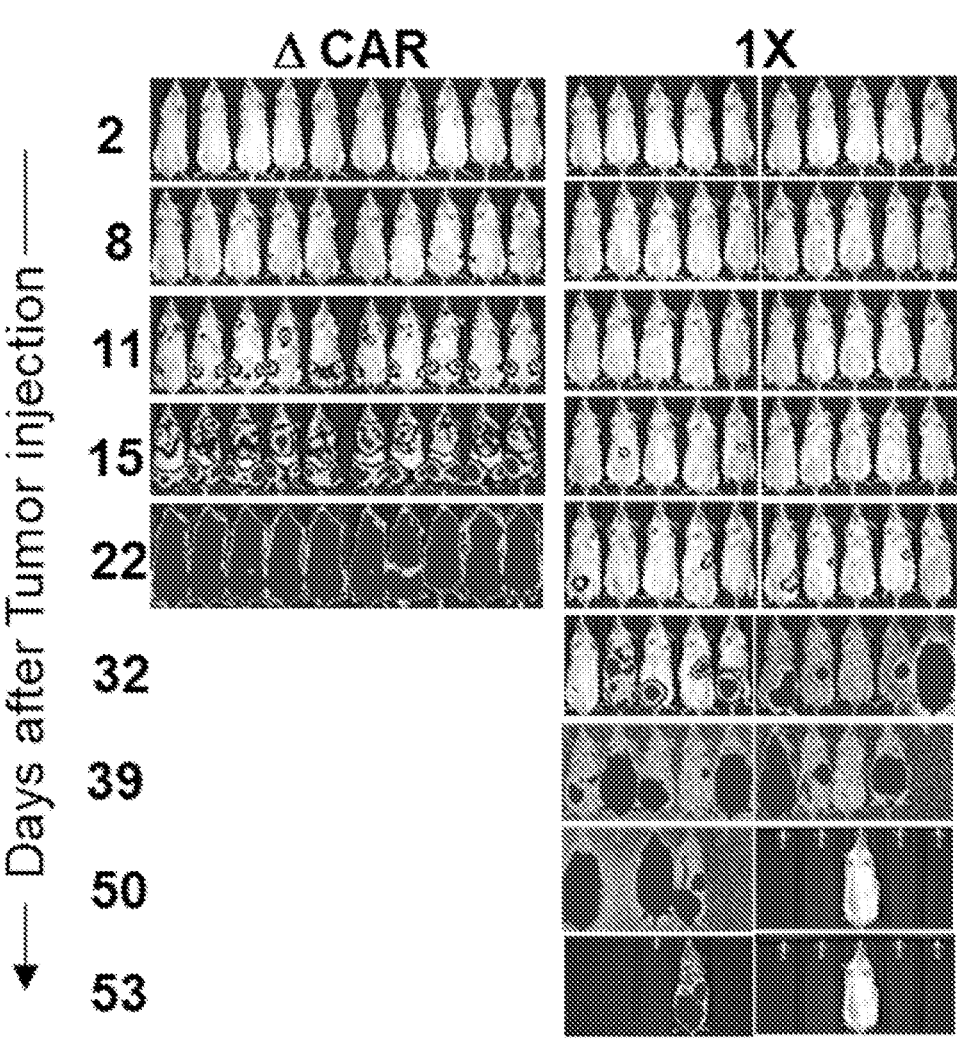
Figure 5C:
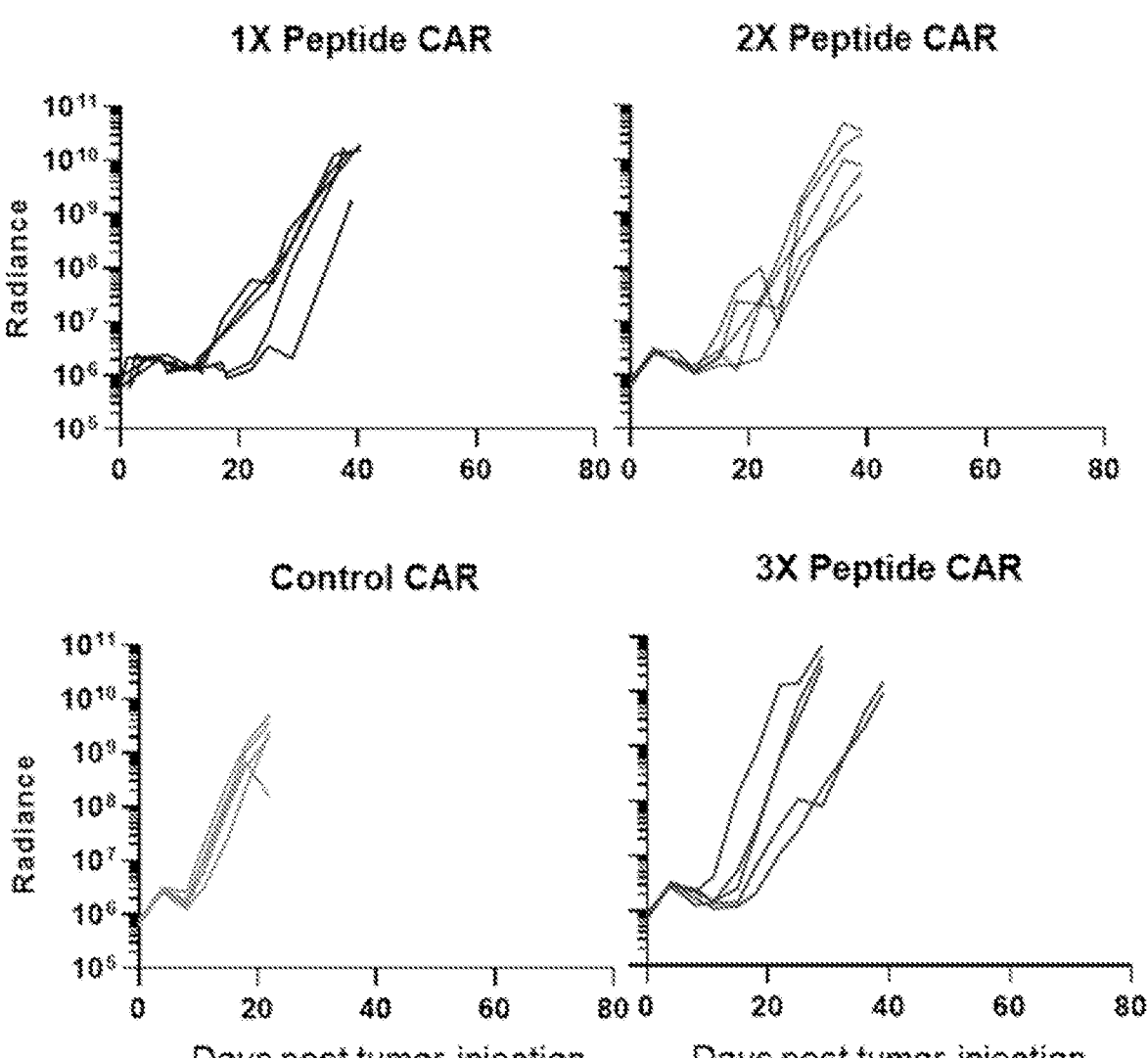
Figure 5D:
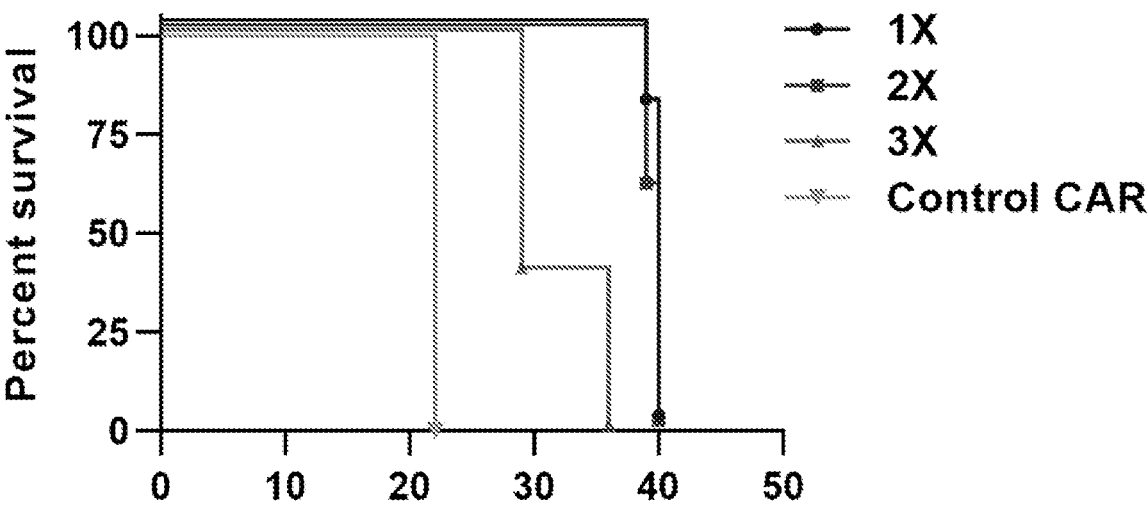
Figure 15:
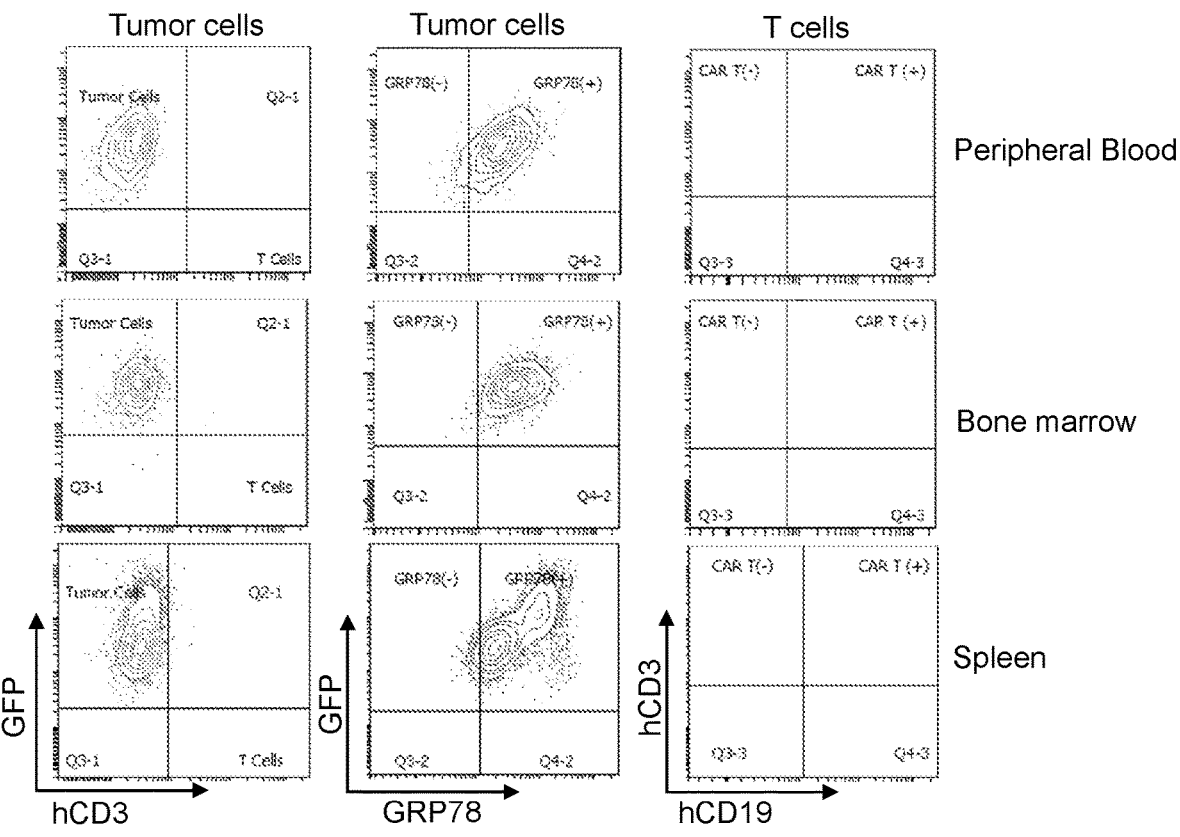
FIG. 15 demonstrates AML progression was due to lack of CAR T cell persistence and not to the development of antigen loss variants. For generation of these data, peripheral blood, spleen and bone marrow was collected from mice on days 39-45 post tumor injection. Single cell suspensions were stained for GRP78, hCD3, and hCD19 and analyzed by flow cytometry to determine the presence of cell surface GRP78+ MOLM13 cells as well as CAR T cells; representative dot plots are shown.

Antitumor efficacy of GRP78-CAR T cells was determined in a highly aggressive AML NSG model using MOLM13 cells expressing firefly luciferase (MOLM13.ffluc), see FIG. 4D. The treatment groups received one of two different doses ($10\times10^6$ and $3\times10^6$) of either control or GRP78-CAR T cells. The GRP78-CAR T cells showed significant anti-AML activity in contrast to the control CAR T cells at both the doses, see FIGS. 4E and 5A-5C. A statistically significant increase in survival was observed in both studies (p value<0.005), see FIG. 4E and FIG. 5D. While GRP78-CAR T cell treated mice at the $10\times10^6$ dose had a significant increase in survival as compared to mice that had received control- or GRP78.ΔCAR T cells (p<0.0001), AML eventually progressed, see e.g., FIG. 4E and FIG. 5B. Progression was due to lack of CAR T cell persistence and not the development of antigen loss variants, since recurrent AML cells continued to express cell surface GRP78, and CAR T cells were not detected in the peripheral blood, bone marrow, and/or spleen at the time of relapse (FIG. 15).

The efficacy of GRP78-CAR T cells in an orthotopic TNBC model was evaluated by injecting MDA-MB468 cells ($0.5\times10^6$ cells/mouse) expressing firefly luciferase (MDA-MB468.ffluc) into the mammary fat pad of NSG mice. The animals subsequently received $10\times10^6$ of either GRP78-CAR T cells or control CAR T cells locally. The group treated with GRP78-CAR T cells achieved complete remission as compared to the control treatment group, see FIG. 4B. This translated into statistically significant extension of overall survival by 50 days (p value<0.0001, N=12) (FIG. 4C).

Figure 4F:
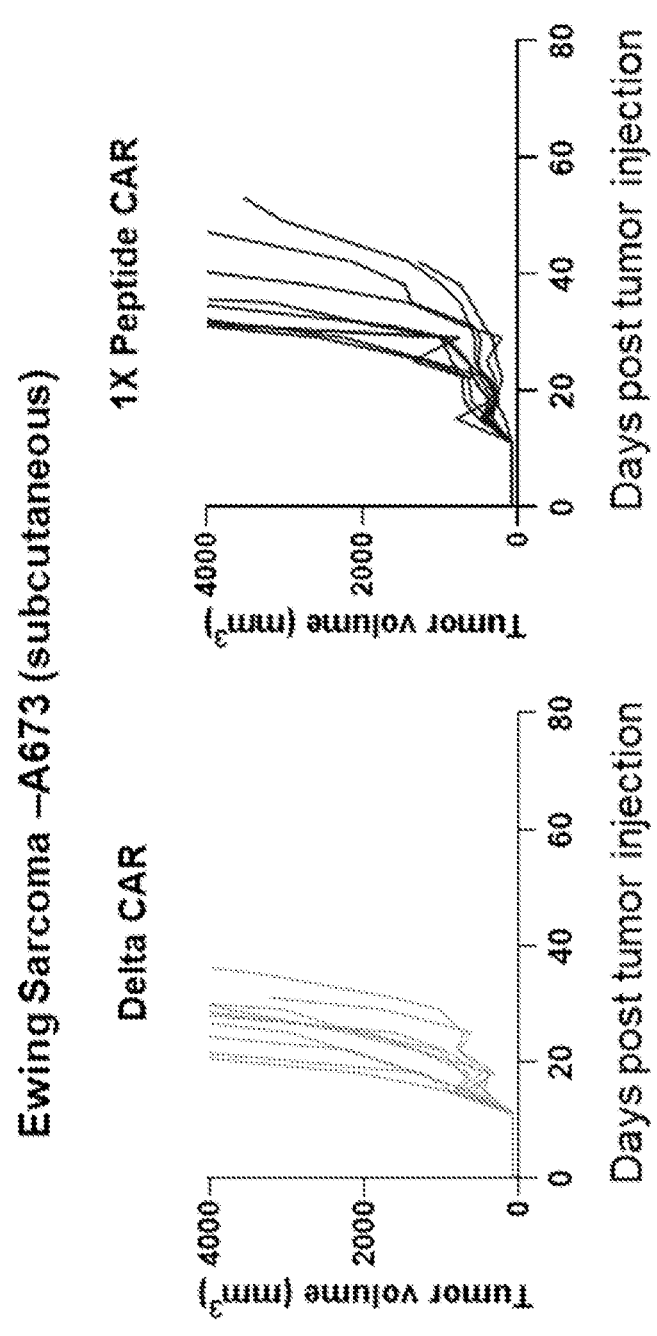
Figure 4G:
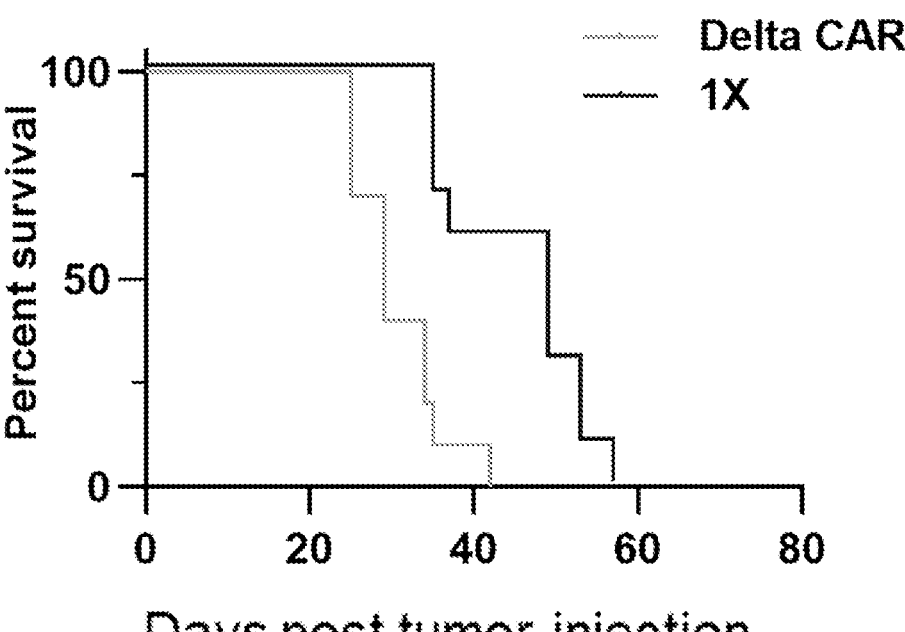
Figure 5E:
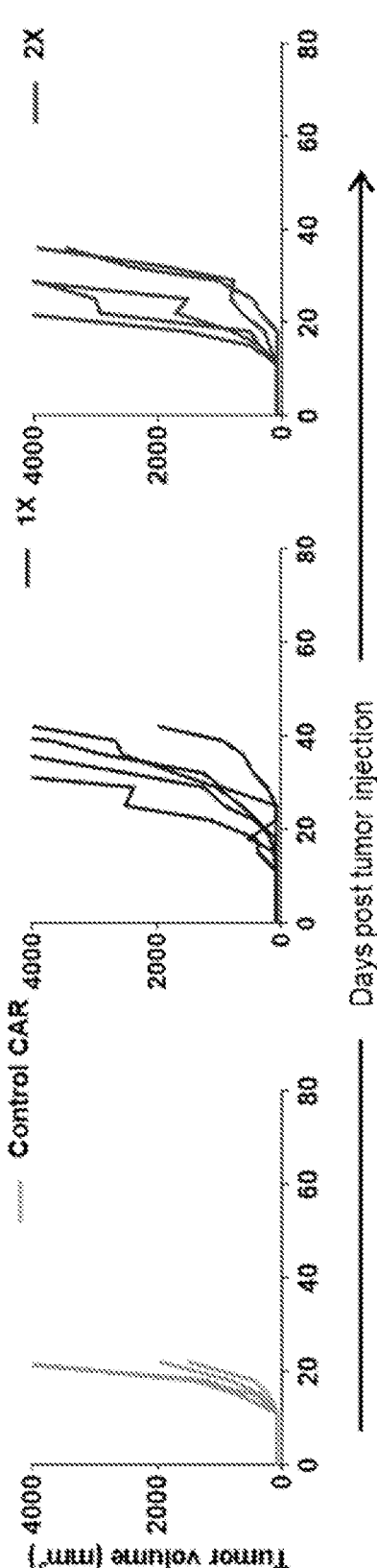
Figure 5F:
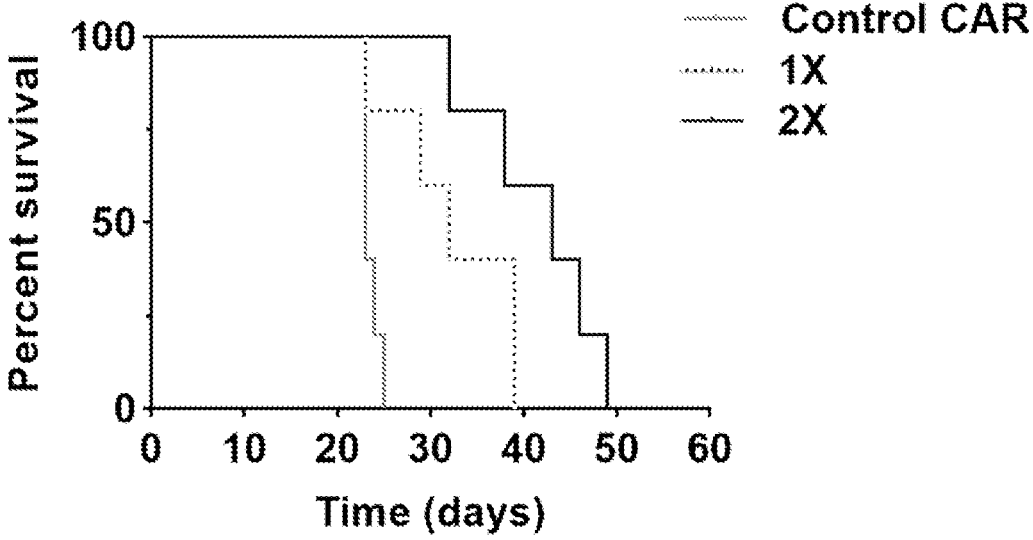

The efficacy of GRP78-CAR T cells in a subcutaneous Ewings sarcoma model, a highly metastatic pediatric tumor [10] was determined, see FIG. 4F. The animals were injected with A673 cells and treated with either $10\times10^6$ or $3\times10^6$ CAR T cells. Animals treated with GRP78 CAR T cells had statistically significantly reduced tumor volumes compared to the control treatment group (N=10, p=0.0002, see FIGS. 4F and 5E. At both doses, the GRP78 CAR T cells were able to significantly improve survival (N=5 p=0.0001), see FIGS. 4G and 5F. Surprisingly, mice treated with the lower dose of

59

$3\times10^6$ GRP78-CAR T cells showed improved survival compared to the mice treated with the higher GRP78-CAR T cell dose.

Figure 10A:
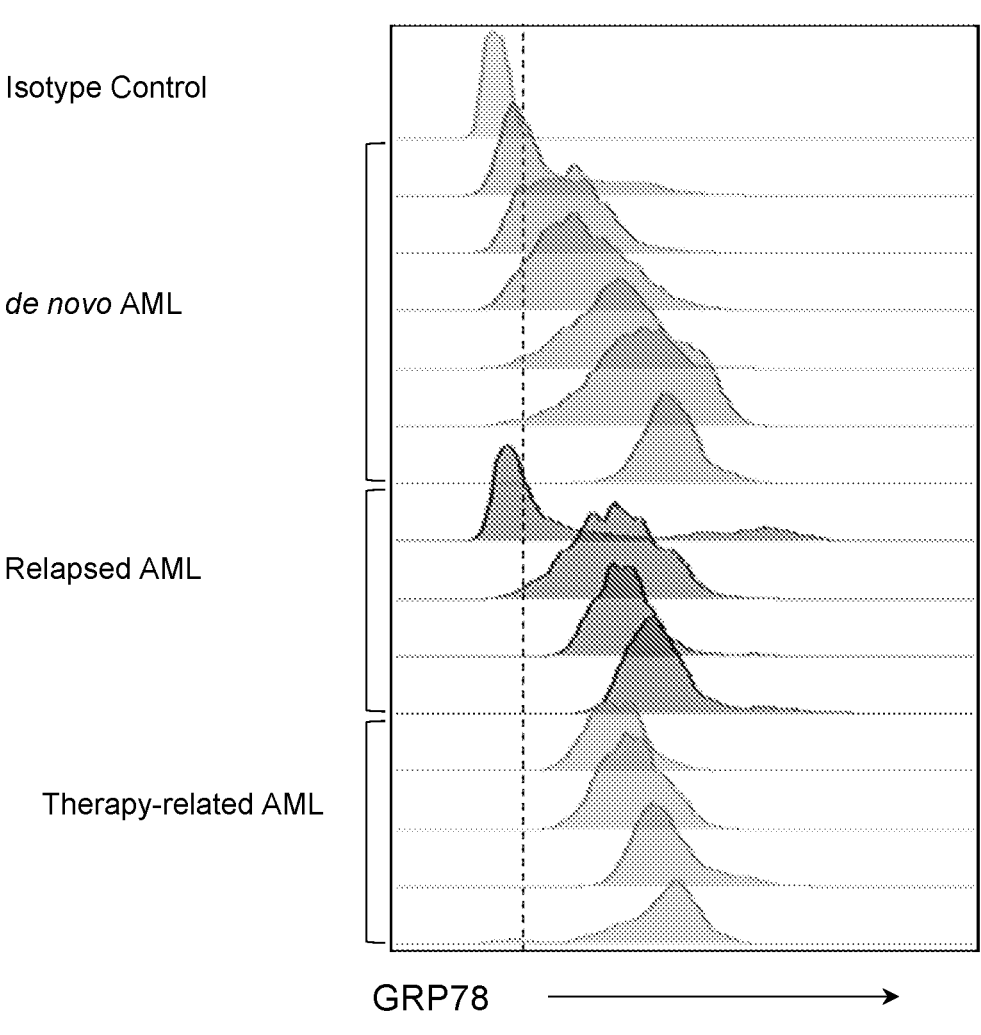
FIGS. 10A-10D demonstrate GRP78 expression on the cell surface on primary AML blasts and PDX samples by flow cytometry.
Figure 10B:
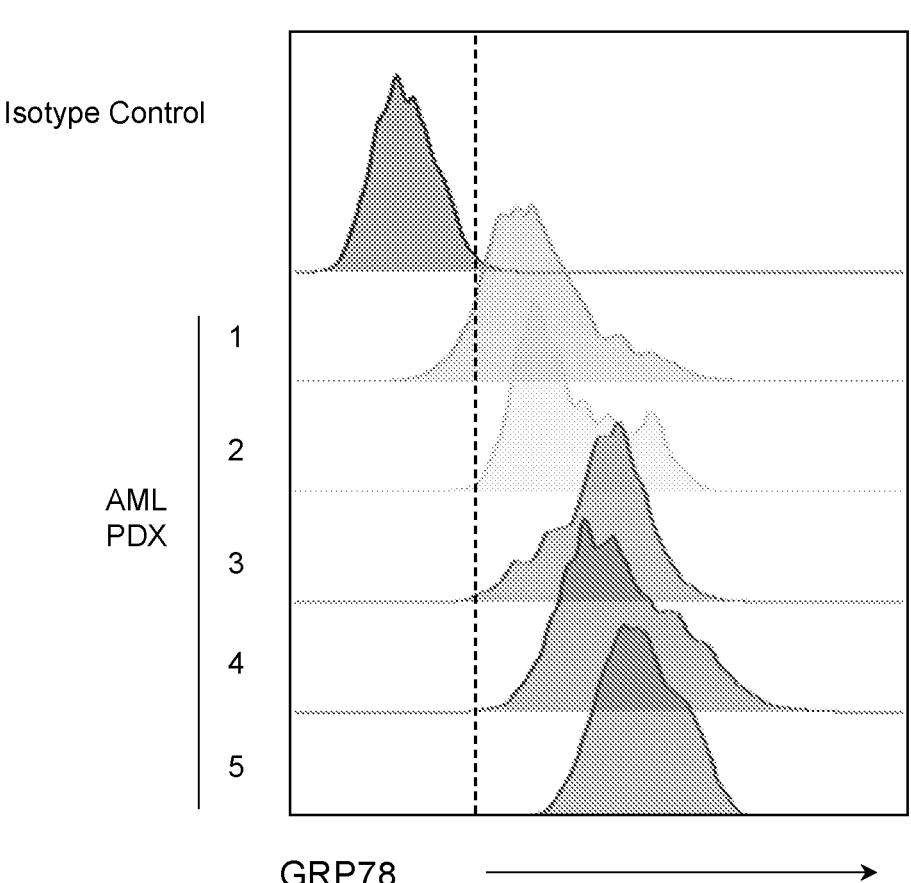
Figure 10C:
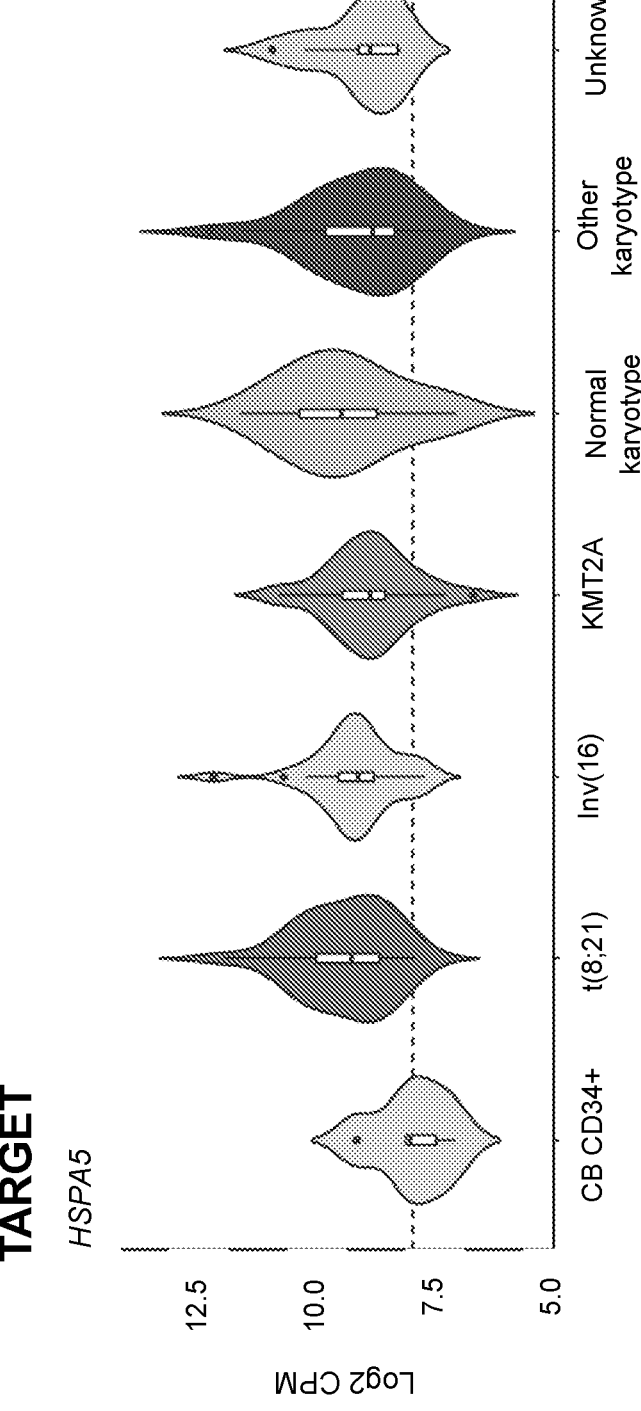
Figure 10D:
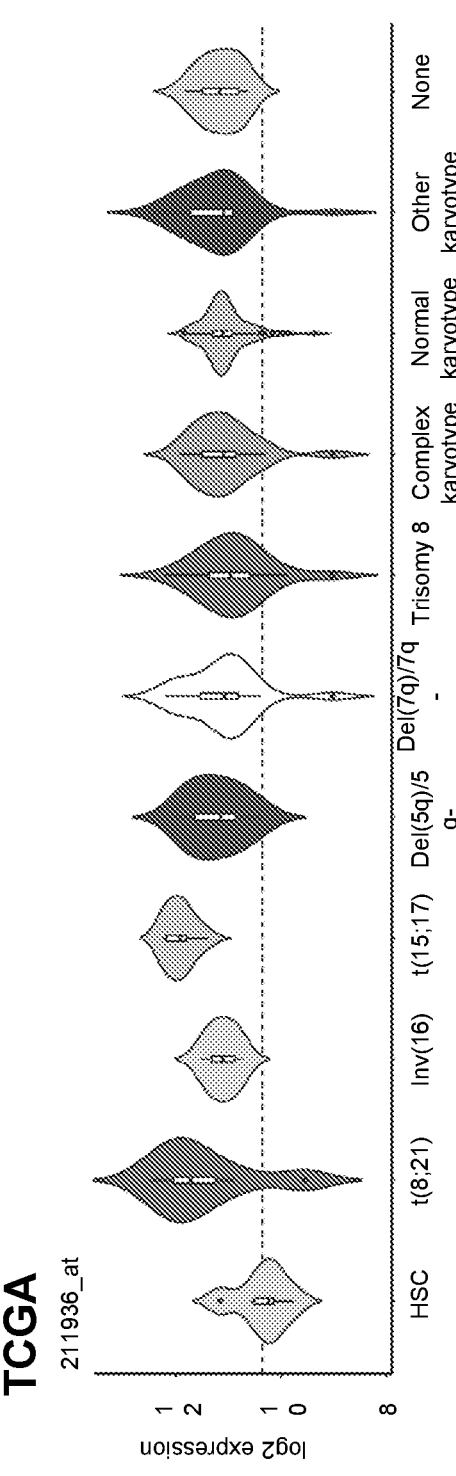

Example 9. GRP78 is Expressed on the Cell Surface on Primary AML Blasts and PDX Samples To demonstrate cell surface expression of GRP78, flow cytometry of AML cell lines (KG1a, MOLM13, THP-1, MV4-11) was initially performed using an antibody specific for the ER retention sequence (KDEL (SEQ ID NO: 92)) at the C-terminus of GRP78 or a biotin-conjugated peptide (Biotin-Ahx-CTVALPGGYVRVC (SEQ ID NO: 71)) that specifically binds GRP78 [1]. All AML cell lines expressed higher levels of cell surface GRP78 in comparison to non-transduced (NT) T cells and CD34+ adult bone marrow cells, which served as control (See Example 1). In the present experiment, it was then further demonstrated that GRP78 was highly expressed on the cell surface of >50% of 14 primary AML samples screened (de novo: N=6, relapsed: N=4, therapy-related: N=4) (FIG. 10A), and in all 5 AML PDX samples (FIG. 10B). To demonstrate that GRP78 was also overexpressed in AML blasts by gene expression analysis, samples from three publicly available databases were utilized (RNAseq from TARGET [28](pediatric): N=159; microarray data from TCGA [29] (adult): N=244 and MILE study [30] (adult and pediatric): N=252, downloaded from Bloodspot [31] (FIG. 10C and FIG. 10D, FIG. 11) in comparison to cord blood (CB) for RNAseq or HPC from adult bone marrow [32] for microarray. GRP78 was differentially overexpressed in pediatric AML blasts, independently of the underlying mutation in all samples (TARGET: AML subgroup vs. CB CD34+p<0.05) (FIG. 10C). Likewise, GRP78 was expressed at significant higher levels in AML blasts of all subtypes present in the MILE study (p<0.0001) (FIG. 11) and TCGA database (p<0.05) with the exception of the Trisomy 8 TCGA subgroup (p=0.0875) (FIG. 10D).

Figure 14A:
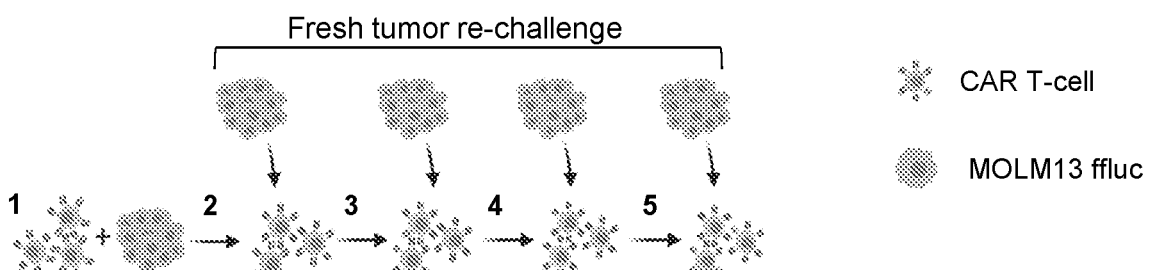
FIGS. 14A-14C show GRP78-CAR T cells sequentially kill tumor cells and secrete cytokines.
Figure 14B:
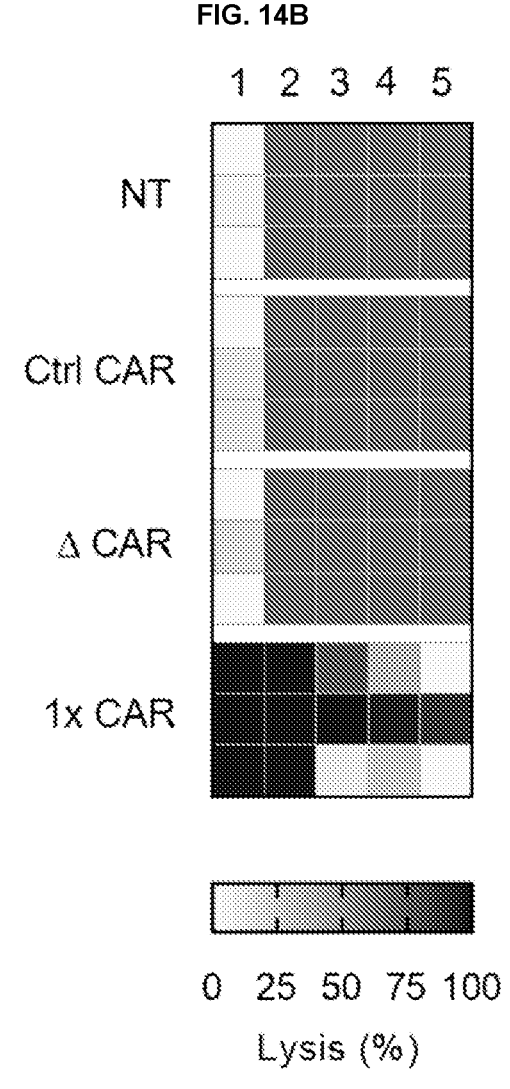
Figure 14C:
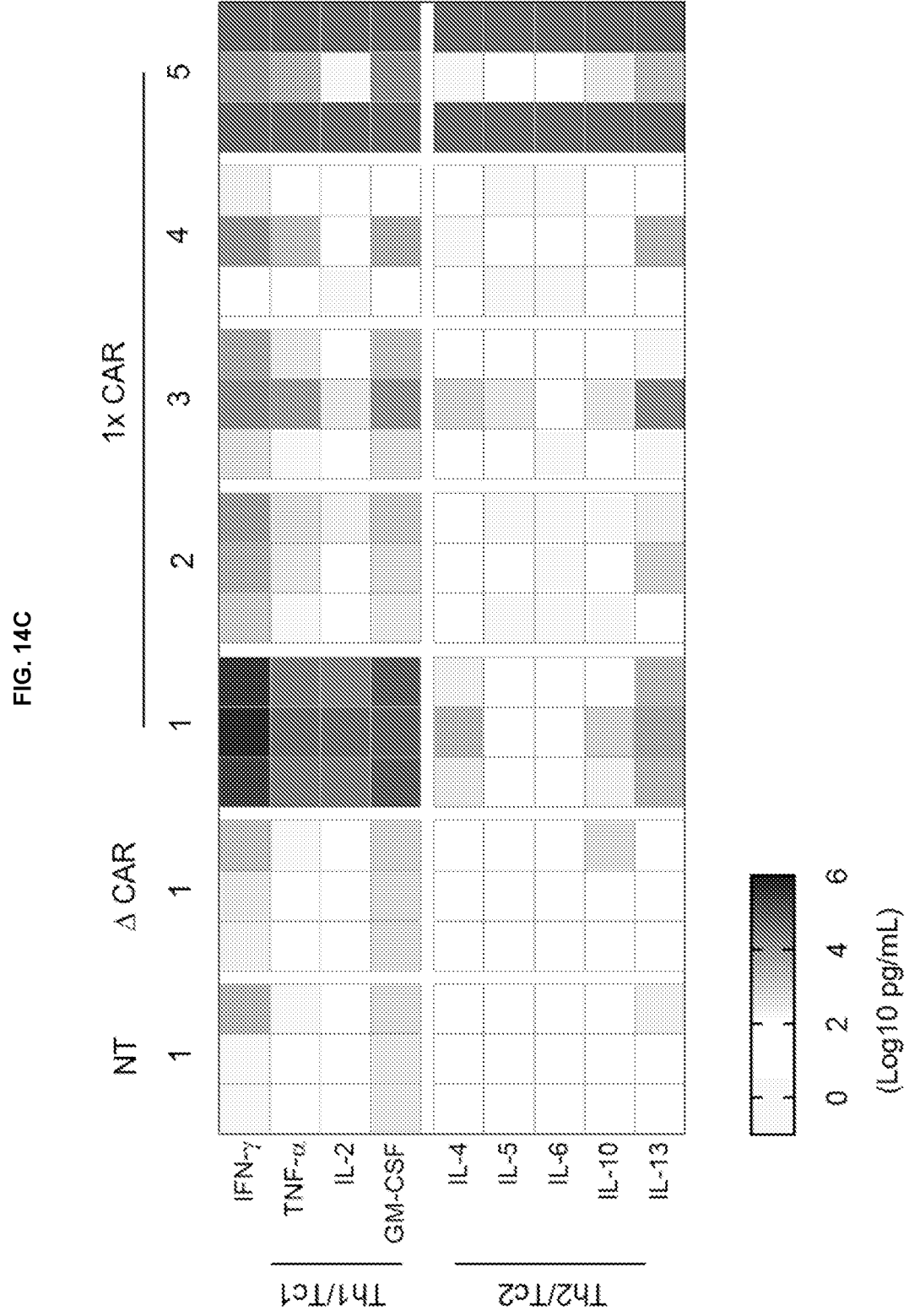

Example 10. GRP78-CAR T Cells Sequentially Kill Tumor Cells and Secrete Cytokines To evaluate if GRP78.1x-CAR T cells were able to sequentially kill AML cells and produce cytokines, a repeat stimulation assay in which NT, GRP78.ΔCAR, or GRP78.1x-CAR T cells were stimulated every three days with MOLM13.GFP.ffluc cells was performed (FIG. 14A). Before re-stimulation, percentage of viable tumor cells was evaluated by performing a luciferase assay, and co-culture supernatant collected for cytokine analysis. Depending on the donor, GRP78.1xCAR T cells killed tumor cells between 2 and 5 times (FIG. 14B). GRP78.1x-CAR T cells also consistently produced Th1/Tc1 (IFN-γ, TNF-α, GMCSF, and/or IL-2) cytokines for at least three stimulations, although there was a significant decrease with each stimulation (FIG. 14C). While GRP78.1x-CAR T cells also produced Th2/Tc2 (IL-4, IL-5, IL-6, IL10, and/or IL13) cytokines, expression was significantly lower than Th1/Tc1 cytokines (FIG. 14C), confirming findings with MV-4-11 cells.

REFERENCES

1. Kim, Y., et al. Targeting heat shock proteins on cancer cells: selection, characterization, and cell-penetrating properties of a peptidic GRP78 ligand. *Biochemistry* 45, 9434-9444 (2006).

2. Jonnalagadda, M., et al. Chimeric antigen receptors with mutated IgG4 Fc spacer avoid fc receptor binding and improve T cell persistence and antitumor efficacy. *Mol Ther* 23, 757-768 (2015).

3. Brown, C. E., et al. Optimization of IL13Ralpha2-Targeted Chimeric Antigen Receptor T Cells for Improved Anti-tumor Efficacy against Glioblastoma. *Mol Ther* 26, 31-44 (2018).

4. Burikhanov, R., et al. The tumor suppressor Par-4 activates an extrinsic pathway for apoptosis. *Cell* 138, 377-388 (2009).

5. Staquicini, D. I., et al. Therapeutic targeting of membrane-associated GRP78 in leukemia and lymphoma: preclinical efficacy in vitro and formal toxicity study of BMTP-78 in rodents and primates. *Pharmacogenomics J* 18, 436-443 (2018).

6. Miao, Y. R., et al. Inhibition of established micrometastases by targeted drug delivery via cell surface-associated GRP78. *Clin Cancer Res* 19, 2107-2116 (2013).

7. Misra, U. K., Deedwania, R. & Pizzo, S. V. Activation and cross-talk between Akt, NF-kappaB, and unfolded protein response signaling in 1-LN prostate cancer cells consequent to ligation of cell surface-associated GRP78. *J Biol Chem* 281, 13694-13707 (2006).

8. Zhang, J., et al. Association of elevated GRP78 expression with increased lymph node metastasis and poor prognosis in patients with gastric cancer. *Clin Exp Metastasis* 23, 401-410 (2006).

9. Niu, Z., et al. Elevated GRP78 expression is associated with poor prognosis in patients with pancreatic cancer. *Sci Rep* 5, 16067 (2015).

10. Grunewald, T. G. P., et al. Ewing sarcoma. *Nat Rev Dis Primers* 4, 5 (2018).

11. Kozutsumi, Y., Segal, M., Normington, K., Gething, M. J. & Sambrook, J. The presence of malfolded proteins in the endoplasmic reticulum signals the induction of glucose-regulated proteins. *Nature* 332, 462-464 (1988).

12. Shuda, M., et al. Activation of the ATF6, XBP1 and grp78 genes in human hepatocellular carcinoma: a possible involvement of the ER stress pathway in hepatocarcinogenesis. *J Hepatol* 38, 605-614 (2003).

13. Auf, G., et al. Inositol-requiring enzyme 1alpha is a key regulator of angiogenesis and invasion in malignant glioma. *Proc Natl Acad Sci USA* 107, 15553-15558 (2010).

14. Verfaillie, T., et al. PERK is required at the ER-mitochondrial contact sites to convey apoptosis after ROS-based ER stress. *Cell Death Differ* 19, 1880-1891 (2012).

15. Chung-man Ho, J., Zheng, S., Comhair, S. A., Farver, C. & Erzurum, S. C. Differential expression of manganese superoxide dismutase and catalase in lung cancer. *Cancer Res* 61, 8578-8585 (2001).

16. Shiu, R. P., Pouyssegur, J. & Pastan, I. Glucose depletion accounts for the induction of two transformation-sensitive membrane proteinsin Rous sarcoma virus-transformed chick embryo fibroblasts. *Proc Natl Acad Sci USA* 74, 3840-3844 (1977).

17. Schroder, M. & Kaufman, R. J. The mammalian unfolded protein response. *Annu Rev Biochem* 74, 739-789 (2005).

18. Tseng, C. C., Zhang, P. & Lee, A. S. The COOH-Terminal Proline-Rich Region of GRP78 Is a Key Regulator of Its Cell Surface Expression and Viability of Tamoxifen-Resistant Breast Cancer Cells. *Neoplasia* 21, 837-848 (2019).

19. Tsai, Y. L., et al. Characterization and mechanism of stress-induced translocation of 78-kilodalton glucose-regulated protein (GRP78) to the cell surface. *J Biol Chem* 290, 8049-8064 (2015).

20. Xu, Y et al. Closely related T-memory stem cells correlate with in vivo expansion of CAR.CD19-T cells and are preserved by IL-7 and IL-15. *Blood* (2014).

21. Ahmed, N et al. Regression of Experimental Medulloblastoma following Transfer of HER2-Specific T Cells. *Cancer Research* (2007).

22. Vera J. et al. T lymphocytes redirected against the kappa light chain of human immunoglobulin efficiently kill mature B lymphocyte-derived malignant cells. *Blood* (2006).

23. Bonifant C L. et al. CD123-Engager T Cells as a Novel Immunotherapeutic for Acute Myeloid Leukemia. *Mol Ther* (2016).

24. Faber Z J, Chen X, Gedman A L, et al. The genomic landscape of core-binding factor acute myeloid leukemias. *Nat Genet.* 2016; 48(12):1551-1556.

25. Anders S, Pyl P T, Huber W. HTSeq—a Python framework to work with high-throughput sequencing data. *Bioinformatics.* 2015; 31(2):166-169.

26. Ritchie M E, Phipson B, Wu D, et al. limma powers differential expression analyses for RNA-sequencing and microarray studies. *Nucleic Acids Res.* 2015; 43(7): e47.

27. Kim Y, Lillo A M, Steiniger S C, et al. Targeting heat shock proteins on cancer cells: selection, characterization, and cell-penetrating properties of a peptidic GRP78 ligand. *Biochemistry.* 2006; 45(31):9434-9444.

28. Bolouri H, Farrar J E, Triche T, Jr., et al. The molecular landscape of pediatric acute myeloid leukemia reveals recurrent structural alterations and age-specific mutational interactions. *Nat Med.* 2018; 24(1): 103-112.

29. Cancer Genome Atlas Research N, Ley T J, Miller C, et al. Genomic and epigenomic landscapes of adult de novo acute myeloid leukemia. *N Engl J Med.* 2013; 368(22):2059-2074.

30. Haferlach T, Kohlmann A, Wieczorek L, et al. Clinical utility of microarray-based gene expression profiling in the diagnosis and subclassification of leukemia: report from the International Microarray Innovations in Leukemia Study Group. *J Clin Oncol.* 2010; 28(15):2529-2537.

31. Bagger F O, Sasivarevic D, Sohi S H, et al. Blood-Spot: a database of gene expression profiles and transcriptional programs for healthy and malignant haematopoiesis. *Nucleic Acids Res.* 2016; 44(D1):D917-924.

32. Rapin N, Bagger F O, Jendholm J, et al. Comparing cancer vs normal gene expression profiles identifies new disease entities and common transcriptional programs in AML patients. *Blood.* 2014; 123(6):894-904.

33. Klco J M, Spencer D H, Miller C A, et al. Functional heterogeneity of genetically defined subclones in acute myeloid leukemia. *Cancer Cell.* 2014; 25(3):379-392.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

---

What is claimed is:

1. A polynucleotide encoding a chimeric antigen receptor (CAR) comprising
    a) an extracellular target-binding domain comprising one or more glucose-regulated-protein 78 (GRP78)-binding moieties, wherein the GRP78-binding moiety comprises the amino acid sequence of SEQ ID NO: 1;
    b) transmembrane domain; and
    c) a cytoplasmic domain comprising a signaling domain.

2. The polynucleotide of claim 1, wherein the nucleotide sequence encoding the GRP78-binding moiety comprises the nucleotide sequence of SEQ ID NO: 2.

3. The polynucleotide of claim 1, wherein the extracellular target-binding domain comprises one, two or three GRP78-binding moieties.

4. The polynucleotide of claim 1, wherein when more than one GRP78-binding moiety is used, each GRP78-binding moiety is linked via a linker sequence.

5. The polynucleotide of claim 4, wherein the linker sequence comprises the amino acid sequence of SEQ ID NO: 5; or the nucleotide encoding the linker sequence comprises the nucleotide sequence of SEQ ID NO: 6.

6. The polynucleotide of claim 1, wherein the extracellular target-binding domain further comprises a leader sequence.

7. The polynucleotide of claim 6, wherein the leader sequence is derived from human immunoglobulin (IgG) heavy chain variable region or CD8α.

8. The polynucleotide of claim 1, wherein the transmembrane domain is derived from CD28, CD8α, CD8, CD4, CD3ζ, CD40, CD134 (OX-40), or CD7.

9. The polynucleotide of claim 1, wherein the extracellular target binding domain further comprises a hinge domain between the GRP78-binding moiety and the transmembrane domain.

10. The polynucleotide of claim 9, wherein the hinge domain is derived from a mutated IgG4 hinge, CD8α, CD28, a chimeric mouse IgG4/CD8α hinge, an IgG1-derived hinge-CH3 spacer, an IgG1-derived hinge-CH2-CH3 spacer, or an IgG1-derived modified hinge-CH2-CH3 spacer.

11. The polynucleotide of claim 10, wherein the hinge domain comprises the amino acid sequence of SEQ ID NO: 7, 85, 87, 89, or an amino acid sequence having at least 80% sequence identity thereof.

12. The polynucleotide of claim 10, wherein the nucleotide sequence encoding the hinge domain comprises the nucleotide sequence of SEQ ID NO: 8, 86, 88, or 90, or a nucleotide sequence having at least 80% sequence identity thereof.

13. The polynucleotide of claim 1, wherein the signaling domain is derived from CD3ζ, DAP10, DAP12, Fc ε receptor I γ chain (FCER1G), CD3δ, CD3ε, CD3γ, CD226, or CD79A.

14. The polynucleotide of claim 1, wherein the cytoplasmic domain further comprises one or more costimulatory domains.

15. The polynucleotide of claim 14, wherein the one or more costimulatory domains are derived from CD28, CD27, CD40, CD134, CD226, CD79A, ICOS, 41BB, OX40 or MyD88, or any combination thereof.

16. The polynucleotide of claim 1, wherein the CAR comprises the amino acid sequence of any one of SEQ ID NOs: 29, 31, or 33, or an amino acid sequence having at least 80% sequence identity thereof; or the nucleotide sequence encoding the CAR comprises the nucleotide sequence of any one of SEQ ID NOs: 30, 32, or 34, or a nucleotide sequence having at least 80% sequence identity thereof.

17. The polynucleotide of claim 1, wherein the polynucleotide further encodes at least one additional polypeptide.

18. The polynucleotide of claim 17, wherein the at least one polypeptide is a transduced host cell selection marker, an in vivo tracking marker, a cytokine, or a safety switch gene.

19. The polynucleotide of claim 1, wherein the sequence encoding the CAR is operably linked to the sequence encoding at least an additional polypeptide sequence via a sequence encoding a self-cleaving peptide and/or an internal ribosomal entry site (IRES).

20. A chimeric antigen receptor (CAR) encoded by the polynucleotide of claim 1.

21. A recombinant vector comprising the polynucleotide of claim 1.

22. An isolated host cell comprising the polynucleotide of claim 1 or a recombinant vector comprising the polynucleotide.

23. An isolated host cell comprising a chimeric antigen receptor (CAR) encoded by the polynucleotide of claim 1.

24. A pharmaceutical composition comprising the host cell of claim 22 and a pharmaceutically acceptable carrier and/or excipient.

25. A method of generating the isolated host cell of claim 22, said method comprising genetically modifying the host cell with the polynucleotide or a recombinant vector comprising the polynucleotide.

26. A method for killing a cancer cell expressing GRP78, said method comprising contacting said cell with the host cell(s) of claim 22 or a pharmaceutical composition comprising the host cell and a pharmaceutically acceptable carrier and/or excipient.

27. A method for treating a cancer in a subject in need thereof, wherein one or more cells of the cancer express GRP78, said method comprising administering to the subject a therapeutically effective amount of the host cell(s) of claim 22 or a pharmaceutical composition comprising the host cell and a pharmaceutically acceptable carrier and/or excipient.

* * * * *